United States Patent
Liu et al.

(10) Patent No.: US 9,598,367 B2
(45) Date of Patent: Mar. 21, 2017

(54) HETEROCYCLIC COMPOUNDS AS BROMODOMAIN INHIBITORS

(71) Applicant: Zenith Epigenetics Corp., Calgary (CA)

(72) Inventors: Shuang Liu, Schenectady, NY (US); Bryan Cordell Duffy, Glenmont, NY (US); John Frederick Quinn, Albany, NY (US); May Xiaowu Jiang, Guilderland, NY (US); Ruifang Wang, Schenectady, NY (US); Gregory Scott Martin, Colonie, NY (US); He Zhao, Madison, CT (US); Bruce Francis Molino, Slingerlands, NY (US); Peter Ronald Young, San Francisco, CA (US)

(73) Assignee: Zenith Epigenetics Ltd., Calgary, AB (CA)

( * ) Notice: Subject to any disclaimer, the term of this patent is extended or adjusted under 35 U.S.C. 154(b) by 0 days.

(21) Appl. No.: 14/997,213

(22) Filed: Jan. 15, 2016

(65) Prior Publication Data
US 2016/0130228 A1 May 12, 2016

Related U.S. Application Data

(63) Continuation of application No. 14/134,793, filed on Dec. 19, 2013, now Pat. No. 9,271,978.

(60) Provisional application No. 61/745,274, filed on Dec. 21, 2012.

(51) Int. Cl.
| | |
|---|---|
| *C07D 213/64* | (2006.01) |
| *C07D 413/04* | (2006.01) |
| *C07D 413/14* | (2006.01) |
| *C07D 237/14* | (2006.01) |
| *C07D 237/22* | (2006.01) |
| *C07D 417/04* | (2006.01) |
| *C07D 213/74* | (2006.01) |
| *C07D 237/32* | (2006.01) |
| *A61K 31/4439* | (2006.01) |
| *A61K 31/496* | (2006.01) |
| *A61K 31/50* | (2006.01) |
| *A61K 31/501* | (2006.01) |
| *A61K 45/06* | (2006.01) |
| *C07D 237/04* | (2006.01) |
| *C07D 401/12* | (2006.01) |

(52) U.S. Cl.
CPC ........ *C07D 213/64* (2013.01); *A61K 31/4439* (2013.01); *A61K 31/496* (2013.01); *A61K 31/50* (2013.01); *A61K 31/501* (2013.01); *A61K 45/06* (2013.01); *C07D 213/74* (2013.01); *C07D 237/04* (2013.01); *C07D 237/14* (2013.01); *C07D 237/22* (2013.01); *C07D 237/32* (2013.01); *C07D 401/12* (2013.01); *C07D 413/04* (2013.01); *C07D 413/14* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 6,380,235 B1 | 4/2002 | Zhang et al. | |
| 8,053,440 B2 | 11/2011 | Hansen | |
| 8,093,273 B2 | 1/2012 | Wong et al. | |
| 8,735,586 B2 | 5/2014 | Alonso et al. | |
| 9,073,878 B2 | 7/2015 | Fairfax et al. | |
| 9,271,978 B2 | 3/2016 | Liu et al. | |
| 9,278,940 B2 | 3/2016 | Fairfax et al. | |
| 2002/0019395 A1 | 2/2002 | Zhu et al. | |
| 2003/0036545 A1 | 2/2003 | Castelhano et al. | |
| 2004/0166137 A1 | 8/2004 | Lackey | |
| 2005/0176775 A1 | 8/2005 | Devadas et al. | |
| 2005/0176858 A1 | 8/2005 | Nohara et al. | |
| 2007/0134161 A1 | 6/2007 | Brown | |
| 2007/0213323 A1 | 9/2007 | Imogai et al. | |
| 2007/0275984 A1 | 11/2007 | Imogai et al. | |
| 2008/0015196 A1 | 1/2008 | Doller et al. | |
| 2010/0063104 A1* | 3/2010 | Nakai .................... | A61K 31/00 514/340 |
| 2010/0234354 A1 | 9/2010 | Dorsch et al. | |
| 2010/0267714 A1 | 10/2010 | Jorgensen et al. | |
| 2011/0136819 A1 | 6/2011 | Dorsch et al. | |
| 2011/0136834 A1 | 6/2011 | Critchley et al. | |
| 2011/0257181 A1 | 10/2011 | Stieber et al. | |
| 2012/0028912 A1 | 2/2012 | Zhou et al. | |
| 2012/0157428 A1 | 6/2012 | Albrecht et al. | |
| 2012/0208798 A1 | 8/2012 | Demont et al. | |

(Continued)

FOREIGN PATENT DOCUMENTS

| | | |
|---|---|---|
| CA | 2440211 A1 | 9/2002 |
| CA | 2818187 A1 | 6/2012 |

(Continued)

OTHER PUBLICATIONS

Aiello, R.J., et al., "Monocyte chemoattractant protein-1 accelerates atherosclerosis in apolipoprotein E-deficient mice" *Arterioscler Thromb. Vasc. Biol.* 19(6): 1518-25 (1999).
Alexandraki, K. et al., "Inflammatory process in type 2 diabetes: The role of cytokines" *Ann N Y Acad Sci*, 2006. 1084:89-117.
Ambinter, "2(1H)-Pyridone, 1-[(4-chlorophenyl)methyl]-5-(1,3,4-oxadiazol-2-yl)-" Chemical Abstracts Record No. 1209999-95-0 [online], entered into STN Registry File Mar. 15, 2010.
Antonelli, A. et al., "Serum levels of proinflammatory cytokines interleukin-1beta, interleukin-6, and tumor necrosis factor alpha in mixed cryoglobulinemia" *Arthritis Rheum*, 2009. 60(12):3841-7.
Aricha, R. et al., "Blocking of IL-6 suppresses experimental autoimmune myasthenia gravis" *J Autoimmun*, 2011. 36(2):135-41.
Arif, M. et al., "Protein lysine acetylation in cellular function and its role in cancer manifestation" *Biochim Biophys Acta*, 2010. 1799(10-12):702-16.
Ash, Z. and P. Emery, "The role of tocilizumab in the management of rheumatoid arthritis" *Expert Opin Biol Ther*, 2012. 12(9): 1277-89.

(Continued)

*Primary Examiner* — Dennis Heyer
(74) *Attorney, Agent, or Firm* — Finnegan, Henderson, Farabow, Garrett & Dunner, LLP

(57) ABSTRACT

The present disclosure relates to compounds, which are useful for inhibition of BET protein function by binding to bromodomains, and their use in therapy.

4 Claims, No Drawings

(56) References Cited

U.S. PATENT DOCUMENTS

| | | |
|---|---|---|
| 2012/0208800 A1 | 8/2012 | Chung et al. |
| 2012/0208814 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0140956 A1 | 5/2014 | Fairfax et al. |
| 2014/0142102 A1 | 5/2014 | Fairfax et al. |
| 2014/0162971 A1 | 6/2014 | Wang et al. |
| 2014/0171462 A1 | 6/2014 | Demont et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0344442 A1 | 12/2015 | Fairfax et al. |
| 2016/0145248 A1 | 5/2016 | Liu et al. |

FOREIGN PATENT DOCUMENTS

| | | |
|---|---|---|
| CN | 102731409 A | 10/2012 |
| EP | 2 196 465 A1 | 6/2010 |
| EP | 2 390 250 A2 | 11/2011 |
| EP | 2 792 355 A1 | 10/2014 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/067675 A2 | 9/2002 |
| WO | WO 02/076976 A2 | 10/2002 |
| WO | WO 02/078708 A1 | 10/2002 |
| WO | WO 2004/078733 A1 | 9/2004 |
| WO | WO 2005/075432 A1 | 8/2005 |
| WO | WO 2005/090317 A1 | 9/2005 |
| WO | WO 2005/117876 A1 | 12/2005 |
| WO | WO 2006/038734 A1 | 4/2006 |
| WO | WO 2006/119400 A2 | 11/2006 |
| WO | WO 2007/016525 A2 | 2/2007 |
| WO | WO 2007/093901 A1 | 8/2007 |
| WO | WO 2008/054599 A2 | 5/2008 |
| WO | WO 2008/072784 A1 | 6/2008 |
| WO | WO 2009/024221 A1 | 2/2009 |
| WO | WO 2009/054790 A1 | 4/2009 |
| WO | WO 2009/099801 A1 | 8/2009 |
| WO | WO 2009/158258 A1 | 12/2009 |
| WO | WO 2010/068483 A2 | 6/2010 |
| WO | WO 2010/072296 A1 | 7/2010 |
| WO | WO 2010/077275 A1 | 7/2010 |
| WO | WO 2010/104851 A1 | 9/2010 |
| WO | WO 2010/106436 A2 | 9/2010 |
| WO | WO 2010/123975 A1 | 10/2010 |
| WO | WO 2011/054843 A1 | 5/2011 |
| WO | WO 2011/054846 A1 | 5/2011 |
| WO | WO 2011/143669 A2 | 11/2011 |
| WO | WO 2011/156626 A1 | 12/2011 |
| WO | WO 2011/159926 A1 | 12/2011 |
| WO | WO 2012/009258 A2 | 1/2012 |
| WO | WO 2012/021382 A1 | 2/2012 |
| WO | WO 2012/040499 A2 | 3/2012 |
| WO | WO 2012/075456 A1 | 6/2012 |
| WO | WO 2012/143413 A1 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/031928 A2 | 2/2014 |
| WO | WO 2014/043246 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/004534 A2 | 1/2015 |
| WO | WO 2015/011084 A1 | 1/2015 |
| WO | WO 2015/013635 A2 | 1/2015 |
| WO | WO 2015/015318 | 2/2015 |

OTHER PUBLICATIONS

Bandukwala, H.S. et al., "Selective inhibition of CD4+ T-cell cytokine production and autoimmunity by BET protein and c-Myc inhibitors" *Proc Natl Aced Sci USA*, 2012. 109(36):14532-7.

Bandyopadhyay, K. et al., "Spermidinyl-CoA-based HAT inhibitors block DNA repair and provide cancer-specific chemo- and radiosensitization" *Cell Cycle*, 2009. 8(17):2779-88. (Author's manuscript, 19 pages).

Banerjee, C. et al., "BET bromodomain inhibition as a novel strategy for reactivation of HIV-1" *J Leukoc Biol*, 2012. 92(6):1147-54.

Baron, P. et al., "Production of IL-6 by human myoblasts stimulated with Abeta: relevance in the pathogenesis of IBM" *Neurology*, 2001. 57(9):1561-5.

Bartholomeeusen, K. et al., "BET bromodomain inhibition activates transcription via a transient release of P-TEFb from 7SK snRNP" JBC in Press, 2012. M112.410746, 16 pages. Final publication in: *J Biol Chem*, 287:36609-16.

Bassiouny, D.A. and O. Shaker, "Role of interleukin-17 in the pathogenesis of vitiligo" *Clin Exp Dermatol*, 2011. 36(3):292-7.

Bayraktaroğlu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.

Belanger, D.B. et al., "Discovery of imidazo[1,2-a]pyrazine-based Aurora kinase inhibitors" *Bioorg. Med. Chem. Lett.*, 20:5170-5174 (2010).

Belkina, A.C. and G.V. Denis, "BET domain co-regulators in obesity, inflammation and cancer" *Nat Rev Cancer*, 2012. 12(7):465-77.

Bellan, C. et al., "CDK9/CYCLIN T1 expression during normal lymphoid differentiation and malignant transformation" *J. Pathol.*, 2004. 203(4):946-52.

Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.

Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.

(56) References Cited

OTHER PUBLICATIONS

Besnard, A.G. et al., "Inflammasome-IL-1-Th17 response in allergic lung inflammation" *J Mol Cell Biol*, 2012. 4(1):3-10.
Boring, L. et al., "Decreased lesion formation in CCR2-/- mice reveals a role for chemokines in the initiation of atherosclerosis" *Nature*, 1998. 394(6696):894-7.
Bradley, D.T. and S.E. Kountakis, "Role of interleukins and transforming growth factor-beta in chronic rhinosinusitis and nasal polyposis" *Laryngoscope*, 2005. 115(4):684-6.
Brennan, P., "Isoxazole Inhibitors of Bromodomains" presented at the *RSC Advances in Synthesis and Medicinal Chemistry Conference*, BioPark, Welwyn Garden City, UK, May 1, 2012 (46 pages).
Brodmerkel, C.M. et al., "Discovery and pharmacological characterization of a novel rodent-active CCR2 antagonist, INCB3344" *J Immunol*, 2005. 175(8):5370-8.
Brühl, H. et al., "Dual role of CCR2 during initiation and progression of collagen-induced arthritis: evidence for regulatory activity of CCR2+ T cells" *J Immunol*, 2004. 172(2):890-8.
ChemDiv, Inc. in Chemical Abstracts Record No. 1340694-11-8, Entered into the Registry File Nov. 4, 2011.
Chen, L. et al., "IL-17RA aptamer-mediated repression of IL-6 inhibits synovium inflammation in a murine model of osteoarthritis" *Osteoarthritis Cartilage*, 2011. 19(6):711-8.
Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.
Chung, C.W., "Small Molecule Bromodomain Inhibitors: Extending the Druggable Genome" *Progr. Med. Chem.*, 51:1-55 (2012).
Chung, C.W. et al., "Discovery and characterization of small molecule inhibitors of the BET family bromodomains" *J Med Chem*, 2011. 54(11):3827-38.
Chung, C.W. et al., "Bromodomains: a new target class for small molecule drug discovery" *Drug Discovery Today: Therapeutic Strategies* 9(2-3):e111-e120 (2012).
Cid, J.M. et al., "Discovery of 1,5-Disubstituted Pyridones: A New Class of Positive Allosteric Modulators of the Metabotropic Glutamate 2 Receptor" *ACS Chem. Neurosci.* 1:788-795 (2010).
Costello, J.F. et al., "Cyclin-dependent kinase 6 (CDK6) amplification in human gliomas identified using two-dimensional separation of genomic DNA" *Cancer Res*, 1997. 57(7):1250-4.
D'Auria, L. et al., "Cytokines and bullous pemphigoid" *Eur Cytokine Netw*, 1999. 10(2):123-34.
Dawson, J. et al., "Targeting monocyte chemoattractant protein-1 signalling in disease" *Expert Opin Ther Targets*, 2003. 7(1):35-48.
Dawson, M.A. et al., "Inhibition of BET Recruitment to Chromatin as as Effective Treatment for MLL-fusion Leukaemia", *Nature*, 2011, 478:529-533.
De Falco, G. et al., "Cdk9 regulates neural differentiation and its expression correlates with the differentiation grade of neuroblastoma and PNET tumors" *Cancer Biol Ther*, 2005. 4(3):277-81.
De Lemos, J.A. et al., "Association between plasma levels of monocyte chemoattractant protein-1 and long-term clinical outcomes in patients with acute coronary syndromes" *Circulation*, 2003. 107(5):690-5.
De Paiva, C.S. et al., "IL-17 disrupts corneal barrier following desiccating stress" *Mucosal Immunol*, 2009. 2(3):243-53.
Degoma, E.M. and D.J. Rader, "Novel HDL-directed pharmacotherapeutic strategies" *Nat Rev Cardiol*, 2011. 8(5):266-77.
Delmore, J.E. et al., "BET bromodomain inhibition as a therapeutic strategy to target c-Myc" *Cell*, 2011. 146(6):904-17.
Deng, J. et al., "Th17 and Th1 T-cell responses in giant cell arteritis" *Circulation*, 2010. 121(7):906-15.
Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).
Denis, G.V., "Bromodomain coactivators in cancer, obesity, type 2 diabetes, and inflammation" *Discov Med*, 2010. 10(55):489-99.

Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.
Dias, P.M. and G. Banerjee, "The Role of Th17/IL-17 on Eosinophilic Inflammation" *J Autoimmun*, 2012. Article in Press: http://dx.doi.org/10.1016/j.jaut.2012.07.004, 12 pages.
Elliott, D.A. et al., "Apolipoproteins in the brain: implications for neurological and psychiatric disorders" *Clin Lipidol*, 2010. 51(4):555-573. (Author manuscript, 28 pages).
El-Osta, H.E. and R. Kurzrock, "Castleman's disease: from basic mechanisms to molecular therapeutics" *Oncologist*, 2011. 16(4):497-511.
European Patent Application No. 13864406.7, by Zenith Epigenetics Corp.: Extended European Search Report, including Search Opinion, dated Mar. 30, 2016 (6 pages).
Fife, B.T. et al., "CC chemokine receptor 2 is critical for induction of experimental autoimmune encephalomyelitis" *J Exp Med*, 2000. 192(6):899-905.
Figueroa-Vega, N. et al., "Increased circulating pro-inflammatory cytokines and Th17 lymphocytes in Hashimoto's thyroiditis" *J Clin Endocrinol Metab*, 2010. 95(2):953-62.
Filippakopoulos, P. et al., "Selective Inhibition of BET Bromodomains", *Nature*, 2010, 468:1067-1073.
Filippakopoulos, P. and S. Knapp, "Targeting bromodomains: epigenetic readers of lyine acetylation" *Nature Reviews*, 13:337-356 (2014).
Fish, P.V. et al., "Identification of a chemical probe for bromo and extra C-terminal bromodomain inhibition through optimization of a fragment-derived hit" *J. Med. Chem.* 55:9831-9837 (2012).
French, C.A., "NUT midline carcinoma" *Cancer Genet Cytogenet*, 2010. 203(1):16-20. (Author manuscript, 9 pages).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*, 2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19):3809-20.
Gloddek, B. et al., "Pharmacological influence on inner ear endothelial cells in relation to the pathogenesis of sensorineural hearing loss" *Adv Otorhinolaryngol*, 2002. 59:75-83.
Gong, J.-H. et al., "An antagonist of monocyte chemoattractant protein 1 (MCP-1) inhibits arthritis in the MRL-lpr mouse model" *J Exp Med*, 1997. 186(1):131-7.
Gong, J.-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production After Lipopolysaccharide Stimulation in Patients with X-linked Agammaglobulinemia" *J Clin Immunol*, 2012. 32(5):967-74.
Gosling, J. et al., "MCP-1 deficiency reduces susceptibility to atherosclerosis in mice that overexpress human apolipoprotein B" *J Clin Invest*, 1999. 103(6):773-8.
Graber, J.J. et al., "Interleukin-17 in transverse myelitis and multiple sclerosis" *J Neuroimmunol*, 2008. 196(1-2):124-32.
Greenwald, R.J. et al., "E mµ-BRD2 transgenic mice develop B-cell lymphoma and leukemia" *Blood*, 2004. 103(4):1475-84.
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*, 1998. 2(2):275-81.
Gu, Y. et al., "Interleukin (IL)-17 promotes macrophages to produce IL-8, IL-6 and tumour necrosis factor-alpha in aplastic anaemia" *Br J Haematol*, 2008. 142(1):109-14.

(56) References Cited

OTHER PUBLICATIONS

Harada, K. et al., "Periductal interleukin-17 production in association with biliary innate immunity contributes to the pathogenesis of cholangiopathy in primary biliary cirrhosis" *Clin Exp Immunol*, 2009. 157(2):261-70.

Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.

Hay et al., "The design and synthesis of 5- and 6-isoxazolylbenzimidazoles as selective inhibitors of the BET bromodomains" *Med. Chem. Commun.* 4:140-144 (2013).

Hay, D.A. et al., "Discovery and Optimization of Small-Molecule Ligands for the CBP/p300 Bromodomains" *J. Am. Chem. Soc.* 136:9308-9319 (2014).

Hewings et al., "3,5-Dimethylisoxazoles Act as Acetyl-lysine-mimetic Bromodomain Ligands" *J. Med. Chem.* 54:6761-6770 (2011).

Hewings et al., "Progress in the development and application of small molecule inhibitors of bromodomain-acetyl-lysine interactions" *J. Med. Chem.* 55:9393-9413 (2012).

Hewings et al., "3,5-Dimethylisoxazoles inhibit the bromodomain-histone protein-protein interaction" *243rd National Spring Meeting of the American-Chemical-Society (Symposium on Ionic Liquids—Science and Applications)*, San Diego, CA. General Poster Session, Mar. 28, 2012, Poster 326 Abstract [online]. Retrieved from: http://acselb-529643017.us-west-2.elb.amazonaws.com/chem/243nm/program/view.php?pub_num=326&par=MEDI.

Hewings et al., "Optimization of 3,5-Dimethylisoxazole Derivatives as Potent Bromodomain Ligands" *J. Med. Chem.* 56:3217-3227 (2013).

Hintermann, S. et al., "Identification of a series of highly potent activators of the Nurr 1 signaling pathway" *Bioorg Med Chem Lett*, 17:193-196 (2007).

Hohki, S. et al., "Blockade of interleukin-6 signaling suppresses experimental autoimmune uveoretinitis by the inhibition of inflammatory Th17 responses" *Exp Eye Res*, 2010. 91(2):162-70.

Hölttä, V. et al., "IL-23/IL-17 immunity as a hallmark of Crohn's disease" *Inflamm Bowel Dis*, 2008. 14(9):1175-84.

Hoshino, I. and H. Matsubara, "Recent advances in histone deacetylase targeted cancer therapy" *Surg Today*, 2010. 40(9):809-15.

Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med*, 2001. 193(6):713-26.

Içöz, S. et al., "Enhanced IL-6 production in aquaporin-4 antibody positive neuromyelitis optica patients" *Int J Neurosci*, 2010. 120(1):71-5.

International Search Report and Written Opinion issued in International Application No. PCT/IB2013/000968; Date of Mailing: Sep. 13, 2013.

International Search Report and Written Opinion issued in International Application No. PCT/IB2013/001026; Date of Mailing: Sep. 30, 2013.

International Search Report and Written Opinion issued in International Application No. PCT/IB2013/001232; Date of Mailing: Sep. 6, 2013.

International Search Report and Written Opinion issued in International Application No. PCT/IB2013/003122; Date of Mailing: Jul. 9, 2014.

International Search Report and Written Opinion issued in International Application No. PCT/IB2013/003126; Date of Mailing: Jun. 26, 2014.

International Search Report and Written Opinion issued in International Application No. PCT/IB2013/003202; Date of Mailing: Jul. 17, 2014.

International Search Report and Written Opinion issued in International Application No. PCT/IB2014/002238; Date of Mailing: Apr. 23, 2015.

International Search Report and Written Opinion issued in International Application No. PCT/IB2014/002240; Date of Mailing: Mar. 10, 2015.

International Search Report and Written Opinion issued in International Application No. PCT/IB2014/002510; Date of Mailing: Apr. 15, 2015.

International Search Report and Written Opinion issued in International Application No. PCT/IB2015/002429; Date of Mailing: Apr. 13, 2016.

International Search Report and Written Opinion issued in International Application No. PCT/IB2015/002490; Date of Mailing: Apr. 1, 2016.

International Search Report and Written Opinion issued in International Application No. PCT/US2014/043423; Date of Mailing: Jan. 12, 2005.

Ishizu, T. et al., "CSF cytokine and chemokine profiles in acute disseminated encephalomyelitis" *J Neuroimmunol*, 2006. 175(1-2):52-58.

Ito, Y. et al., "Pathogenic significance of interleukin-6 in a patient with antiglomerular basement membrane antibody-induced glomerulonephritis with multinucleated giant cells" *Am J Kidney Dis*, 1995. 26(1):72-9.

Jadidi-Niaragh, F. and A. Mirshafiey, "Th17 cell, the new player of neuroinflammatory process in multiple sclerosis" *Scand J Immunol*, 2011. 74(1):1-13.

Jahagirdar, R. et al., "An Orally Bioavailable Small Molecule RVX-297 Significantly Decreases Disease in a Mouse Modelof Multiple Sclerosis" (Poster Presentation). World Congress of Inflammation, Paris, France, 2011, 1 page.

Jen, H-Y. et al., "Increased serum interleukin-17 and peripheral Th17 cells in children with acute Henoch-Schonlein purpura" *Pediatr Allergy Immunol*, 2011. 22(8):862-8.

Jia, S., et al., "The T helper type 17/regulatory T cell imbalance in patients with acute Kawasaki disease" *Clin Exp Immunol*, 2010. 162(1):131-7.

Johnson, R.B. et al., "Interleukin-11 and IL-17 and the pathogenesis of periodontal disease" *J Periodontol*, 2004. 75(1):37-43.

Kahawita, I.P. and D.N. Lockwood, "Towards understanding the pathology of erythema nodosum leprosum" *Trans R Soc Trop Med Hyg*, 2008. 102(4):329-37.

Kallen, K.J. et al., "New developments in IL-6 dependent biology and therapy: where do we stand and what are the options?" *Expert Opin Investig Drugs*, 1999. 8(9):1327-49.

Kaplanski, G. et al., "Jarisch-Herxheimer reaction complicating the treatment of chronic Q fever endocarditis: elevated TNFalpha and IL-6 serum levels" *J Infect*, 1998. 37(1):83-4.

Kappel, L.W. et al., "IL-17 contributes to CD4-mediated graft-versus-host disease" *Blood*, 2009. 113(4):945-52.

Katsifis, G.E. et al., "Systemic and local interleukin-17 and linked cytokines associated with Sjogren's syndrome immunopathogenesis" *Am J Pathol*, 2009. 175(3):1167-77.

Kawai, M. et al., "Sustained response to tocilizumab, anti-interleukin-6 receptor antibody, in two patients with refractory relapsing polychondritis" *Rheumatology*, 2009. 48(3):318-9.

Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol*, 2009. 104(9):2363-4.

Kawakami, T. et al., "Serum levels of interleukin-6 in patients with cutaneous polyarteritis nodosa" *Acta Derm Venereol*, 2012. 92(3):322-3.

Kelly, P.N. and A. Strasser, "The role of Bcl-2 and its pro-survival relatives in tumourigenesis and cancer therapy" *Cell Death Differ*, 2011. 18(9):1414-24.

Kim, S.E. et al., "Increased serum interleukin-17 in Graves' ophthalmopathy" *Graefes Arch Clin Exp Ophthalmol*, 2012. 250(10):1521-6.

Kimura, A. and T. Kishimoto, "IL-6: regulator of Treg/Th17 balance" *Eur J Immunol*, 2010. 40(7):1830-5.

(56) References Cited

OTHER PUBLICATIONS

Koch, A.E. et al., "Enhanced production of monocyte chemoattractant protein-1 in rheumatoid arthritis" *J Clin Invest*, 1992. 90(3):772-9.

Kyburz, D. and M. Corr, "Th17 cells generated in the absence of TGF-beta induce experimental allergic encephalitis upon adoptive transfer" *Expert Rev Clin Immunol*, 2011. 7(3):283-5.

Lahdenperä, A.I. et al., "Up-regulation of small intestinal interleukin-17 immunity in untreated coeliac disease but not in potential coeliac disease or in type 1 diabetes" *Clin Exp Immunol*, 2012.167(2):226-34.

Lamale, L.M. et al., "Interleukin-6, histamine, and methylhistamine as diagnostic markers for interstitial cystitis" *Urology*, 2006. 68(4):702-6.

Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041. Final publication as: Seal, J. et al., "Identification of a novel series of BET family bromodomain inhibitors: binding mode and profile of I-BET151 (GSK1210151A)" *Bioorg Med Chem Lett*, 2012. 22(8):2968-72.

Latifi, S.Q. et al., "Persistent elevation of serum interleukin-6 in intraabdominal sepsis identifies those with prolonged length of stay" *J Pediatr Surg*, 2004. 39(10):1548-52.

Lee, D.K. et al., "Androgen receptor interacts with the positive elongation factor P-TEFb and enhances the efficiency of transcriptional elongation" *J Biol Chem*, 2001. 276(13):9978-84.

Li, Z., et al., "The BET bromodomain inhibitor JQ1 activates HIV latency through antagonizing Brd4 inhibition of Tat-transactivation" *Nucleic Acids Res Advance Access*, 2012. DOI:10.1093/nar/gks976, 11 pages.

Lin, F.J. et al., "Imbalance of regulatory T cells to Th17 cells in IgA nephropathy" *Scand J Clin Lab Invest*, 2012. 72(3):221-9.

Linhares, U.C. et al., "The Ex Vivo Production of IL-6 and IL-21 by CD4(+) T Cells is Directly Associated with Neurological Disability in Neuromyelitis Optica Patients" *J Clin Immunol*, 2012, DOI 10.1007/s10875-012-9780-2, 11 pages.

Lopez-Robles, E. et al., "TNFalpha and IL-6 are mediators in the blistering process of pemphigus" *Int J Dermatol*, 2001. 40(3):185-8.

Lu, M.O. and J. Zhu, "The role of cytokines in Guillain-Barre syndrome" *J Neurol*, 2011. 258(4):533-48.

Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.

Mahad, D.J. and R.M. Ransohoff, "The role of MCP-1 (CCL2) and CCR2 in multiple sclerosis and experimental autoimmune encephalomyelitis (EAE)" *Semin Immunol*, 2003. 15(1):23-32.

Matzuk, M.M. et al., "Small-Molecule Inhibition of BRDT for Male Contraception" *Cell*, 2012. 150(4):673-684, with supplemental pp. S1-S8.

McKinley, L. et al., "TH17 cells mediate steroid-resistant airway inflammation and airway hyperresponsiveness in mice" *J Immunol*, 2008. 181(6):4089-97.

Medina-Franco, J.L. et al., "Pyridin-2(1H)-ones: A Promising Class of HIV-f1 Non-nucleoside Reverse Transcriptase Inhibitors" *ChemMedChem*, 2:1141-1147 (2007).

Mendrzyk, F. et al., "Genomic and protein expression profiling identifies CDK6 as novel independent prognostic marker in medulloblastoma" *J Clin Oncol*, 2005. 23(34):8853-62.

Mertz, Jennifer A., "Targeting MYC Dependence in Cancer by Inhibiting BET Bromodomains", *PNAS*, 2011, 108(40):16669-16674.

Min, C.K. et al., "Cutaneous leucoclastic vasculitis (LV) following bortezomib therapy in a myeloma patient; association with proinflammatory cytokines" *Eur J Haematol*, 2006. 76(3):265-8.

Mirguet, O. et al., "From ApoA1 upregulation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-2967.

Mitsuyama, K. et al., "STAT3 activation via interleukin 6 trans-signalling contributes to ileitis in SAMP1/Yit mice" *Gut*, 2006. 55(9):1263-9.

Miyazaki, et al. "Intravenous Injection of Rabbit Apolipoprotein A-I Inhibits the Progression of Atherosclerosis in Cholesterol-Fed Rabbits" *Arterioscler Thromb. Vasc. Biol.* 15: 1882-1888 (1995).

Mok, M.Y. et al., "The relation of interleukin 17 (IL-17) and IL-23 to Th1/Th2 cytokines and disease activity in systemic lupus erythematosus" *J Rheumatol*, 2010. 37(10):2046-52.

Morin, R.D. et al., "Frequent mutation of histone-modifying genes in non-Hodgkin lymphoma" *Nature*, 2011. 476(7360):298-303. (Author manuscript, 17 pages).

Mudter, J. and M.F. Neurath, "IL-6 signaling in inflammatory bowel disease: pathophysiological role and clinical relevance" *Inflamm Bowel Dis*, 2007. 13(8):1016-23.

Muller Kobold, A.C. et al., "In vitro up-regulation of E-selectin and induction of interleukin-6 in endothelial cells by autoantibodies in Wegener's granulomatosis and microscopic polyangiitis" *Clin Exp Rheumatol*, 1999. 17(4):433-40.

Muller, S. et al., "Bromodomains as therapeutic targets" *Expert Rev Mol Med*, 2011. 13: e29, 21 pages.

Nakahama, H. et al., "Distinct responses of interleukin-6 and other laboratory parameters to treatment in a patient with Wegener's granulomatosis" *Intern Med*, 1993. 32(2):189-92.

Narayana, B.L. et al., "Synthesis of New 2-Substituted Pyrido[2,3-d]pyrimidine-4(1H)-ones and Their Antibacterial Activity" *Eur. J. Med. Chem.* 44(3):1369-1376 (2009).

Nelken, N.A. et al., "Monocyte chemoattractant protein-1 in human atheromatous plaques" *J Clin Invest*, 1991. 88(4):1121-7.

Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).

Nicodeme et al., "Suppression of inflammation by a synthetic histone mimic" *Nature* 468:1119-1123 (2010).

Niu, J. and P.E. Kolattukudy, "Role of MCP-1 in cardiovascular disease: molecular mechanisms and clinical implications" *Clin Sci*, 2009. 117(3):95-109.

Ooi, J.D. et al, "Review: T helper 17 cells: their role in glomerulonephritis" *Nephrology*, 2010. 15(5):513-21.

Ortiz-Lucas, M. et al., "Irritable bowel syndrome immune hypothesis. Part two: the role of cytokines" *Rev Esp Enferm Dig*, 2010. 102(12):711-7.

Ott, C.J. et al., "BET bromodomain inhibition targets both c-Myc and IL7R in high-risk acute lymphoblastic leukemia" *Blood*, 2012. 120(14):2843-52.

Palermo, R.D. et al., RNA polymerase II stalling promotes nucleosome occlusion and pTEFb recruitment to drive immortalization by Epstein-Barr virus. *PLoS Pathog*, 2011. 7(10): e1002334, 15 pages.

Paquet, P. and G.E. Pierard, "Interleukin-6 and the skin" *Int Arch Allergy Immunol*, 1996. 109(4):308-17.

Peserico, A. and C. Simone, "Physical and functional HAT/HDAC interplay regulates protein acetylation balance" *J Biomed Biotechnol*, 2011. 371832, 10 pages.

Poreba, E. et al., "Epigenetic mechanisms in virus-induced tumorigenesis" *Clin Epigenetics*, 2011. 2(2):233-47.

Prabakaran, K. et al., "Iridium bromide catalysed, ultrasound-assisted, region-selective synthesis of ethyl-5- (trifluoromethyl)-1-(3-substituted-isoguinolin-I-yl)-1H-pyrazole-4-carboxylates", *Res. Chem. Intermed.*, 38:429-441 (2012).

Prinjha, R.K. et al., "Place your BETs: the therapeutic potential of bromodomains" *Trends Pharmacol Sci*, 2012. 33(3):146-53.

Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.

Ramsay, R.G. and T.J. Gonda, "MYB function in normal and cancer cells" *Nat Rev Cancer*, 2008. 8(7):523-34.

Raychaudhuri, S.P. et al., "IL-17 receptor and its functional significance in psoriatic arthritis" *Mol Cell Biochem*, 2012. 359(1-2):419-29.

(56) References Cited

OTHER PUBLICATIONS

Rhodus, N.L. et al., "Proinflammatory cytokine levels in saliva before and after treatment of (erosive) oral lichen planus with dexamethasone" *Oral Dis*, 2006. 12(2):112-6.

Rodriguez, R.M. et al., "Aberrant epigenetic regulation of bromodomain BRD4 in human colon cancer" *J Mol Med*, 2012. 90(5):587-95.

Roger, V.L. et al., "Heart disease and stroke statistics—2012 update: a report from the American Heart Association" *Circulation*, 2012. 125(1):3-e220.

Ruden, M. and N. Puri, "Novel anticancer therapeutics targeting telomerase" *Cancer Treat Rev*, 2012. Article in Press: http://dx.doi.org/10.1016/j.ctrv.2012.06.007, 13 pages.

Rudloff, U. and Y. Samuels, "TYRO3-mediated regulation of MITF: a novel target in melanoma?" *Pigment Cell Melanoma Res*, 2010. 23(1):9-11.

Sanchez, R. and M.M. Zhou, "The role of human bromodomains in chromatin biology and gene transcription" *Curr Opin Drug Discov Devel*, 2009. 12(5):659-65. (Author manuscript, 12 pages.).

Scanlan, M.J. et al., "Expression of cancer-testis antigens in lung cancer: definition of bromodomain testis-specific gene (BRDT) as a new CT gene, CT9" *Cancer Lett*, 2000. 150(2):155-64.

Seal, J. et al., "Identification of a novel series of BET family bromodomain inhibitors: Binding mode and profile of I-BET15I(GSK121051A)" *Bioorg. Med. Chem. Lett.*, 22:2968-2972 (2012).

Segura, M.F. et al., "BRD4 is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1, Abstract 2185.

Shang, E. et al., "The first bromodomain of Brdt, a testis-specific member of the BET sub-family of double-bromodomain-containing proteins, is essential for male germ cell differentiation" *Development*, 2007. 134(19):3507-15.

Shibuya, M. et al., "Successful treatment with tocilizumab in a case of Cogan's syndrome complicated with aortitis" *Mod Rheumatol*, 2012, online: DOI 10.1007/s10165-012-0691-0, 5 pages.

Simmons, E.M. et al., "Plasma cytokine levels predict mortality in patients with acute renal failure" *Kidney Int*, 2004. 65(4):1357-65.

Simone, C. and A. Giordano, "Abrogation of signal-dependent activation of the cdk9/cyclin T2a complex in human RD rhabdomyosarcoma cells" *Cell Death Differ*, 2007. 14(1):192-5.

Soltesz, P. et al., "Immunological features of primary anti-phospholipid syndrome in connection with endothelial dysfunction" *Rheumatology*, 2008. 47(11):1628-34.

Stenman, G. et al., "New tricks from an old oncogene: gene fusion and copy number alterations of MYB in human cancer" *Cell Cycle*, 2010. 9(15):2986-95.

Sun, Y. et al., "MMP-9 and IL-6 are potential biomarkers for disease activity in Takayasu's arteritis" *Int J Cardiol*, 2012. 156(2):236-8.

Taylan, A. et al., "Evaluation of the T helper 17 axis in ankylosing spondylitis" *Rheumatol Int*, 2012. 32(8):2511-5.

Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.

Traves, S.L. and L.E. Donnelly, "Th17 cells in airway diseases" *Curr. Mol. Med.*, 2008. 8(5):416-26.

Uchida, T. et al., "Antitumor effect of bcl-2 antisense phosphorothioate oligodeoxynucleotides on human renal-cell carcinoma cells in vitro and in mice" *Mol Urol*, 2001. 5(2):71-8.

Urano, W. et al., "The inflammatory process in the mechanism of decreased serum uric acid concentrations during acute gouty arthritis" *J Rheumatol*, 2002. 29(9):1950-3.

Velisek, L. et al., "GABAergic neuron deficit as an idiopathic generalized epilepsy mechanism: the role of BRD2 haploinsufficiency in juvenile myoclonic epilepsy" *PLoS One*, 2011. 6(8): e23656, 8 pages.

Vernarecci, S. et al., "Tuning acetylated chromatin with HAT inhibitors: a novel tool for therapy" *Epigenetics*, 2010. 5(2): p. 105-11.

Vidal, B. et al., "Discovery and Characterization of 4'-(2-Furyl)-N-pyridin-3-yl-4,5'-bipyrimidin-2'-amine (LAS38096), a Potent, Selective, and Efficacious $A_{2B}$ Adenosine Receptor Antagonist" *J. Med. Chem.* 50:2732-2736 (2007).

Vidler, L.R. et al., "Discovery of Novel Small-Molecule Inhibitors of BRD4 Using Structure-Based Virtual Screening" *J Med Chem*, 56:8073-8088 (2013).

Vita, M. and M. Henriksson, "The Myc oncoprotein as a therapeutic target for human cancer" *Semin Cancer Biol*, 2006. 16(4):318-30.

Voitenko et al., "Esters of o-(4-oxo-3,4-dihydro-2-quinazolinyl)benzoic acid and 5,11-dihydroisoindolo[2,1-a]quinazolinone-5 derivatives as β-cyclodextrin modifiers" *Dopovidi Natsional'noi Akademii Nauk Uraini* (*Reports of the National Academy of Sciences of Ukraine*), 8:132-138 (2005) English abstract on p. 132.

Wang, F. et al., "Brd2 disruption in mice causes severe obesity without Type 2 diabetes" *Biochem J*, 2010. 425(1): p. 71-83, with supplemental online material, 2 pages.

Wang, G. et al., "Increased cyclin-dependent kinase 6 expression in bladder cancer" *Oncol Lett*, 2012. 4(1): p. 43-46.

Wang, S. and P.M. Fischer, "Cyclin-dependent kinase 9: a key transcriptional regulator and potential drug target in oncology, virology and cardiology" *Trends Pharmacol Sci*, 2008. 29(6):302-13.

Watson, J.D., "Curing 'incurable' cancer" *Cancer Discov*, 2011. 1(6):477-80.

Wu, S.Y. and C.M. Chiang, "The double bromodomain-containing chromatin adaptor Brd4 and transcriptional regulation" *J Biol Chem*, 2007. 282(18):13141-5.

Xing, W. et al., "Discovery of novel 2,6-disubstituted pyridazinone derivatives as acetylcholinesterase inhibitors" *Eur. J. Med. Chem.* 63:95-103 (2013).

Xu, L. et al., "Critical role of Th17 cells in development of autoimmune hemolytic anemia" *Exp Hematol*, 2012. Article in Press: http://dx.doi.org/10.1016/j.exphem.2012.08.008, 15 pages.

Yamaguchi, M. et al., "Novel Antiasthmatic Agents with Dual Activities of Thromboxane $A_2$ Synthetase Inhibition and Bronchodilation. 2. 4-(3-Pyridyl)-1(2H)-phthalazinones" *J. Med. Chem.*, 36:4061-4068 (1993).

Yamashita, T. et al., "IL-6-mediated Th17 differentiation through RORγt is essential for the initiation of experimental autoimmune myocarditis" *Cardiovasc Res*, 2011. 91(4):640-8.

Yoshii, T. et al., "Local levels of interleukin-1beta, -4, -6 and tumor necrosis factor alpha in an experimental model of murine osteomyelitis due to *Staphylococcus aureus*" *Cytokine*, 2002. 19(2): p. 59-65.

Yoshimura, T. et al., "Involvement of Th17 cells and the effect of anti-IL-6 therapy in autoimmune uveitis" *Rheumatology*, 48(4):347-354 (2009).

You, J. et al., "Kaposi's sarcoma-associated herpesvirus latency-associated nuclear antigen interacts with bromodomain protein Brd4 on host mitotic chromosomes" *J Virol*, 2006. 80(18):8909-19.

Yu et al., "Toll-Like Receptor 7 Agonists: Chemical Feature Based Pharmacophore Identification and Molecular Docking Studies" *PLoS One* 8(3):e56514, doi:10.1371/journal.pone.0056514 (2013).

Zhang, G. et al., "Down-regulation of NF-kappaB Transcriptional Activity in HIVassociated Kidney Disease by BRD4 Inhibition" *JBC Papers in Press*, 2012. M112.359505 with supplement, 38 pages. Final publication in: *J Biol Chem*, 287(34):28840-51.

Zhang, W.S. et al., "Bromodomain-Containing-Protein 4 (BRD4) Regulates RNA Polymerase II Serine 2 Phosphorylation in Human CD4+ T Cells" JBC Papers in Press, 2012. M112.413047, 30 pages. Final publication in: *J Biol Chem*, 287:43137-55.

Zhao, L. et al., "Interleukin-17 contributes to the pathogenesis of autoimmune hepatitis through inducing hepatic interleukin-6 expression" *PLoS One*, 2011. 6(4):e18909, 8 pages.

Zhou, M. et al., "Bromodomain protein Brd4 regulates human immunodeficiency virus transcription through phosphorylation of CDK9 at threonine 29" *J Virol*, 2009. 83(2):1036-44.

(56) References Cited

OTHER PUBLICATIONS

Zhu, J. et al., "Reactivation of Latent HIV-1 by Inhibition of BRD4" *Cell Rep*, 2012. 2:1-10, with supplemental pp. S1-S7.
Zuber, J. et al., "RNAi screen identifies Brd4 as a therapeutic target in acute myeloid leukaemia" *Nature*, 2011. 478(7370):524-8.

* cited by examiner

HETEROCYCLIC COMPOUNDS AS BROMODOMAIN INHIBITORS

This patent application is a continuation of U.S. application Ser. No. 14/134,793, filed on Dec. 19, 2013 (now U.S. Pat. No. 9,271,978, issued Mar. 1, 2016), which claims the benefit of priority to U.S. Provisional Application No. 61/745,274, filed on Dec. 21, 2012, the entirety of each of which is incorporated herein by reference.

The present disclosure relates to novel compounds, pharmaceutical compositions containing such compounds, and their use in prevention and treatment of diseases and conditions.

Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs) [1]. Small molecule inhibitors of HDACs and HATs are being investigated as cancer therapy [2-5]. Histone acetylation controls gene expression by recruiting protein complexes that bind directly to acetylated lysine via bromodomains [6]. One such family, the bromodomain and extra terminal domain (BET) proteins, comprises Brd2, Brd3, Brd4, and BrdT, each of which contains two bromodomains in tandem that can independently bind to acetylated lysines, as reviewed in [7].

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis [8].

BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections [8, 9].

Autoimmune diseases, which are often chronic and debilitating, are a result of a dysregulated immune response, which leads the body to attack its own cells, tissues, and organs. Pro-inflammatory cytokines including IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy [10].

BET inhibitors are expected to have anti-inflammatory and immunomodulatory properties [8, 9]. BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells [11-13]. The mechanism for these anti-inflammatory effects may involve BET inhibitor disruption of Brd4 co-activation of NF-κB-regulated pro-inflammatory cytokines and/or displacement of BET proteins from cytokine promoters, including IL-6 [12, 14, 15]. In addition, because Brd4 is involved in T-cell lineage differentiation, BET inhibitors may be useful in inflammatory disorders characterized by specific programs of T cell differentiation [16].

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders [12]. A BET inhibitor has been shown to ameliorate inflammation and kidney injury in HIV-1 transgenic mice, an animal model for HIV-associated nephropathy, in part through inhibition of Brd4 interaction with NF-κB [14]. The utility of BET inhibition in autoimmune disease was demonstrated in a mouse model of multiple sclerosis, where BET inhibition resulted in abrogation of clinical signs of disease, in part, through inhibition of IL-6 and IL-17 [17]. These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells [18].

BET inhibitors may be useful in the treatment of a variety of chronic autoimmune inflammatory conditions. Examples of autoimmune and inflammatory diseases, disorders, and syndromes that may be treated using the compounds and methods include but are not limited to, inflammatory pelvic disease, urethritis, skin sunburn, sinusitis, pneumonitis, encephalitis, meningitis, myocarditis, nephritis [14], osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis [9], Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis [18], scleroderma, vasculitis, autoimmune hemolytic and thrombocytopenic states, Goodpasture's syndrome, atherosclerosis, Addison's disease, Parkinson's disease, Alzheimer's disease, Type I diabetes [8], septic shock [12], systemic lupus erythematosus (SLE) [9], rheumatoid arthritis [19], psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions including but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock [12], systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus [8].

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs [20, 21].

The present disclosure provides a method for treating human cancer, including, but not limited to, cancers that result from aberrant translocation or overexpression of BET proteins (e.g., NUT midline carcinoma (NMC) [22]) and B-cell lymphoma [23]). NMC tumor cell growth is driven by a translocation of the Brd4 or Brd3 gene to the nutlin 1 gene[24]. BET inhibition has demonstrated potent antitumor activity in murine xenograft models of NMC, a rare but lethal form of cancer [24].

The present disclosure provides a method for treating human cancers, including, but not limited to, cancers dependent on a member of the myc family of oncoproteins including c-myc, MYCN, and L-myc [25]. These cancers include Burkitt's lymphoma, acute myelogenous leukemia, multiple myeloma, and aggressive human medulloblastoma [25]. Cancers in which c-myc is overexpressed may be particularly susceptible to BET protein inhibition; it has been shown that treatment of tumors that have activation of c-myc with a BET inhibitor resulted in tumor regression through inactivation of c-myc transcription [26-30].

The present disclosure provides a method for treating human cancers including cancers that rely on BET proteins and pTEFb (Cdk9/CyclinT) to regulate oncogenes [31], and cancers that can be treated by inducing apoptosis or senescence by inhibiting Bcl2, cyclin-dependent kinase 6 (CDK6) [26], or human telomerase reverse transcriptase (hTERT) [27, 32].

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia [26, 28, 30], adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia [29], B-cell chronic lymphocytic leukemia, B-cell prolymphocytic leukemia, B-cell lymphoma [23], basal cell carcinoma, biliary tract cancer, bladder cancer, blastoma, bone cancer, Brenner tumor, Brown tumor, Burkitt's lymphoma [28], breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia [28], chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma [33], meningioma, Merkel cell cancer, mesothelioma, metastatic urothelial carcinoma, mixed Mullerian tumor, mixed lineage leukemia [26], mucinous tumor, multiple myeloma [27], muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma [24], ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis.

Cardiovascular disease (CVD) is the leading cause of mortality and morbidity in the United States [34]. Atherosclerosis, an underlying cause of CVD, is a multifactoral disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL [11, 35].

Up-regulation of ApoA-I is considered to be a useful strategy in treatment of atherosclerosis and CVD [36]. BET inhibitors have been shown to increase ApoA-I transcription and protein expression [11, 35]. It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis [36], and Alzheimer's disease and other neurological disorders [37].

BET inhibitors may be useful in the prevention and treatment of conditions associated with ischemia-reperfusion injury such as, but not limited to, myocardial infarction, stroke, acute coronary syndromes [9], renal reperfusion injury, organ transplantation, coronary artery bypass grafting, cardio-pulmonary bypass procedures, hypertension, pulmonary, renal, hepatic, gastro-intestinal, or peripheral limb embolism.

Obesity-associated inflammation is a hallmark of type II diabetes, insulin resistance, and other metabolic disorders [8, 19]. Consistent with the ability of BET inhibitors to inhibit inflammation, gene disruption of Brd2 in mice ablates inflammation and protects animals from obesity-induced insulin resistance [38]. It has been shown that Brd2 interacts with PPARγ and opposes its transcriptional function. Knockdown of Brd2 in vitro promotes transcription of PPARγ-regulated networks, including those controlling adipogenesis [39]. In addition Brd2 is highly expressed in pancreatic β-cells and regulates proliferation and insulin transcription [38]. Taken together, the combined effects of BET inhibitors on inflammation and metabolism decrease insulin resistance and may be useful in the treatment of pre-diabetic and type II diabetic individuals as well as patients with other metabolic complications [8].

Host-encoded BET proteins have been shown to be important for transcriptional activation and repression of viral promoters. Brd4 interacts with the E2 protein of human papilloma virus (HPV) to enable E2 mediated transcription of E2-target genes [40]. Similarly, Brd2, Brd3, and Brd4 all bind to latent nuclear antigen 1 (LANA1), encoded by Kaposi's sarcoma-associated herpes virus (KSHV), promoting LANA-dependent proliferation of KSHV-infected cells [41]. A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies [42]. Also, a BET inhibitor reactivated HIV in models of latent T cell infection and latent monocyte infection, potentially allowing for viral eradication by complementary anti-retroviral therapy [43-46].

BET inhibitors may be useful in the prevention and treatment of episome-based DNA viruses including, but not limited to, human papillomavirus, herpes virus, Epstein-Barr virus, human immunodeficiency virus [8], adenovirus, poxvirus, hepatitis B virus, and hepatitis C virus.

Some central nervous system (CNS) diseases are characterized by disorders in epigenetic processes. Brd2 haploinsufficiency has been linked to neuronal deficits and epilepsy [47].

SNPs in various bromodomain-containing proteins have also been linked to mental disorders including schizophrenia and bipolar disorders [9]. In addition, the ability of BET inhibitors to increase ApoA-I transcription may make BET inhibitors useful in Alzheimer's disease therapy considering the suggested relationship between increased ApoA-I and Alzheimer's disease and other neurological disorders [37].

BRDT is the testis-specific member of the BET protein family which is essential for chromatin remodeling during spermatogenesis [48, 49]. Genetic depletion of BRDT or inhibition of BRDT interaction with acetylated histones by a BET inhibitor resulted in a contraceptive effect in mice, which was reversible when small molecule BET inhibitors were used [50, 51]. These data suggest potential utility of BET inhibitors as a novel and efficacious approach to male contraception.

Monocyte chemotactic protein-1 (MCP-1, CCL2) plays an important role in cardiovascular disease [52]. MCP-1, by its chemotactic activity, regulates recruitment of monocytes from the arterial lumen to the subendothelial space, where they develop into macrophage foam cells, and initiate the formation of fatty streaks which can develop into atherosclerotic plaque [53]. The critical role of MCP-1 (and its cognate receptor CCR2) in the development of atherosclerosis has been examined in various transgenic and knockout mouse models on a hyperlipidemic background [54-57]. These reports demonstrate that abrogation of MCP-1 signaling results in decreased macrophage infiltration to the arterial wall and decreased atherosclerotic lesion development.

The association between MCP-1 and cardiovascular disease in humans is well-established [52]. MCP-1 and its receptor are overexpressed by endothelial cells, smooth muscle cells, and infiltrating monocytes/macrophages in human atherosclerotic plaque [58]. Moreover, elevated circulating levels of MCP-1 are positively correlated with most cardiovascular risk factors, measures of coronary atherosclerosis burden, and the incidence of coronary heart disease (CHD) [59]. CHD patients with among the highest levels of MCP-1 are those with acute coronary syndrome (ACS) [60]. In addition to playing a role in the underlying inflammation associated with CHD, MCP-1 has been shown to be involved in plaque rupture, ischemic/reperfusion injury, restenosis, and heart transplant rejection [52].

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients [61]. Blockade of MCP-1 and MCP-1 signaling in animal models of RA have also shown the importance of MCP-1 to macrophage accumulation and proinflammatory cytokine expression associated with RA [62-65].

Overexpression of MCP-1, in the brain, cerebrospinal fluid (CSF), and blood, has also been associated with chronic and acute MS in humans [66]. MCP-1 is overexpressed by a variety of cell types in the brain during disease progression and contributes to the infiltration of macrophages and lymphocytes which mediate the tissue damage associated with MS [66]. Genetic depletion of MCP-1 or CCR2 in the experimental autoimmune encephalomyelitis (EAE) mouse model, a model resembling human MS, results in resistance to disease, primarily because of decreased macrophage infiltration to the CNS [67, 68].

Preclinical data have suggested that small- and large-molecule inhibitors of MCP-1 and CCR2 have potential as therapeutic agents in inflammatory and autoimmune indications.

The present disclosure includes compounds that are useful for inhibition of BET protein function by binding to bromodomains, and their use in the treatment and prevention of diseases and conditions, including, but not limited to, cancer, autoimmune, and cardiovascular diseases.

The first aspect of the present disclosure includes compounds of Formula I and methods of administering a therapeutically effective amount of those compounds to a mammal (e.g., a human) in need thereof.

The present invention includes compounds that are useful for inhibition of BET protein function by binding to bromodomains, and their use in the treatment and prevention of diseases and conditions, including, but not limited to, cancer, autoimmune, and cardiovascular diseases.

The first aspect of the invention includes compounds of Formula I and methods of administering a therapeutically effective amount of those compounds to a mammal (e.g., a human) in need thereof:

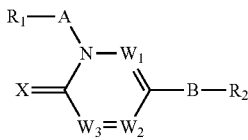

Formula I or a stereoisomer, tautomer, pharmaceutically acceptable salt, or hydrate thereof,
wherein:
$W_1$ is selected from N and $CR_5$;
$W_2$ is selected from N and $CR_4$;
$W_3$ is selected from N and $CR_3$;
each W may be the same or different from each other;
$R_1$ is selected from a carbocycles or heterocycles;
$R_2$ is selected from a 5- or 6-membered monocyclic carbocycle or a 5- or 6-membered monocyclic heterocycle;
$R_3$, $R_4$, and $R_5$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN;
$R_3$ and $R_4$ may be connected to form an optionally substituted 5-, 6-, or 7-membered carbocycle or heterocycle;
$R_4$ may be connected to B or $R_2$ to form a carbocycle or heterocycle;
X is selected from O and S;
A is selected from —$CR_xR_y$—, C=O, —C(O)$CR_xR_y$—, —$CR_xR_yCR_zR_v$—, —SO$_2$—, —$CR_xR_yCR_zR_vO$—, —$CR_xR_yCR_zR_vN$—, —$CR_xR_yCR_zR_vS$—, and —$CR_xR_yCR_zR_vCR_QR_R$—;
$R_x$, $R_y$, $R_z$, $R_v$, $R_Q$, and $R_R$ are each independently selected from hydrogen, alkyl($C_1$-$C_8$), halogen, —OH, —CF$_3$, amino, alkoxy ($C_1$-$C_8$), carboxyl, —CN, sulfone, and sulfoxide, carbocycle, heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;

B is selected from —(CR$_a$R$_b$)$_n$—, —(CR$_a$R$_b$CR$_c$R$_d$)—, —O—, —OCR$_a$R$_b$—, —CR$_a$R$_b$O—, —NH—, —NHCR$_a$R$_b$—, —CR$_a$R$_b$NH—, —S—, —SCR$_a$R$_b$—, —CR$_a$R$_b$S—, —S(O)—, —S(O)CR$_a$R$_b$—, —CR$_a$R$_b$S(O)—, —SO$_2$—, —SO$_2$CR$_a$R$_b$—, and —CR$_a$R$_b$SO$_2$—;

n is selected from 0 and 1, meaning if n=0 then B is absent and $R_2$ is connected directly to the center ring;

$R_a$, $R_b$, $R_c$, and $R_d$ are each independently selected from hydrogen, alkyl($C_1$-$C_3$), and alkoxy($C_1$-$C_3$).

In another aspect of the invention, a pharmaceutical composition comprising a compound of Formula I, or a pharmaceutically acceptable salt thereof and one or more pharmaceutically acceptable carriers, diluents or excipients is provided.

In yet another aspect of the invention there is provided a compound of Formula I, or a pharmaceutically acceptable salt thereof for use in therapy, in particular in the treatment of diseases or conditions for which a bromodomain inhibitor is indicated.

In yet another aspect of the invention there is provided a compound of Formula I, or a pharmaceutically acceptable salt thereof in the manufacture of a medicament for the treatment of diseases or conditions for which a bromodomain inhibitor is indicated.

DEFINITIONS

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2\text{-}C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1\text{-}C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1\text{-}C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2\text{-}C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —NR$_a$C(O)(R$_b$)— or —C(O)NR$_b$R$_c$, wherein R$_a$, R$_b$ and R$_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, R$_b$, or R$_c$. The amide also may be cyclic, for example R$_b$ and R$_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —NR$_d$R$_e$ or —N(R$_d$)R$_e$—, where R$_d$ and R$_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example any two of R$_d$ and R$_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of R$_d$ or R$_e$ is an alkyl group. In some embodiments Rd and Re each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl."

The term "carbamate" as used herein refers to the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of Rj or Rk is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "$(C_2-C_5)$heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetra hydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —R$_n$—C(O)—R$_o$—. The ketone can be attached to another group through R$_n$ or R$_o$. R$_n$ or R$_o$ can be alkyl, alkenyl, alkynyl, cycloalkyl, heterocyclyl or aryl, or R$_n$ or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{3-7}$ cycloalkyl; $C_{1-8}$ alkoxy; $C_6$ aryloxy; —CN; —OH; oxo; halo, carboxy; amino, such as —NH ($C_{1-8}$ alkyl), —N($C_{1-8}$ alkyl)$_2$, —NH(($C_6$)aryl), or —N(($C_6$) aryl)$_2$; formyl; ketones, such as —CO($C_{1-8}$ alkyl), —CO(($C_6$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

EXEMPLARY EMBODIMENTS

In a preferred aspect of Formula I, the invention is directed to a compound according to Formula II:

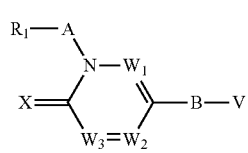

Formula II or a stereoisomer, tautomer, pharmaceutical acceptable salt, or hydrate thereof, wherein:
$W_1$ is selected from N and $CR_5$;
$W_2$ is selected from N and $CR_4$;
$W_3$ is selected from N and $CR_3$, with the proviso that if $W_3$ is N then neither $R_5$ nor $R_4$ is —OH;
each W may be the same or different from each other;
$R_1$ is a carbocycle or heterocycle;
V is selected from a 5-membered monocyclic carbocycle or monocyclic heterocycle, where the heterocycle is connected to the rest of the molecule via a carbon-carbon bond,
with the proviso that V cannot be unsubstituted thiophene, cyclopentyl, cyclopentenyl, ribofuranosyl, or furan,
and with the proviso that if $W_1$=$CR_5$ and V is an optionally substituted

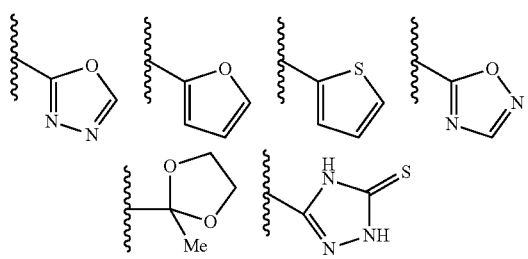

then at least one of $R_3$ and $R_4$ are different from hydrogen, or if $W_3$=N, then $R_4$ is different from hydrogen,
and with the proviso that if $W_1$=$CR_5$ and V is

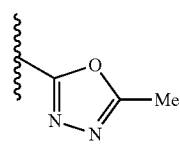

then $R_1$ is different from

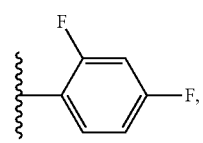 [SMILES: *c1ccc(F)cc1F]

and with the proviso that if $W_1$=$CR_5$ and V is

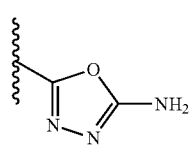 [SMILES: *c1nnc(N)o1]

then $R_1$ is not N

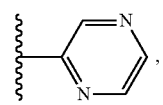

and with the proviso that if $W_1$=N and V is an optionally substituted

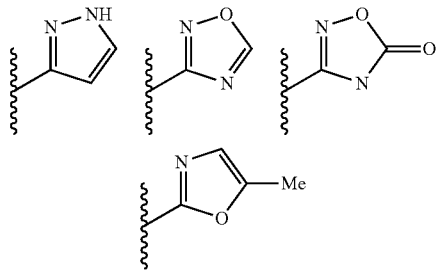

then at least one of $R_3$ and $R_4$ are different from hydrogen, or if $W_3$=N, then $R_4$ is different from hydrogen, and with the proviso that if $W_1$=N and V is an optionally substituted

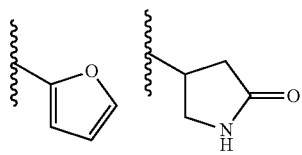

then $R_1$-A is different from

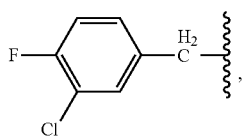

and with the proviso that if $W_1$=N and V is

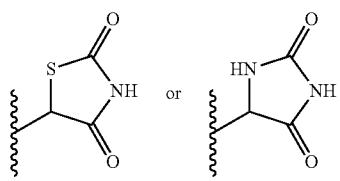 [SMILES: *C1SC(=O)NC1=O ; *C1NC(=O)NC1=O]

then $R_3$ and $R_4$ cannot be

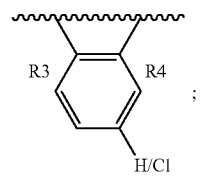

$R_3$, $R_4$, and $R_5$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN, with the proviso that if $R_5$ is —COOMe then V is not a substituted thiophene, and with the proviso that if $R_5$ is methyl then $R_2$ is not

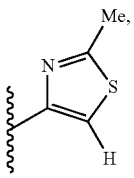

and with the proviso that if B is present (meaning n is different from zero) then neither $R_4$ or $R_5$ can be hydroxyl;

$R_3$ and $R_4$ may be connected to form an optionally substituted 5-, 6-, or 7-membered carbocycle or heterocycle;

$R_4$ may be connected to B or V to form a carbocycle or heterocycle;

X is selected from O and S;

A is selected from —CR$_x$R$_y$—, C=O, —C(O)CR$_x$R$_y$—, —CR$_x$R$_y$CR$_z$R$_v$—, —SO$_2$—, —CR$_x$R$_y$CR$_z$R$_v$O—, —CR$_x$R$_y$CR$_z$R$_v$N—, —CR$_x$R$_y$CR$_z$R$_v$S—, and —CR$_x$R$_y$CR$_z$R$_v$CR$_Q$R$_R$—;

with the proviso that R$_x$ and R$_y$ cannot both be an unsubstituted phenyl ring, and with the proviso that if A is —CH$_2$CH$_2$CH$_2$— and W$_3$ is N then R$_4$ is not —OH, and with the proviso that if A is —CH$_2$CH$_2$O— or —CH$_2$C(O)NH— then V is not a substituted

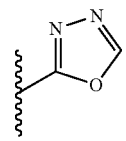 [SMILES: *c1nnco1]

or a substituted

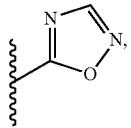

and with the proviso that if A is —CH$_2$CH$_2$O— the R$_1$ is not

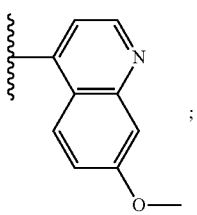 [SMILES: *c1ccnc2cc(OC)ccc12]

R$_x$, R$_y$, R$_z$, R$_v$, R$_Q$ and R$_R$ are each independently selected from hydrogen, alkyl(C$_1$-C$_8$), halogen, —OH, —CF$_3$, amino, alkoxy (C$_1$-C$_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;

B is selected from —$(CR_aR_b)_n$—, —$(CR_aR_bCR_cR_d)$—, —O—, —$OCR_aR_b$—, —$CR_aR_bO$—, —NH—, —$NHCR_aR_b$—, —$CR_aR_bNH$—, —S—, —$SCR_aR_b$—, —$CR_aR_bS$—, —S(O)—, —$S(O)CR_aR_b$—, —$CR_aR_bS(O)$—, —$SO_2$—, —$SO_2CR_aR_b$—, and —$CR_aR_bSO_2$—;

n is selected from 0 and 1, meaning if n=0 then B is absent; and $R_a$, $R_b$, $R_c$, and $R_d$ are each independently selected from hydrogen, alkyl($C_1$-$C_3$), and alkoxy($C_1$-$C_3$).

In some embodiments, according to Formula II, V is selected from an optionally substituted 5-membered monocyclic heterocycle, such as, but not limited to:

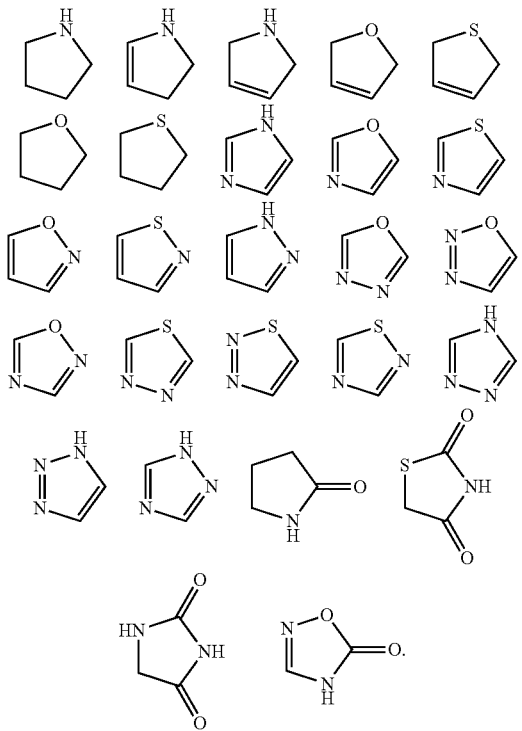

In some embodiments according to Formula II, V is optionally substituted with hydrogen, alkyl ($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu—$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —$C(O)NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments according to Formula II, V is selected from an optionally substituted 5-membered monocyclic heterocycle containing one oxygen and one or two nitrogens, where the heterocycle is connected to the rest of the molecule via a carbon-carbon bond.

In some embodiments, according to Formula II, V is an optionally substituted isoxazole.

In some embodiments, according to Formula II, V is

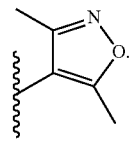 [SMILES: *c1c(C)noc1C]

In some embodiments, according to Formula II, $W_1$ is $CR_5$.

In some embodiments, according to Formula II, $W_2$ is $CR_4$.

In some embodiments, according to Formula II, X is oxygen.

In some embodiments, according to Formula II, n=0, meaning B is absent.

In some embodiments, according to Formula II, A is selected from C=O and —$CR_xR_y$—.

In some embodiments, according to Formula II, $R_1$ is selected from an optionally substituted 3-, 4-, 5-, and 6-membered carbocycle or heterocycle (such as cyclopropyl, phenyl, pyridyl, thiophene, cyclobutyl, piperidine, piperazine, cyclopentyl, or cyclohexyl).

In some embodiments, according to Formula II, $R_1$ is selected from an optionally substituted 5- and 6-membered carbocycle and heterocycle (such as phenyl, pyridyl, thiophene, or cyclopentyl).

In some embodiments, according to Formula II, $R_1$ is selected from an optionally substituted phenyl or pyridyl ring.

In some embodiments, according to Formula II, $R_3$, $R_4$, and $R_5$ are each independently selected from hydrogen, alkyl ($C_1$-$C_8$), —OH, —$NH_2$, thioalkyl ($C_1$-$C_8$), alkoxy($C_1$-$C_8$) (such as methoxy, ethoxy, —OPr, or -OiPr), ketone($C_1$-$C_8$), ester, carboxylic acid, urea, carbamate, carbonate, amino, amide, halogen (such as F, Cl, Br), carbocycle (such as cyclopropyl, cyclopentyl, phenyl), alkenyl($C_1$-$C_8$), alkynyl ($C_1$-$C_8$), heterocycle, sulfone, sulfoxide, sulfide, sulfonamide, and —CN, which may be optionally substituted.

In some embodiments, according to Formula II, $R_5$ is selected from hydrogen, methyl, —$CF_3$, Ethyl, propyl, isopropyl, methoxy, ethoxy, propoxy, —NHMe, —NHEthyl, —NHAc, $NH_2$, and —CN.

In some embodiments, according to Formula II, $R_3$ is selected from hydrogen, —CN, —$NH_2$, amino (such as —NHMe, —NHethyl, —NHcyclopropyl, —NHPh, —NHBn, —$NMe_2$, —NHpyridyl, —NHcyclopentyl), amido (such as —NHAc, —NHC(O)Et, —NHC(O)Pr, —NHC(O)phenyl, —C(O)NHMe, —$C(O)NH_2$, —C(O)NHEt, —$C(O)NMe_2$), sulfone, Sulfoxide, sulfonamide (such as —$SO_2NH_2$, —$NHSO_2$Me), carbocycle (for example, phenyl, cyclopropyl, cyclobutyl, or cyclopentyl), or heterocycle, which may be optionally substituted.

In some embodiments, according to Formula II, $R_3$ is selected from hydrogen, —$NH_2$, amino (such as —NHMe, —NHEt, —NHcyclopropyl, —NHPh, —NHBn, —$NMe_2$, —NHpyridyl, —NHcyclopentyl), and —NHheterocycle or heterocycle (such as

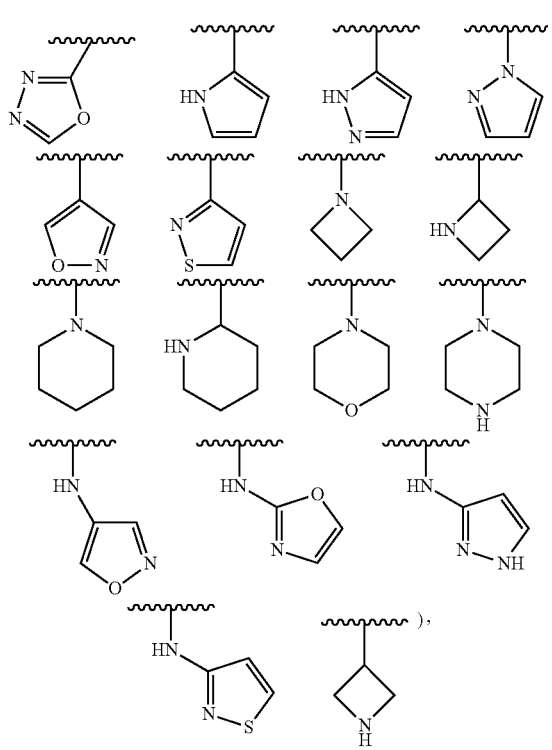

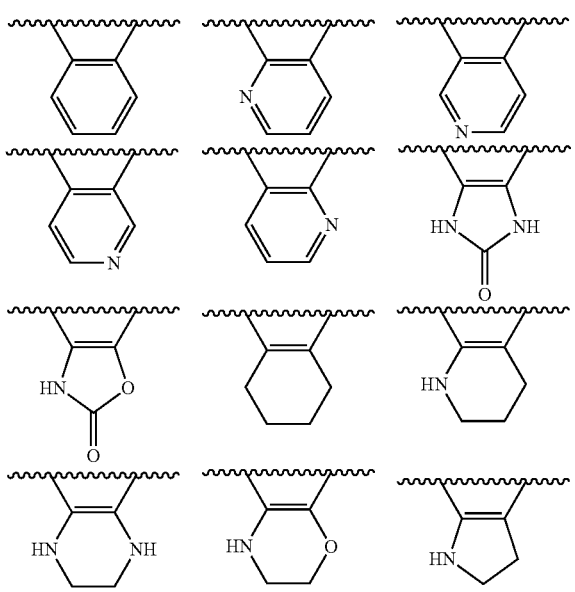

which may be optionally substituted with groups independently selected from hydrogen, alkyl (C₁-C₃), —OH, —NH₂, thioalkyl (C₁-C₃), alkoxy (C₁-C₃), ketone (C₁-C₃), ester, carboxylic acid, urea, carbamate, carbonate, amino, amide, and halogen.

In some embodiments, according to Formula II, $R_3$, $R_4$, and $R_5$ may be optionally substituted with groups independently selected from hydrogen, alkyl, —OH, —NH₂, thioalkyl, alkoxy, ketone, ester, carboxylic acid, urea, carbamate, carbonate, amino, amide, and halogen.

In some embodiments, according to Formula II, $R_3$ and $R_4$ may be connected to form an optionally substituted 5-, 6-, or 7-membered carbocycle or heterocycle such as In some embodiments, according to Formula II, $R_x$ and $R_y$ are selected from hydrogen, alkyl(C₁-C₃); halogen (such as F and Cl), —CF₃, amino (such as —NHMe, —NHEt, —NHiPr), alkoxy (such as —OMe, OEt, OPr), and —CN.

In some embodiments, according to Formula II, $R_x$ and $R_y$ are independently selected from hydrogen, methyl, and —CF₃.

In some embodiments, according to Formula II, $R_z$ and $R_v$ are independently selected from hydrogen, methyl, and —CF₃.

In some embodiments, according to Formula II, $R_a$, $R_b$, $R_c$, and $R_d$ are independently selected from hydrogen, methyl, methoxy, and —CF₃.

In some embodiments, according to Formula II, B is selected from —(CR$_a$R$_b$)$_n$—, —O—, —NH—, —S—, —S(O)—, and —SO₂—, where n is 0 or 1, meaning if n=0 then B is absent.

In some embodiments, according to Formula II, B is selected from —(CR$_a$R$_b$)$_n$—, —O—, —NH—, and —S—, where n is 0 or 1, meaning if n=0 then B is absent.

In certain embodiments of the invention, the compound of Formula II is selected from: 6-(3,5-Dimethylisoxazol-4-yl)-2-phenethylpyridazin-3(2H)-one (Example 1);
6-(3,5-Dimethylisoxazol-4-yl)-2-(pyridin-2-ylmethyl) pyridazin-3(2H)-one (Example 2);
6-(3,5-Dimethylisoxazol-4-yl)-2-(pyrimidin-2-ylmethyl) pyridazin-3(2H)-one (Example 3);
5-(3,5-Dimethylisoxazol-4-yl)-1-(3-(trifluoromethyl)benzyl)pyridin-2(1H)-one (Example 4);
5-(3,5-Dimethylisoxazol-4-yl)-1-(4-(trifluoromethoxy)benzyl)pyridin-2(1H)-one (Example 5);
1-Benzyl-5-(3,5-dimethylisoxazol-4-yl)pyrazin-2(1H)-one (Example 6);
5-(3,5-Dimethylisoxazol-4-yl)-1-(4-(trifluoromethyl)benzyl)pyridin-2(1H)-one (Example 7);
1-Benzyl-5-(3,5-dimethylisoxazol-4-yl)pyrimidin-2(1H)-one (Example 8);
1-(4-((Dimethylamino)methyl)benzyl)-5-(3,5-dimethylisoxazol-4-yl)pyridin-2(1H)-one hydrochloric acid (Example 9);
5-(3,5-Dimethylisoxazol-4-yl)-1-(piperidin-4-ylmethyl) pyridin-2(1H)-one hydrochloric acid (Example 10);
5-(3,5-Dimethylisoxazol-4-yl)-1-((3,5-dimethylisoxazol-4-yl)methyl)pyridin-2(1H)-one (Example 11);
1-Benzyl-5-(3,5-dimethylisoxazol-4-yl)-4-methylpyridin-2 (1H)-one (Example 12);
4-((5-(3,5-Dimethylisoxazol-4-yl)-2-oxopyridin-1(2H)-yl) methyl)benzamide (Example 13);
2-Benzyl-6-(3,5-dimethylisoxazol-4-yl)pyridazin-3(2H)-one (Example 14);
5-(3,5-Dimethylisoxazol-4-yl)-1-(quinoxalin-6-ylmethyl) pyridin-2(1H)-one (Example 18);
6-(3,5-Dimethylisoxazol-4-yl)-2-(1-phenylethyl)pyridazin-3(2H)-one (Example 19);

2-Benzyl-4-methyl-6-(5-methylisoxazol-4-yl)pyridazin-3 (2H)-one (Example 20);
2-Benzyl-6-(3,5-dimethylisoxazol-4-yl)-4-methylpyridazin-3(2H)-one (example 21);
6-(3,5-Dimethylisoxazol-4-yl)-2-(3-fluorobenzyl) pyridazin-3(2H)-one (Example 22);
2-(3-Chlorobenzyl)-6-(3,5-dimethylisoxazol-4-yl) pyridazin-3(2H)-one (Example 23);
2-((3-(3,5-Dimethylisoxazol-4-yl)-6-oxopyridazin-1(6H)-yl)methyl)benzonitrile (Example 24);
2-(4-Chlorobenzyl)-6-(3,5-dimethylisoxazol-4-yl) pyridazin-3(2H)-one (Example 25);
2-(2-Chlorobenzyl)-6-(3,5-dimethylisoxazol-4-yl) pyridazin-3(2H)-one (Example 26);
5-(3,5-Dimethylisoxazol-4-yl)-1-(2-fluorobenzyl)pyridin-2 (1H)-one (Example 27);
6-(3,5-Dimethylisoxazol-4-yl)-2-(2-methylbenzyl) pyridazin-3(2H)-one (Example 28);
6-(3,5-Dimethylisoxazol-4-yl)-2-(4-methylbenzyl) pyridazin-3(2H)-one (Example 29);
6-(3,5-Dimethylisoxazol-4-yl)-2-(3-methylbenzyl) pyridazin-3(2H)-one (Example 30);
6-(3,5-Dimethylisoxazol-4-yl)-2-(3-(trifluoromethyl)benzyl)pyridazin-3(2H)-one (Example 31);
6-(3,5-Dimethylisoxazol-4-yl)-2-(3-fluoro-5-methylbenzyl) pyridazin-3(2H)-one (Example 32);
6-(3,5-Dimethylisoxazol-4-yl)-2-(4-methoxybenzyl) pyridazin-3(2H)-one (Example 33);
6-(3,5-Dimethylisoxazol-4-yl)-2-(1-(2-(trifluoromethyl) phenyl)ethyl)pyridazin-3(2H)-one (Example 34);
6-(3,5-Dimethylisoxazol-4-yl)-2-(3-methoxybenzyl) pyridazin-3(2H)-one (Example 35);
6-(3,5-Dimethylisoxazol-4-yl)-2-(3(trifluoromethoxy)benzyl pyridazin-3(2H)-one (Example 36);
6-(3,5-Dimethylisoxazol-4-yl)-2-((tetrahydro-2H-pyran-4-yl)methyl)pyridazin-3(2H)-one (Example 37);
5-(3,5-Dimethylisoxazol-4-yl)-1-(1-(2-(trifluoromethyl) phenyl)ethyl)pyridin-2(1H)-one (Example 38);
6-(3,5-Dimethylisoxazol-4-yl)-2-(2-(trifluoromethoxy)benzyl)pyridazin-3(2H)-one (Example 39);
5-(3,5-Dimethylisoxazol-4-yl)-1-(2-(trifluoromethoxy)benzyl)pyridin-2(1H)-one (Example 40);
5-(3,5-Dimethylisoxazol-4-yl)-1-(4-methylbenzyl)pyridin-2 (1H)-one (Example 41);
5-(3,5-Dimethylisoxazol-4-yl)-1-(3-fluorobenzyl)pyridin-2 (1H)-one (Example 42);
5-(3,5-Dimethylisoxazol-4-yl)-1-(1-phenylpropyl)pyridin-2 (1H)-one (Example 43);
5-(3,5-Dimethylisoxazol-4-yl)-1-(pyridin-3-ylmethyl)pyridin-2(1H)-one (Example 44);
2-(Cyclopropylmethyl)-6-(3,5-dimethylisoxazol-4-yl) pyridazin-3(2H)-one (Example 45);
5-(3,5-Dimethylisoxazol-4-yl)-1-((6-methylpyridin-2-yl) methyl)pyridin-2(1H)-one (Example 46);
5-(3,5-Dimethylisoxazol-4-yl)-1-(quinolin-8-ylmethyl)pyridin-2(1H)-one (Example 47);
1-(Cyclopropylmethyl)-5-(3,5-dimethylisoxazol-4-yl)pyridin-2(1H)-one (Example 48);
1-(Cyclobutylmethyl)-5-(3,5-dimethylisoxazol-4-yl)pyridin-2(1H)-one (Example 49);
1-(3-(Difluoromethyl)benzyl)-5-(3,5-dimethylisoxazol-4-yl)pyridin-2(1H)-one (Example 50);
5-(3,5-Dimethylisoxazol-4-yl)-1-(2-phenoxyethyl)pyridin-2 (1H)-one (Example 51);
1-((5-Chloropyridin-2-yl)methyl-5-(3,5-dimethylisoxazol-4-yl)pyridin-2(1H)-one (Example 55);
1-Benzyl-5-(3,5-dimethylisoxazol-4-yl)pyridin-2(1H)-one (Example 56);
1-Benzyl-5-(5-methyl isoxazol-4-yl)pyridin-2(1H)-one (Example 57);
1-Benzyl-5-(isoxazol-4-yl)pyridin-2(1H)-one (Example 58);
1-Benzyl-5-(isothiazol-4-yl)pyridin-2(1H)-one (Example 59);
2-Benzyl-6-((3,5-dimethylisoxazol-4-yl)amino)pyridazin-3 (2H)-one (Example 61);
1-Benzyl-5-(3,5-dimethylisoxazol-4-yl)-3-fluoropyridin-2 (1H)-one (Example 63);
1-Benzyl-3-chloro-5-(3,5-dimethylisoxazol-4-yl)pyridin-2 (1H)-one (Example 64);
1-Benzyl-5-(3,5-dimethylisoxazol-4-yl)-3-methylpyridin-2 (1H)-one (Example 66);
1-Benzyl-3-cyclopropyl-5-(3,5-dimethylisoxazol-4-yl)pyridin-2(1H)-one (Example 67);
5-(3,5-Dimethylisoxazol-4-yl)-1-(4-fluorobenzoyl)pyridin-2(1H)-one (Example 68);
1-(4-Chlorobenzoyl)-5-(3,5-dimethylisoxazol-4-yl)pyridin-2(1H)-one (Example 69);
1-Benzyl-5-(3,5-dimethylisoxazol-4-yl)-3-(4-fluorophenyl) pyridin-2(1H)-one (Example 70);
N-(1-Benzyl-5-(3,5-dimethylisoxazol-4-yl)-2-oxo-1,2-dihydropyridin-3-yl)acetamide (Example 71);
1-Benzyl-5-(3,5-dimethylisoxazol-4-yl)-3-(phenylamino) pyridin-2(1H)-one (Example 72);
3-Amino-1-benzyl-5-(3,5-dimethylisoxazol-4-yl)pyridin-2 (1H)-one (Example 73);
1-Benzyl-3-(benzylamino)-5-(3,5-dimethylisoxazol-4-yl) pyridin-2(1H)-one (Example 74);
1-Benzyl-5-(3,5-dimethylisoxazol-4-yl)-3-(methylamino) pyridin-2(1H)-one (Example 75);
6-(3,5-Dimethylisoxazol-4-yl)-2-(4-(trifluoromethoxy)benzyl)pyridazin-3(2H)-one (Example 76);
6-(3,5-Dimethylisoxazol-4-yl)-2-(naphthalen-2-ylmethyl) pyridazin-3(2H)-one (Example 77);
5-(3,5-Dimethyl isoxazol-4-yl)-1-(3-methoxybenzyl)pyridin-2(1H)-one (Example 78);
5-(3,5-Dimethylisoxazol-4-yl)-1-(thiophen-3-ylmethyl) pyridin-2(1H)-one (Example 79);
1-Benzyl-5-(thiazol-5-yl)pyridin-2(1H)-one (Example 80);
1-Benzyl-5-(5-methyl-1H-imidazol-4-yl)pyridin-2(1H)-one (Example 81);
6-(3,5-Dimethylisoxazol-4-yl)-2-(2-fluorobenzyl)-4-methylpyridazin-3(2H)-one (Example 84);
2-(Cyclopropylmethyl)-6-(3,5-dimethylisoxazol-4-yl)-4-methylpyridazin-3(2H)-one (Example 85);
2-Benzyl-6-(3,5-dimethyl-1H-pyrazol-4-yl)pyridazin-3 (2H)-one (Example 86);
6-(3,5-Dimethylisoxazol-4-yl)-4-methyl-2-(pyridin-4-ylmethyl)pyridazin-3(2H)-one (Example 87);
2-(Cyclobutylmethyl)-6-(3,5-dimethylisoxazol-4-yl) pyridazin-3(2H)-one (Example 88);
4-((3-(3,5-Dimethylisoxazol-4-yl)-6-oxopyridazin-1(6H)-yl)methyl)-N-methylbenzamide (Example 89);
2-(2,6-Difluorobenzyl)-6-(3,5-dimethylisoxazol-4-yl) pyridazin-3(2H)-one (Example 90);
6-(3,5-Dimethylisoxazol-4-yl)-2-(4-(trifluoromethyl)benzyl)pyridazin-3(2H)-one (Example 91);
6-(3,5-Dimethylisoxazol-4-yl)-2-(2,4,6-trifluorobenzyl) pyridazin-3(2H)-one (Example 92);
6-(3,5-Dimethylisoxazol-4-yl)-2-(2-fluorobenzyl) pyridazin-3(2H)-one (Example 93);
6-(3,5-Dimethylisoxazol-4-yl)-2-(2-(trifluoromethyl)benzyl)pyridazin-3(2H)-one (Example 94);

6-(3,5-Dimethylisoxazol-4-yl)-2-(1-(2-fluorophenyl)ethyl)pyridazin-3(2H)-one (Example 95);
2-(2-Chloro-6-fluorobenzyl)-6-(3,5-dimethylisoxazol-4-yl)pyridazin-3(2H)-one (Example 96);
6-(3,5-Dimethylisoxazol-4-yl)-2-(isoxazol-4-ylmethyl)pyridazin-3(2H)-one (Example 97);
5-(5-Amino-3-methylisoxazol-4-yl)-1-benzylpyridin-2(1H)-one trifluoroacetic acid (Example 98);
5-(3,5-Dimethylisoxazol-4-yl)-1-(1-(4-fluorophenyl)ethyl)pyridin-2(1H)-one (Example 101);
6-(3,5-Dimethylisoxazol-4-yl)-2-(quinolin-8-ylmethyl)pyridazin-3(2H)-one (Example 102);
1-(1-(2-Chlorophenyl)ethyl)-5-(3,5-dimethylisoxazol-4-yl)pyridin-2(1H)-one (Example 103);
5-(3,5-Dimethylisoxazol-4-yl)-1-(1-(3-fluorophenyl)ethyl)pyridin-2(1H)-one (Example 104);
1-(1-(4-Chlorophenyl)ethyl)-5-(3,5-dimethylisoxazol-4-yl)pyridin-2(1H)-one (Example 105);
5-(3,5-Dimethylisoxazol-4-yl)-1-(2-phenylpropan-2-yl)pyridin-2(1H)-one (Example 106);
6-(3,5-Dimethylisoxazol-4-yl)-2-(thiophen-3-ylmethyl)pyridazin-3(2H)-one (Example 107);
(R)-6-(3,5-Dimethylisoxazol-4-yl)-2-(1-phenylethyl)pyridazin-3(2H)-one (Example 108);
(S)-6-(3,5-Dimethylisoxazol-4-yl)-2-(1-phenylethyl)pyridazin-3(2H)-one (Example 109);
(S)-5-(3,5-Dimethylisoxazol-4-yl)-1-(1-(4-fluorophenyl)ethyl)pyridin-2(1H)-one (Example 110);
(R)-5-(3,5-Dimethylisoxazol-4-yl)-1-(1-(4-fluorophenyl)ethyl)pyridin-2(1H)-one (Example 111);
5-(3,5-Dimethylisoxazol-4-yl)-1-(1-(pyridin-2-yl)ethyl)pyridin-2(1H)-one (Example 112);
1-(1-(3-Chlorophenyl)ethyl)-5-(3,5-dimethylisoxazol-4-yl)pyridin-2(1H)-one (Example 113);
1-Benzyl-6-chloro-5-(3,5-dimethylisoxazol-4-yl)pyridin-2(1H)-one (Example 114);
1-Benzyl-5-(3,5-dimethylisoxazol-4-yl)-6-methylpyridin-2(1H)-one (Example 115);
5-(3,5-Dimethylisoxazol-4-yl)-1-(2-methylbenzyl)pyridin-2(1H)-one (Example 121);
5-(3,5-Dimethylisoxazol-4-yl)-1-(3-methylbenzyl)pyridin-2(1H)-one (Example 122);
5-(3,5-Dimethylisoxazol-4-yl)-1-(2-(trifluoromethyl)benzyl)pyridin-2(1H)-one (Example 123);
5-(3,5-Dimethylisoxazol-4-yl)-1-(1-(2-fluorophenyl)ethyl)pyridin-2(1H)-one (Example 124);
5-(3,5-Dimethylisoxazol-4-yl)-1-(1-phenylethyl)pyridin-2(1H)-one (Example 125);
1-(3-Chlorobenzyl)-5-(3,5-dimethylisoxazol-4-yl)pyridin-2(1H)-one (Example 126);
1-(2-Chlorobenzyl)-5-(3,5-dimethylisoxazol-4-yl)pyridin-2(1H)-one (Example 127);
1-(4-Chlorobenzyl)-5-(3,5-dimethylisoxazol-4-yl)pyridin-2(1H)-one (Example 128);
5-(3,5-Dimethylisoxazol-4-yl)-1-(pyridin-4-ylmethyl)pyridin-2(1H)-one (Example 129);
5-(3,5-Dimethylisoxazol-4-yl)-1-(4-methoxybenzyl)pyridin-2(1H)-one (Example 130);
1-(3,4-Dimethoxybenzyl)-5-(3,5-dimethylisoxazol-4-yl)pyridin-2(1H)-one (Example 131);
5-(3,5-Dimethylisoxazol-4-yl)-1-(4-fluorobenzyl)pyridin-2(1H)-one (Example 132);
(S)-5-(3,5-Dimethylisoxazol-4-yl)-1-(1-phenylethyl)pyridin-2(1H)-one (Example 133);
(R)-5-(3,5-Dimethylisoxazol-4-yl)-1-(1-phenylethyl)pyridin-2(1H)-one (Example 134);
2-((5-(3,5-Dimethylisoxazol-4-yl)-2-oxopyridin-1(2H)-yl)methyl)benzonitrile (Example 135);
1-(2,4-Dichlorobenzyl)-5-(3,5-dimethylisoxazol-4-yl)pyridin-2(1H)-one (Example 136);
4-((5-(3,5-Dimethylisoxazol-4-yl)-2-oxopyridin-1(2H)-yl)methyl)benzonitrile (Example 137);
1-(2,4-Difluorobenzyl)-5-(3,5-dimethylisoxazol-4-yl)pyridin-2(1H)-one (Example 138);
1-(4-Chloro-2-fluorobenzyl)-5-(3,5-dimethylisoxazol-4-yl)pyridin-2(1H)-one (Example 139);
1-(2-Chloro-4-fluorobenzyl)-5-(3,5-dimethylisoxazol-4-yl)pyridin-2(1H)-one (Example 140);
1-(4-Chloro-3-fluorobenzyl)-5-(3,5-dimethylisoxazol-4-yl)pyridin-2(1H)-one (Example 141);
5-(3,5-Dimethylisoxazol-4-yl)-1-(3,4,5-trifluorobenzyl)pyridin-2(1H)-one (Example 142);
2-((1H-Benzo[d]imidazol-5-yl)methyl)-6-(3,5-dimethylisoxazol-4-yl)pyridazin-3(2H)-one (Example 143);
6-(3,5-Dimethylisoxazol-4-yl)-2-(3,4,5-trifluorobenzyl)pyridazin-3(2H)-one (Example 144);
5-(3,5-Dimethylisoxazol-4-yl)-1-(4-(methylsulfonyl)benzyl)pyridin-2(1H)-one (Example 145);
1-((1H-Benzo[d]imidazol-5-yl)methyl)-5-(3,5-dimethylisoxazol-4-yl)pyridin-2(1H)-one (Example 146);
1-(3-Chloro-4-fluorobenzyl)-5-(3,5-dimethylisoxazol-4-yl)pyridin-2(1H)-one (Example 147);
1-((1H-Indazol-5-yl)methyl)-5-(3,5-dimethylisoxazol-4-yl)pyridin-2(1H)-one (Example 148);
1-((1H-Indol-4-yl)methyl)-5-(3,5-dimethylisoxazol-4-yl)pyridin-2(1H)-one (Example 149);
1-((4-Chlorophenyl)sulfonyl)-5-(3,5-dimethylisoxazol-4-yl)pyridin-2(1H)-one (Example 150);
5-(3-Amino-5-methylisoxazol-4-yl)-1-benzylpyridin-2(1H)-one (Example 151);
3-Amino-1-(4-chlorobenzyl)-5-(3,5-dimethylisoxazol-4-yl)pyridin-2(1H)-one (Example 152);
1-Benzyl-5-(3,5-dimethylisoxazol-4-yl)-3-(4-methylpiperazin-1-yl)pyridin-2(1H)-one Hydrochloride (Example 153);
1-Benzyl-5-(3,5-dimethylisoxazol-4-yl)-4-methoxypyridin-2(1H)-one (Example 154);
1-(3,4-Dichlorobenzyl)-5-(3,5-dimethylisoxazol-4-yl)pyridin-2(1H)-one (Example 155);
1-Benzyl-5-(3,5-dimethylisoxazol-4-yl)-3-((4-fluorophenyl)amino)pyridin-2(1H)-one (Example 156);
1-Benzyl-5-(3,5-dimethylisoxazol-4-yl)-3-((3-fluorophenyl)amino)pyridin-2(1H)-one (Example 157);
1-Benzyl-5-(3-(hydroxymethyl)-5-methylisoxazol-4-yl)pyridin-2(1H)-one (Example 158);
1-(4-Chlorobenzyl)-5-(3-(hydroxymethyl)-5-methylisoxazol-4-yl)pyridin-2(1H)-one (Example 159);
1-Benzyl-5-(3-methylisothiazol-4-yl)pyridin-2(1H)-one (Example 160);
1-Benzyl-5-(3,5-dimethylisoxazol-4-yl)-3-(piperazin-1-yl)pyridin-2(1H)-one Hydrochloride (Example 161);
5-(3,5-Dimethylisoxazol-4-yl)-1-(2-methoxybenzyl)pyridin-2(1H)-one (Example 162);
5-(3,5-Dimethylisoxazol-4-yl)-1-(pyrimidin-2-ylmethyl)pyridin-2(1H)-one (Example 163);
2-Benzyl-4-(3,5-dimethylisoxazol-4-yl)isoquinolin-1(2H)-one (Example 167);
2-Benzyl-4-(3,5-dimethylisoxazol-4-yl)-2H-phthalazin-1-one (Example 170);
6-Benzyl-8-(3,5-dimethylisoxazol-4-yl)-1,6-naphthyridin-5(6H)-one (Example 173);
7-Benzyl-5-(3,5-dimethylisoxazol-4-yl)-1,7-naphthyridin-8(7H)-one (Example 174);

2-Benzyl-4-(3,5-dimethylisoxazol-4-yl)-2,7-naphthyridin-1(2H)-one (Example 175);
2-Benzyl-4-(3,5-dimethylisoxazol-4-yl)-2,6-naphthyridin-1(2H)-one (Example 176);
3-amino-5-(3,5-dimethylisoxazol-4-yl)-1-(4-fluorobenzyl)pyridin-2(1H)-one (Example 180);
3-chloro-5-(3,5-dimethylisoxazol-4-yl)-1-(4-fluorobenzyl)pyridin-2(1H)-one (Example 181);
5-(3,5-dimethylisoxazol-4-yl)-1-(4-fluorobenzyl)-3-(phenylamino)pyridin-2(1H)-one (Example 182);
3-(azetidin-1-yl)-1-benzyl-5-(3,5-dimethylisoxazol-4-yl)pyridin-2(1H)-one (Example 183);
1-benzyl-5-(3,5-dimethylisoxazol-4-yl)-3-((1-methyl-1H-pyrazol-3-yl)amino)pyridin-2(1H)-one (Example 184);
3-(1-benzyl-5-(3,5-dimethylisoxazol-4-yl)-2-oxo-1,2-dihydropyridin-3-yl)benzamide (Example 185);
1-benzyl-5-(3,5-dimethylisoxazol-4-yl)-3-(ethylamino)pyridin-2(1H)-one (Example 186);
1-benzyl-5-(3-(methoxymethyl)-5-methylisoxazol-4-yl)pyridin-2(1H)-one (Example 187);
1-(4-chlorobenzyl)-5-(3,5-dimethylisoxazol-4-yl)-3-(phenylamino)pyridin-2(1H)-one (Example 188);
3-amino-1-benzyl-5-(3-(hydroxymethyl)-5-methylisoxazol-4-yl)pyridin-2(1H)-one (Example 189);
1-benzyl-5-(3,5-dimethylisoxazol-4-yl)-3-morpholinopyridin-2(1H)-one (Example 190);
1-benzyl-3-(benzyloxy)-5-(3,5-dimethylisoxazol-4-yl)pyridin-2(1H)-one (Example 191);
1-benzyl-5-(3,5-dimethylisoxazol-4-yl)-3-(isopropylamino)pyridin-2(1H)-one (Example 192);
1-benzyl-5-(3,5-dimethylisoxazol-4-yl)-3-(pyridin-2-ylamino)pyridin-2(1H)-one (Example 193);
1-benzyl-5-(3,5-dimethylisoxazol-4-yl)-3-(pyridin-3-ylamino)pyridin-2(1H)-one (Example 194);
1-benzyl-5-(3,5-dimethylisoxazol-4-yl)-3-(pyridin-4-ylamino)pyridin-2(1H)-one (Example 195);
1-benzyl-5-(3,5-dimethylisothiazol-4-yl)pyridin-2(1H)-one (Example 196);
1-benzyl-5-(3,5-dimethylisoxazol-4-yl)-2-oxo-1,2-dihydropyridine-3-carbonitrile (Example 198);
methyl 4-(1-(4-chlorobenzyl)-6-oxo-1,6-dihydropyridin-3-yl)-5-methylisoxazole-3-carboxylate (Example 199);
N-(1-benzyl-5-(3,5-dimethylisoxazol-4-yl)-2-oxo-1,2-dihydropyridin-3-yl)methanesulfonamide (Example 200);
2-benzyl-6-(((3,5-dimethylisoxazol-4-yl)methyl)amino)pyridazin-3(2H)-one (Example 201);
4-(1-(4-chlorobenzyl)-6-oxo-1,6-dihydropyridin-3-yl)-5-methylisoxazole-3-carboxamide (Example 202);
3-amino-1-(4-chloro-3-fluorobenzyl)-5-(3,5-dimethylisoxazol-4-yl)pyridin-2(1H)-one (Example 203);
1-benzyl-5-(3,5-dimethylisoxazol-4-yl)-3-(1H-imidazol-1-yl)pyridin-2(1H)-one (Example 204);
3-amino-1-(4-chlorobenzyl)-5-(3-(hydroxymethyl)-5-methylisoxazol-4-yl)pyridin-2(1H)-one (Example 205);
3-amino-1-(4-chloro-2-fluorobenzyl)-5-(3,5-dimethylisoxazol-4-yl)pyridin-2(1H)-one (Example 206);
3-amino-1-(2-chloro-4-fluorobenzyl)-5-(3,5-dimethylisoxazol-4-yl)pyridin-2(1H)-one (Example 207);
1-benzyl-3-(cyclopentylamino)-5-(3,5-dimethylisoxazol-4-yl)pyridin-2(1H)-one (Example 208);
1-benzyl-5-(3,5-dimethylisoxazol-4-yl)-3-hydroxypyridin-2(1H)-one (Example 209);
1-benzyl-5-(3,5-dimethylisoxazol-4-yl)-3-methoxypyridin-2(1H)-one (Example 210);
3-amino-1-(3,4-difluorobenzyl)-5-(3,5-dimethylisoxazol-4-yl)pyridin-2(1H)-one (Example 211);
3-amino-1-(3-chloro-4-fluorobenzyl)-5-(3,5-dimethylisoxazol-4-yl)pyridin-2(1H)-one (Example 212);
3-amino-1-(3,4-dichlorobenzyl)-5-(3,5-dimethylisoxazol-4-yl)pyridin-2(1H)-one (Example 213);
1-benzyl-5-(5-(hydroxymethyl)-3-methylisoxazol-4-yl)pyridin-2(1H)-one (Example 214);
3-amino-5-(3,5-dimethylisoxazol-4-yl)-1-(thiazol-2-ylmethyl)pyridin-2(1H)-one (Example 215);
4-((3-amino-5-(3,5-dimethylisoxazol-4-yl)-2-oxopyridin-1(2H)-yl)methyl)benzonitrile (Example 216);
1-benzyl-5-(3,5-dimethylisoxazol-4-yl)-3-((3,5-dimethylisoxazol-4-yl)amino)pyridin-2(1H)-one (Example 217);
5-(3,5-dimethylisoxazol-4-yl)-1-(4-vinylbenzyl)pyridin-2(1H)-one (Example 218);
3-amino-5-(3,5-dimethylisoxazol-4-yl)-1-(thiophen-3-ylmethyl)pyridin-2(1H)-one (Example 219);
3-amino-5-(3,5-dimethylisoxazol-4-yl)-1-(4-methoxybenzyl)pyridin-2(1H)-one (Example 220);
1-benzyl-5-(3,5-dimethylisoxazol-4-yl)-3-(pyridazin-3-ylamino)pyridin-2(1H)-one (Example 221);
3-amino-1-((5-chlorothiophen-2-yl)methyl)-5-(3,5-dimethylisoxazol-4-yl)pyridin-2(1H)-one (Example 222);
1-benzyl-5-(3,5-dimethylisoxazol-4-yl)-3-((5-fluoropyridin-3-yl)amino)pyridin-2(1H)-one (Example 223);
3-amino-5-(3,5-dimethylisoxazol-4-yl)-1-methylpyridin-2(1H)-one (Example 224);
4-(1-(4-chlorobenzyl)-6-oxo-1,6-dihydropyridin-3-yl)-5-methylisoxazole-3-carboxylic acid (Example 225);
3-amino-5-(3,5-dimethylisoxazol-4-yl)-1-(4-(trifluoromethoxy)benzyl)pyridin-2(1H)-one (Example 226);
3-amino-1-(2-chlorobenzyl)-5-(3,5-dimethylisoxazol-4-yl)pyridin-2(1H)-one (Example 227);
3-amino-5-(3,5-dimethylisoxazol-4-yl)-1-(4-(trifluoromethyl)benzyl)pyridin-2(1H)-one (Example 228);
1-benzyl-5-(3,5-dimethylisoxazol-4-yl)-2-oxo-1,2-dihydropyridine-3-carboxylic acid (Example 229);
1-benzyl-5-(3,5-dimethylisoxazol-4-yl)-2-oxo-1,2-dihydropyridine-3-carboxamide (Example 230);
1-benzyl-5-(3,5-dimethylisoxazol-4-yl)-3-((5-methoxypyridin-3-yl)amino)pyridin-2(1H)-one (Example 231);
5-((1-benzyl-5-(3,5-dimethylisoxazol-4-yl)-2-oxo-1,2-dihydropyridin-3-yl)amino)picolinonitrile (Example 232);
4-amino-2-(4-chlorobenzyl)-6-(3,5-dimethylisoxazol-4-yl)pyridazin-3(2H)-one (Example 233);
1-benzyl-5-(3,5-dimethylisoxazol-4-yl)-3-((6-methoxypyridin-3-yl)amino)pyridin-2(1H)-one (Example 234);
1-benzyl-5-(3,5-dimethylisoxazol-4-yl)-3-(pyrazin-2-ylamino)pyridin-2(1H)-one (Example 235);
1-benzyl-5-(3,5-dimethylisoxazol-4-yl)-3-(pyrimidin-5-ylamino)pyridin-2(1H)-one (Example 236);
3-amino-1-(4-(azetidin-1-yl)benzyl)-5-(3,5-dimethylisoxazol-4-yl)pyridin-2(1H)-one (Example 237);
3-amino-5-(3,5-dimethylisoxazol-4-yl)-1-(4-morpholinobenzyl)pyridin-2(1H)-one (Example 238);
1-benzyl-5-(3,5-dimethylisoxazol-4-yl)-3-(pyrrolidin-3-ylamino)pyridin-2(1H)-one (Example 239);
3-amino-5-(3,5-dimethylisoxazol-4-yl)-1-((3-methylisoxazol-5-yl)methyl)pyridin-2(1H)-one (Example 240);
3-amino-1-(4-bromobenzyl)-5-(3,5-dimethylisoxazol-4-yl)pyridin-2(1H)-one (Example 241);
3-amino-5-(3,5-dimethylisoxazol-4-yl)-1-(4-isopropylbenzyl)pyridin-2(1H)-one (Example 242);
1-(4-chlorobenzyl)-5-(3,5-dimethylisoxazol-4-yl)-3-((2,2,2-trifluoroethyl)amino)pyridin-2(1H)-one (Example 243);
3-amino-5-(3,5-dimethylisoxazol-4-yl)-1-((6-methylpyridin-2-yl)methyl)pyridin-2(1H)-one (Example 244);

1-benzyl-5-(3,5-dimethylisoxazol-4-yl)-3-((6-methylpyridin-3-yl)amino)pyridin-2(1H)-one (Example 245);
1-benzyl-5-(3,5-dimethylisoxazol-4-yl)-3-((5-methylpyridin-3-yl)amino)pyridin-2(1H)-one (Example 246);
1-((1H-indol-4-yl)methyl)-3-amino-5-(3,5-dimethylisoxazol-4-yl)pyridin-2(1H)-one (Example 247);
2-benzyl-6-(3,5-dimethylisoxazol-4-yl)-4-(pyridin-3-ylamino)pyridazin-3(2H)-one (Example 248);
4-(1-benzyl-6-oxo-1,6-dihydropyridin-3-yl)-N-methoxy-N,5-dimethylisoxazole-3-carboxamide (Example 249);
4-amino-2-benzyl-6-(3,5-dimethylisoxazol-4-yl)pyridazin-3(2H)-one (Example 250);
3-amino-5-(3,5-dimethylisoxazol-4-yl)-1-((2,5-dimethylthiophen-3-yl)methyl)pyridin-2(1H)-one (Example 251);
3-amino-1-((5-chloropyridin-3-yl)methyl)-5-(3,5-dimethylisoxazol-4-yl)pyridin-2(1H)-one (Example 252);
3-amino-1-((3-chloropyridin-4-yl)methyl)-5-(3,5-dimethylisoxazol-4-yl)pyridin-2(1H)-one (Example 253);
3-amino-1-((3-chloropyridin-2-yl)methyl)-5-(3,5-dimethylisoxazol-4-yl)pyridin-2(1H)-one (Example 254);
3-amino-1-((5-chloropyridin-2-yl)methyl)-5-(3,5-dimethylisoxazol-4-yl)pyridin-2(1H)-one (Example 255);
3-amino-1-(benzo[d][1,3]dioxol-5-ylmethyl)-5-(3,5-dimethylisoxazol-4-yl)pyridin-2(1H)-one (Example 256);
3-amino-1-(benzo[d][1,3]dioxol-4-ylmethyl)-5-(3,5-dimethylisoxazol-4-yl))pyridin-2(1H)-one (Example 257);
3-amino-5-(3,5-dimethylisoxazol-4-yl)-1-((6-methylpyridin-3-yl)methyl)pyridin-2(1H)-one (Example 258);
methyl 4-(1-(4-chlorobenzyl)-6-oxo-1,6-dihydropyridin-3-yl)-3-methylisoxazole-5-carboxylate (Example 259);
4-(1-(4-chlorobenzyl)-6-oxo-1,6-dihydropyridin-3-yl)-3-methylisoxazole-5-carboxylic acid (Example 260);
4-((3-amino-5-(3,5-dimethylisoxazol-4-yl)-2-oxopyridin-1(2H)-yl)methyl)-3-fluorobenzonitrile (Example 261);
4-((3-amino-5-(3,5-dimethylisoxazol-4-yl)-2-oxopyridin-1(2H)-yl)methyl)-2-fluorobenzonitrile (Example 262);
3-amino-5-(3,5-dimethylisoxazol-4-yl)-1-(1-phenylethyl)pyridin-2(1H)-one (Example 263);
5-((3-amino-5-(3,5-dimethylisoxazol-4-yl)-2-oxopyridin-1(2H)-yl)methyl)thiophene-2-carbonitrile (Example 264);
4-(1-(4-chlorobenzyl)-6-oxo-1,6-dihydropyridin-3-yl)-N,3-dimethylisoxazole-5-carboxamide (Example 265);
3-(aminomethyl)-1-benzyl-5-(3,5-dimethylisoxazol-4-yl)pyridin-2(1H)-one (Example 266);
3-amino-5-(3,5-dimethylisoxazol-4-yl)-1-(4-iodobenzyl)pyridin-2(1H)-one (Example 267);
1-benzyl-5-(5-oxopyrrolidin-3-yl)pyridin-2(1H)-one (Example 268);
4-(1-(3-amino-5-(3,5-dimethylisoxazol-4-yl)-2-oxopyridin-1(2H)-yl)ethyl)benzonitrile (Example 269);
1-((1H-indol-3-yl)methyl)-3-amino-5-(3,5-dimethylisoxazol-4-yl)pyridin-2(1H)-one (Example 270);
3-amino-5-(3,5-dimethylisoxazol-4-yl)-1-((3-methyl-1H-indol-4-yl)methyl)pyridin-2(1H)-one (Example 271);
5-((3-amino-5-(3,5-dimethylisoxazol-4-yl)-2-oxopyridin-1(2H)-yl)methyl)-2-bromobenzonitrile (Example 272);
4-((3-amino-5-(3,5-dimethylisoxazol-4-yl)-2-oxopyridin-1(2H)-yl)methyl)-2-bromobenzonitrile (Example 276); and
3-amino-5-(3,5-dimethylisoxazol-4-yl)-1-(quinolin-5-ylmethyl)pyridin-2(1H)-one (Example 274).

In certain embodiments of the disclosure, the compound of formula I is 1-(4-chlorobenzyl)-5-(3,5-dimethyl-4H-1,2,4-triazol-4-yl)pyridin-2(1H)-one (Example 197).

In a second aspect of Formula I, the invention is directed to a compound according to Formula III:

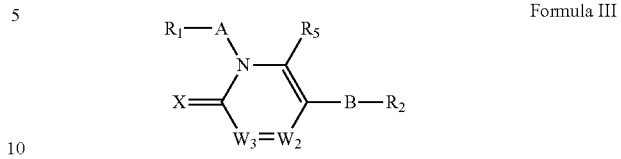

Formula III or a stereoisomer, tautomer, pharmaceutical acceptable salt, or hydrate thereof,
wherein:
$W_2$ is selected from N and $CR_4$,
with the proviso that if $W_2$ is N and $R_2$ is

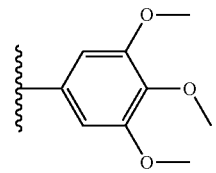 [SMILES: *c1cc(OC)c(OC)c(OC)c1]

then $R_5$ is not hydrogen;
$W_3$ is selected from N and $CR_3$,
with the proviso that if $W_3$ is N then neither $R_5$ or $R_4$ can be —OH;
each W may be the same or different from each other;
$R_1$ is a carbocycle or heterocycle,
with the proviso $R_1$-A is not

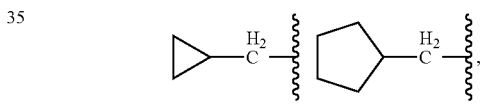

and with the proviso that if $R_1$-A is

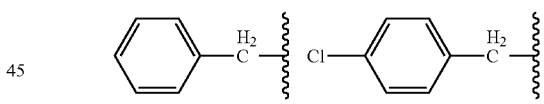

then at least one of $Q_1$, $Q_2$, $Q_3$, or $Q_4$ is different from hydrogen,
and with the proviso that if $R_1$-A is

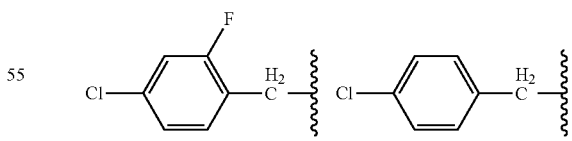

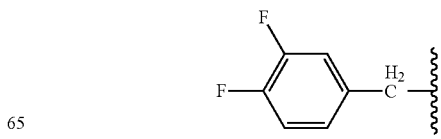

then at least one of $R_3$ and $R_4$ is not hydrogen,
and with the proviso that if $R_1$ is

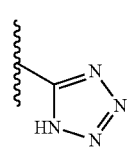 [SMILES: *c1nnn[nH]1]

then $R_2$ is not

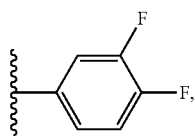 [SMILES: *c1ccc(F)c(F)c1]

and with the proviso that if $R_1$ is

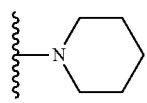

then $R_2$ is not

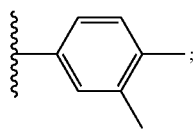 [SMILES: *c1ccc(C)c(C)c1]

$R_2$ is selected from a 6-membered monocyclic carbocycle or monocyclic heterocycle,
with the proviso that $R_2$ is not

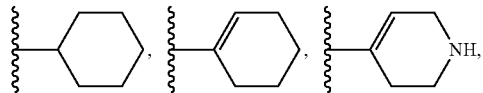

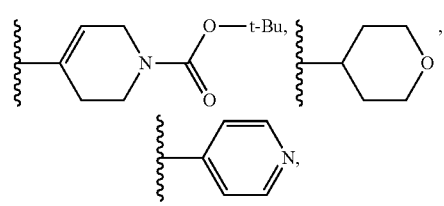

or an optionally substituted

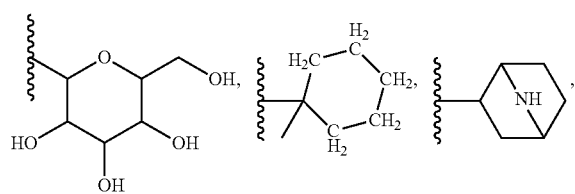

and with the proviso that if $R_2$ is

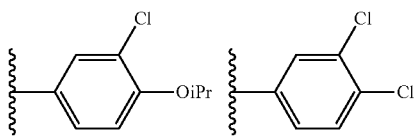

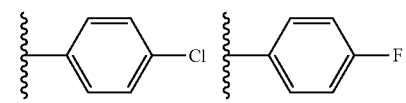

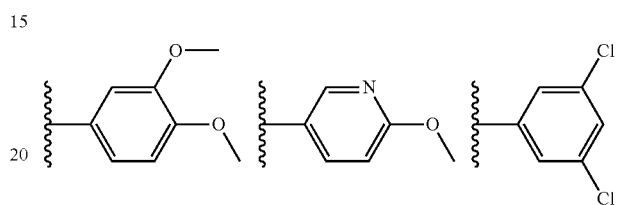

then at least one of $R_3$ and $R_4$ is not hydrogen,
and with the proviso that if $R_3$ is —CN, then $R_2$ is not

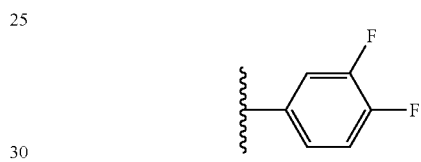

and with the proviso that if $R_2$ is

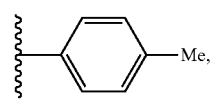

then $R_1$ is not

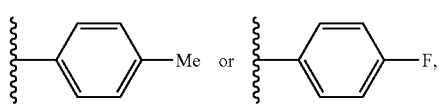

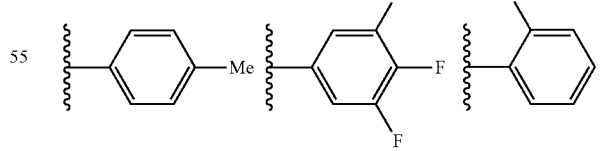

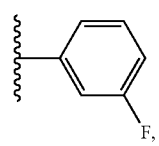

and with the proviso that if $R_2$ is

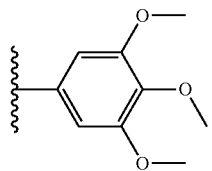 [SMILES: *c1cc(OC)c(OC)c(OC)c1]

then $R_5$ is not —COOMe
and with the proviso that if $R_4$ is —NH$_2$ then $R_2$ is not

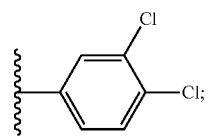

$R_3$, $R_4$, and $R_5$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN,
with the proviso that $R_4$ is not —OH and $R_5$ is not —COOH or -ester;
$R_3$ and $R_4$ may be connected to form an optionally substituted 5-, 6-, or 7-membered carbocycle or heterocycle;
$R_4$ may be connected to B or $R_2$ to form a carbocycle or heterocycle;
X is selected from O and S;
A is selected from —CR$_x$R$_y$—, C=O, —C(O)CR$_x$R$_y$—, —CR$_x$R$_y$CR$_z$R$_v$—, —SO$_2$—, —CR$_x$R$_y$CR$_z$R$_v$O—, —CR$_x$R$_y$CR$_z$R$_v$N—, —CR$_x$R$_y$CR$_z$R$_v$S—, and —CR$_x$R$_y$CR$_z$R$_v$CR$_Q$R$_R$—;
with the proviso that $R_x$ and $R_y$ cannot both be an unsubstituted phenyl ring,
and with the proviso that if A is —CH$_2$CH$_2$CH$_2$— and $W_3$ is N then $R_4$ is not —OH,
and with the proviso that if A is —CH$_2$CH$_2$O— the $R_1$ is not

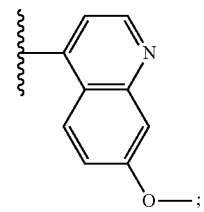 [SMILES: *c1ccnc2cc(OC)ccc12]

$R_x$, $R_y$, $R_z$, $R_v$, $R_Q$, and $R_R$ are each independently selected from hydrogen, alkyl(C$_1$-C$_8$), halogen, —OH, —CF$_3$, amino, alkoxy (C$_1$-C$_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;
B is selected from —(CR$_a$R$_b$)$_n$—, —(CR$_a$R$_b$CR$_c$R$_d$)—, —O—, —OCR$_a$R$_b$—, —CR$_a$R$_b$O—, —NH—, —NHCR$_a$R$_b$—, —CR$_a$R$_b$NH—, —S—, —SCR$_a$R$_b$—, —CR$_a$R$_b$S—, —S(O)—, —S(O)CR$_a$R$_b$—, —CR$_a$R$_b$S(O)—, —SO$_2$—, —SO$_2$CR$_a$R$_b$—, and —CR$_a$R$_b$SO$_2$—;
n is selected from 0 and 1, meaning if n=0 then B is absent;
and $R_a$, $R_b$, $R_c$, and $R_d$ are each independently selected from hydrogen, alkyl(C$_1$-C$_3$), and alkoxy(C$_1$-C$_3$).

In some embodiments, according to Formula III, $R_2$ is selected from an optionally substituted 6-membered monocyclic carbocycle (such as phenyl) or heterocycle (such as pyridyl, pyrimidine, pyrazine, and triazine), where the heterocycle is connected to the rest of the molecule via a carbon-carbon bond.

In some embodiments, according to Formula III, $R_2$ is selected from

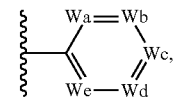

wherein:
$W_a$ is selected from N and CQ$_1$;
$W_b$ is selected from N and CQ$_2$;
$W_c$ is selected from N and CQ$_3$;
$W_d$ is selected from N and CQ$_4$;
$W_e$ is selected from N and CQ$_5$;
Each W may be the same or different from each other;
$Q_1$, $Q_2$, $Q_4$, $Q_5$ are each independently selected from hydrogen, —OH, —NH$_2$, halogen, —CF$_3$, —CN, —Ac, alkyl (C$_1$-C$_3$), alkoxy(C$_1$-C$_3$), —S(O)Alkyl(C$_1$-C$_3$), —SO$_2$Alkyl (C$_1$-C$_3$), —Salkyl(C$_1$-C$_3$), —NHAlkyl(C$_1$-C$_3$), —N(Alkyl)$_2$ (C$_1$-C$_3$), which may be optionally substituted with groups independently selected from F, Cl, Br, —OH, —NH$_2$, —OMe, —OEt, —NHMe, —SMe, —S(O)Me, -Me, and -Et;
$Q_3$ is selected from —OH, —NH$_2$, F, Cl, alkyl(C$_1$-C$_3$), alkoxy(C$_1$-C$_3$), —S(O)Alkyl(C$_1$-C$_3$), —SO$_2$Alkyl(C$_1$-C$_3$), —Salkyl(C$_1$-C$_3$), —NHAlkyl(C$_1$-C$_3$), and —N(Alkyl)$_2$ (C$_1$-C$_3$), which may be optionally substituted with groups independently selected from F, Cl, —OH, —NH$_2$, —OMe, —OEt, -Me, and -Et.

In some embodiments, according to Formula III, $R_2$ is selected from

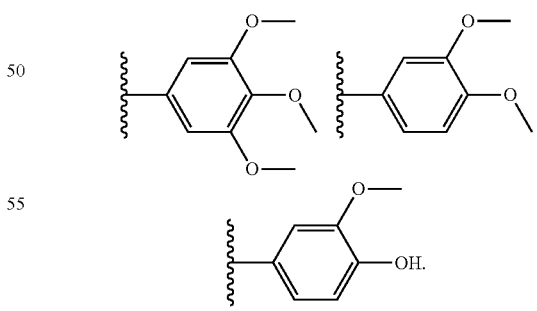

In some embodiments, according to Formula III, $R_1$ is selected from a 3-, 4-, 5-, or 6-membered carbocycle or heterocycle.

In some embodiments, according to Formula III, $R_1$ is selected from an optionally substituted phenyl.

In some embodiments, according to Formula III, $R_1$ is optionally substituted with hydrogen, —OH, —NH$_2$, halogen, —CF₃, —CN, —Ac, Alkyl(C₁-C₃), Alkoxy(C₁-C₃), —S(O)Alkyl(C₁-C₃), —SO₂Alkyl(C₁-C₃), —SAlkyl(C₁-C₃), —NHAlkyl(C₁-C₃), and —N(Alkyl)₂ (C₁-C₃), which may be optionally substituted.

In some embodiments, according to Formula III, R₃ is selected from hydrogen, —CN, —NH₂, amino (such as —NHMe, —NHethyl, —NHcyclopropyl, —NHPh, —NHBn, —NMe₂, —NHpyridyl, —NHcyclopentyl), amido (such as —NHAc, —NHC(O)Et, —NHC(O)Pr, —NHC(O)phenyl, —C(O)NHMe, —C(O)NH₂, —C(O)NHEt, —C(O)NMe₂), sulfone, Sulfoxide, sulfonamide (such as —SO₂NH₂, —NHSO₂Me), carbocycle (phenyl, cyclopropyl, cyclobutyl, or cyclopentyl), and heterocycle, which may be optionally substituted.

In some embodiments, according to Formula III, R₃ is selected from hydrogen, —NH₂, amino (such as —NHMe, —NHEt, —NHcyclopropyl, —NHPh, —NHBn, —NMe₂, —NHpyridyl, or —NHcyclopentyl), and —NHheterocycle or heterocycle (such as,

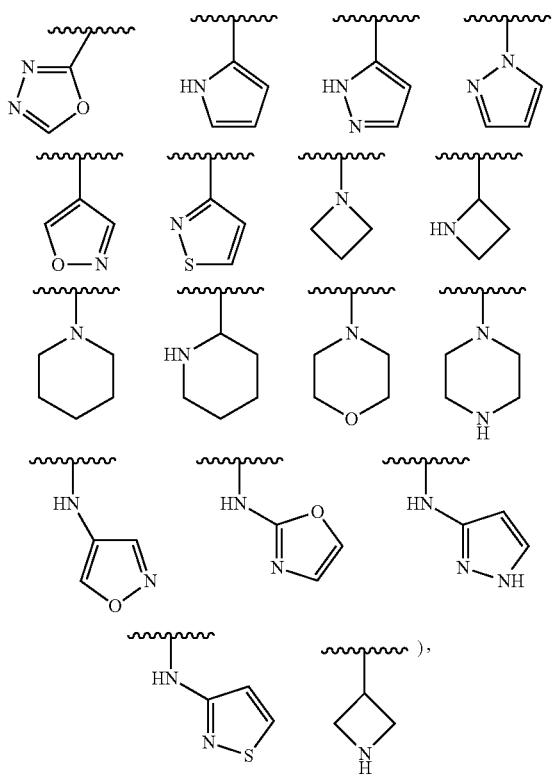

which may be optionally substituted with groups independently selected from hydrogen, alkyl, —OH, —NH₂, thioalkyl, alkoxy, ketone, ester, carboxylic acid, urea, carbamate, carbonate, amino, amide, halogen, oxo, and thio-oxo.

In some embodiments, according to Formula III, R₃, R₄, and R₅ may be optionally substituted with groups independently selected from hydrogen, alkyl, —OH, —NH₂, thioalkyl, alkoxy, ketone, ester, carboxylic acid, urea, carbamate, carbonate, amino, amide, and halogen.

In some embodiments, according to Formula III, R₃ and R₄ may be connected to form an optionally substituted 5-, 6-, or 7-membered carbocycle or heterocycle such as

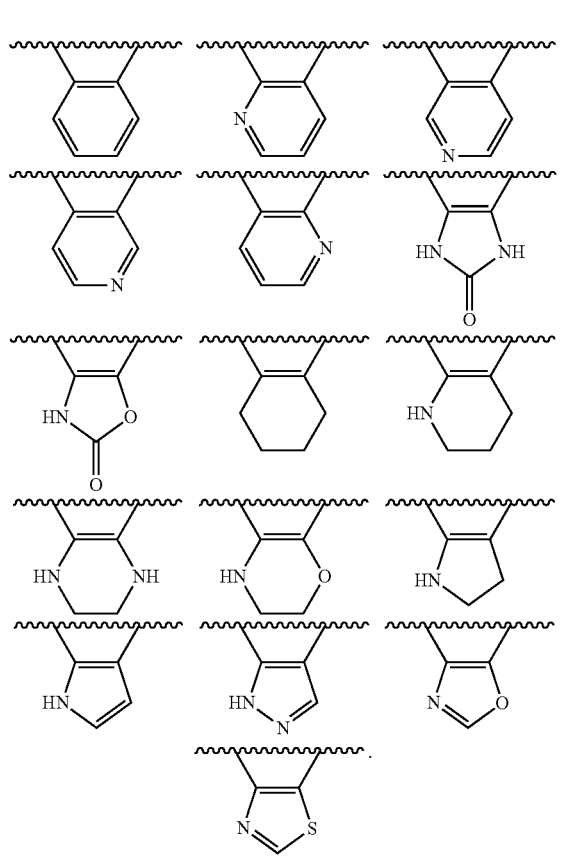

In some embodiments, according to Formula III, R₅ is hydrogen.

In some embodiments, according to Formula III, R₄ is hydrogen.

In some embodiments, according to Formula III, X is oxygen.

In some embodiments, according to Formula III, n=0, meaning B is absent.

In some embodiments, according to Formula III, B is selected from —(CR_aR_b)_n—, —O—, —NH—, —S—, where n is 0 or 1, meaning if n=0 then B is absent.

In some embodiments, according to Formula III, A is selected from C=O and —CR_xR_y—

In certain embodiments of the invention, the compound of Formula III is selected from: 1-Benzyl-5-(3,4,5-trimethoxyphenyl)pyridin-2(1H)-one (Example 52);

2-((2-Oxo-5-(3,4,5-trimethoxyphenyl)pyridin-1(2H)-yl)methyl)benzonitrile (Example 53);

1-Benzyl-2'-hydroxy-[3,4'-bipyridin]-6(1H)-one (Example 62);

1-Benzyl-5-((3,4-dimethoxyphenyl)amino)pyridin-2(1H)-one (Example 65);

2-Benzyl-4-(3,4-dimethoxyphenyl)isoquinolin-1(2H)-one (Example 166);

2-Benzyl-4-(3,4,5-trimethoxyphenyl)isoquinolin-1(2H)-one (Example 168);

2-Benzyl-4-(4-hydroxy-3-methoxyphenyl)isoquinolin-1(2H)-one (Example 169); and

2-Benzyl-4-((3,4,5-trimethoxyphenyl)amino)isoquinolin-1(2H)-one (Example 172).

In a third aspect of Formula I, the invention concerns a compound according to Formula IV:

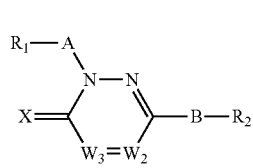

Formula IV or a stereoisomer, tautomer, pharmaceutically acceptable salt, or hydrate thereof,
wherein:
$W_2$ is selected from N and $CR_4$,
with the proviso that if $W_2$ is N and $R_2$ is

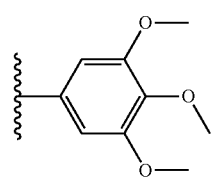 [SMILES: *c1cc(OC)c(OC)c(OC)c1]

then $R_5$ is not hydrogen;
$W_3$ is selected from N and $CR_3$,
with the proviso that if $W_3$ is N then neither $R_5$ or $R_4$ can be —OH;
each W may be the same or different from each other;
$R_1$ is a carbocycle or heterocycle,
with the proviso that $R_1$ is different from an amino group with nitrogen attached to A (such as

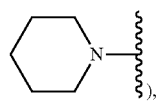

a substituted napthyl, or cyclohexyl,
and with the proviso that $R_1$-A is not

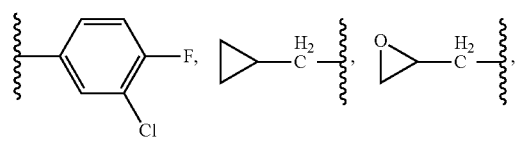

and with the proviso that if $R_1$-A is

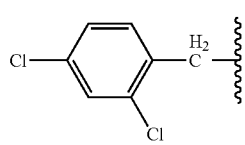

then $R_2$ is not an optionally substituted

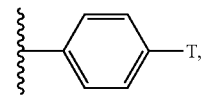

where T is halogen,
and with the proviso that if $R_1$-A is

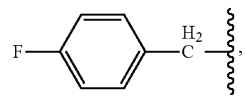

then $R_2$ is not

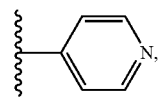

and with the proviso that if $R_1A$ is

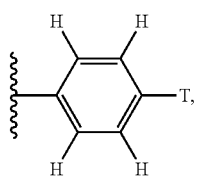

then $R_2$ is not substituted with —OH or —NH$_2$;
$R_2$ is selected from a 6-membered monocyclic carbocycle or monocyclic heterocycle,
with the proviso that $R_2$ is not unsubstituted thiophene, furane, cyclopentyl, cyclohexyl, or

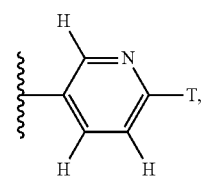

where T can be any atom,
and with the proviso that $R_2$ is not where T is Cl, Br, —OMe, or Me,
and with the proviso that R$_2$ is not

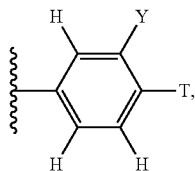

where T and Y are independently selected from Cl, F, -Me, —CN, and —OH,
and with the proviso that R$_2$ is not

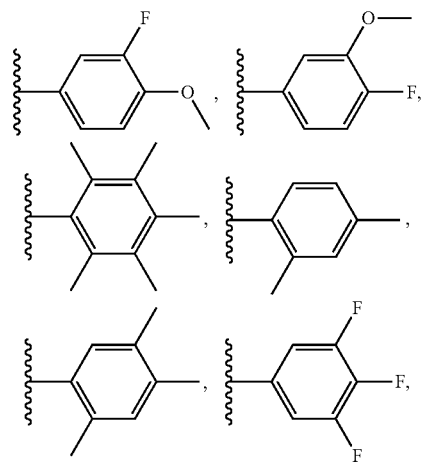

and with the proviso that if R$_2$ is

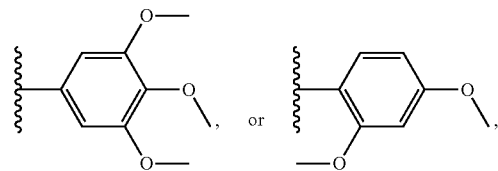 [SMILES: *c1cc(OC)c(OC)c(OC)c1 ; *c1ccc(OC)cc1OC]

then R$_1$-A is not

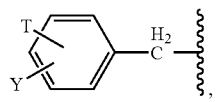

where T and Y are independently selected from hydrogen, F, Cl, Br, —CF$_3$, and -Me, and R$_1$ is not unsubstituted pyridyl, substituted furane, or unsubstituted naphthyl,
and with the proviso that if R$_2$ is

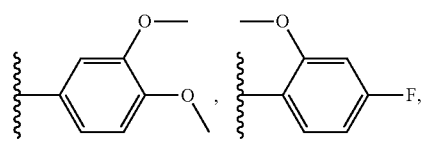

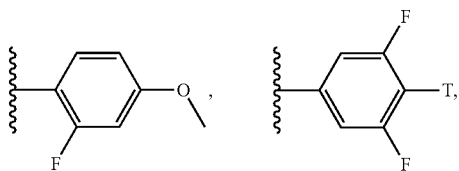

where T is an —OH, Alkoxy, —OAcyl, —NH$_2$, amino, amide, carbamate, or urea, substituent, then at least one of R$_3$ and R$_4$ is different from hydrogen,
and with the proviso that if R$_2$ is an unsubstituted pyridyl, then at least one of R$_3$ and R$_4$ is different from hydrogen, or R$_1$-A is different from

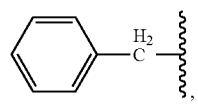

or R$_3$ and R$_4$ are not connected to form an unsubstituted benzene ring,
and with the proviso that if R$_2$ is

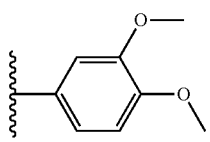 [SMILES: *c1ccc(OC)c(OC)c1]

then R$_3$ is not methyl, at least one of R$_3$ and R$_4$ cannot be connected to

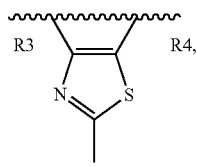

or R$_1$-A cannot be

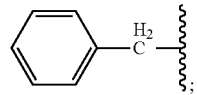

R$_3$ and R$_4$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN,
with the proviso that R$_4$ is not —OH;
R$_3$ and R$_4$ may be connected to form an optionally substituted 5-, 6-, or 7-membered carbocycle or heterocycle, with the proviso that $R_3$ and $R_4$ are not connected to form

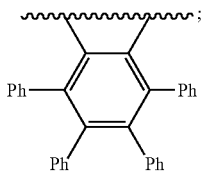

$R_4$ may be connected to B or $R_2$ to form a carbocycle or heterocycle;

X is selected from O and S;

A is selected from —$CR_xR_y$—, C=O, —$C(O)CR_xR_y$—, —$CR_xR_yCR_zR_v$—, —$SO_2$—, —$CR_xR_yCR_zR_vO$—, —$CR_xR_yCR_zR_vN$—, —$CR_xR_yCR_zR_vS$—, and —$CR_xR_yCR_zR_vCR_QR_R$—;

with the proviso that if A is C=O, then $R_2$ is not an optionally substituted

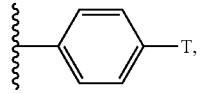

where T is halogen, and with the proviso that $R_x$ and $R_y$ cannot both be an unsubstituted phenyl ring, and with the proviso that if A is —$CH_2CH_2CH_2$— and $W_3$ is N then $R_4$ is not —OH, and with the proviso that if A is —$CH_2CH_2O$— the $R_1$ is not

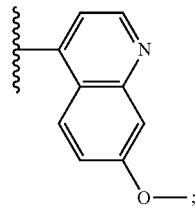 [SMILES: *c1ccnc2cc(OC)ccc12]

$R_x$, $R_y$, $R_z$, $R_v$, $R_Q$, and $R_R$ are each independently selected from hydrogen, alkyl($C_1$-$C_8$), halogen, —OH, —$CF_3$, amino, alkoxy ($C_1$-$C_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;

B is selected from —$(CR_aR_b)_n$—, —$(CR_aR_bCR_cR_d)$—, —O—, —$OCR_aR_b$—, —$CR_aR_bO$—, —NH—, —$NHCR_aR_b$—, —$CR_aR_bNH$—, —S—, —$SCR_aR_b$—, —$CR_aR_bS$—, —S(O)—, —$S(O)CR_aR_b$—, —$CR_aR_bS(O)$—, —$SO_2$—, —$SO_2CR_aR_b$—, and —$CR_aR_bSO_2$—;

n is selected from 0 and 1, meaning if n=0 then B is absent;

$R_a$, $R_b$, $R_c$, and $R_d$ are each independently selected from hydrogen, alkyl($C_1$-$C_3$), and alkoxy($C_1$-$C_3$).

In some embodiments, according to Formula IV, $R_2$ is selected from an optionally substituted 6-membered monocyclic carbocycle (such as phenyl) or heterocycle (such as pyridyl, pyrimidine, pyrazine, and triazine), where the heterocycle is connected to the rest of the molecule via a carbon-carbon bond.

In some embodiments, according to Formula IV, $R_2$ is selected from

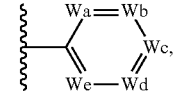

wherein:

$W_a$ is selected from N and $CQ_1$;
$W_b$ is selected from N and $CQ_2$;
$W_c$ is selected from N and $CQ_3$;
$W_d$ is selected from N and $CQ_4$;
$W_e$ is selected from N and $CQ_5$;
Each of $W_a$, $W_b$, $W_c$, $W_d$, and $W_e$ may be the same or different from each other;
$Q_1$, $Q_2$, $Q_4$, $Q_5$ are each independently selected from hydrogen, —OH, —$NH_2$, halogen, —$CF_3$, —CN, —Ac, alkyl ($C_1$-$C_3$), alkoxy($C_1$-$C_3$), —S(O)Alkyl($C_1$-$C_3$), —$SO_2$Alkyl ($C_1$-$C_3$), —Salkyl($C_1$-$C_3$), —NHAlkyl($C_1$-$C_3$), and —N(Alkyl)$_2$($C_1$-$C_3$), which may be optionally substituted with groups independently selected from F, Cl, Br, —OH, —$NH_2$, —OMe, —OEt, —NHMe, —SMe, —S(O)Me, -Me, and -Et;
$Q_3$ is selected from —OH, —$NH_2$, F, Cl, alkyl($C_1$-$C_3$), alkoxy($C_1$-$C_3$), —S(O)Alkyl($C_1$-$C_3$), —$SO_2$Alkyl($C_1$-$C_3$), —Salkyl($C_1$-$C_3$), —NHAlkyl($C_1$-$C_3$), and —N(Alkyl)$_2$ ($C_1$-$C_3$), which may be optionally substituted with groups independently selected from F, Cl, —OH, —$NH_2$, —OMe, —OEt, -Me, and -Et.

In some embodiments, according to Formula IV, $R_2$ is selected from

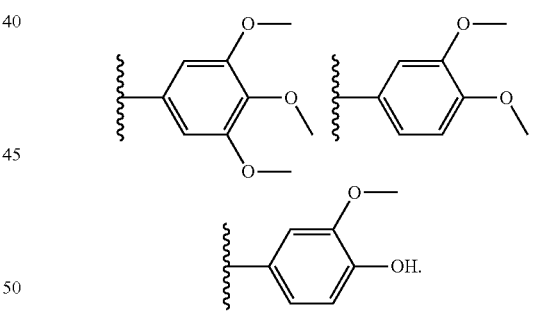

In some embodiments, according to Formula IV, $R_1$ is selected from a 3-, 4-, 5-, or 6-membered carbocycle or heterocycle.

In some embodiments, according to Formula IV, $R_1$ is selected from an optionally substituted phenyl.

In some embodiments, according to Formula IV, $R_1$ is optionally substituted with hydrogen, —OH, —$NH_2$, halogen, —$CF_3$, —CN, —Ac, Alkyl($C_1$-$C_3$), Alkoxy($C_1$-$C_3$), —S(O)Alkyl($C_1$-$C_3$), —$SO_2$Alkyl($C_1$-$C_3$), —SAlkyl($C_1$-$C_3$), —NHAlkyl($C_1$-$C_3$), and —N(Alkyl)$_2$ ($C_1$-$C_3$), which may be optionally substituted.

In some embodiments, according to Formula IV, $R_3$ is selected from hydrogen, —CN, —$NH_2$, amino (such as —NHMe, —NHethyl, —NHcyclopropyl, —NHPh, —NHBn, —NMe$_2$, —NHpyridyl, —NHcyclopentyl), amido (such as —NHAc, —NHC(O)Et, —NHC(O)Pr, —NHC(O)phenyl, —C(O)NHMe, —C(O)NH$_2$, —C(O)NHEt, —C(O)NMe$_2$), sulfone, Sulfoxide, sulfonamide (such as —SO$_2$NH$_2$, —NHSO$_2$Me), carbocycle (phenyl, cyclopropyl, cyclobutyl, cyclopentyl), and heterocycle, which may be optionally substituted.

In some embodiments, according to Formula IV, R$_3$ is selected from hydrogen, —NH$_2$, amino (such as —NHMe, —NHEt, —NHcyclopropyl, —NHPh, —NHBn, —NMe$_2$, —NHpyridyl, —NHcyclopentyl), and —NHheterocycle or heterocycle (such as,

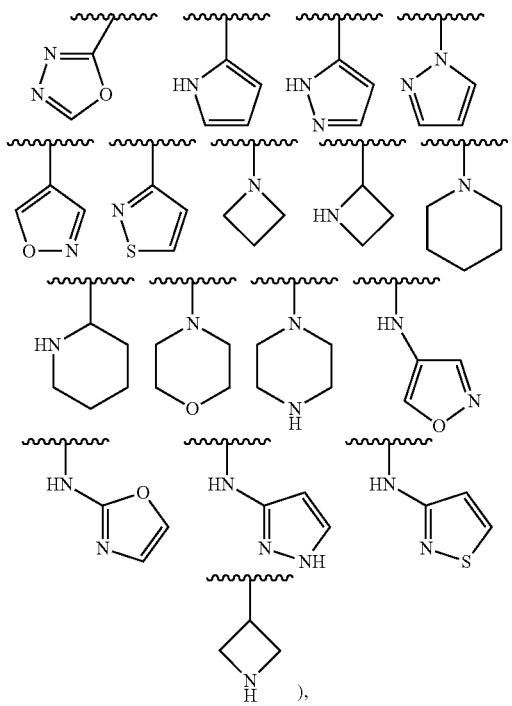
), which may be optionally substituted with groups independently selected from hydrogen, alkyl, —OH, —NH$_2$, thioalkyl, alkoxy, ketone, ester, carboxylic acid, urea, carbamate, carbonate, amino, amide, and halogen.

In some embodiments, according to Formula IV, R$_3$, R$_4$, and R$_5$ may be optionally substituted with groups independently selected from hydrogen, alkyl, —OH, —NH$_2$, thioalkyl, alkoxy, ketone, ester, carboxylic acid, urea, carbamate, carbonate, amino, amide, and halogen.

In some embodiments, according to Formula IV, R$_3$ and R$_4$ may be connected to form an optionally substituted 5-, 6-, or 7-membered carbocycle or heterocycle such

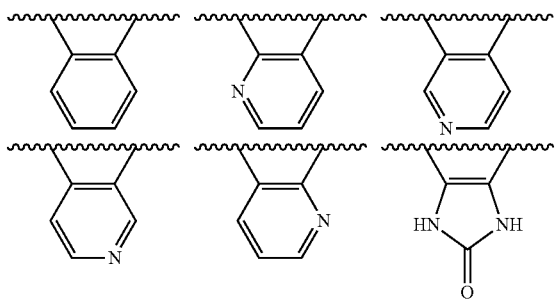

as,

[additional structures]

In some embodiments, according to Formula IV, R$_4$ is hydrogen.

In some embodiments, according to Formula IV, X is oxygen.

In some embodiments, according to Formula IV, n=0, meaning B is absent.

In some embodiments, according to Formula IV, B is selected from —(CR$_a$R$_b$)$_n$—, —O—, —NH—, —S—, where n is 0 or 1, meaning if n=0 then B is absent.

In some embodiments, according to Formula IV, A is selected from C=O and —CR$_x$R$_y$—

In certain embodiments of the invention, the compound of Formula IV is selected from: 3-((6-Oxo-3-(3,4,5-trimethoxyphenyl)pyridazin-1(6H)-yl)methyl)benzonitrile (Example 15);
4-((6-Oxo-3-(3,4,5-trimethoxyphenyl)pyridazin-1(6H)-yl)methyl)benzonitrile (Example 16);
N-(3-((6-Oxo-3-(3,4,5-trimethoxyphenyl)pyridazin-1(6H)-yl)methyl)phenyl)acetamide (Example 17);
2-Benzyl-6-((3,4,5-trimethoxyphenyl)amino)pyridazin-3(2H)-one (Example 54);
2-Benzyl-6-((3,4-dimethoxyphenyl)amino)pyridazin-3(2H)-one (Example 60); N-(4-((6-Oxo-3-(3,4,5-trimethoxyphenyl)pyridazin-1(6H)-yl)methyl)phenyl)acetamide (Example 82);
2-Benzyl-6-(4-hydroxy-3-methoxyphenyl)pyridazin-3(2H)-one (Example 83);
2-Benzyl-6-((5,6-dimethoxypyridin-2-yl)amino)pyridazin-3(2H)-one (Example 99);
2-Benzyl-6-(3,4-dimethoxyphenoxy)pyridazin-3(2H)-one (Example 100);
2-(4-(Methylsulfonyl)benzyl)-6-(3,4,5-trimethoxyphenyl)pyridazin-3(2H)-one (Example 116);
2-(4-Methoxybenzyl)-6-(3,4,5-trimethoxyphenyl)pyridazin-3(2H)-one (Example 117);

2-((6-Oxo-3-(3,4,5-trimethoxyphenyl)pyridazin-1(6H)-yl) methyl)benzonitrile (Example 118);
2-(3-Methoxybenzyl)-6-(3,4,5-trimethoxyphenyl)pyridazin-3(2H)-one (Example 119);
2-(4-(tert-Butyl)benzyl)-6-(3,4,5-trimethoxyphenyl) pyridazin-3(2H)-one (Example 120);
2-Benzyl-4-(2-hydroxy-3,4-dimethoxyphenyl)phthalazin-1 (2H)-one (Example 164);
2-Benzyl-4-(4-hydroxy-3-methoxyphenyl)-2H-phthalazin-1-one (Example 165);
2-Benzyl-4-(3,4,5-trimethoxyphenylamino)-2H-phthalazin-1-one (Example 171);
2-Benzyl-4-(2,3,4-trimethoxyphenyl)phthalazin-1(2H)-one (Example 177);
6-(4-hydroxyphenyl)-2-(1-phenylethyl)pyridazin-3(2H)-one (Example 178); and
2-benzyl-6-(4-methyl-3-oxopiperazin-1-yl)pyridazin-3 (2H)-one (Example 179).

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formulae I-IV.

In one embodiment, because of potent effects of BET inhibitors in vitro on IL-6 and IL-17 transcription, BET inhibitor compounds of Formulae I-IV may be used as therapeutics for inflammatory disorders in which IL-6 and/or IL-17 have been implicated in disease. The following autoimmune diseases are amenable to therapeutic use of BET inhibition by administration of a compound of Formulae I-IV because of a prominent role of IL-6 and/or IL-17: Acute Disseminated Encephalomyelitis [69], Agammaglobulinemia [70], Allergic Disease [71], Ankylosing spondylitis [72], Anti-GBM/Anti-TBM nephritis [73], Anti-phospholipid syndrome [74], Autoimmune aplastic anemia [75], Autoimmune hepatitis [76], Autoimmune inner ear disease [77], Autoimmune myocarditis [78], Autoimmune pancreatitis [79], Autoimmune retinopathy [80], Autoimmune thrombocytopenic purpura [81], Behcet's Disease [82], Bullous pemphigoid [83], Castleman's Disease [84], Celiac Disease [85], Churg-Strauss syndrome [86], Crohn's Disease [87], Cogan's syndrome [88], Dry eye syndrome [89], Essential mixed cryoglobulinemia [90], Dermatomyositis [91], Devic's Disease [92], Encephalitis [93], Eosinophlic esophagitis [94], Eosinophilic fasciitis [94], Erythema nodosum [95], Giant cell arteritis [96], Glomerulonephritis [97], Goodpasture's syndrome [73], Granulomatosis with Polyangiitis (Wegener's) [98], Graves' Disease [99], Guillain-Barre syndrome [100], Hashimoto's thyroiditis [101], Hemolytic anemia [102], Henoch-Schonlein purpura [103], IgA nephropathy [104], Inclusion body myositis [105], Type I diabetes [8], Interstitial cystitis [106], Kawasaki's Disease [107], Leukocytoclastic vasculitis [108], Lichen planus [109], Lupus (SLE) [110], Microscopic polyangitis [111], Multiple sclerosis [112], Myasthenia gravis [113], myositis [91], Optic neuritis [114], Pemphigus [115], POEMS syndrome [116], Polyarteritis nodosa [117], Primary biliary cirrhosis [118], Psoriasis [119], Psoriatic arthritis [120], Pyoderma gangrenosum [121], Relapsing polychondritis [122], Rheumatoid arthritis [123], Sarcoidosis [124], Scleroderma [125], Sjogren's syndrome [126], Takayasu's arteritis [127], Transverse myelitis [128], Ulcerative colitis [129], Uveitis [130], and Vitiligo [131].

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis [132], pneumonitis [133], osteomyelitis [134], gastritis [135], enteritis [136], gingivitis [137], appendicitis [138], irritable bowel syndrome [139], tissue graft rejection [140], chronic obstructive pulmonary disease (COPD) [141], septic shock (toxic shock syndrome, SIRS, bacterial sepsis, etc) [12], osteoarthritis [142], acute gout [143], acute lung injury [141], acute renal failure [144], burns [145], Herxheimer reaction [146], and SIRS associated with viral infections [8].

In one embodiment, BET inhibitor compounds of Formulae I-IV may be used for treating rheumatoid arthritis (RA) and multiple sclerosis (MS). Strong proprietary data exist for the utility of BET inhibitors in preclinical models of RA and MS [17]. Both RA and MS are characterized by a dysregulation of the IL-6 and IL-17 inflammatory pathways [10] and thus would be especially sensitive to BET inhibition. In another embodiment, BET inhibitor compounds of Formulae I-IV may be used for treating sepsis and associated afflictions. BET inhibition has been shown to inhibit development of sepsis, in part, by inhibiting IL-6 expression, in preclinical models in both published [12] and proprietary data.

In one embodiment, BET inhibitor compounds of Formulae I-IV may be used to treat cancer. Cancers that have an overexpression, translocation, amplification, or rearrangement c-myc or other myc family oncoproteins (MYCN, L-myc) are particularly sensitive to BET inhibition [27, 28]. These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma [25].

In one embodiment, BET inhibitor compounds of Formulae I-IV may be used to treat cancers that result from an aberrant regulation (overexpression, translocation, etc) of BET proteins. These include, but are not limited to, NUT midline carcinoma (Brd3 or Brd4 translocation to nutlin 1 gene) [22], B-cell lymphoma (Brd2 overexpression) [23], non-small cell lung cancer (BrdT overexpression) [147, 148], esophageal cancer and head and neck squamous cell carcinoma (BrdT overexpression) [147], and colon cancer (Brd4) [149].

In one embodiment, because BET inhibitors decrease Brd-dependent recruitment of pTEFb to genes involved in cell proliferation, BET inhibitor compounds of Formulae I-IV may be used to treat cancers that rely on pTEFb (Cdk9/cyclin T) and BET proteins to regulate oncogenes. These include, but are not limited to, chronic lymphocytic leukemia and multiple myeloma [150], follicular lymphoma, diffuse large B cell lymphoma with germinal center phenotype, Burkitt's lymphoma, Hodgkin's lymphoma, follicular lymphomas and activated, anaplastic large cell lymphoma [151], neuroblastoma and primary neuroectodermal tumor [152], rhabdomyosarcoma [153], prostate cancer [154], and breast cancer [45].

In one embodiment, BET inhibitor compounds of Formulae I-IV may be used to treat cancers in which BET-responsive genes, such as CDK6, Bcl2, TYRO3, MYB, and hTERT are up-regulated [26, 27]. These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma [32, 155-162].

Published and proprietary data have shown direct effects of BET inhibition on cell proliferation in various cancers. In one embodiment, BET inhibitor compounds of Formulae I-IV may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), and non-Hodgkin's lymphoma [24, 26-30, 33]. Examples provided within this application have also shown a direct effect of BET inhibition on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formulae I-IV may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, because of their ability to up-regulate ApoA-1 transcription and protein expression [11, 35], BET inhibitor compounds of Formulae I-IV may be used to treat cardiovascular diseases that are generally associated with including dyslipidemia, atherosclerosis, hypercholesterolemia, and metabolic syndrome [8, 19]. In another embodiment, BET inhibitor compounds of Formulae I-IV may be used to treat non-cardiovascular disease characterized by deficits in ApoA-1, including Alzheimer's disease [37].

In one embodiment, BET inhibitor compounds of Formulae I-IV may be used in patients with insulin resistance and type II diabetes [8, 19, 38, 39]. The anti-inflammatory effects of BET inhibition would have additional value in decreasing inflammation associated with diabetes and metabolic disease [163].

In one embodiment, because of their ability to down-regulate viral promoters, BET inhibitor compounds of Formulae I-IV may be used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV) [40-42, 164]. In another embodiment, because of their ability to reactivate HIV-1 in models of latent T cell infection and latent monocyte infection, BET inhibitors could be used in combination with anti-retroviral therapeutics for treating HIV [43-46].

In one embodiment, because of the role of epigenetic processes and bromodomain-containing proteins in neurological disorders, BET inhibitor compounds of Formulae I-IV may be used to treat diseases including, but not limited to, Alzheimer's disease, Parkinson's disease, Huntington disease, bipolar disorder, schizophrenia, Rubinstein-Taybi syndrome, and epilepsy [9, 165].

In one embodiment, because of the effect of BRDT depletion or inhibition on spermatid development, BET inhibitor compounds of Formulae I-IV may be used as reversible, male contraceptive agents [50, 51].

Pharmaceutical Compositions

Pharmaceutical compositions of the present disclosure comprise at least one compound of Formulae I-IV, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formulae I-IV or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection.

Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formulae I-IV or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

Equivalent Surface Area Dosage Factors:

| From: | To: | | | | |
| --- | --- | --- | --- | --- | --- |
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formulae I-IV or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylureabased drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formulae I-IV or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprednisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

REFERENCES

1. Peserico, A. and C. Simone, *Physical and functional HAT/HDAC interplay regulates protein acetylation balance.* J Biomed Biotechnol, 2011. 2011: p. 371832.
2. Hoshino, I. and H. Matsubara, *Recent advances in histone deacetylase targeted cancer therapy.* Surg Today, 2010. 40(9): p. 809-15.
3. Vernarecci, S., F. Tosi, and P. Filetici, *Tuning acetylated chromatin with HAT inhibitors: a novel tool for therapy.* Epigenetics, 2010. 5(2): p. 105-11.
4. Bandyopadhyay, K., et al., *Spermidinyl-CoA-based HAT inhibitors block DNA repair and provide cancer-specific chemo-and radiosensitization.* Cell Cycle, 2009. 8(17): p. 2779-88.
5. Arif, M., et al., *Protein lysine acetylation in cellular function and its role in cancer manifestation.* Biochim Biophys Acta, 2010. 1799(10-12): p. 702-16.
6. Sanchez, R. and M. M. Zhou, *The role of human bromodomains in chromatin biology and gene transcription.* Curr Opin Drug Discov Devel, 2009. 12(5): p. 659-65.
7. Wu, S. Y. and C. M. Chiang, *The double bromodomain-containing chromatin adaptor Brd4 and transcriptional regulation.* J Biol Chem, 2007. 282(18): p. 13141-5.
8. Belkina, A. C. and G. V. Denis, *BET domain co-regulators in obesity, inflammation and cancer.* Nat Rev Cancer, 2012. 12(7): p. 465-77.
9. Prinjha, R. K., J. Witherington, and K. Lee, *Place your BETs: the therapeutic potential of bromodomains.* Trends Pharmacol Sci, 2012. 33(3): p. 146-53.
10. Kimura, A. and T. Kishimoto, *IL-6: regulator of Treg/Th17 balance.* Eur J Immunol, 2010. 40(7): p. 1830-5.
11. Mirguet, O., et al., *From ApoA1 upregulation to BET family bromodomain inhibition: discovery of I-BET151.* Bioorg Med Chem Lett, 2012. 22(8): p. 2963-7.
12. Nicodeme, E., et al., *Suppression of inflammation by a synthetic histone mimic.* Nature, 2010. 468(7327): p. 1119-23.
13. Seal, J., et al., *Identification of a novel series of BET family bromodomain inhibitors: binding mode and profile of I-BET151 (GSK1210151A).* Bioorg Med Chem Lett, 2012. 22(8): p. 2968-72.
14. Zhang, G., et al., *Down-regulation of NF-kappaB Transcriptional Activity in HIV associated Kidney Disease by BRD4 Inhibition.* J Biol Chem, 2012. 287(34): p. 28840-51.
15. Zhou, M., et al., *Bromodomain protein Brd4 regulates human immunodeficiency virus transcription through phosphorylation of CDK9 at threonine 29.* J Virol, 2009. 83(2): p. 1036-44.
16. Zhang, W. S., et al., *Bromodomain-Containing-Protein 4 (BRD4) Regulates RNA Polymerase II Serine 2 Phosphorylation in Human CD4+ T Cells.* J Biol Chem, 2012.
17. R. Jahagirdar, S. M., S. Attwell, K. G. McLure, P. R. Young, H. C. Hansen, R. Yu, K. Norek, G. S. Wagner, *An Orally Bioavailable Small Molecule RVX-297 Significantly Decreases Disease in a Mouse Model of Multiple Sclerosis (Poster Presentation).* World Congress of Inflammation, Paris, France, 2011.
18. Bandukwala, H. S., et al., *Selective inhibition of CD4+ T-cell cytokine production and autoimmunity by BET protein and c-Myc inhibitors.* Proc Natl Acad Sci USA, 2012. 109(36): p. 14532-7.
19. Denis, G. V., *Bromodomain coactivators in cancer, obesity, type 2 diabetes, and inflammation.* Discov Med, 2010. 10(55): p. 489-99.
20. Watson, J. D., *Curing "incurable" cancer.* Cancer Discov, 2011. 1(6): p. 477-80.
21. Morin, R. D., et al., *Frequent mutation of histone-modifying genes in non-Hodgkin lymphoma.* Nature, 2011. 476(7360): p. 298-303.
22. French, C. A., *NUT midline carcinoma.* Cancer Genet Cytogenet, 2010. 203(1): p. 16-20.
23. Greenwald, R. J., et al., *E mu-BRD2 transgenic mice develop B-cell lymphoma and leukemia.* Blood, 2004. 103(4): p. 1475-84.
24. Filippakopoulos, P., et al., *Selective inhibition of BET bromodomains.* Nature, 2010. 468(7327): p. 1067-73.
25. Vita, M. and M. Henriksson, *The Myc oncoprotein as a therapeutic target for human cancer.* Semin Cancer Biol, 2006. 16(4): p. 318-30.
26. Dawson, M. A., et al., *Inhibition of BET recruitment to chromatin as an effective treatment for MLL-fusion leukaemia.* Nature, 2011. 478(7370): p. 529-33.
27. Delmore, J. E., et al., *BET bromodomain inhibition as a therapeutic strategy to target c-Myc.* Cell, 2011. 146(6): p. 904-17.
28. Mertz, J. A., et al., *Targeting MYC dependence in cancer by inhibiting BET bromodomains.* Proc Natl Acad Sci USA, 2011. 108(40): p. 16669-74.
29. Ott, C. J., et al., *BET bromodomain inhibition targets both c-Myc and IL7R in highrisk acute lymphoblastic leukemia.* Blood, 2012. 120(14): p. 2843-52.
30. Zuber, J., et al., *RNAi screen identifies Brd4 as a therapeutic target in acute myeloid leukaemia.* Nature, 2011. 478(7370): p. 524-8.
31. Wang, S. and P. M. Fischer, *Cyclin-dependent kinase 9: a key transcriptional regulator and potential drug target in oncology, virology and cardiology.* Trends Pharmacol Sci, 2008. 29(6): p. 302-13.
32. Ruden, M. and N. Puri, *Novel anticancer therapeutics targeting telomerase.* Cancer Treat Rev, 2012.
33. Miguel F. Segura, R. D. M., Guangtao Zhang, Weijia Zhang, Iman Osman, Ming-Ming Zhou, Eva Hernando,

*BRD4 is a novel therapeutic target in melanoma (Poster Presentation).* Cancer Research, 2012. 72(8): p. Supplement 1.
34. Roger, V. L., et al., *Heart disease and stroke statistics—2012 update: a report from the American Heart Association.* Circulation, 2012. 125(1): p. e2-e220.
35. Chung, C. W., et al., *Discovery and characterization of small molecule inhibitors of the BET family bromodomains.* J Med Chem, 2011. 54(11): p. 3827-38.
36. Degoma, E. M. and D. J. Rader, *Novel HDL-directed pharmacotherapeutic strategies.* Nat Rev Cardiol, 2011. 8(5): p. 266-77.
37. Elliott, D. A., C. S. Weickert, and B. Garner, *Apolipoproteins in the brain: implications for neurological and psychiatric disorders.* Clin Lipidol, 2010. 51(4): p. 555-573.
38. Wang, F., et al., *Brd2 disruption in mice causes severe obesity without Type 2 diabetes.* Biochem J, 2010. 425(1): p. 71-83.
39. Denis, G. V., B. S. Nikolajczyk, and G. R. Schnitzler, *An emerging role for bromodomain-containing proteins in chromatin regulation and transcriptional control of adipogenesis.* FEBS Lett, 2010. 584(15): p. 3260-8.
40. Gagnon, D., et al., *Proteasomal degradation of the papillomavirus E2 protein is inhibited by overexpression of bromodomain-containing protein 4.* J Virol, 2009. 83(9): p. 4127-39.
41. You, J., et al., *Kaposi's sarcoma-associated herpesvirus latency-associated nuclear antigen interacts with bromodomain protein Brd4 on host mitotic chromosomes.* J Virol, 2006. 80(18): p. 8909-19.
42. Palermo, R. D., H. M. Webb, and M. J. West, *RNA polymerase II stalling promotes nucleosome occlusion and pTEFb recruitment to drive immortalization by Epstein-Barr virus.* PLoS Pathog, 2011. 7(10): p. e1002334.
43. Zhu, J., et al., *Reactivation of Latent HIV-1 by Inhibition of BRD4.* Cell Rep, 2012.
44. Banerjee, C., et al., *BET bromodomain inhibition as a novel strategy for reactivation of HIV-1.* J Leukoc Biol, 2012.
45. Bartholomeeusen, K., et al., *BET bromodomain inhibition activates transcription via a transient release of P-TEFb from 7SK snRNP.* J Biol Chem, 2012.
46. Li, Z., et al., *The BET bromodomain inhibitor JQ1 activates HIV latency through antagonizing Brd4 inhibition of Tat-transactivation.* Nucleic Acids Res, 2012.
47. Velisek, L., et al., *GABAergic neuron deficit as an idiopathic generalized epilepsy mechanism: the role of BRD2 haploinsufficiency in juvenile myoclonic epilepsy.* PLoS One, 2011. 6(8): p. e23656.
48. Gaucher, J., et al., *Bromodomain-dependent stage-specific male genome programming by Brdt.* EMBO J, 2012. 31(19): p. 3809-20.
49. Shang, E., et al., *The first bromodomain of Brdt, a testis-specific member of the BET sub-family of double-bromodomain-containing proteins, is essential for male germ cell differentiation.* Development, 2007. 134(19): p. 3507-15.
50. Matzuk, M. M., et al., *Small-Molecule Inhibition of BRDT for Male Contraception.* Cell, 2012. 150(4): p. 673-684.
51. Berkovits, B. D., et al., *The testis-specific double bromodomain-containing protein BRDT forms a complex with multiple spliceosome components and is required for mRNA splicing and 3'-UTR truncation in round spermatids.* Nucleic Acids Res, 2012. 40(15): p. 7162-75.
52. Niu, J. and P. E. Kolattukudy, *Role of MCP-1 in cardiovascular disease: molecular mechanisms and clinical implications.* Clin Sci (Lond), 2009. 117(3): p. 95-109.
53. Dawson, J., et al., *Targeting monocyte chemoattractant protein-1 signalling in disease.* Expert Opin Ther Targets, 2003. 7(1): p. 35-48.
54. Boring, L., et al., *Decreased lesion formation in CCR2-/- mice reveals a role for chemokines in the initiation of atherosclerosis.* Nature, 1998. 394(6696): p. 894-7.
55. Gosling, J., et al., *MCP-1 deficiency reduces susceptibility to atherosclerosis in mice that overexpress human apolipoprotein B.* J Clin Invest, 1999. 103(6): p. 773-8.
56. Gu, L., et al., *Absence of monocyte chemoattractant protein-1 reduces atherosclerosis in low density lipoprotein receptor-deficient mice.* Mol Cell, 1998. 2(2): p. 275-81.
57. Aiello, R. J., et al., *Monocyte chemoattractant protein-1 accelerates atherosclerosis in apolipoprotein E-deficient mice.* Arterioscler Thromb Vasc Biol, 1999. 19(6): p. 1518-25.
58. Nelken, N. A., et al., *Monocyte chemoattractant protein-1 in human atheromatous plaques.* J Clin Invest, 1991. 88(4): p. 1121-7.
59. Deo, R., et al., *Association among plasma levels of monocyte chemoattractant protein-1, traditional cardiovascular risk factors, and subclinical atherosclerosis.* J Am Coil Cardiol, 2004. 44(9): p. 1812-8.
60. de Lemos, J. A., et al., *Association between plasma levels of monocyte chemoattractant protein-1 and long-term clinical outcomes in patients with acute coronary syndromes.* Circulation, 2003. 107(5): p. 690-5.
61. Koch, A. E., et al., *Enhanced production of monocyte chemoattractant protein-1 in rheumatoid arthritis.* J Clin Invest, 1992. 90(3): p. 772-9.
62. Brodmerkel, C. M., et al., *Discovery and pharmacological characterization of a novel rodent-active CCR2 antagonist, INCB3344.* J Immunol, 2005. 175(8): p. 5370-8.
63. Bruhl, H., et al., *Dual role of CCR2 during initiation and progression of collagen-induced arthritis: evidence for regulatory activity of CCR2+ T cells.* J Immunol, 2004. 172(2): p. 890-8.
64. Gong, J. H., et al., *An antagonist of monocyte chemoattractant protein 1 (MCP-1) inhibits arthritis in the MRL-Ipr mouse model.* J Exp Med, 1997. 186(1): p. 131-7.
65. Gong, J. H., et al., *Post-onset inhibition of murine arthritis using combined chemokine antagonist therapy.* Rheumatology (Oxford), 2004. 43(1): p. 39-42.
66. Mahad, D. J. and R. M. Ransohoff, *The role of MCP-1 (CCL2) and CCR2 in multiple sclerosis and experimental autoimmune encephalomyelitis (EAE).* Semin Immunol, 2003. 15(1): p. 23-32.
67. Fife, B. T., et al., *CC chemokine receptor 2 is critical for induction of experimental autoimmune encephalomyelitis.* J Exp Med, 2000. 192(6): p. 899-905.
68. Huang, D. R., et al., *Absence of monocyte chemoattractant protein 1 in mice leads to decreased local macrophage recruitment and antigen-specific T helper cell type 1 immune response in experimental autoimmune encephalomyelitis.* J Exp Med, 2001. 193(6): p. 713-26.
69. Ishizu, T., et al., *CSF cytokine and chemokine profiles in acute disseminated encephalomyelitis.* J Neuroimmunol, 2006. 175(1-2): p. 52-8.
70. Gonzalez-Serrano, M. E., et al., *Increased Pro-inflammatory Cytokine Production After Lipopolysaccharide*

*Stimulation in Patients with X-linked Agammaglobulinemia.* J Clin Immunol, 2012. 32(5): p. 967-74.
71. McKinley, L., et al., *TH17 cells mediate steroid-resistant airway inflammation and airway hyperresponsiveness in mice.* J Immunol, 2008. 181(6): p. 4089-97.
72. Taylan, A., et al., *Evaluation of the T helper 17 axis in ankylosing spondylitis.* Rheumatol Int, 2012. 32(8): p. 2511-5.
73. Ito, Y., et al., *Pathogenic significance of interleukin-6 in a patient with antiglomerular basement membrane antibody-induced glomerulonephritis with multinucleated giant cells.* Am J Kidney Dis, 1995. 26(1): p. 72-9.
74. Soltesz, P., et al., *Immunological features of primary anti-phospholipid syndrome in connection with endothelial dysfunction.* Rheumatology (Oxford), 2008. 47(11): p. 1628-34.
75. Gu, Y., et al., *Interleukin (IL)-17 promotes macrophages to produce IL-8, IL-6 and tumour necrosis factor-alpha in aplastic anaemia.* Br J Haematol, 2008. 142(1): p. 109-14.
76. Zhao, L., et al., *Interleukin-17 contributes to the pathogenesis of autoimmune hepatitis through inducing hepatic interleukin-6 expression.* PLoS One, 2011. 6(4): p. e18909.
77. Gloddek, B., K. Lamm, and W. Arnold, *Pharmacological influence on inner ear endothelial cells in relation to the pathogenesis of sensorineural hearing loss.* Adv Otorhinolaryngol, 2002. 59: p. 75-83.
78. Yamashita, T., et al., *IL-6-mediated Th17 differentiation through RORgammat is essential for the initiation of experimental autoimmune myocarditis.* Cardiovasc Res, 2011. 91(4): p. 640-8.
79. Ni, J., et al., *Involvement of Interleukin-17A in Pancreatic Damage in Rat Experimental Acute Necrotizing Pancreatitis.* Inflammation, 2012.
80. Hohki, S., et al., *Blockade of interleukin-6 signaling suppresses experimental autoimmune uveoretinitis by the inhibition of inflammatory Th17 responses.* Exp Eye Res, 2010. 91(2): p. 162-70.
81. Ma, D., et al., *Profile of Th17 cytokines (IL-17, TGF-beta, IL-6) and Th1 cytokine (IFN-gamma) in patients with immune thrombocytopenic purpura.* Ann Hematol, 2008. 87(11): p. 899-904.
82. Yoshimura, T., et al., *Involvement of Th17 cells and the effect of anti-IL-6 therapy in autoimmune uveitis.* Rheumatology (Oxford), 2009. 48(4): p. 347-54.
83. D'Auria, L., P. Cordiali Fei, and F. Ameglio, *Cytokines and bullous pemphigoid.* Eur Cytokine Netw, 1999. 10(2): p. 123-34.
84. El-Osta, H. E. and R. Kurzrock, *Castleman's disease: from basic mechanisms to molecular therapeutics.* Oncologist, 2011. 16(4): p. 497-511.
85. Lahdenpera, A. I., et al., *Up-regulation of small intestinal interleukin-17 immunity in untreated coeliac disease but not in potential coeliac disease or in type 1 diabetes.* Clin Exp Immunol, 2012. 167(2): p. 226-34.
86. Fujioka, A., et al., *The analysis of mRNA expression of cytokines from skin lesions in Churg-Strauss syndrome.* J Dermatol, 1998. 25(3): p. 171-7.
87. Holtta, V., et al., *IL-23/IL-17 immunity as a hallmark of Crohn's disease.* Inflamm Bowel Dis, 2008. 14(9): p. 1175-84.
88. Shibuya, M., et al., *Successful treatment with tocilizumab in a case of Cogan's syndrome complicated with aortitis.* Mod Rheumatol, 2012.
89. De Paiva, C. S., et al., *IL-17 disrupts corneal barrier following desiccating stress.* Mucosal Immunol, 2009. 2(3): p. 243-53.
90. Antonelli, A., et al., *Serum levels of proinflammatory cytokines interleukin-1beta, interleukin-6, and tumor necrosis factor alpha in mixed cryoglobulinemia.* Arthritis Rheum, 2009. 60(12): p. 3841-7.
91. Chevrel, G., et al., *Interleukin-17 increases the effects of IL-1 beta on muscle cells: arguments for the role of T cells in the pathogenesis of myositis.* J Neuroimmunol, 2003. 137(1-2): p. 125-33.
92. Linhares, U. C., et al., *The Ex Vivo Production of IL-6 and IL-21 by CD4(+) T Cells is Directly Associated with Neurological Disability in Neuromyelitis Optica Patients.* J Clin Immunol, 2012.
93. Kyburz, D. and M. Corr, *Th17 cells generated in the absence of TGF-beta induce experimental allergic encephalitis upon adoptive transfer.* Expert Rev Clin Immunol, 2011. 7(3): p. 283-5.
94. Dias, P. M. and G. Banerjee, *The Role of Th17/IL-17 on Eosinophilic Inflammation.* J Autoimmun, 2012.
95. Kahawita, I. P. and D. N. Lockwood, *Towards understanding the pathology of erythema nodosum leprosum.* Trans R Soc Trop Med Hyg, 2008. 102(4): p. 329-37.
96. Deng, J., et al., *Th17 and Th1 T-cell responses in giant cell arteritis.* Circulation, 2010. 121(7): p. 906-15.
97. Ooi, J. D., A. R. Kitching, and S. R. Holdsworth, *Review: T helper 17 cells: their role in glomerulonephritis.* Nephrology (Carlton), 2010. 15(5): p. 513-21.
98. Nakahama, H., et al., *Distinct responses of interleukin-6 and other laboratory parameters to treatment in a patient with Wegener's granulomatosis.* Intern Med, 1993. 32(2): p. 189-92.
99. Kim, S. E., et al., *Increased serum interleukin-17in Graves' ophthalmopathy.* Graefes Arch Clin Exp Ophthalmol, 2012. 250(10): p. 1521-6.
100. Lu, M. O. and J. Zhu, *The role of cytokines in Guillain-Barre syndrome.* J Neurol, 2011. 258(4): p. 533-48.
101. Figueroa-Vega, N., et al., *Increased circulating pro-inflammatory cytokines and Th17 lymphocytes in Hashimoto's thyroiditis.* J Clin Endocrinol Metab, 2010. 95(2): p. 953-62.
102. Xu, L., et al., *Critical role of Th17 cells in development of autoimmune hemolytic anemia.* Exp Hematol, 2012.
103. Jen, H. Y., et al., *Increased serum interleukin-17 and peripheral Th17 cells in children with acute Henoch-Schonlein purpura.* Pediatr Allergy Immunol, 2011. 22(8): p. 862-8.
104. Lin, F. J., et al., *Imbalance of regulatory T cells to Th17 cells in IgA nephropathy.* Scand J Clin Lab Invest, 2012. 72(3): p. 221-9.
105. Baron, P., et al., *Production of IL-6 by human myoblasts stimulated with Abeta: relevance in the pathogenesis of IBM.* Neurology, 2001. 57(9): p. 1561-5.
106. Lamale, L. M., et al., *Interleukin-6, histamine, and methylhistamine as diagnostic markers for interstitial cystitis.* Urology, 2006. 68(4): p. 702-6.
107. Jia, S., et al., *The T helper type 17/regulatory T cell imbalance in patients with acute Kawasaki disease.* Clin Exp Immunol, 2010. 162(1): p. 131-7.
108. Min, C. K., et al., *Cutaneous leucoclastic vasculitis (LV) following bortezomib therapy in a myeloma patient; association with pro-inflammatory cytokines.* Eur J Haematol, 2006. 76(3): p. 265-8.

109. Rhodus, N. L., et al., *Proinflammatory cytokine levels in saliva before and after treatment of (erosive) oral lichen planus with dexamethasone*. Oral Dis, 2006. 12(2): p. 112-6.

110. Mok, M. Y., et al., *The relation of interleukin 17 (IL-17) and IL-23 to Th1/Th2 cytokines and disease activity in systemic lupus erythematosus*. J Rheumatol, 2010. 37(10): p. 2046-52.

111. Muller Kobold, A. C., et al., *In vitro up-regulation of E-selectin and induction of interleukin-6 in endothelial cells by autoantibodies in Wegener's granulomatosis and microscopic polyangiitis*. Clin Exp Rheumatol, 1999. 17(4): p. 433-40.

112. Jadidi-Niaragh, F. and A. Mirshafiey, *Th17 cell, the new player of neuroinflammatory process in multiple sclerosis*. Scand J Immunol, 2011. 74(1): p. 1-13.

113. Aricha, R., et al., *Blocking of IL-6 suppresses experimental autoimmune myasthenia gravis*. J Autoimmun, 2011. 36(2): p. 135-41.

114. Icoz, S., et al., *Enhanced IL-6 production in aquaporin-4 antibody positive neuromyelitis optica patients*. Int J Neurosci, 2010. 120(1): p. 71-5.

115. Lopez-Robles, E., et al., *TNFalpha and IL-6 are mediators in the blistering process of pemphigus*. Int J Dermatol, 2001. 40(3): p. 185-8.

116. Kallen, K. J., P. R. Galle, and S. Rose-John, *New developments in IL-6 dependent biology and therapy: where do we stand and what are the options?* Expert Opin Investig Drugs, 1999. 8(9): p. 1327-49.

117. Kawakami, T., S. Takeuchi, and Y. Soma, *Serum levels of interleukin-6 in patients with cutaneous polyarteritis nodosa*. Acta Derm Venereol, 2012. 92(3): p. 322-3.

118. Harada, K., et al., *Periductal interleukin-17 production in association with biliary innate immunity contributes to the pathogenesis of cholangiopathy in primary biliary cirrhosis*. Clin Exp Immunol, 2009. 157(2): p. 261-70.

119. Fujishima, S., et al., *Involvement of IL-17F via the induction of IL-6 in psoriasis*. Arch Dermatol Res, 2010. 302(7): p. 499-505.

120. Raychaudhuri, S. P., S. K. Raychaudhuri, and M. C. Genovese, *IL-17 receptor and its functional significance in psoriatic arthritis*. Mol Cell Biochem, 2012. 359(1-2): p. 419-29.

121. Kawakami, T., M. Yamazaki, and Y. Soma, *Reduction of interleukin-6, interleukin-8, and anti-phosphatidylserine-prothrombin complex antibody by granulocyte and monocyte adsorption apheresis in a patient with pyoderma gangrenosum and ulcerative colitis*. Am J Gastroenterol, 2009. 104(9): p. 2363-4.

122. Kawai, M., et al., *Sustained response to tocilizumab, anti-interleukin-6 receptor antibody, in two patients with refractory relapsing polychondritis*. Rheumatology (Oxford), 2009. 48(3): p. 318-9.

123. Ash, Z. and P. Emery, *The role of tocilizumab in the management of rheumatoid arthritis*. Expert Opin Biol Ther, 2012. 12(9): p. 1277-89.

124. Belli, F., et al., *Cytokines assay in peripheral blood and bronchoalveolar lavage in the diagnosis and staging of pulmonary granulomatous diseases*. Int J Immunopathol Pharmacol, 2000. 13(2): p. 61-67.

125. Radstake, T. R., et al., *The pronounced Th17 profile in systemic sclerosis (SSc) together with intracellular expression of TGFbeta and IFNgamma distinguishes SSc phenotypes*. PLoS One, 2009. 4(6): p. e5903.

126. Katsifis, G. E., et al., *Systemic and local interleukin-17 and linked cytokines associated with Sjogren's syndrome immunopathogenesis*. Am J Pathol, 2009. 175(3): p. 1167-77.

127. Sun, Y., et al., *MMP-9 and IL-6 are potential biomarkers for disease activity in Takayasu's arteritis*. Int J Cardiol, 2012. 156(2): p. 236-8.

128. Graber, J. J., et al., *Interleukin-17 in transverse myelitis and multiple sclerosis*. J Neuroimmunol, 2008. 196(1-2): p. 124-32.

129. Mudter, J. and M. F. Neurath, *Il-6 signaling in inflammatory bowel disease: pathophysiological role and clinical relevance*. Inflamm Bowel Dis, 2007. 13(8): p. 1016-23.

130. Haruta, H., et al., *Blockade of interleukin-6 signaling suppresses not only th17 but also interphotoreceptor retinoid binding protein-specific Th1 by promoting regulatory T cells in experimental autoimmune uveoretinitis*. Invest Ophthalmol Vis Sci, 2011. 52(6): p. 3264-71.

131. Bassiouny, D. A. and O. Shaker, *Role of interleukin-17 in the pathogenesis of vitiligo*. Clin Exp Dermatol, 2011. 36(3): p. 292-7. 115. Bradley, D. T. and S. E. Kountakis, *Role of interleukins and transforming growth factor-beta in chronic rhinosinusitis and nasal polyposis*. Laryngoscope, 2005. 115(4): p. 684-6.

132. Bradley, D. T. and S. E. Kountakis, *Role of interleukins and transforming growth factor-beta in chronic rhinosinusitis and nasal polyposis*. Laryngoscope, 2005. 115(4): p. 684-6.

133. Besnard, A. G., et al., *Inflammasome-IL-1-Th17 response in allergic lung inflammation*. J Mol Cell Biol, 2012. 4(1): p. 3-10.

134. Yoshii, T., et al., *Local levels of interleukin-1beta, -4, -6 and tumor necrosis factor alpha in an experimental model of murine osteomyelitis due to staphylococcus aureus*. Cytokine, 2002. 19(2): p. 59-65.

135. Bayraktaroglu, T., et al., *Serum levels of tumor necrosis factor-alpha, interleukin-6 and interleukin-8 are not increased in dyspeptic patients with Helicobacter pylori-associated gastritis*. Mediators Inflamm, 2004. 13(1): p. 25-8.

136. Mitsuyama, K., et al., *STAT3 activation via interleukin 6 trans-signalling contributes to ileitis in SAMP1/Yit mice*. Gut, 2006. 55(9): p. 1263-9.

137. Johnson, R. B., N. Wood, and F. G. Serio, *Interleukin-11 and IL-17 and the pathogenesis of periodontal disease*. J Periodontol, 2004. 75(1): p. 37-43.

138. Latifi, S. Q., et al., *Persistent elevation of serum interleukin-6 in intraabdominal sepsis identifies those with prolonged length of stay*. J Pediatr Surg, 2004. 39(10): p. 1548-52.

139. Ortiz-Lucas, M., P. Saz-Peiro, and J. J. Sebastian-Domingo, *Irritable bowel syndrome immune hypothesis. Part two: the role of cytokines*. Rev Esp Enferm Dig, 2010. 102(12): p. 711-7.

140. Kappel, L. W., et al., *IL-17 contributes to CD4-mediated graft-versus-host disease*. Blood, 2009. 113(4): p. 945-52.

141. Traves, S. L. and L. E. Donnelly, *Th17 cells in airway diseases*. Curr Mol Med, 2008. 8(5): p. 416-26.

142. Chen, L., et al., *IL-17RA aptamer-mediated repression of IL-6 inhibits synovium inflammation in a murine model of osteoarthritis*. Osteoarthritis Cartilage, 2011. 19(6): p. 711-8.

143. Urano, W., et al., *The inflammatory process in the mechanism of decreased serum uric acid concentrations during acute gouty arthritis.* J Rheumatol, 2002. 29(9): p. 1950-3.
144. Simmons, E. M., et al., *Plasma cytokine levels predict mortality in patients with acute renal failure.* Kidney Int, 2004. 65(4): p. 1357-65.
145. Paquet, P. and G. E. Pierard, *Interleukin-6 and the skin.* Int Arch Allergy Immunol, 1996. 109(4): p. 308-17.
146. Kaplanski, G., et al., *Jarisch-Herxheimer reaction complicating the treatment of chronic Q fever endocarditis: elevated TNFalpha and IL-6 serum levels.* J Infect, 1998. 37(1): p. 83-4.
147. Scanlan, M. J., et al., *Expression of cancer-testis antigens in lung cancer: definition of bromodomain testis-specific gene (BRDT) as a new CT gene, CT9.* Cancer Lett, 2000. 150(2): p. 155-64.
148. Grunwald, C., et al., *Expression of multiple epigenetically regulated cancer/germline genes in nonsmall cell lung cancer.* Int J Cancer, 2006. 118(10): p. 2522-8.
149. Rodriguez, R. M., et al., *Aberrant epigenetic regulation of bromodomain BRD4 in human colon cancer.* J Mol Med (Berl), 2012. 90(5): p. 587-95.
150. Tong, W. G., et al., *Phase I and pharmacologic study of SNS-032, a potent and selective Cdk2, 7, and 9 inhibitor, in patients with advanced chronic lymphocytic leukemia and multiple myeloma.* J Clin Oncol, 2010. 28(18): p. 3015-22.
151. Bellan, C., et al., *CDK9/CYCLIN T1 expression during normal lymphoid differentiation and malignant transformation.* J Pathol, 2004. 203(4): p. 946-52.
152. De Falco, G., et al., *Cdk9 regulates neural differentiation and its expression correlates with the differentiation grade of neuroblastoma and PNET tumors.* Cancer Biol Ther, 2005. 4(3): p. 277-81.
153. Simone, C. and A. Giordano, *Abrogation of signal-dependent activation of the cdk9/cyclin T2a complex in human RD rhabdomyosarcoma cells.* Cell Death Differ, 2007. 14(1): p. 192-5.
154. Lee, D. K., H. O. Duan, and C. Chang, *Androgen receptor interacts with the positive elongation factor P-TEFb and enhances the efficiency of transcriptional elongation.* J Biol Chem, 2001. 276(13): p. 9978-84.
155. Kelly, P. N. and A. Strasser, *The role of Bcl-2 and its pro-survival relatives in tumourigenesis and cancer therapy.* Cell Death Differ, 2011. 18(9): p. 1414-24.
156. Costello, J. F., et al., *Cyclin-dependent kinase 6 (CDK6) amplification in human gliomas identified using two-dimensional separation of genomic DNA.* Cancer Res, 1997. 57(7): p. 1250-4.
157. Mendrzyk, F., et al., *Genomic and protein expression profiling identifies CDK6 as novel independent prognostic marker in medulloblastoma.* J Clin Oncol, 2005. 23(34): p. 8853-62.
158. Ramsay, R. G. and T. J. Gonda, *MYB function in normal and cancer cells.* Nat Rev Cancer, 2008. 8(7): p. 523-34.
159. Rudloff, U. and Y. Samuels, *TYRO3-mediated regulation of MITF: a novel target in melanoma?* Pigment Cell Melanoma Res, 2010. 23(1): p. 9-11.
160. Stenman, G., M. K. Andersson, and Y. Andren, *New tricks from an old oncogene: gene fusion and copy number alterations of MYB in human cancer.* Cell Cycle, 2010. 9(15): p. 2986-95.
161. Wang, G., et al., *Increased cyclin-dependent kinase 6 expression in bladder cancer.* Oncol Lett, 2012. 4(1): p. 43-46.
162. Uchida, T., et al., *Antitumor effect of bcl-2 antisense phosphorothioate oligodeoxynucleotides on human renal-cell carcinoma cells in vitro and in mice.* Mol Urol, 2001. 5(2): p. 71-8.
163. Alexandraki, K., et al., *Inflammatory process in type 2 diabetes: The role of cytokines.* Ann N Y Acad Sci, 2006. 1084: p. 89-117.
164. Poreba, E., J. K. Broniarczyk, and A. Gozdzicka-Jozefiak, *Epigenetic mechanisms in virus-induced tumorigenesis.* Clin Epigenetics, 2011. 2(2): p. 233-47.
165. Muller, S., P. Filippakopoulos, and S. Knapp, *Bromodomains as therapeutic targets.* Expert Rev Mol Med, 2011. 13: p. e29.

EXAMPLES

General Procedure A

Preparation of 2-Benzyl-6-(3,5-dimethylisoxazol-4-yl)pyridazin-3(2H)-one (Example 14)

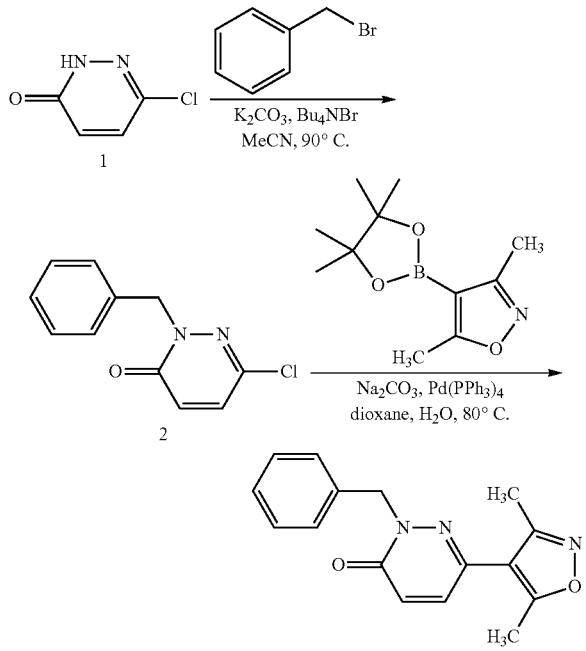

Example 14

Step 1:

To a solution of 1 (2.0 g, 15.3 mmol) in acetonitrile (30 mL) was added benzyl bromide (2.18 mL, 18.4 mmol), tetrabutylammoniumbromide (0.25 g, 0.77 mmol) and potassium carbonate (5.3 g, 38.3 mmol). The reaction was heated at 90° C. for 16 h. The reaction mixture was cooled to room temperature, concentrated and purified by chromatography (silica gel, 0-20% ethyl acetate/hexanes) to give 2 (2.2 g, 60%) as a white solid: $^1$H NMR (300 MHz, CDCl$_3$) δ 7.47-7.40 (m, 2H), 7.39-7.28 (m, 3H), 7.16 (d, J=9.6 Hz, 1H), 6.91 (d, J=9.6 Hz, 1H).

Step 2:

To a solution of 2 (100 mg, 0.45 mmol) in 1,4-dioxane (3 mL) was added 3,5-dimethyl-4-(4,4,5,5-tetramethyl-1,3,2-dioxaborolan-2-yl)isoxazole (103 mg, 0.46 mmol), sodium carbonate (2.0 M in H$_2$O, 0.27 mL, 0.54 mmol) and tetrakis(triphenylphosphine)palladium(0) (25 mg, 0.023 mmol).

The reaction mixture was purged with nitrogen and heated at 80° C. for 16 h. The mixture was diluted with methylene chloride (20 mL) and washed with brine (15 mL). The organic layer was dried over sodium sulfate, filtered and concentrated. Purification by chromatography (silica gel, 0-40% ethyl acetate/hexanes) afforded Example 14 (65 mg, 51%) as an off-white solid: $^1$H NMR (300 MHz, CDCl$_3$) δ 7.48-7.40 (m, 2H), 7.40-7.27 (m, 4H), 7.02 (d, J=9.6 Hz, 1H), 5.36 (s, 2H), 2.46 (s, 3H), 2.32 (s, 3H); ESI m/z 282 [M+H]$^+$.

General Procedure B

Preparation of 2-Benzyl-6-((5,6-dimethoxypyridin-2-yl)amino)pyridazin-3(2H)-one (Example 99)

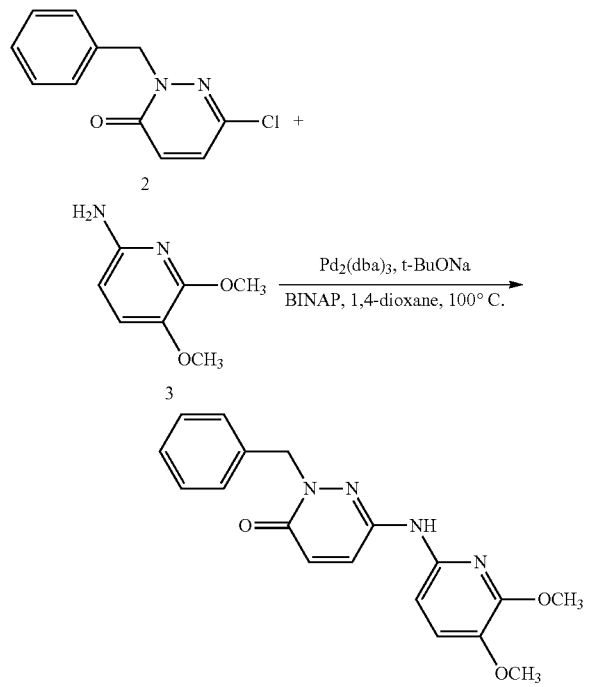

Example 99

A mixture of 2-benzyl-6-chloropyridazin-3(2H)-one (2) (220 mg, 1.0 mmol), 5,6-dimethoxypyridin-2-amine (3) (231 mg, 1.5 mmol), BINAP (125 mg, 0.2 mmol) and sodium tert-butoxide (106 mg, 1.1 mmol) in 1,4-dioxane (15 mL) was purged with nitrogen for 5 minutes. Tris(dibenzylideneacetone)dipalladium(0) (92 mg, 0.1 mmol) was added and the reaction mixture was heated to 100° C. for 16 h. The reaction was diluted with EtOAc (100 mL), washed with brine (50 mL) and the ethyl acetate solution was separated, dried (Na$_2$SO$_4$) and concentrated. The residue was purified by chromatography (silica gel, 10%-60% EtOAc/CH$_2$Cl$_2$) to yield Example 99 (153 mg, 45%) as a yellow solid: $^1$H NMR (300 MHz, DMSO-d$_6$) δ 9.26 (s, 1H), 7.52 (d, J=9.9 Hz, 1H), 7.36-7.25 (m, 7H), 6.93 (d, J=9.9 Hz, 1H), 5.15 (s, 2H), 3.84 (s, 3H), 3.72 (s, 3H); ESI MS m/z 339 [M+H]$^+$.

General Procedure C

Preparation of 2-Benzyl-6-(3,5-dimethylisoxazol-4-yl)pyridazin-3(2H)-one (Example 28)

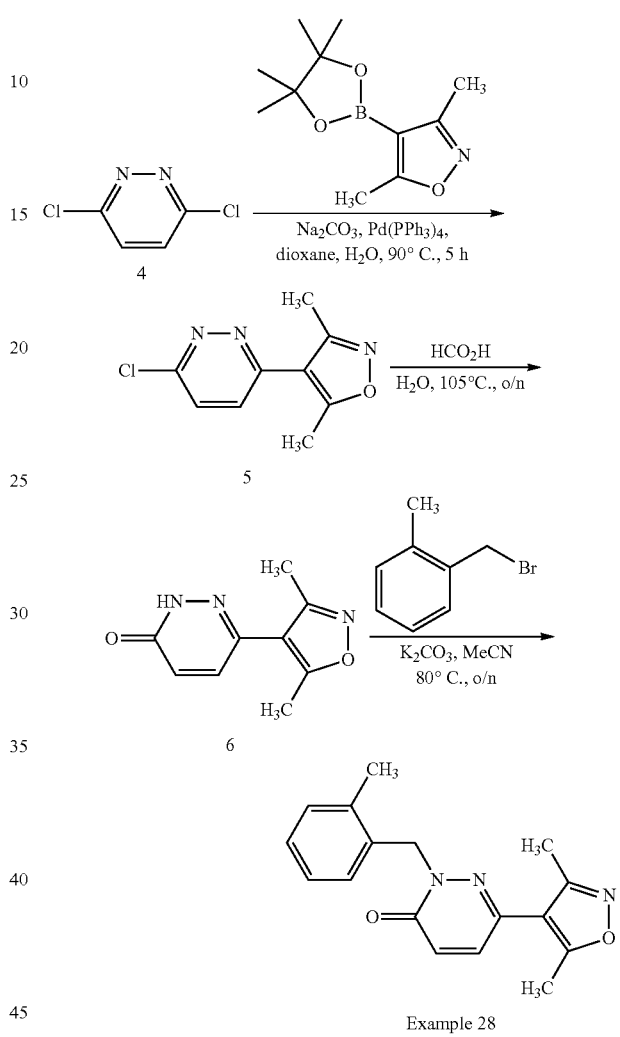

Example 28

Step 1:
To a solution of 4 (5.5 g, 36.9 mmol) in ethanol (170 mL) was added 3,5-dimethyl-4-(4,4,5,5-tetramethyl-1,3,2-dioxaborolan-2-yl)isoxazole (9.88 g, 44.3 mmol), sodium carbonate (2.0 M in H$_2$O, 36.9 mL, 73.8 mmol) and tetrakis(triphenylphosphine)palladium(0) (1.0 g, 1.85 mmol). The reaction mixture was purged with nitrogen and then heated at 90° C. for 5 h. The mixture was concentrated to half of the volume, then diluted with ethyl acetate (200 mL) and washed with brine (2×30 mL). The ethyl acetate layer was dried over sodium sulfate, filtered and concentrated. Purification by chromatography (silica gel, 0-40% ethyl acetate/hexanes) afforded 5 (4.26 g, 55%) as a yellow solid: $^1$H NMR (300 MHz, DMSO-d$_6$) δ 8.04 (d, J=9.0 Hz, 1H), 7.99 (d, J=9.0 Hz, 1H), 2.59 (s, 3H), 2.39 (s, 3H).

Step 2:
To a solution of 5 (4.26 g, 20.4 mmol) in water (25 mL) was added acetic acid (25 mL). The reaction mixture was refluxed at 105° C. for 16 h. The reaction was cooled to room temperature and neutralized with 6 N aq. sodium hydroxide solution (100 mL). The solids were collected, washed with water and dried in a vacuum oven to afford 6 (2.8 g, 75%) as a yellow solid: $^1$H NMR (300 MHz, DMSO-$d_6$) δ 13.26 (s, 1H), 7.63 (d, J=9.6 Hz, 1H), 6.99 (d, J=9.6 Hz, 1H), 2.49 (s, 3H), 2.29 (s, 3H).

Step 3:

To a solution of 6 (40 mg, 0.21 mmol) in acetonitrile (2 mL) was added 2-methylbenzyl bromide (0.034 ml, 0.25 mmol) and potassium carbonate (58 mg, 0.42 mmol). The reaction was heated at 80° C. for 16 h. The reaction mixture was cooled to room temperature, concentrated and purified by chromatography (silica gel, 0-50% ethyl acetate/hexanes) to afford Example 28 (39 mg, 62%) as a brown-red solid: $^1$H NMR (300 MHz, DMSO-$d_6$) δ 7.69 (d, J=9.0 Hz, 1H), 7.25-7.06 (m, 5H), 5.31 (s, 2H), 2.40 (s, 3H), 2.31 (s, 3H), 2.15 (s, 3H); ESI m/z 296 [M+H]$^+$.

General Procedure D

Preparation of 5-(3,5-Dimethylisoxazol-4-yl)-1-(2-fluorobenzyl)pyridin-2(1H)-one (Example 27)

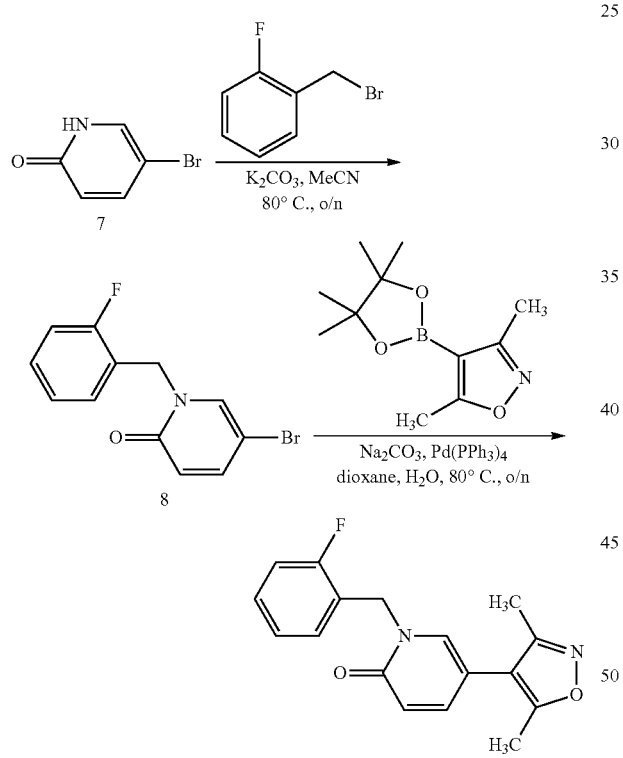

Example 27

Step 1:

To a solution of 7 (150 mg, 0.86 mmol) in acetonitrile (3 mL) was added 1-(bromomethyl)-2-fluorobenzene (0.13 ml, 1.03 mmol) and potassium carbonate (237 mg, 1.72 mmol). The reaction was heated at 80° C. for 16 h. The reaction mixture was cooled to room temperature, concentrated and purified by chromatography (silica gel, 0-20% ethyl acetate/hexanes) to give 8 (180 mg, 74%) as a white solid: $^1$H NMR (300 MHz, DMSO-$d_6$) δ 8.10 (d, J=2.8 Hz, 1H), 7.58 (dd, J=9.9, 2.8 Hz, 1H), 7.42-7.30 (m, 1H), 7.28-7.08 (m, 3H), 6.42 (d, J=9.7 Hz, 1H), 5.12 (s, 2H).

Step 2:

To a solution of 8 (180 mg, 0.64 mmol) in 1,4-dioxane (4 mL) was added 3,5-dimethyl-4-(4,4,5,5-tetramethyl-1,3,2-dioxaborolan-2-yl)isoxazole (170 mg, 0.76 mmol), 2 M aq. sodium carbonate (0.48 mL, 0.95 mmol) and tetrakis(triphenylphosphine)palladium(0) (37 mg, 0.032 mmol). The reaction mixture was purged with nitrogen and heated at 80° C. for 16 h. The mixture was diluted with methylene chloride (30 mL) and washed with brine (2×10 mL). The organic layer was dried over sodium sulfate, filtered and concentrated. Purification by chromatography (silica gel, 0-45% ethyl acetate/hexanes) afforded Example 27 (48 mg, 25%) as a white solid: $^1$H NMR (300 MHz, DMSO-$d_6$) δ 7.88 (d, J=2.4 Hz, 1H), 7.54 (dd, J=6.6 Hz, 2.7 Hz, 1H), 7.41-7.30 (m, 1H), 7.29-7.14 (m, 3H), 6.51 (d, J=9.3 Hz, 1H), 5.18 (s, 2H), 2.20 (s, 3H), 1.99 (s, 3H); ESI m/z 299 [M+H]$^+$.

General Procedure E

Preparation of 5-(3,5-Dimethylisoxazol-4-yl)-1-(1-(3-fluorophenyl)ethyl)pyridin-2(1H)-one (Example 104)

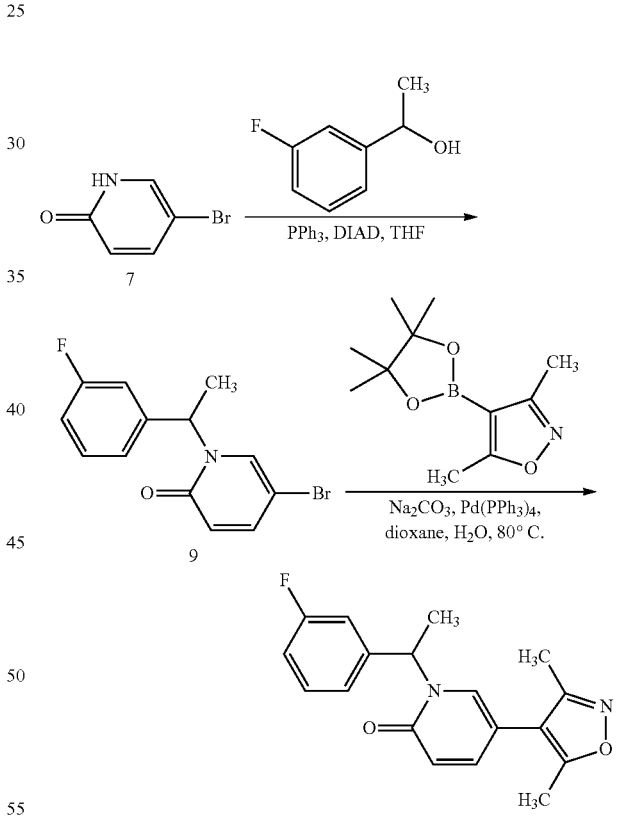

Example 104

Step 1:

A solution of 7 (522 mg, 3.0 mmol), 1-(3-fluorophenyl)ethanol (631 mg, 14.5 mmol) and PPh$_3$ (1.18 g, 4.5 mmol) in THF (10 mL) was cooled to 0° C. DIAD (0.87 mL, 4.5 mmol) was added dropwise and the reaction was stirred at room temperature for 3 h. The mixture was concentrated and purified by chromatography (silica gel, 50% ethyl acetate/hexanes) to give 9 (257 mg, 29%) as a white solid: $^1$H NMR (300 MHz, CDCl$_3$) δ 7.39-7.30 (m, 2H), 7.17 (d, J=2.7 Hz, 1H), 7.11-7.06 (m, 2H), 7.02 (dd, J=9.9, 1.2 Hz, 1H), 6.54 (dd, J=9.9, 1.2 Hz, 1H), 6.36 (q, J=7.2 Hz, 1H), 1.71 (d, J=7.2 Hz, 3H).

Step 2:

To a solution of 9 (148 mg, 0.50 mmol) in 1,4-dioxane (6 mL) was added 3,5-dimethyl-4-(4,4,5,5-tetramethyl-1,3,2-dioxaborolan-2-yl)isoxazole (167 mg, 0.75 mmol), 2 M aq. $Na_2CO_3$ (0.50 mL, 1.0 mmol) and tetrakis(triphenylphosphine)palladium(0) (29 mg, 0.025 mmol). The reaction mixture was purged with nitrogen and then heated at 80° C. for 6 h. The mixture was diluted with EtOAc (50 mL) and washed with brine (20 mL). The ethyl acetate layer was dried over sodium sulfate, filtered and concentrated. Purification by chromatography (silica gel, 20-80% ethyl acetate/hexanes) followed by recrystallization from ethyl acetate/hexanes afforded Example 104 (84 mg, 54%) as an off-white solid: $^1$H NMR (300 MHz, DMSO-$d_6$) δ 7.70 (d, J=2.4 Hz, 1H), 7.47 (dd, J=9.3, 2.4 Hz, 1H), 7.40 (dd, J=7.8, 6.0 Hz, 1H), 7.26-7.12 (m, 3H), 6.52 (d, J=9.3 Hz, 1H), 6.20 (q, J=7.2 Hz, 1H), 2.29 (s, 3H), 2.12 (s, 3H), 1.75 (d, J=7.2 Hz, 3H); ESI-MS m/z 313 $[M+H]^+$.

General Procedure F

Preparation of 1-Benzyl-5-(thiazol-5-yl)pyridin-2(1H)-one (Example 80)

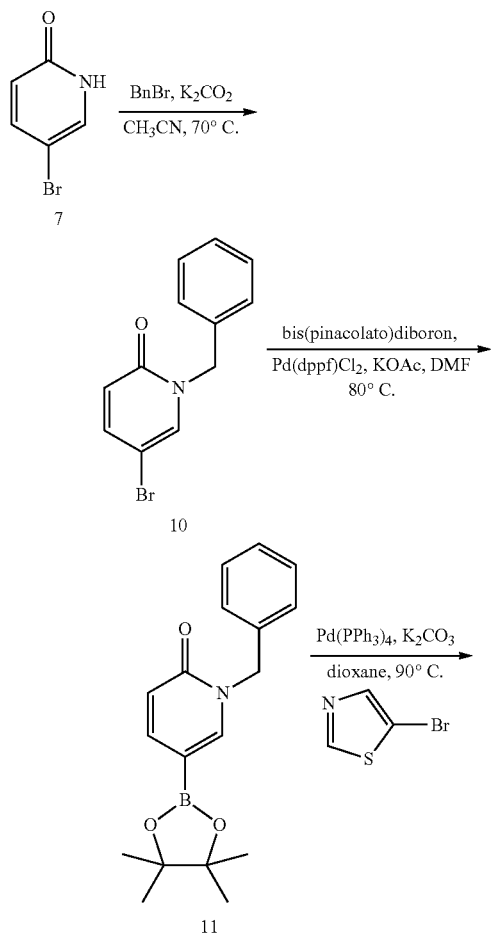

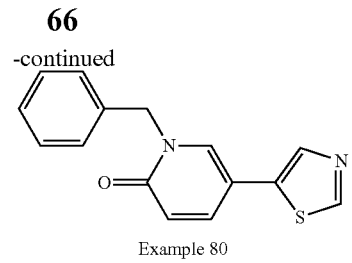

Example 80

Step 1:

A mixture of 5-bromopyridin-2(1H)-one (7, 3.0 g, 17.2 mmol), benzyl bromide (4.4 g, 25.8 mmol), potassium carbonate (4.8 g, 34.5 mmol) and acetonitrile (150 mL) was heated at 70° C. for 3 h under nitrogen. The mixture was allowed to cool to room temperature and the solvent was removed under reduced pressure. The residue was purified by chromatography (silica gel, eluting with 0-75% EtOAc/hexanes), to provide 10 (3.84 g, 84%) as a white solid: $^1$H NMR (500 MHz, $CDCl_3$) δ 7.38-7.29 (m, 7H), 6.53 (d, J=9.4 Hz, 1H), 5.09 (s, 2H).

Step 2:

A mixture of bis(pinacolato)diboron (2.23, 9.94 mmol), 10 (500 mg, 2.19 mmol), $Pd(dppf)Cl_2$ (390 mg, 0.47 mmol), KOAc (2.79 g, 28.4 mmol) and DMF (15 mL) was heated at 80° C. under nitrogen for 16 h. The reaction mixture was then cooled and poured over ice. The mixture was extracted with EtOAc (3×100 mL) and the combined extracts were dried over sodium sulfate and filtered. The solvent was removed under reduced pressure and the residue was purified by chromatography (silica gel, 0-50% EtOAc in hexanes) to provide 11 (2.3 g, 78%) as an off-white solid: $^1$H NMR (500 MHz, $CDCl_3$) δ 7.78 (d, J=1.9 Hz, 1H), 7.59 (dd, J=2.0, 9.1 Hz, 1H), 7.33-7.28 (m, 5H), 6.56 (d, J=9.1 Hz, 1H), 5.15 (s, 2H), 1.28 (s, 12H).

Step 3:

A mixture of 11 (200 mg, 0.64 mmol), 5-bromothiazole (157 mg, 0.96 mmol), potassium carbonate (177 mg, 1.28 mmol), tetrakis(triphenylphosphine)palladium(0) (38 mg, 0.04 mmol), dioxane (6 mL) and water (1 mL) was heated at 90° C. for 16 h. The reaction mixture was cooled and concentrated under reduced pressure. The residue was purified by chromatography (silica gel, 0-100% EtOAc in hexanes) to provide Example 80 (38 mg, 22%) as a white solid: $^1$H NMR (500 MHz, $CDCl_3$) δ 8.69 (s, 1H), 7.82 (s, 1H), 7.53 (dd, J=2.1, 9.1 Hz, 1H), 7.50 (d, J=2.4 Hz, 1H), 7.38-7.32 (m, 5H), 6.71 (d, J=9.5 Hz, 1H), 5.12 (s, 2H); ESI MS m/z 269 $[M+H]^+$.

General Procedure G

Preparation of 1-(3-(Difluoromethyl)benzyl)-5-(3,5-dimethylisoxazol-4-yl)pyridin-2(1H)-one (Example 50)

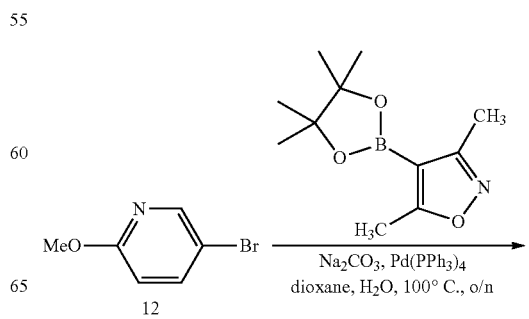

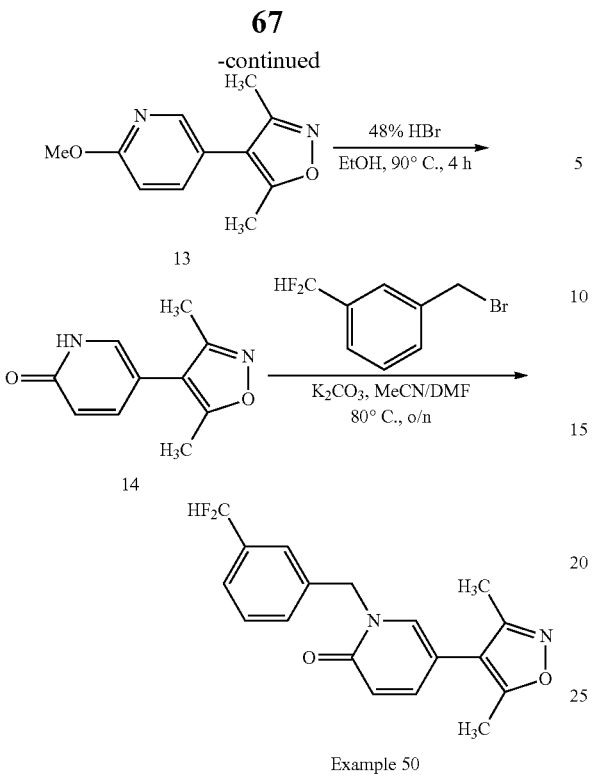

Example 50

Step 1:

To a solution of 12 (5.6 g, 29.9 mmol) in 1,4-dioxane (120 mL) and water (24 mL) was added 3,5-dimethyl-4-(4,4,5,5-tetramethyl-1,3,2-dioxaborolan-2-yl)isoxazole (8.0 g, 35.9 mmol), sodium carbonate (6.34 g, 59.8 mmol) and tetrakis(triphenylphosphine)palladium(0) (863 mg, 0.75 mmol). The reaction mixture was purged with nitrogen and was heated at 100° C. for 16 h. The mixture was diluted with methylene chloride (200 mL) and washed with brine (2×50 mL). The combined extracts were dried over sodium sulfate, filtered and concentrated. Purification by chromatography (silica gel, 0-15% ethyl acetate/hexanes) afforded 13 (5.4 g, 89%) as a yellow solid: $^1$H NMR (300 MHz, DMSO-d$_6$) δ 7.20 (dd, J=2.5 Hz, 0.6 Hz, 1H), 7.76 (dd, J=8.6 Hz, 2.5 Hz, 1H), 6.93 (dd, J=8.5 Hz, 0.7 Hz, 1H), 3.89 (s, 3H), 2.39 (s, 3H), 2.21 (s, 3H).

Step 2:

To a solution of 13 (4.40 g, 21.5 mmol) in ethanol (130 mL) was added hydrobromic acid (48%, 44 mL) and the reaction mixture was refluxed at 90° C. for 4 h. The reaction mixture was cooled to room temperature and concentrated. The residue was dissolved in methanol and neutralized to pH 8 by adding potassium carbonate. After stirring the mixture for 30 min, the suspension was filtered and the filtrate was concentrated. Purification by chromatography (silica gel, 0-10% methanol/ethyl acetate) afforded 14 (3.5 g, 85%) as a yellow solid: $^1$H NMR (300 MHz, DMSO-d$_6$) δ 11.85 (br s, 1H), 7.50-7.40 (m, 2H), 6.41 (dd, J=9.2 Hz, 0.8 Hz, 1H), 2.34 (s, 3H), 2.17 (s, 3H).

Step 3:

To a solution of 14 (100 mg, 0.53 mmol) in acetonitrile (2 mL) and N,N-dimethyl formamide (1 mL) was added 1-(bromomethyl)-3-(difluoromethyl)benzene (174 mg, 0.79 mmol) and potassium carbonate (219 mg, 1.59 mmol). The reaction was heated at 80° C. for 16 h. The reaction mixture was cooled to room temperature, concentrated and purified by chromatography (silica gel, 0-65% ethyl acetate/hexanes) to give Example 50 (150 mg, 86%) as a yellow solid: $^1$H NMR (300 MHz, DMSO-d$_6$) δ 7.99 (d, J=2.1 Hz, 1H), 7.57 (s, 1H), 7.55-7.47 (m, 4H), 7.04 (q, J=56 Hz, 1H), 6.52 (d, J=9.3 Hz, 1H), 5.19 (s, 2H), 2.36 (s, 3H), 2.19 (s, 3H); ESI m/z 331 [M+H]$^+$.

General Procedure H

Preparation of 5-(3,5-Dimethylisoxazol-4-yl)-1-(4-fluorobenzoyl)pyridin-2(1H)-one (Example 68

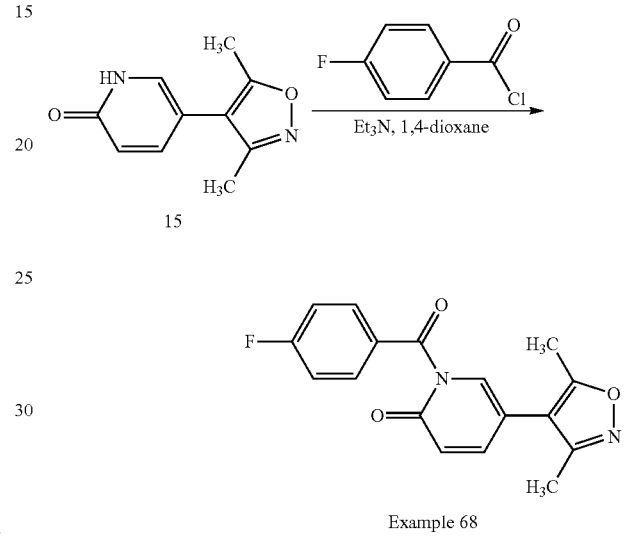

Example 68

A mixture of 5-(3,5-dimethylisoxazol-4-yl)pyridin-2(1H)-one (15, 60 mg, 0.32 mmol), NEt$_3$ (64 mg, 2 equiv.) and 4-fluorobenzoyl chloride (75 mg, 1.5 equiv.) in 1,4-dioxane (5 mL) was stirred at room temperature for 16 h. The reaction mixture was concentrated and purified by chromatography (silica gel, 0-40% EtOAc in hexanes) to afford the Example 68 (75 mg, 76%) as an off-white solid: $^1$H NMR (300 MHz, CDCl$_3$) δ 8.37 (d, J=2.4 Hz, 1H), 8.25-8.30 (m, 2H), 7.76 (dd, J=2.4, 8.4 Hz, 1H), 7.33 (d, J=8.4 Hz, 2H), 7.19-7.24 (m, 2H), 2.46 (s, 3H), 2.31 (s, 3H). ESI MS m/z 313 [M+H]$^+$.

General Procedure I

Preparation of 1-Benzyl-5-(3,5-dimethylisoxazol-4-yl)-3-(4-fluorophenyl)pyridin-2(1H)-one (Example 70)

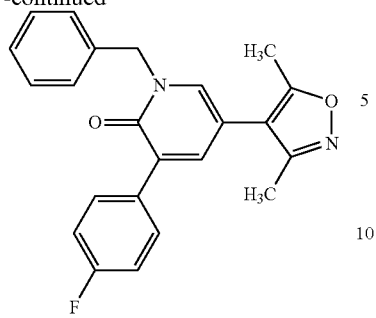

Example 70

A mixture of 1-benzyl-3-chloro-5-(3,5-dimethylisoxazol-4-yl)pyridin-2(1H)-one (16, 130 mg, 0.41 mmol), 4-fluorophenylboronic acid (115 mg, 2 equiv.), Pd(OAc)$_2$ (28 mg, 0.1 equiv), S-Phos (34 mg, 0.2 equiv.) and K$_3$PO$_4$ (174 mg, 2 equiv.) in wet toluene (5 mL mixed with 0.5 mL H$_2$O) was stirred at 100° C. for 16 h. The reaction mixture was allowed to cool to room temperature and filtered through a layer of Celite. The filtrate was concentrated and then purified by chromatography (silica gel, 0-20% EtOAc in CH$_2$Cl$_2$) to afford Example 70 (58 mg, 38%) as a pale red solid: $^1$H NMR (300 MHz, CDCl$_3$) δ 7.67-7.72 (m, 2H), 7.36-7.40 (m, 5H), 7.34 (d, J=2.4 Hz, 1H), 7.18 (d, J=2.7 Hz, 1H), 7.08-7.14 (m, 2H), 5.25 (s, 2H), 2.34 (s, 3H), 2.20 (s, 3H). ESI MS m/z 375 [M+H]$^+$.

General Procedure J

Preparation of 1-Benzyl-5-(3,5-dimethylisoxazol-4-yl)-3-(phenylamino)pyridin-2(1H)-one (Example 72)

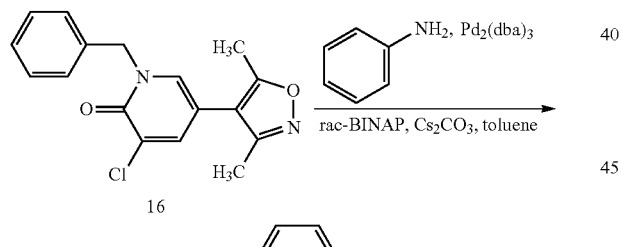

Example 72

A mixture of 1-benzyl-3-chloro-5-(3,5-dimethylisoxazol-4-yl)pyridin-2(1H)-one (16, 90 mg, 0.29 mmol), aniline (54 mg, 2 equiv.), Pd$_2$(dba)$_3$ (27 mg, 0.1 equiv), rac-BINAP (36 mg, 0.2 equiv.) and Cs$_2$CO$_3$ (189 mg, 2 equiv.) in toluene (4 mL) was stirred at 110° C. for 16 h. The reaction mixture was allowed to cool to room temperature and was filtered through a layer of Celite. The filtrate was concentrated and purified by chromatography (silica gel, 0-50% EtOAc in hexanes) to afford Example 72 (61 mg, 57%) as a yellow solid: $^1$H NMR (300 MHz, DMSO-d$_6$) δ 7.87 (s, 1H); 7.43-7.34 (m, 5H); 7.25-7.32 (m, 5H); 6.98 (d, J=2.1 Hz, 1H); 6.90-6.96 (m, 1H); 5.22 (s, 2H); 2.36 (s, 3H); 2.19 (s, 3H); ESI MS m/z 372 [M+H]$^+$.

General Procedure K

Chiral Separation of Example 110 and Example 111

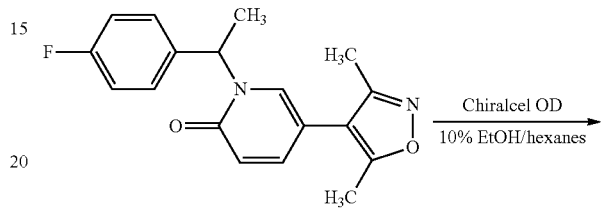

Example 101

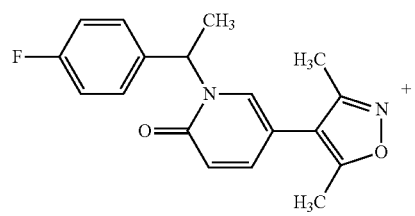

Example 110
Enantiomer A

+

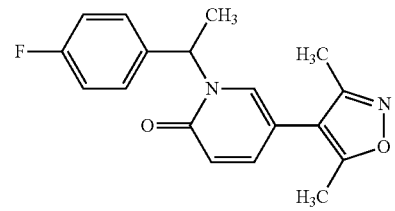

Example 111
Enantiomer B

The enantiomeric mixture of received as Example 101 (80 mg) were separated by preparative HPLC (column: Chiralcel OD, 5 cm×50 cm, 20 micron); mobile phase: 10% EtOH in hexanes; flow rate: 80 mL/min; detection: 254 nm) to afford Example 110 (the first eluting enantiomer, white solid, 30 mg, 38%) and Example 111 (the second eluting enantiomer, white solid, 21 mg, 26%). Example 110: $^1$H NMR (300 MHz, DMSO-d$_6$) δ 7.65 (d, J=2.1 Hz, 1H), 7.48-7.41 (m, 3H), 7.23-7.17 (m, 2H), 6.51 (d, J=9.3 Hz, 1H), 6.20 (q, J=7.2 Hz, 1H), 2.27 (s, 3H), 2.11 (s, 3H), 1.73 (d, J=7.2 Hz, 3H); ESI MS m/z 313 [M+H]$^+$; Chiralcel OD (10% EtOH in heptane, 0.8 mL/min): $t_R$=11.07 min. Example 111: $^1$H NMR (300 MHz, DMSO-d$_6$) δ 7.65 (d, J=2.1 Hz, 1H), 7.48-7.41 (m, 3H), 7.23-7.17 (m, 2H), 6.51 (d, J=9.3 Hz, 1H), 6.20 (q, J=7.2 Hz, 1H), 2.27 (s, 3H), 2.11 (s, 3H), 1.73 (d, J=7.2 Hz, 3H); ESI MS m/z 313 [M+H]$^+$; Chiralcel OD (10% EtOH in heptane, 0.8 mL/min): $t_R$=18.19 min.

General Procedure L

Preparation of 1-((1H-benzo[d]imidazol-5-yl)methyl)-5-(3,5-dimethylisoxazol-4-yl)pyridin-2(1H)-one (Example 146)

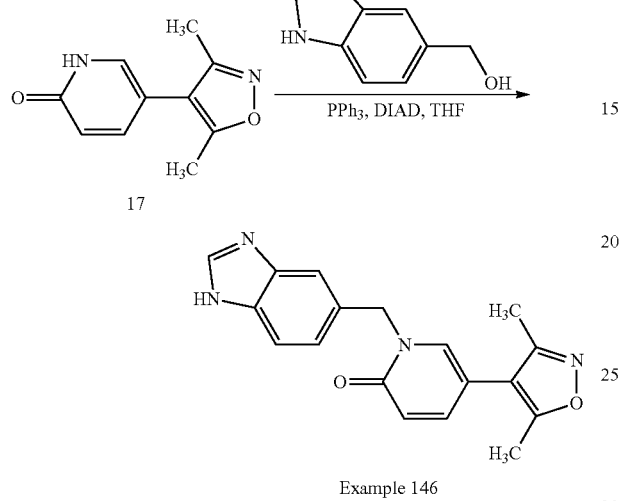

To a solution of 17 (100 mg, 0.53 mmol), (1H-benzo[d]imidazol-5-yl)methanol (234 mg, 1.58 mmol) and triphenylphosphine (689 mg, 2.63 mmol) in THF (30 mL) at 60° C. was added diisopropylazodicarboxylate (531 mg, 2.63 mmol) dropwise. The reaction was stirred at room temperature for 1 h. The reaction mixture was concentrated and purified by chromatography (silica gel, $CH_2Cl_2$ to 1:1 $CH_2Cl_2$/92:7:1 $CHCl_3$/MeOH/concentrated $NH_4OH$). A portion of this material was further purified by reverse phase HPLC eluting with 10-90% $CH_3CN$ in $H_2O$ to give Example 146 (46 mg, 27%) as an off-white solid: $^1H$ NMR (500 MHz, DMSO-$d_6$) δ 8.19 (s, 1H), 7.96 (d, J=2.5 Hz, 1H), 7.62 (s, 1H), 7.55 (d, J=8.3 Hz, 1H), 7.47 (dd, J=2.6, 9.3 Hz, 1H), 7.27 (dd, J=1.6, 8.3 Hz, 1H), 6.54 (d, J=9.3 Hz, 1H), 5.23 (s, 2H), 2.34 (s, 3H), 2.17 (s, 3H). ESI MS m/z 321 [M+H]$^+$.

General Procedure M

Preparation of 1-Benzyl-5-(3,5-dimethylisoxazol-4-yl)-3-(piperazin-1-yl)pyridin-2(1H)-one Hydrochloride (Example 161)

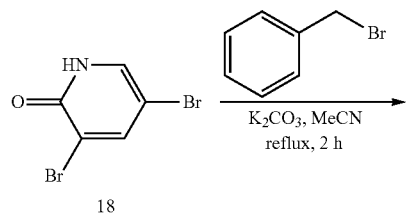

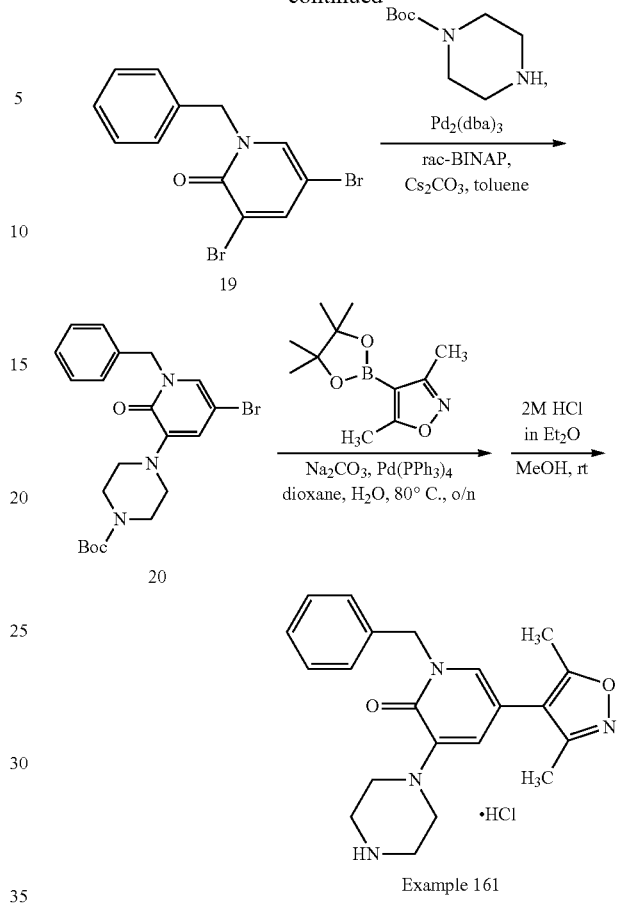

Step 1:

A mixture of 3,5-dibromopyridin-2(1H)-one (18, 3.0 g, 11.9 mmol), benzyl bromide (1.7 mL, 14.2 mmol), potassium carbonate (4.9 g, 35.6 mmol) and acetonitrile (90 mL) was heated at reflux for 2 h under nitrogen. The mixture was allowed to cool to room temperature and the solvent was removed under reduced pressure. The residue was purified by chromatography (silica gel, eluting with 0-55% EtOAc/hexanes) to provide 19 (3.42 g, 84%) as a light yellow solid: $^1H$ NMR (500 MHz, CDCl$_3$) δ 7.77 (d, J=2.5 Hz, 1H), 7.39 (d, J=2.5 Hz, 1H), 7.38-7.32 (m, 5H), 5.14 (s, 2H).

Step 2:

A mixture of 1-benzyl-3,5-dibromopyridin-2(1H)-one (19, 98 mg, 0.29 mmol), tert-butyl piperazine-1-carboxylate (107 mg, 2 equiv.), Pd$_2$(dba)$_3$ (27 mg, 0.1 equiv), rac-BINAP (36 mg, 0.2 equiv.) and Cs$_2$CO$_3$ (189 mg, 2 equiv.) in toluene (4 mL) was stirred at 110° C. for 16 h. The reaction mixture was allowed to cool to room temperature and was filtered through a layer of Celite. The filtrate was concentrated and purified by chromatography (silica gel, 0-50% EtOAc in hexanes) to afford 20 (69 mg, 54%) as a green viscous oil: $^1H$ NMR (500 MHz, CDCl$_3$) δ 7.35-7.29 (m, 5H), 7.10 (d, J=2.4 Hz, 1H), 6.62 (d, J=2.4 Hz, 1H), 5.10 (s, 2H), 3.61-3.59 (m, 4H), 3.11-3.09 (m, 4H), 1.48 (s, 9H); ESI MS m/z 448 [M+H]$^+$.

Step 3:

To a solution of 20 (68 mg, 0.15 mmol) in 1,4-dioxane (3 mL) was added 3,5-dimethyl-4-(4,4,5,5-tetramethyl-1,3,2-dioxaborolan-2-yl)isoxazole (51 mg, 0.23 mmol), sodium carbonate (2.0 M in H$_2$O, 0.5 mL, 1.0 mmol) and tetrakis(triphenylphosphine)-palladium(0) (9 mg, 0.0076 mmol).

The reaction mixture was purged with nitrogen and heated at 80° C. for 15 h. The mixture was diluted with methylene chloride (20 mL) and washed with brine (15 mL). The methylene chloride layer was dried over sodium sulfate, filtered and the filtrate was concentrated. Purification by chromatography (silica gel, 0-50% ethyl acetate/hexanes) afforded a yellow viscous oil (41 mg, 58%). This material was dissolved in methanol (1 mL) and 2 M HCl in diethyl ether (1 mL) was added. After stirring at room temperature for 18 h, the residue was dried in vacuo to afford Example 161 (32 mg, 90%) as a yellow solid: $^1$H NMR (500 MHz, DMSO-$d_6$) δ 8.96 (br s, 2H), 7.65 (d, J=2.2 Hz, 1H), 7.35-7.28 (m, 5H), 6.80 (d, J=2.2 Hz, 1H), 5.15 (s, 2H), 3.37-3.28 (m, 4H), 3.24-3.14 (m, 4H), 2.37 (s, 3H), 2.20 (s, 3H); ESI m/z 365 [M+H]$^+$.

General Procedure N

Preparation of 3-amino-5-(3,5-dimethylisoxazol-4-yl)-1-(4-fluorobenzyl)pyridin-2(1H)-one (Example 180)

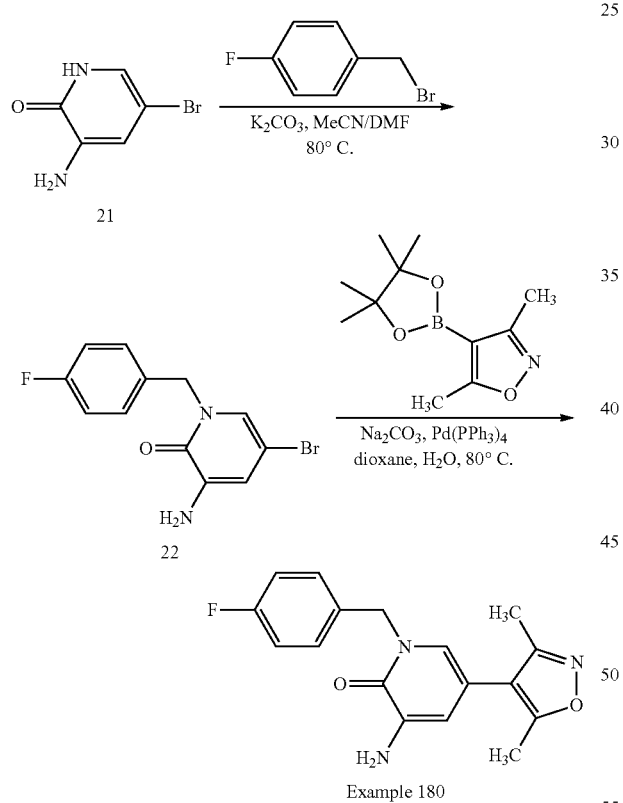

Example 180

Step 1:
To a solution of 21 (500 mg, 2.65 mmol) in acetonitrile (7 mL) and DMF (3.5 mL) was added 1-(bromomethyl)-4-fluorobenzene (0.39 ml, 3.18 mmol) and potassium carbonate (731 mg, 5.30 mmol). The reaction was heated at 80° C. for 5 h. The reaction mixture was cooled to room temperature, diluted with ethyl acetate (200 mL) and washed with brine (2×100 mL). The ethyl acetate layer was dried over sodium sulfate, filtered and concentrated. Purification by chromatography (silica gel, 0-40% ethyl acetate/hexanes) provided 22 (360 mg, 46%) as a white solid: $^1$H NMR (300 MHz, DMSO-$d_6$) δ 7.41-7.36 (m, 2H), 7.30 (d, J=2.4 Hz, 1H), 7.20-7.14 (m, 2H), 6.46 (d, J=2.4 Hz, 1H), 5.54 (br s, 2H), 5.04 (s, 2H).

Step 2:
To a solution of 22 (360 mg, 1.21 mmol) in 1,4-dioxane (12 mL) was added 3,5-dimethyl-4-(4,4,5,5-tetramethyl-1,3,2-dioxaborolan-2-yl)isoxazole (323 mg, 1.45 mmol), 2 M aq. sodium carbonate (1.21 mL, 2.42 mmol) and tetrakis(triphenylphosphine)palladium(0) (70 mg, 0.061 mmol). The reaction mixture was purged with nitrogen and heated at 80° C. for 16 h. The mixture was diluted with ethyl acetate (100 mL) and washed with brine (50 mL). The organic layer was dried over sodium sulfate, filtered and concentrated. Purification by chromatography (silica gel, 10-40% ethyl acetate/hexanes) followed by trituration with ethyl acetate/hexanes afforded Example 180 (234 mg, 62%) as an off-white solid: $^1$H NMR (300 MHz, DMSO-$d_6$) δ 7.45-7.40 (m, 2H), 7.21-7.15 (m, 2H), 7.13 (d, J=2.4 Hz, 1H), 6.44 (d, J=2.4 Hz, 1H), 5.29 (s, 2H), 5.11 (s, 2H), 2.35 (s, 3H), 2.18 (s, 3H); ESI m/z 314 [M+H]$^+$.

General Procedure O

Preparation of 3-Amino-5-(3,5-dimethylisoxazol-4-yl)-1-((3-methyl-1H-indol-4-yl)methyl)pyridin-2(1H)-one (Example 271)

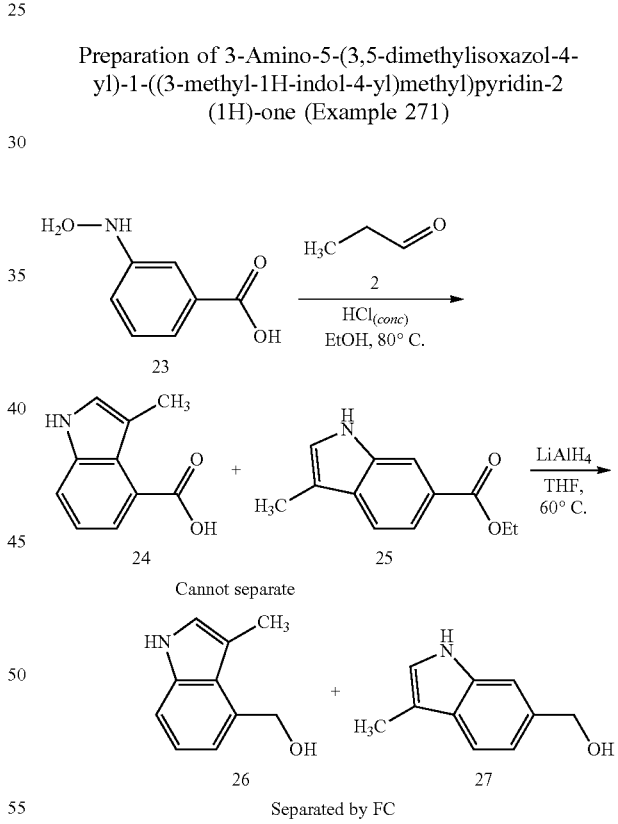

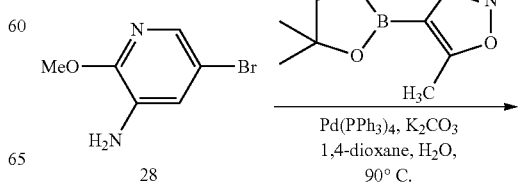

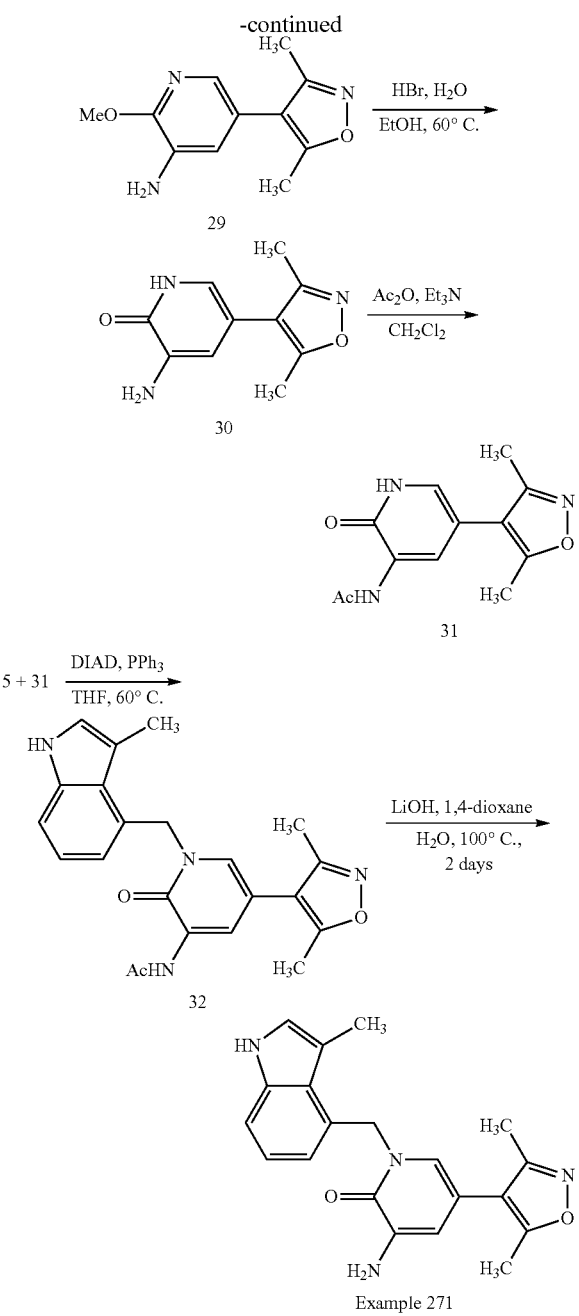

Example 271

Step 1:
To a solution of 23 (1.52 g, 10.0 mmol) in ethanol (10 mL) was added propionaldehyde (696 mg, 12.0 mmol) at room temperature. The mixture was heated at 80° C. for 1 h and cooled at room temperature. Then concentrated hydrochloric acid (2.5 mL) was added and heated at 80° C. overnight. The mixture was concentrated under vacuum. The residue was dissolved in MeOH and basified with sodium carbonate (20% in water). The mixture was concentrated and purified by chromatography (silica gel, 0-50% ethyl acetate/hexanes) to give a mixture of 24 and 25 (650 mg, 32%) as an orange oil.

Step 2:
To a solution of LiAlH$_4$ (1 M in THF, 12.8 mL, 12.8 mmol) in tetrahydrofuran (50 mL) was added a mixture of 24 and 25 (650 mg, 3.20 mmol) in tetrahydrofuran (10 mL) at 0° C. under nitrogen. The reaction mixture was heated at 65° C. for 30 min and then cooled to 0° C. Water (1 mL), 2N aq. NaOH (2 mL), and silica gel (5 g) were then added sequentially. The mixture was concentrated and purified by chromatography (silica gel, 0-100% ethyl acetate/hexanes) to give: Compound 26 (94 mg, 18%) as a yellow solid: $^1$H NMR (500 MHz, CDCl$_3$) δ 7.96 (s, 1H), 7.31 (dd, J=8.1, 0.8 Hz, 1H), 7.14 (t, J=7.2 Hz, 1H), 7.08 (d, J=7.2 Hz, 1H), 6.99 (q, J=1.1 Hz, 1H), 5.06 (d, J=5.8 Hz, 2H), 2.53 (d, J=1.0 Hz, 3H), 1.56 (t, J=5.9 Hz, 1H). Compound 27 (147 mg, 29%) as an orange solid: $^1$H NMR (500 MHz, CDCl$_3$) δ 7.90 (s, 1H), 7.56 (d, J=8.0 Hz, 1H), 7.35 (d, J=0.5 Hz, 1H), 7.12 (dd, J=8.1, 1.3 Hz, 1H), 6.97 (q, J=1.0 Hz, 1H), 4.78 (d, J=5.4 Hz, 2H), 2.33 (d, J=1.1 Hz, 3H), 1.61 (t, J=5.7 Hz, 1H).

Step 3:
To a solution of 28 (10.0 g, 49.3 mmol) in 1,4-dioxane (400 mL) and water (40 mL) was added 3,5-dimethyl-4-(4,4,5,5-tetramethyl-1,3,2-dioxaborolan-2-yl)isoxazole (13.2 g, 59.1 mmol), potassium carbonate (13.6 g, 98.6 mmol), and tetrakis(triphenylphosphine)palladium(0) (1.71 g, 1.48 mmol). The reaction mixture was purged with nitrogen and heated at 90° C. overnight. The reaction mixture was cooled to room temperature, concentrated and purified by chromatography (silica gel, 0-50% ethyl acetate/hexanes) to give 29 (9.26 g, 86%) as a yellow solid: $^1$H NMR (500 MHz, CDCl$_3$) δ 7.45 (d, J=2.0 Hz, 1H), 6.75 (d, J=2.0 Hz, 1H), 4.02 (s, 3H), 3.87 (s, 2H), 2.37 (s, 3H), 2.23 (s, 3H).

Step 4:
A mixture of 29 (4.00 g, 18.3 mmol), ethanol (15 mL), and 48% HBr (20 mL) was heated at 85° C. for 1 h under nitrogen. The reaction mixture was concentrated under vacuum to give crude 30 (6.40 g) that was used in the next step without further purification.

Step 5:
To a solution of 30 (6.40 g, 18.3 mmol) and triethylamine (12.7 mL, 91.5 mmol) in methylene chloride (100 mL) was added acetic anhydride (3.73 g, 36.6 mmol). The mixture was stirred at room temperature for 17 h, methanol (20 mL) was added, and the material was concentrated and purified by chromatography (silica gel, 0-20% ethyl acetate/methanol). The product was further purified by dissolving in methanol (300 mL) and precipitation by the addition of water (1000 mL) to give 31 (3.90 g, 86%) as a green solid: $^1$H NMR (500 MHz, DMSO-d$_6$) δ 12.17 (s, 1H), 9.35 (s, 1H), 8.23 (d, J=2.3 Hz, 1H), 7.14 (d, J=2.3 Hz, 1H), 2.35 (s, 3H), 2.17 (s, 3H), 2.12 (s, 3H); ESI m/z 248 [M+H]$^+$.

Step 6:
To a solution of 5 (94 mg, 0.58 mmol), 31 (120 mg, 0.49 mmol), and triphenylphosphine (321 mg, 1.23 mmol) in tetrahydrofuran (10 mL) at 65° C. under nitrogen was added diisopropyl azodicarboxylate (247 mg, 1.23 mmol). The mixture was cooled to room temperature, concentrated, and purified by chromatography (silica gel, 0-100% ethyl acetate/hexanes) to give crude 32 (230 mg, contained Ph$_3$PO).

Step 7:
A solution of crude 32 (230 mg, 0.490 mmol) and LiOH (118 mg, 4.90 mmol) in 1,4-dioxane (10 mL) and water (10 mL) was heated at 100° C. for 17 h under nitrogen. The reaction mixture was cooled to room temperature, concentrated and purified by chromatography (silica gel, 0-100% hexanes/ethyl acetate). It was further purified by reverse phase HPLC on a Polaris column eluting with 10-90% CH$_3$CN in H$_2$O to give Example 271 (32 mg, 19% over 2 steps) as an off-white solid: $^1$H NMR (500 MHz, DMSO-d$_6$) δ 10.85 (s, 1H), 7.26 (d, J=7.8 Hz, 1H), 7.12-7.95 (m, 1H), 6.97 (t, J=7.4 Hz, 1H), 6.69 (d, J=2.5 Hz, 1H), 6.50 (d, J=2.5 Hz, 1H), 6.44 (d, J=7.8 Hz, 1H), 5.58 (s, 2H), 5.28 (s, 2H), 2.37 (d, J=0.5 Hz, 3H), 2.22 (s, 3H), 2.05 (s, 3H); ESI m/z 349 [M+H]+.

General Procedure P

Preparation of 3-Amino-5-(3,5-dimethylisoxazol-4-yl)-1-(4-isopropylbenzyl)pyridin-2(1H)-one (Example 242)

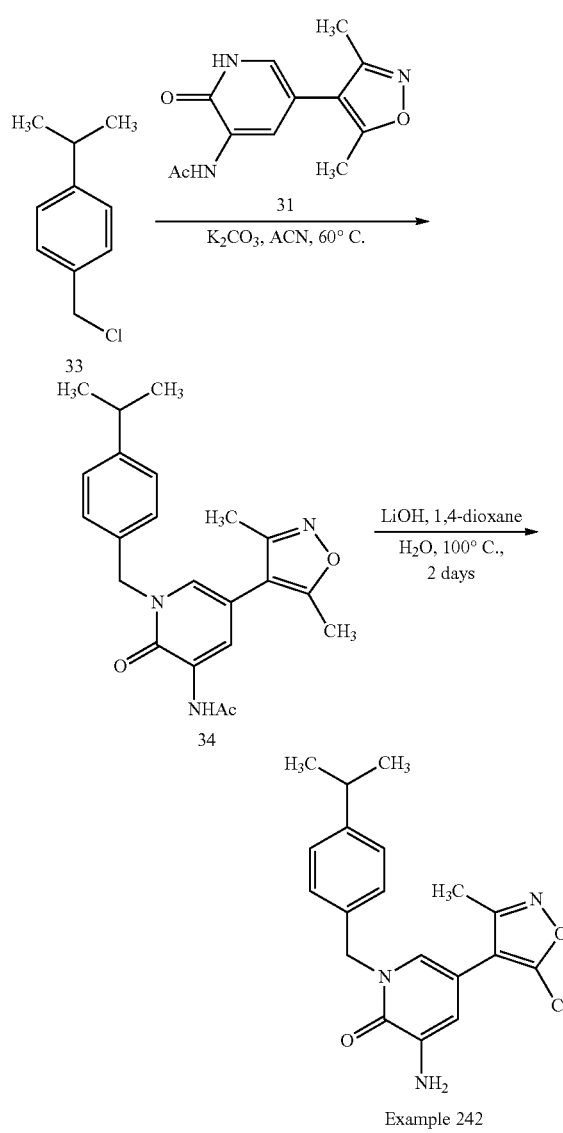

Example 242

Step 1:
To a solution of N-(5-(3,5-dimethylisoxazol-4-yl)-2-oxo-1,2-dihydropyridin-3-yl)acetamide 31 (200 mg, 50% pure, 0.405 mmol) in acetonitrile (10 mL) was added 33 (136 mg, 0.810 mmol) and potassium carbonate (168 mg, 1.22 mmol). The reaction was heated at 60° C. for 17 h. The reaction mixture was cooled to room temperature, concentrated, and purified by chromatography (silica gel, 0-100% ethyl acetate/hexanes) to afford 34 (120 mg, 78%) as an off-white solid: $^1$H NMR (500 MHz, CDCl$_3$) δ 8.43 (s, 1H), 8.34 (d, J=2.3 Hz, 1H), 7.23 (s, 4H), 6.85 (d, J=2.3 Hz, 1H), 5.17 (s, 2H), 2.90 (octet, J=6.9 Hz, 1H), 2.31 (s, 3H), 2.20 (s, 3H), 2.18 (s, 3H), 1.23 (d, J=6.9 Hz, 6H); ESI m/z 380 [M+H]+.

Step 2:
A solution of 34 (100 mg, 0.264 mmol) and LiOH (40 mg, 1.58 mmol) in 1,4-dioxane (4 mL) and water (2 mL) was heated at 100° C. for 17 h under nitrogen. The reaction mixture was cooled to room temperature, treated with acetic acid (0.5 mL), and concentrated. The residue was purified by reverse phase HPLC on a Polaris column eluting with 10-90% CH$_3$CN in H$_2$O to give Example 242 (75 mg, 84%) as a yellow solid: $^1$H NMR (500 MHz, DMSO-d$_6$) δ 7.27 (d, J=8.1 Hz, 2H), 7.20 (d, J=8.1 Hz, 2H), 7.08 (d, J=2.2 Hz, 1H), 6.43 (d, J=2.2 Hz, 1H), 5.25 (s, 2H), 5.08 (s, 2H), 2.84 (octet, J=6.9 Hz, 1H), 2.34 (s, 3H), 2.17 (s, 3H), 1.17 (d, J=6.9 Hz, 6H); ESI m/z 338 [M+H]+.

Example 100

Preparation of 2-Benzyl-6-(3,4-dimethoxyphenoxy)pyridazin-3(2H)-one

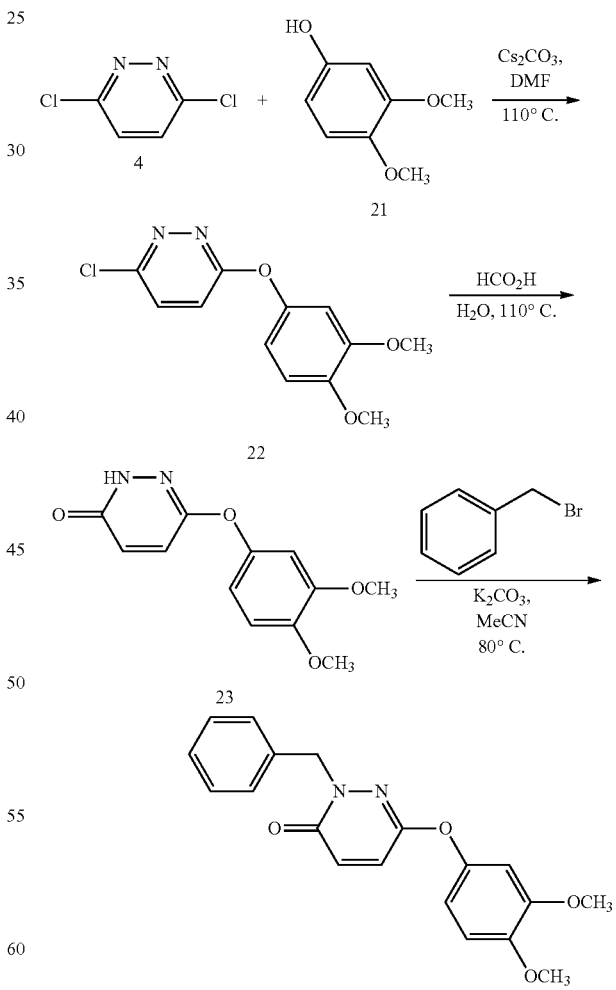

Example 100

Step 1:
To a solution of 4 (600 mg, 4.0 mmol) in DMF (10 mL) was added 3,4-dimethoxyphenol (21, 925 mg, 6.0 mmol)

and Cs₂CO₃ (3.91 g, 12.0 mmol). The reaction mixture was heated at 110° C. for 10 h. The mixture was diluted with ethyl acetate (150 mL) and washed with brine (2×30 mL). The ethyl acetate layer was dried over sodium sulfate, filtered and concentrated. Purification by chromatography (silica gel, 0-40% ethyl acetate/hexanes) afforded 22 (480 mg, 45%) as a yellow solid: ¹H NMR (300 MHz, DMSO-d₆) δ 7.92 (d, J=9.3 Hz, 1H), 7.51 (d, J=9.0 Hz, 1H), 7.00 (d, J=8.7 Hz, 1H), 6.92 (d, J=2.7 Hz, 1H), 6.76 (dd, J=8.7, 2.7 Hz, 1H), 3.77 (s, 3H), 3.73 (s, 3H).

Step 2:

A suspension of 22 (480 mg, 1.80 mmol) in water (4 mL) and formic acid (4 mL) was heated to reflux for 10 h. The reaction mixture was cooled to room temperature and adjusted to pH 8 with 6 N aq. NaOH. Solids were collected, washed with water and dried to afford 23 (250 mg, 56%) as an off-white solid: ¹H NMR (300 MHz, DMSO-d₆) δ 12.23 (s, 1H), 7.36 (d, J=9.9 Hz, 1H), 6.98 (d, J=8.7 Hz, 1H), 6.94 (d, J=9.0 Hz, 1H), 6.85 (d, J=3.0 Hz, 1H), 6.68 (dd, J=8.7, 2.7 Hz, 1H), 3.74 (s, 3H), 3.73 (s, 3H).

Step 3:

To a solution of 23 (75 mg, 0.30 mmol) in acetonitrile (5 mL) was added benzyl bromide (0.043 ml, 0.36 mmol) and potassium carbonate (83 mg, 0.60 mmol). The reaction was heated at 80° C. for 16 h. The reaction mixture was cooled to room temperature and the solid filtered was rinsed with CH₂Cl₂ (10 mL). The filtrate was concentrated and purified by chromatography (silica gel, 10-60% ethyl acetate/hexanes) to give Example 100 (52 mg, 51%) as a white solid: ¹H NMR (300 MHz, DMSO-d₆) δ 7.38 (d, J=9.6 Hz, 1H), 7.32-7.20 (m, 5H), 7.09 (d, J=9.6 Hz, 1H), 6.93 (d, J=8.7 Hz, 1H), 6.83 (d, J=2.7 Hz, 1H), 6.67 (dd, J=8.7, 2.7 Hz, 1H), 5.03 (s, 2H), 3.74 (s, 3H), 3.66 (s, 3H); ESI MS m/z 339 [M+H]⁺.

Example 151

Preparation of 5-(3-Amino-5-methylisoxazol-4-yl)-1-benzylpyridin-2(1H)-one

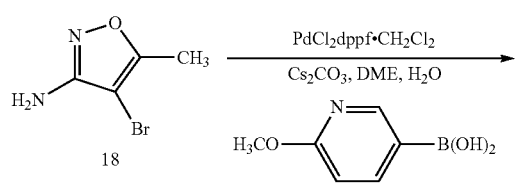

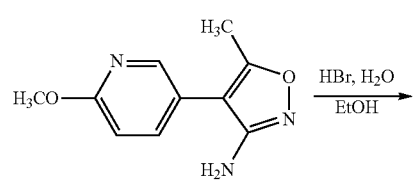

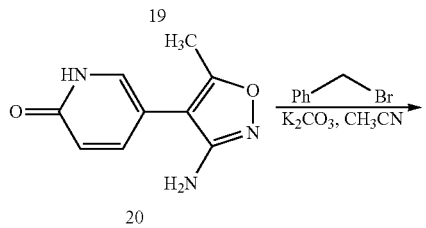

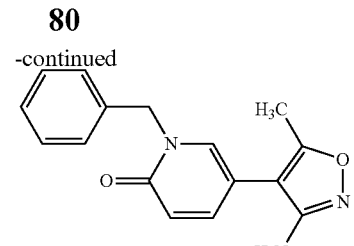

Example 151

Step 1:

A mixture of 4-bromo-5-methylisoxazol-3-amine (18, 0.35 g, 2 mmol), (6-methoxypyridin-3-yl)boronic acid (0.46 g, 1.5 equiv.), PdCl₂dppf·CH₂Cl₂ (146 mg, 0.1 equiv) and Cs₂CO₃ (1.3 g, 2 equiv.) in aqueous DME (6 mL mixed with 0.5 mL H₂O) was stirred at 100° C. for 5 h. The reaction mixture was allowed to cool to room temperature and filtered through a layer of Celite. The filtrate was concentrated and purified by chromatography (silica gel, 0-50% EtOAc in hexanes) to afford 19 (93 mg, 23%) as an off-white solid: ¹H NMR (300 MHz, DMSO-d₆) δ 8.15 (dd, J=0.6, 2.4 Hz, 1H), 7.69 (dd, J=2.4, 8.7 Hz, 1H), 6.90 (dd, J=0.6, 8.4 Hz, 1H), 5.41 (s, 2H), 3.88 (s, 3H), 2.25 (s, 3H). ESI MS m/z 206 [M+H]⁺.

Step 2:

A mixture of 4-(6-methoxypyridin-3-yl)-5-methylisoxazol-3-amine (19, 0.33 g, 1.6 mmol) and HBr (4 mL, 48% aqueous solution) in EtOH (6 mL) was stirred at 85° C. for 8 h. The reaction mixture was allowed to cool to room temperature and Na₂CO₃ was added until pH reached 7-8. The mixture was filtered through a layer of Celite and the filtrate was concentrated. The material was purified by chromatography (silica gel, 0-10% CH₃OH in CH₂Cl₂) to afford 20 (0.22 g, 71%) as an off-white solid: ¹H NMR (300 MHz, DMSO-d₆) δ 11.8 (s, 1H), 7.40 (dd, J=2.7, 9.3 Hz, 1H), 7.32 (d, J=2.1 Hz, 1H), 6.39 (d, J=9.6 Hz, 1H), 5.39 (s, 2H), 2.21 (s, 3H). ESI MS m/z 192 [M+H]⁺.

Step 3:

A mixture of 5-(3-amino-5-methylisoxazol-4-yl)pyridin-2(1H)-one (20, 53 mg, 0.28 mmol), K₂CO₃ (77 mg, 2 equiv.) and benzyl bromide (52 mg, 1.1 equiv.) in CH₃CN (4 mL) was stirred at 85° C. in sealed tube for 12 h. The reaction mixture was allowed to cool to room temperature and was filtered through a layer of Celite. The filtrate was concentrated and purified by trituration with ethyl acetate to afford Example 151 (71 mg, 90%) as an off-white solid: ¹H NMR (300 MHz, DMSO-d₆) δ 7.81 (d, J=2.1 Hz, 1H), 7.42 (dd, J=2.7, 9.3 Hz, 1H), 7.28-7.36 (m, 5H), 5.49 (d, J=9.3 Hz, 1H), 5.43 (s, 2H), 5.13 (s, 2H), 2.21 (s, 3H). ESI MS m/z 282 [M+H]⁺.

Example 183

Preparation of 3-(Azetidin-1-yl)-1-benzyl-5-(3,5-dimethylisoxazol-4-yl)pyridin-2(1H)-one

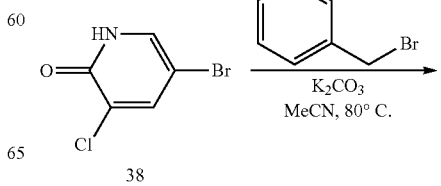

-continued

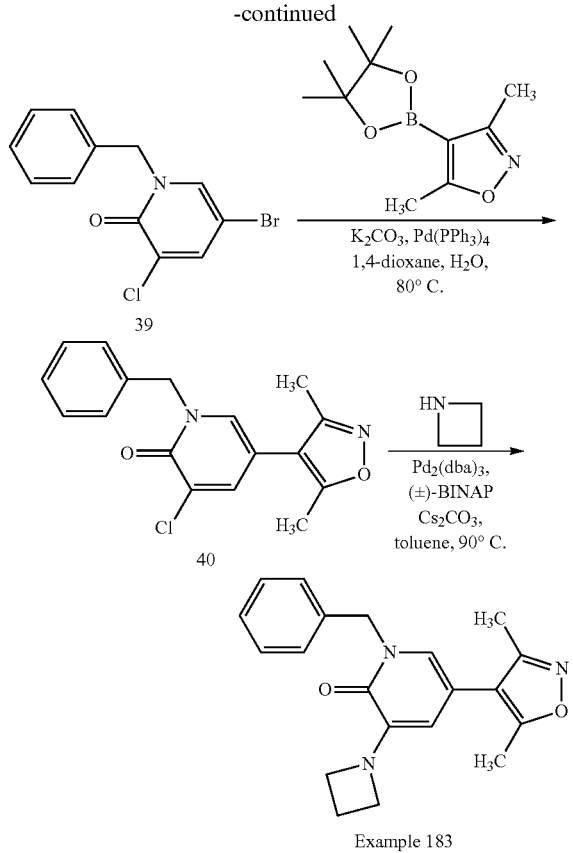

Example 183

Step 1:

To a solution of 38 (3.00 g, 14.4 mmol) in acetonitrile (120 mL) was added benzyl bromide (2.95 g, 17.3 mmol) and potassium carbonate (3.97 g, 28.8 mmol). The reaction was heated at 75° C. for 17 h. The reaction mixture was cooled to room temperature, concentrated, and purified by chromatography (silica gel, 0-50% ethyl acetate/hexanes) to afford 39 (3.70 g, 86%) as a light-brown solid: $^1$H NMR (500 MHz, CDCl$_3$) δ 7.57 (d, J=2.5 Hz, 1H), 7.31-7.41 (m, 6H), 5.14 (s, 2H).

Step 2:

To a solution of 39 (3.70 g, 12.4 mmol) in 1,4-dioxane (180 mL) and water (20 mL) was added 3,5-dimethyl-4-(4,4,5,5-tetramethyl-1,3,2-dioxaborolan-2-yl)isoxazole (3.47 g, 14.9 mmol), potassium carbonate (3.42 g, 24.8 mmol), and tetrakis(triphenylphosphine)palladium(0) (286 mg, 0.248 mmol). The reaction mixture was purged with nitrogen and heated at 90° C. for 17 h. The reaction mixture was cooled to room temperature, concentrated, and purified by chromatography (silica gel, 0-30% ethyl acetate/hexanes) to afford 40 (2.52 g, 65%) as a yellow solid: $^1$H NMR (500 MHz, CDCl$_3$) δ 7.42 (d, J=2.3 Hz, 1H), 7.32-7.41 (m, 5H), 7.08 (d, J=2.3 Hz, 1H), 5.22 (s, 2H), 2.29 (s, 3H), 2.14 (s, 3H); ESI m/z 315 [M+H]$^+$.

Step 3:

To a solution of 40 (100 mg, 0.318 mmol) in toluene (10 mL) under nitrogen atmosphere was added azetidine (36 mg, 0.64 mmol), cesium carbonate (208 mg, 0.640 mmol), racemic 2,2'-bis(diphenylphosphino)-1,1'-binaphthalene (30 mg, 0.048 mmol), and tris(dibenzylideneacetone)dipalladium(0) (29 mg, 0.018 mmol). The reaction mixture was heated at 90° C. for 17 h, cooled to room temperature, and purified by chromatography (silica gel, 0-50% ethyl acetate/hexanes). It was further purified by reverse phase HPLC on a Polaris column eluting with 10-90% CH$_3$CN in H$_2$O to give Example 183 (13 mg, 12%) as an off-white solid: $^1$H NMR (500 MHz, DMSO-d$_6$) δ 7.25-7.38 (m, 5H), 7.21 (d, J=2.2 Hz, 1H), 6.07 (d, J=2.2 Hz, 1H), 5.07 (s, 2H), 3.89 (t, J=7.2 Hz, 4H), 2.34 (s, 3H), 2.18 (t, J=7.2 Hz, 2H), 2.17 (s, 3H); ESI m/z 336 [M+H]$^+$.

Example 189

Preparation of 3-Amino-1-benzyl-5-(3-(hydroxymethyl)-5-methylisoxazol-4-yl)pyridin-2(1H)-one

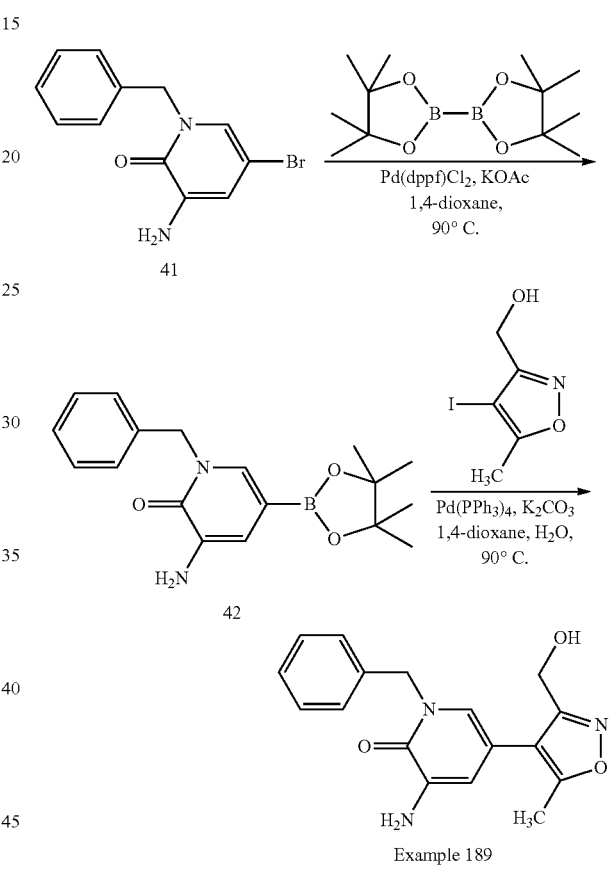

Example 189

Step 1:

To a solution of 41 (950 mg, 3.41 mmol) in 1,4-dioxane (40 mL) was added bis(pinacolato)diboron (1.04 g, 4.09 mmol), potassium acetate (668 mg, 6.82 mmol), and [1,1'-bis(diphenylphosphino)ferrocene]dichloropalladium(II) (125 mg, 0.171 mmol). The reaction mixture was heated at 90° C. for 17 h under nitrogen atmosphere. The reaction mixture was cooled to room temperature, concentrated, and purified by chromatography (silica gel, 0-30% ethyl acetate/hexanes) to give 42 (490 mg, 44%) as an off-white solid: $^1$H NMR (500 MHz, DMSO-d$_6$) δ 7.23-7.36 (m, 6H), 6.61 (d, J=1.6 Hz, 1H), 5.16 (s, 2H), 5.08 (s, 2H), 1.23 (s, 12H).

Step 2:

To a solution of 42 (400 mg, 1.50 mmol) in 1,4-dioxane (20 mL) and water (2 mL) was added (4-iodo-5-methylisoxazol-3-yl)methanol (431 mg, 1.80 mmol), potassium carbonate (414 mg, 3.00 mmol), and tetrakis(triphenylphosphine)palladium(0) (86 mg, 0.075 mmol). The reaction mixture was purged with nitrogen and heated at 90° C.

overnight. The reaction mixture was cooled to room temperature, concentrated, and purified by chromatography (silica gel, 0-50% ethyl acetate/hexanes). It was further purified by reverse phase HPLC on a Polaris column eluting with 10-90% $CH_3CN$ in $H_2O$ to give Example 189 (150 mg, 32%) as a light yellow solid: $^1H$ NMR (500 MHz, DMSO-$d_6$) δ 7.25-7.37 (m, 5H), 7.18 (d, J=2.2 Hz, 1H), 6.57 (d, J=2.2 Hz, 1H), 5.42 (t, J=5.6 Hz, 1H), 5.25 (s, 2H), 5.12 (s, 2H), 4.44 (d, J=5.6 Hz, 2H), 2.37 (s, 3H); ESI m/z 312 $[M+H]^+$.

Example 197

Preparation of 1-(4-Chlorobenzyl)-5-(3,5-dimethyl-4H-1,2,4-triazol-4-yl)pyridin-2(1H)-one

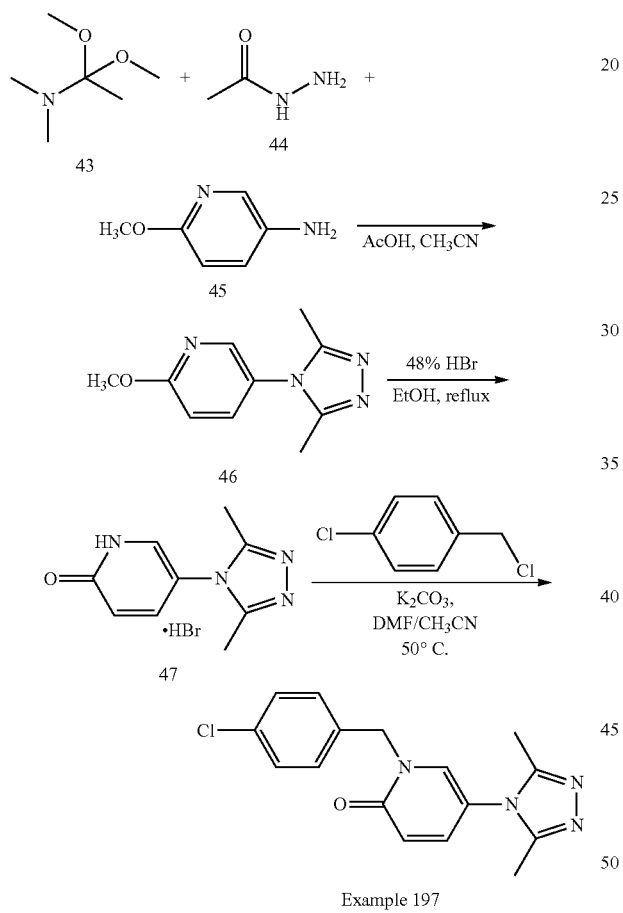

Example 197

Step 1:

To a solution of 43 (400 mg, 5.5 mmol) in $CH_3CN$ (2 mL) was added 44 (0.805 mL, 5.5 mmol). The reaction mixture was heated at 50° C. for 30 minutes, then a solution of 45 (621 mg, 5.0 mmol) in $CH_3CN$ (1 mL) and AcOH (3 mL) were added. The reaction mixture was heated at 120° C. for 2 h. The mixture was diluted with saturated $NaHCO_3$ (100 mL), and was extracted with ethyl acetate (200 mL). The organic layer was dried over sodium sulfate, filtered and concentrated. The residue was triturated with ethyl acetate/hexanes to afford 46 (445 mg, 44%) as a light brown solid: $^1H$ NMR (300 MHz, $CDCl_3$) δ 8.06 (d, J=2.7 Hz, 1H), 7.41 (dd, J=8.7, 2.7 Hz, 1H), 7.00 (dd, J=8.7, 0.6 Hz, 1H), 4.02 (s, 3H), 2.28 (s, 6H).

Step 2:

A solution of 46 (198 mg, 0.97 mmol) in EtOH (4 mL) and 48% HBr (2 mL) was heated to reflux for 1 h. The reaction mixture was concentrated to dryness to afford 47 (265 mg, 100%) as a brown solid: $^1H$ NMR (300 MHz, DMSO-$d_6$) δ 7.94 (d, J=3.0 Hz, 1H), 7.63 (dd, J=9.6, 3.0 Hz, 1H), 6.55 (d, J=9.6 Hz, 1H), 2.43 (s, 6H).

Step 3:

To a solution of 47 (55 mg, 0.20 mmol) in acetonitrile (1 mL) and DMF (3 mL) was added 4-chlorobenzyl chloride (19 mg, 0.12 mmol) and potassium carbonate (83 mg, 0.60 mmol). The reaction was heated at 50° C. for 4 h. The reaction mixture was diluted with ethyl acetate (50 mL) and washed with brine (50 mL). The organic layer was dried over sodium sulfate, filtered and concentrated. The residue was triturated with ethyl acetate to afford Example 197 (28 mg, 73%) as an off-white solid: $^1H$ NMR (300 MHz, DMSO-$d_6$) δ 8.30 (d, J=2.7 Hz, 1H), 7.58 (dd, J=9.6, 2.4 Hz, 1H), 7.45-7.36 (m, 4H), 6.55 (d, J=9.6 Hz, 1H), 5.08 (s, 2H), 2.19 (s, 6H); ESI m/z 315 $[M+H]^+$.

Example 198

Preparation of 1-Benzyl-5-(3,5-dimethylisoxazol-4-yl)-2-oxo-1,2-dihydropyridine-3-carbonitrile

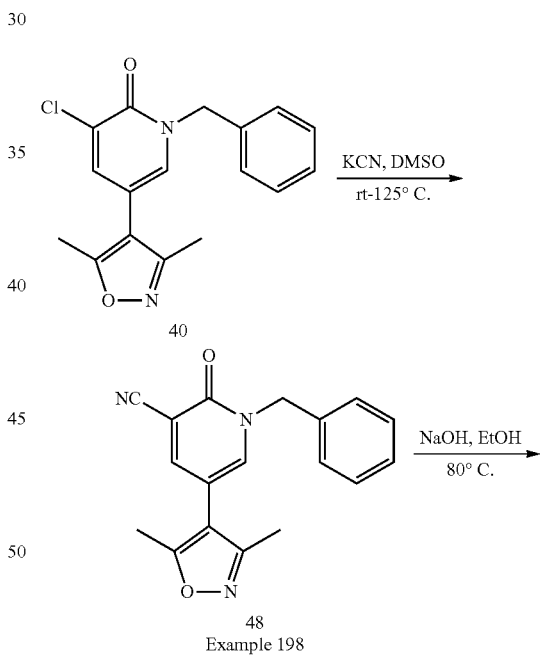

Example 198

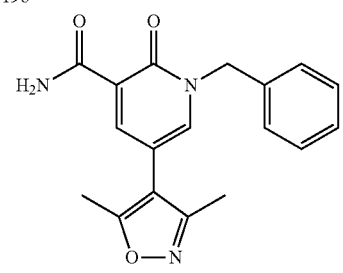

Example 230

-continued

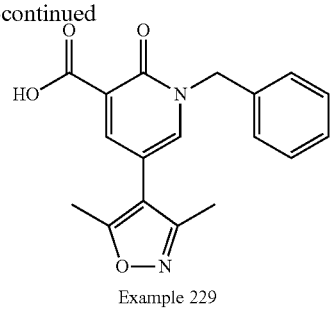

Example 229

A mixture of 1-benzyl-3-chloro-5-(3,5-dimethylisoxazol-4-yl)pyridin-2(1H)-one (50 mg, 0.16 mmol), KCN (104 mg, 1.6 mmol) and DMSO (3 mL) was heated to 120° C. under nitrogen. The reaction mixture was heated at that temperature for 18 hours and then cooled to room temperature. Water (10 mL) was added and the solution was extracted with ethyl acetate (3×20 mL). The combined extracts were dried over sodium sulfate, filtered and concentrated. The product was purified by silica gel chromatography (eluting with 0 to 50% ethyl acetate in hexanes) to provide Example 198 (15 mg, 31%): $^1$H NMR (300 MHz, CDCl$_3$) δ 7.68 (d, J=2.6 Hz, 1H), 7.45-7.33 (m, 6H), 5.21 (s, 2H), 2.28 (s, 3H), 2.13 (s, 3H); ESI MS m/z 306 [M+H]$^+$.

Examples 229 and 230

Preparation of 1-Benzyl-5-(3,5-dimethylisoxazol-4-yl)-2-oxo-1,2-dihydropyridine-3-carboxamide (Example 230) and 1-Benzyl-5-(3,5-dimethylisoxazol-4-yl)-2-oxo-1,2-dihydropyridine-3-carboxylic acid (Example 229)

To a solution of 1-benzyl-5-(3,5-dimethylisoxazol-4-yl)-2-oxo-1,2-dihydropyridine-3-carbonitrile (Example 198, 58 mg, 0.19 mmol) and EtOH (2 mL) was slowly added NaOH (2M, 0.5 mL, 0.95 mmol) at room temperature. The solution was heated at 80° C. for 3 hours and then cooled back to room temperature. The solution was then neutralized with HCl (6N) and extracted with CH$_2$Cl$_2$. The organic layer was dried over sodium sulfate, filtered and concentrated. The products were purified by combiflash (eluting with 0 to 5% methanol in CH$_2$Cl$_2$) to yield 1-benzyl-5-(3,5-dimethylisoxazol-4-yl)-2-oxo-1,2-dihydropyridine-3-carboxylic acid (Example 229) (22 mg, 34%) as the first eluted compound: $^1$H NMR (500 MHz, CDCl$_3$) δ 8.41 (s, 1H), 7.49-7.39 (m, 4H), 7.36-7.33 (m, 2H), 5.28 (s, 2H), 2.32 (s, 3H), 2.15 (s, 3H); ESI MS m/z 325 [M+H]$^+$ and 1-benzyl-5-(3,5-dimethylisoxazol-4-yl)-2-oxo-1,2-dihydropyridine-3-carboxamide (Example 230) (21 mg, 33%) as the second eluted compound: $^1$H NMR (500 MHz, CDCl$_3$) δ 9.55 (s, 1H), 8.45 (d, J=2.7 Hz, 1H), 7.44-7.30 (m, 6H), 5.75 (s, 1H), 5.26 (s, 2H), 2.30 (s, 3H), 2.15 (s, 3H); ESI MS m/z 324 [M+H]$^+$.

Example 200

Preparation of N-(1-Benzyl-5-(3,5-dimethylisoxazol-4-yl)-2-oxo-1,2-dihydropyridin-3-yl)methanesulfonamide

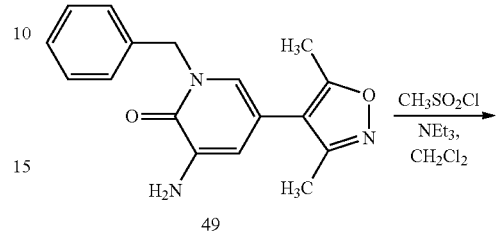

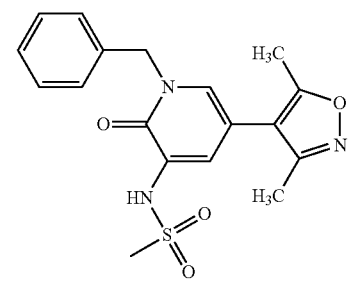

Example 200

To a solution of 49 (85 mg, 0.29 mmol) and triethylamine (0.12 mL, 0.86 mmol) in CH$_2$Cl$_2$ (5 mL) at room temperature was added methanesulfonyl chloride (37 mg, 0.32 mmol). The reaction was stirred at room temperature for 17 h and the mixture was chromatographed on silica gel (40 g) using 0-60% ethyl acetate in hexanes. After concentration, the product residue was further purified by reverse phase HPLC on a Polaris column eluting with 10-90% CH$_3$CN in H$_2$O to give Example 200 (12 mg, 11%) as a white solid: 1H NMR (500 MHz, DMSO-d$_6$): δ 9.02 (s, 1H), 7.78 (d, J=3.5 Hz, 1H), 7.38-7.26 (m, 6H), 5.20 (s, 2H), 3.30 (s, 3H), 2.42 (s, 3H), 2.20 (s, 3H). ESI MS m/z 374 [M+H]$^+$.

Example 201

Preparation of 2-Benzyl-6-(((3,5-dimethylisoxazol-4-yl)methyl)amino)pyridazin-3(2H)-one

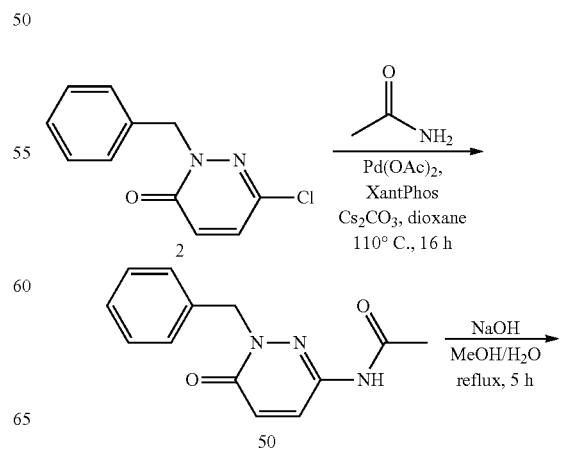

87

-continued

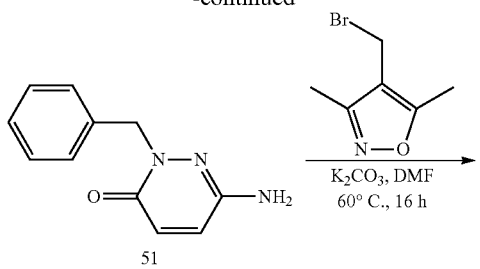

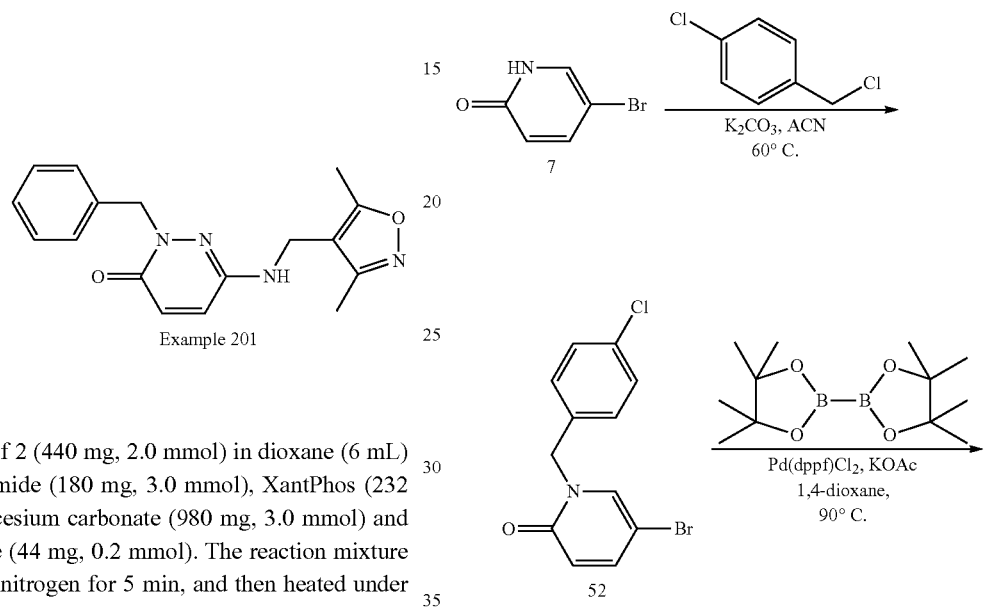

Example 201

Step 1:

To a solution of 2 (440 mg, 2.0 mmol) in dioxane (6 mL) was added acetamide (180 mg, 3.0 mmol), XantPhos (232 mg, 0.4 mmol), cesium carbonate (980 mg, 3.0 mmol) and palladium acetate (44 mg, 0.2 mmol). The reaction mixture was purged with nitrogen for 5 min, and then heated under nitrogen at 110° C. for 16 h. The reaction mixture was cooled to room temperature, concentrated and purified by chromatography (silica gel, 0-100% ethyl acetate/hexanes) to give 50 (451 mg, 93%) as a white solid: $^1$H NMR (500 MHz, CDCl$_3$) δ 8.17 (d, J=16.0 Hz, 1H), 7.51 (s, 1H), 7.39-7.29 (m, 5H), 7.0 (d, J=16.5 Hz, 1H), 5.21 (s, 2H), 2.16 (s, 3H).

Step 2:

To a solution of 50 (439 mg, 1.8 mmol) in MeOH/water (15 mL/5 mL) was added NaOH (360 mg, 9.0 mmol). The reaction mixture was refluxed for 5 h and concentrated. The residue was partitioned between DCM and water, and extracted with DCM. The organic layer was dried over sodium sulfate, filtered and concentrated to give 51 (368 mg, 100%) as a yellow solid: ESI m/z 202 [M+H]$^+$.

Step 3:

To a solution of 51 (20 mg, 0.10 mmol) in DMF (1 mL) was added 4-(bromomethyl)-3,5-dimethylisoxazole (29 mg, 0.15 mmol) and potassium carbonate (28 mg, 0.20 mmol). The reaction was heated at 60° C. for 16 h. The reaction mixture was cooled to room temperature, concentrated and purified by chromatography (silica gel, 0-100% ethyl acetate/hexanes) to afford Example 201 (13 mg, 42%) as a white solid: $^1$H NMR (300 MHz, DMSO-d$_6$) δ 7.41-7.38 (m, 2H), 7.35-7.27 (m, 3H), 6.86 (d, J=16.0 Hz, 1H), 6.69 (d, J=16.0 Hz, 1H), 5.20 (s, 2H), 4.09 (s, 2H), 2.34 (s, 3H), 2.23 (s, 3H); ESI m/z 310 [M+H]$^+$.

88

Examples 199, 202, and 225

Preparation of Methyl 4-(1-(4-chlorobenzyl)-6-oxo-1,6-dihydropyridin-3-yl)-5-methylisoxazole-3-carboxylate (Example 199), 4-(1-(4-Chlorobenzyl)-6-oxo-1,6-dihydropyridin-3-yl)-5-methylisoxazole-3-carboxamide (Example 202) and 4-(1-(4-Chlorobenzyl)-6-oxo-1,6-dihydropyridin-3-yl)-5-methylisoxazole-3-carboxylic acid (Example 225)

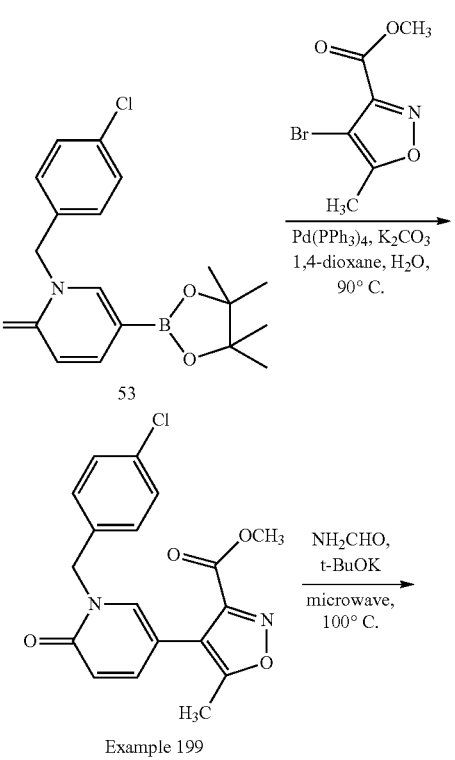

Example 199

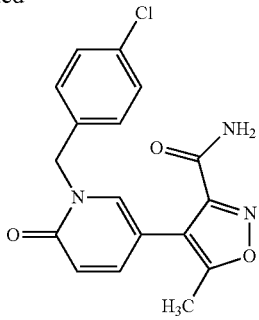

Example 202

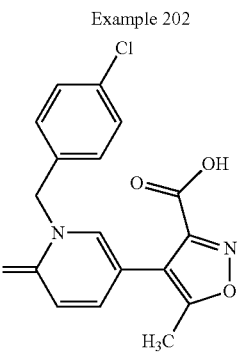

Example 199 →(LiOH, H₂O / 1,4-dioxane, rt)→ Example 225

Step 1:

To a solution of 7 (5.00 g, 28.7 mmol) in acetonitrile (200 mL) was added 1-chloro-4-(chloromethyl)benzene (5.55 g, 34.5 mmol) and potassium carbonate (7.92 g, 57.4 mmol). The reaction was heated at 75° C. for 2 h. The reaction mixture was cooled to room temperature, concentrated, and purified by chromatography (silica gel, 0-50% ethyl acetate/hexanes) to afford 52 (7.32 g, 85%) as an off-white solid: $^1$H NMR (500 MHz, CDCl₃) δ 7.20-7.40 (m, 6H), 6.53 (dd, J=1.3, 8.9 Hz, 1H), 5.05 (s, 2H); ESI m/z 298 [M+H]$^+$.

Step 2:

To a solution of 52 (4.43 g, 14.5 mmol) in 1,4-dioxane (150 mL) was added bis(pinacolato)diboron (4.41 g, 17.4 mmol), potassium acetate (2.84 g, 29.0 mmol), and [1,1'-bis(diphenylphosphino)ferrocene]dichloropalladium(II) (530 mg, 0.725 mmol). The reaction mixture was heated at 100° C. for 17 h under nitrogen atmosphere. The reaction mixture was cooled to room temperature, concentrated, and purified by chromatography (silica gel, 0-50% ethyl acetate/hexanes) to give 53 (3.72 g, 74%) as an off-white solid: $^1$H NMR (500 MHz, CDCl₃) δ 7.75 (d, J=1.7 Hz, 1H), 7.60 (dd, J=1.7, 9.1 Hz, 1H), 7.21-7.34 (m, 4H), 6.56 (d, J=9.1 Hz, 1H), 5.10 (s, 2H), 1.29 (s, 12H); ESI m/z 346 [M+H]$^+$.

Step 3:

To a solution of 53 (1.51 g, 4.36 mmol) in 1,4-dioxane (80 mL) and water (8 mL) was added methyl 4-bromo-5-methylisoxazole-3-carboxylate (800 mg, 3.64 mmol), potassium carbonate (1.01 g, 7.28 mmol), and tetrakis(triphenylphosphine)palladium(0) (210 mg, 0.182 mmol). The reaction mixture was purged with nitrogen and heated at 90° C. for 17 h. The reaction mixture was cooled to room temperature, concentrated and purified by chromatography (silica gel, 0-50% ethyl acetate/hexanes). It was further purified by reverse phase HPLC on a Polaris column eluting with 10-90% CH₃CN in H₂O to give Example 199 (140 mg, 9%) as an off-white solid: $^1$H NMR (500 MHz, DMSO-d₆) δ 7.99 (d, J=2.3 Hz, 1H), 7.50 (dd, J=2.5, 9.3 Hz, 1H), 7.33-7.47 (m, 4H), 6.47 (d, J=9.3 Hz, 1H), 5.09 (s, 2H), 3.79 (s, 3H), 2.44 (s, 3H); ESI m/z 359 [M+H]$^+$.

Step 4:

To a solution of Example 199 (50 mg, 0.14 mmol) in formamide (4 mL) was added potassium tert-butoxide (31 mg, 0.28 mmol). The reaction mixture was purged with nitrogen and heated in the microwave at 100° C. for 30 min. The reaction mixture was cooled to room temperature and treated with acetic acid (25 mg, 0.42 mmol). The mixture was purified by reverse phase HPLC on a Polaris column eluting with 10-90% CH₃CN in H₂O to give Example 202 (47 mg, 97%) as a yellow solid: $^1$H NMR (500 MHz, DMSO-d₆) δ 8.13 (s, 1H), 7.95 (d, J=2.3 Hz, 1H), 7.82 (s, 1H), 7.45 (dd, J=2.5, 9.3 Hz, 1H), 7.34-7.44 (m, 4H), 6.45 (d, J=9.3 Hz, 1H), 5.09 (s, 2H), 2.42 (s, 3H); ESI m/z 344 [M+H]$^+$.

Step 5:

To a solution of Example 199 (30 mg, 0.083 mmol) in 1,4-dioxane (4 mL) and water (1 mL) was added lithium hydroxide (8 mg, 0.3 mmol). The mixture was stirred at room temperature for 17 h and treated with acetic acid (0.5 mL). The mixture was purified by reverse phase HPLC on a Polaris column eluting with 10-90% CH₃CN in H₂O to give Example 225 (25 mg, 87%) as an off-white solid: $^1$H NMR (500 MHz, CD₃OD) δ 7.84 (d, J=2.4 Hz, 1H), 7.56 (dd, J=2.4, 9.3 Hz, 1H), 7.35 (s, 4H), 6.60 (d, J=9.3 Hz, 1H), 5.19 (s, 2H), 2.40 (s, 3H); ESI m/z 345 [M+H]$^+$.

Example 205

Preparation of 3-Amino-1-(4-chlorobenzyl)-5-(3-(hydroxymethyl)-5-methylisoxazol-4-yl)pyridin-2 (1H)-one

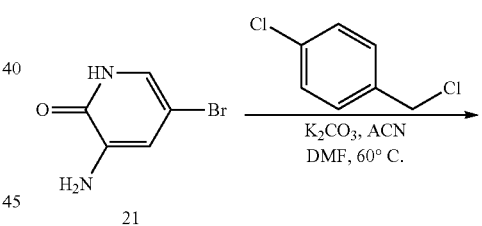

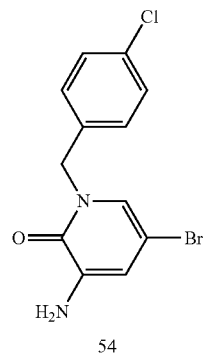

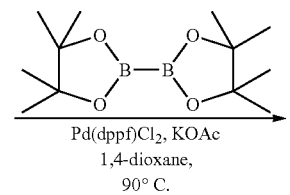

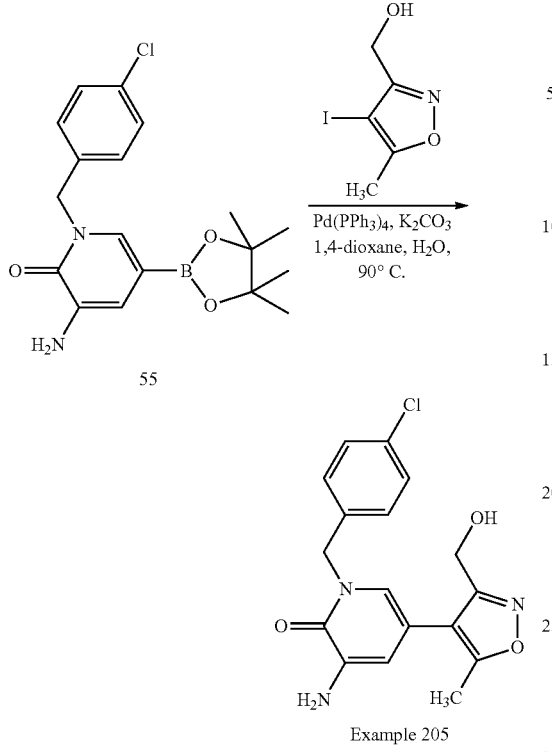

Example 205

Step 1:
To a solution of 21 (700 mg, 3.70 mmol) in acetonitrile (15 mL) and DMF (5 mL) was added 1-chloro-4-(chloromethyl)benzene (596 mg, 3.70 mmol) and potassium carbonate (1.02 g, 7.40 mmol). The reaction was heated at 60° C. for 17 h. The reaction mixture was cooled to room temperature, concentrated, and purified by chromatography (silica gel, 0-50% ethyl acetate/hexanes) to afford 54 (990 mg, 85%) as a light-brown solid: $^1$H NMR (500 MHz, CDCl$_3$) δ 7.20-7.36 (m, 4H), 6.80 (d, J=2.3 Hz, 1H), 6.54 (d, J=2.3 Hz, 1H), 5.07 (s, 2H), 4.38 (s, 2H).

Step 2:
To a solution of 54 (990 mg, 3.16 mmol) in 1,4-dioxane (40 mL) was added bis(pinacolato)diboron (1.12 g, 4.42 mmol), potassium acetate (619 mg, 6.32 mmol), and [1,1'-bis(diphenylphosphino)ferrocene]dichloropalladium(II) (115 mg, 0.158 mmol). The reaction mixture was heated at 90° C. for 17 h under nitrogen atmosphere. The reaction mixture was cooled to room temperature, concentrated, and purified by chromatography (silica gel, 0-50% ethyl acetate/hexanes) to give 55 (710 mg, 62%) as an off-white solid: $^1$H NMR (500 MHz, CDCl$_3$) δ 7.15-7.35 (m, 5H), 6.78 (d, J=1.6 Hz, 1H), 5.10 (s, 2H), 4.12 (s, 2H), 1.28 (s, 12H); ESI m/z 361 [M+H]$^+$.

Step 3:
To a solution of 55 (300 mg, 0.832 mmol) in 1,4-dioxane (15 mL) and water (1.5 mL) was added (4-iodo-5-methyl-isoxazol-3-yl)methanol (239 mg, 0.999 mmol), potassium carbonate (230 mg, 1.66 mmol), and tetrakis(triphenylphosphine)palladium(0) (48 mg, 0.042 mmol). The reaction mixture was purged with nitrogen and heated at 90° C. for 17 h. The reaction mixture was cooled to room temperature, concentrated, and purified by chromatography (silica gel, 0-50% ethyl acetate/hexanes). It was further purified by reverse phase HPLC on a Polaris column eluting with 10-90% CH$_3$CN in H$_2$O to give Example 205 (110 mg, 32%) as a gray solid: $^1$H NMR (500 MHz, DMSO-d$_6$) δ 7.32-7.45 (m, 4H), 7.19 (d, J=2.2 Hz, 1H), 6.57 (d, J=2.2 Hz, 1H), 5.43 (t, J=5.6 Hz, 1H), 5.27 (s, 2H), 5.11 (s, 2H), 4.44 (d, J=5.6 Hz, 2H), 2.38 (s, 3H); ESI m/z 346 [M+H]$^+$.

Example 218

Preparation of 5-(3,5-Dimethylisoxazol-4-yl)-1-(4-vinylbenzyl)pyridin-2(1H)-one

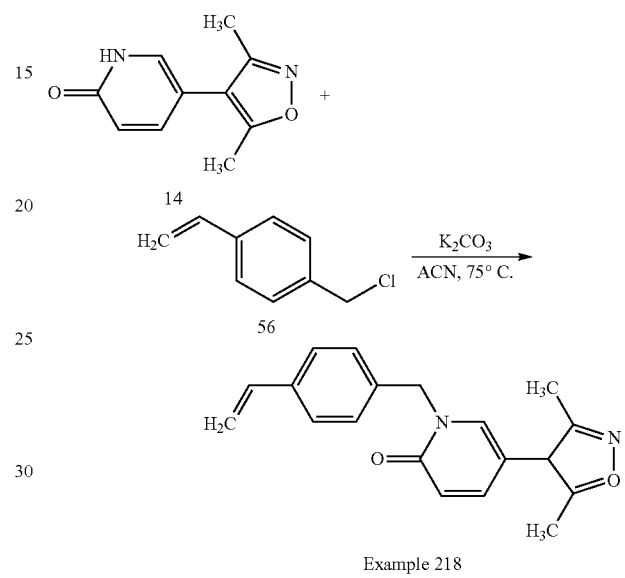

Example 218

To a solution of 14 (150 mg, 0.789 mmol) in acetonitrile (20 mL) was added 1-(chloromethyl)-4-vinylbenzene 56 (145 mg, 0.947 mmol) and potassium carbonate (327 mg, 2.37 mmol). The reaction was heated at 75° C. for 3 h. The reaction mixture was cooled to room temperature, concentrated, and purified by chromatography (silica gel, 0-100% ethyl acetate/hexanes). It was further purified by reverse phase HPLC on a Polaris column eluting with 10-90% CH$_3$CN in H$_2$O to give Example 218 (180 mg, 75%) as an off-white solid: $^1$H NMR (500 MHz, DMSO-d$_6$) δ 7.94 (d, J=2.4 Hz, 1H), 7.50 (dd, J=2.5, 9.3 Hz, 1H), 7.30-7.50 (m, 4H), 6.71 (dd, J=10.9, 17.6 Hz, 1H), 6.51 (d, J=9.3 Hz, 1H), 5.81 (dd, J=0.7, 17.6 Hz, 1H), 5.25 (dd, J=0.63, 10.9 Hz, 1H), 5.11 (s, 2H), 2.35 (s, 3H), 2.18 (s, 3H); ESI m/z 307 [M+H]$^+$.

Example 224

Preparation of 3-Amino-5-(3,5-dimethylisoxazol-4-yl)-1-methylpyridin-2(1H)-one

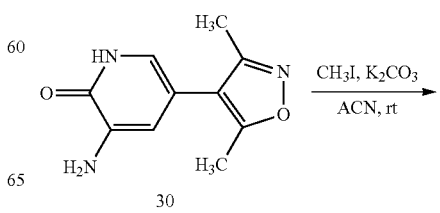

30

-continued

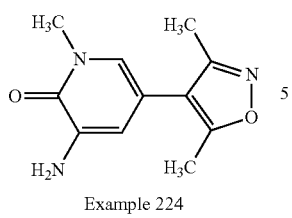

Example 224

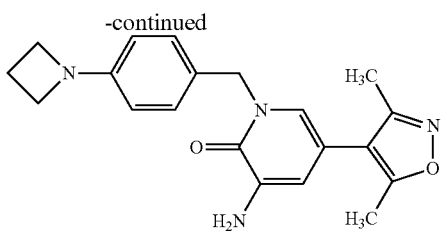

Example 237

To a mixture of 30 (100 mg, 0.488 mmol) and potassium carbonate (135 mg, 0.976 mmol) in acetonitrile (4 mL) at room temperature was added a mixture of iodomethane (69 mg, 0.488 mmol) in acetonitrile (1 mL). The mixture was stirred at room temperature overnight, concentrated, and purified by chromatography (silica gel, 0-100% ethyl acetate/hexanes). It was further purified by reverse phase HPLC on a Polaris column eluting with 10-90% CH$_3$CN in H$_2$O to give Example 224 (31 mg, 29%) as an off-white solid: $^1$H NMR (500 MHz, DMSO-d$_6$) δ 6.97 (d, J=2.2 Hz, 1H), 6.42 (d, J=2.2 Hz, 1H), 5.22 (s, 2H), 3.47 (s, 3H), 2.35 (s, 3H), 2.18 (s, 3H); ESI m/z 220 [M+H]$^+$.

Example 237

Preparation of 3-Amino-1-(4-(azetidin-1-yl)benzyl)-5-(3,5-dimethylisoxazol-4-yl)pyridin-2(1H)-one

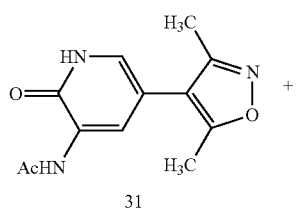

31

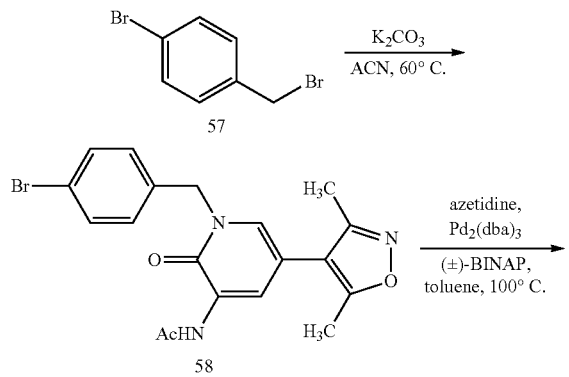

Step 1:
To a solution of 31 (1.38 g, only 50% pure, 2.79 mmol) in acetonitrile (50 mL) was added 57 (1.05 g, 4.19 mmol) and potassium carbonate (1.93 g, 14.0 mmol). The reaction was heated at 60° C. for 2 h. The reaction mixture was cooled to room temperature, concentrated, and purified by chromatography (silica gel, 0-100% ethyl acetate/hexanes) to afford 58 (1.02 g, 88%) as an off-white solid: $^1$H NMR (500 MHz, DMSO-d$_6$) δ 9.43 (s, 1H), 8.24 (d, J=2.3 Hz, 1H), 7.68 (d, J=2.3 Hz, 1H), 7.56 (d, J=8.4 Hz, 2H), 7.34 (d, J=8.4 Hz, 2H), 5.17 (s, 2H), 2.37 (s, 3H), 2.19 (s, 3H), 2.11 (s, 3H); ESI m/z 416 [M+H]$^+$.

Step 2:
To a solution of 58 (70 mg, 0.17 mmol) in toluene (5 mL) under nitrogen atmosphere was added azetidine (39 mg, 0.68 mmol), cesium carbonate (111 mg, 0.340 mmol), racemic 2,2'-bis(diphenylphosphino)-1,1'-binaphthalene (18 mg, 0.026 mmol), and tris(dibenzylideneacetone)dipalladium(0) (15 mg, 0.017 mmol). The reaction mixture was heated at 100° C. for 5 h, cooled to room temperature, and purified by chromatography (silica gel, 0-100% ethyl acetate/hexanes) to afford 59 (48 mg, 72%) as a yellow solid: $^1$H NMR (500 MHz, CDCl$_3$) δ 8.45 (s, 1H), 8.31 (d, J=2.3 Hz, 1H), 7.17 (d, J=8.5 Hz, 2H), 6.84 (d, J=2.3 Hz, 1H), 6.41 (d, J=8.5 Hz, 2H), 5.08 (s, 2H), 3.87 (t, J=7.2 Hz, 4H), 2.36 (quintet, J=7.2 Hz, 2H), 2.31 (s, 3H), 2.20 (s, 3H), 2.17 (s, 3H); ESI m/z 393 [M+H]$^+$.

Step 3:
A solution of 59 (48 mg, 0.12 mmol) and LiOH (12 mg, 0.49 mmol) in 1,4-dioxane (4 mL) and water (2 mL) was heated at 100° C. for 2 days under nitrogen. The reaction mixture was cooled to room temperature, treated with acetic acid (0.5 mL), and concentrated. The residue was purified by reverse phase HPLC on a Polaris column eluting with 10-90% CH$_3$CN in H$_2$O to give Example 237 (32 mg, 76%) as a light yellow solid: $^1$H NMR (500 MHz, DMSO-d$_6$) δ 7.23 (d, J=8.5 Hz, 2H), 7.04 (d, J=2.2 Hz, 1H), 6.04 (d, J=2.2 Hz, 1H), 6.35 (d, J=8.5 Hz, 2H), 5.23 (s, 2H), 4.98 (s, 2H), 3.74 (t, J=7.1 Hz, 4H), 2.33 (s, 3H), 2.26 (quintet, J=7.1 Hz, 2H), 2.16 (s, 3H); ESI m/z 351 [M+H]$^+$.

Example 238

Preparation of 3-Amino-5-(3,5-dimethylisoxazol-4-yl)-1-(4-morpholinobenzyl)pyridin-2(1H)-one

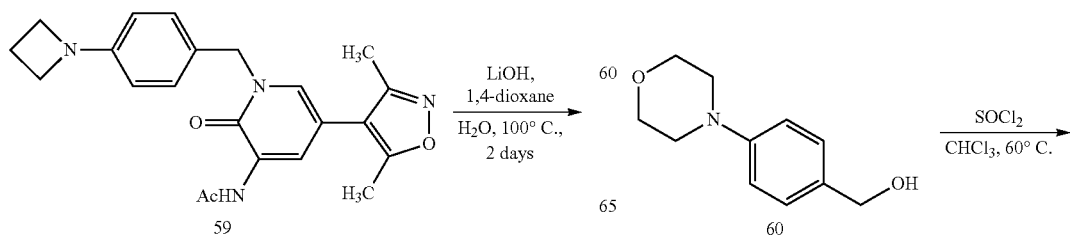

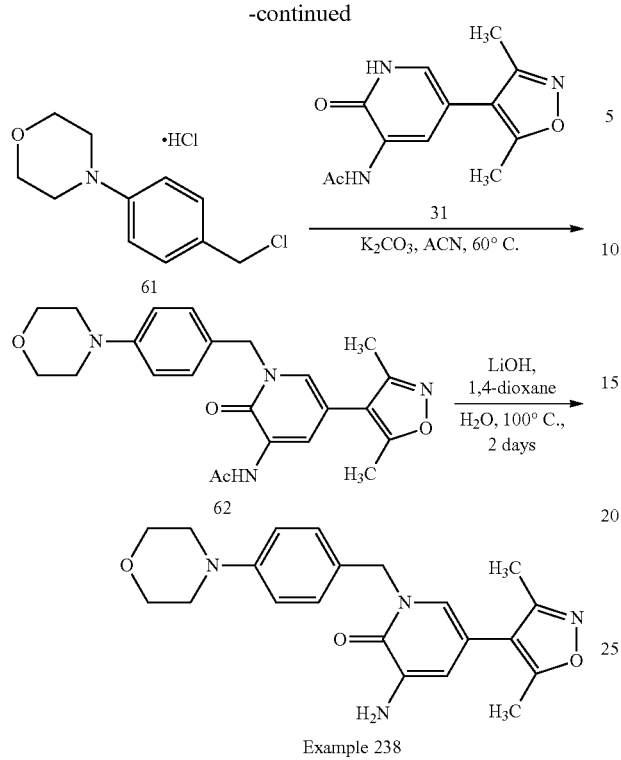

Example 238

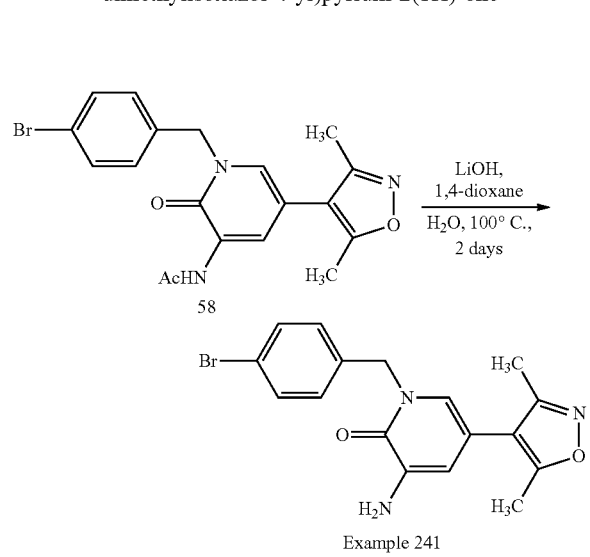

Example 241

Step 1:

To a solution of 60 (450 mg, 2.33 mmol) in chloroform (5 mL) was added thionyl chloride (1.00 mL). The mixture was heated at 60° C. for 2 h and concentrated to afford crude 61 (624 mg, >99%) as a yellow solid.

Step 2:

To a solution of N-(5-(3,5-dimethylisoxazol-4-yl)-2-oxo-1,2-dihydropyridin-3-yl)acetamide 31 (200 mg, 50% pure, 0.405 mmol) in acetonitrile (20 mL) was added 61 (201 mg, 0.810 mmol) and potassium carbonate (335 mg, 2.43 mmol). The reaction was heated at 60° C. for 17 h. The reaction mixture was cooled to room temperature, concentrated, and purified by chromatography (silica gel, 0-100% ethyl acetate/hexanes) to afford 62 (160 mg, 94%) as an off-white solid: $^1$H NMR (500 MHz, CDCl$_3$) δ 8.43 (s, 1H), 8.32 (d, J=2.2 Hz, 1H), 7.24 (d, J=8.7 Hz, 2H), 6.89 (d, J=8.7 Hz, 2H), 6.86 (d, J=2.2 Hz, 1H), 5.12 (s, 2H), 3.84 (t, J=4.9 Hz, 4H), 3.15 (t, J=4.9 Hz, 4H), 2.32 (s, 3H), 2.20 (s, 3H), 2.18 (s, 3H); ESI m/z 423 [M+H]$^+$.

Step 3:

A solution of 62 (100 mg, 0.237 mmol) and LiOH (23 mg, 0.94 mmol) in 1,4-dioxane (4 mL) and water (2 mL) was heated at 100° C. for 17 h under nitrogen. The reaction mixture was cooled at room temperature, treated with acetic acid (0.5 mL), and concentrated. The residue was purified by reverse phase HPLC on a Polaris column eluting with 10-90% CH$_3$CN in H$_2$O to give Example 238 (65 mg, 72%) as an off-white solid: $^1$H NMR (500 MHz, DMSO-d$_6$) δ 7.27 (d, J=8.7 Hz, 2H), 7.07 (d, J=2.2 Hz, 1H), 6.89 (d, J=8.7 Hz, 2H), 6.41 (d, J=2.2 Hz, 1H), 5.24 (s, 2H), 5.01 (s, 2H), 3.70 (t, J=2.2 Hz, 4H), 3.06 (t, J=4.8 Hz, 4H), 2.33 (s, 3H), 2.16 (s, 3H); ESI m/z 381 [M+H]$^+$.

Example 241

Preparation of 3-Amino-1-(4-bromobenzyl)-5-(3,5-dimethylisoxazol-4-yl)pyridin-2(1H)-one A solution of 58 (500 mg, 1.20 mmol) and LiOH (288 mg, 12.0 mmol) in 1,4-dioxane (20 mL) and water (5 mL) was heated at 100° C. for 17 h under nitrogen. The reaction mixture was cooled to room temperature, concentrated, and purified by chromatography (silica gel, 0-100% ethyl acetate/hexanes) to give Example 241 (360 mg, 80%) as a yellow solid: $^1$H NMR (500 MHz, DMSO-d$_6$) δ 7.54 (d, J=8.4 Hz, 2H), 7.31 (d, J=8.4 Hz, 2H), 7.11 (d, J=2.2 Hz, 1H), 6.45 (d, J=2.2 Hz, 1H), 5.27 (s, 2H), 5.10 (s, 2H), 2.34 (s, 3H), 2.17 (s, 3H); ESI m/z 374 [M+H]$^+$.

Example 243

Preparation of 1-(4-Chlorobenzyl)-5-(3,5-dimethylisoxazol-4-yl)-3-((2,2,2-trifluoroethyl)amino)pyridin-2(1H)-one

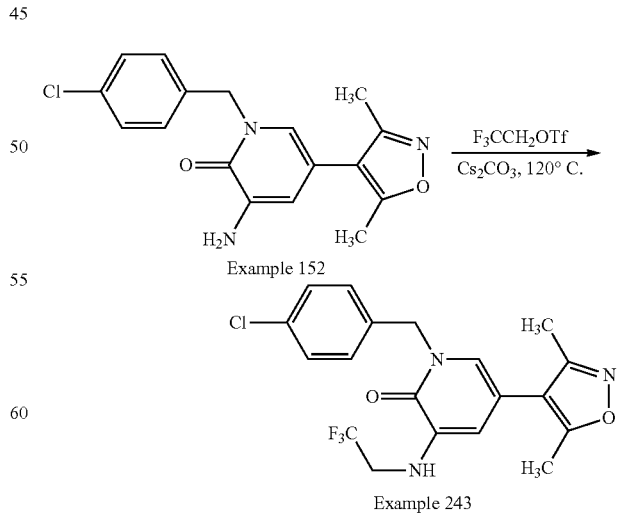

A mixture of Example 152 (50 mg, 0.15 mmol) and cesium carbonate (98 mg, 0.30 mmol) in 2,2,2-trifluoroethyl trifluoromethanesulfonate (1.5 mL) was heated at 120° C. for 8 h. The reaction mixture was cooled to room temperature, concentrated, and purified by chromatography (silica gel, 0-50% ethyl acetate/hexanes). It was further purified by reverse phase HPLC on a Polaris column eluting with 10-90% $CH_3CN$ in $H_2O$ to give Example 243 (31 mg, 50%) as an off-white solid: $^1H$ NMR (500 MHz, DMSO-$d_6$) δ 7.36-7.45 (m, 4H), 7.23 (d, J=2.1 Hz, 1H), 6.55 (d, J=1.7 Hz, 1H), 6.11 (t, J=7.1 Hz, 1H), 5.14 (s, 2H), 3.93-4.04 (m, 2H), 2.35 (s, 3H), 2.18 (s, 3H); ESI m/z 412 [M+H]$^+$.

Example 247

Preparation of 1-((1H-Indol-4-yl)methyl)-3-amino-5-(3,5-dimethylisoxazol-4-yl)pyridin-2(1H)-one

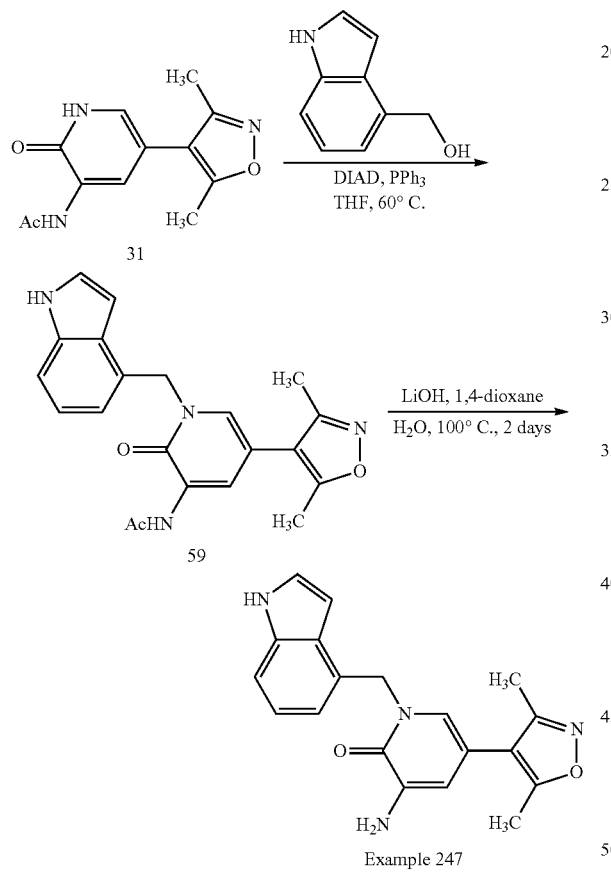

Step 1:
To a solution of 31 (700 mg, 2.83 mmol), (1H-indol-4-yl)methanol (1.25 g, 8.50 mmol), and triphenylphosphine (2.97 g, 11.3 mmol) in tetrahydrofuran (30 mL) at 60° C. under nitrogen atmosphere was added diisopropyl azodicarboxylate (1.43 g, 7.07 mmol). The mixture was cooled to room temperature, concentrated, and purified by chromatography (silica gel, 0-100% ethyl acetate/hexanes) to give crude 59 (1.94 g, contained $Ph_3PO$).

Step 2:
A solution of crude 59 (1.94 g, 5.16 mmol) and LiOH (1.24 g, 51.6 mmol) in 1,4-dioxane (30 mL) and water (30 mL) was heated at 100° C. for 17 h under nitrogen atmosphere. The reaction mixture was cooled to room temperature, concentrated and purified by chromatography (silica gel, 0-100% ethyl acetate/hexanes). It was further purified by reverse phase HPLC on a Polaris column eluting with 10-90% $CH_3CN$ in $H_2O$ to give Example 247 (285 mg, 30% over 2 steps) as an off-white solid: $^1H$ NMR (500 MHz, DMSO-$d_6$) δ 11.17 (s, 1H), 7.31-7.36 (m, 2H), 7.03 (t, J=7.3 Hz, 1H), 6.63 (d, J=2.3 Hz, 1H), 6.87 (d, J=7.0 Hz, 1H), 6.59-6.62 (m, 1H), 6.43 (d, J=2.3 Hz, 1H), 5.40 (s, 2H), 5.28 (s, 2H), 2.25 (s, 3H), 2.08 (s, 3H); ESI m/z 335 [M+H]$^+$.

Example 266

Preparation of 3-(Aminomethyl)-1-benzyl-5-(3,5-dimethylisoxazol-4-yl)pyridin-2(1H)-one

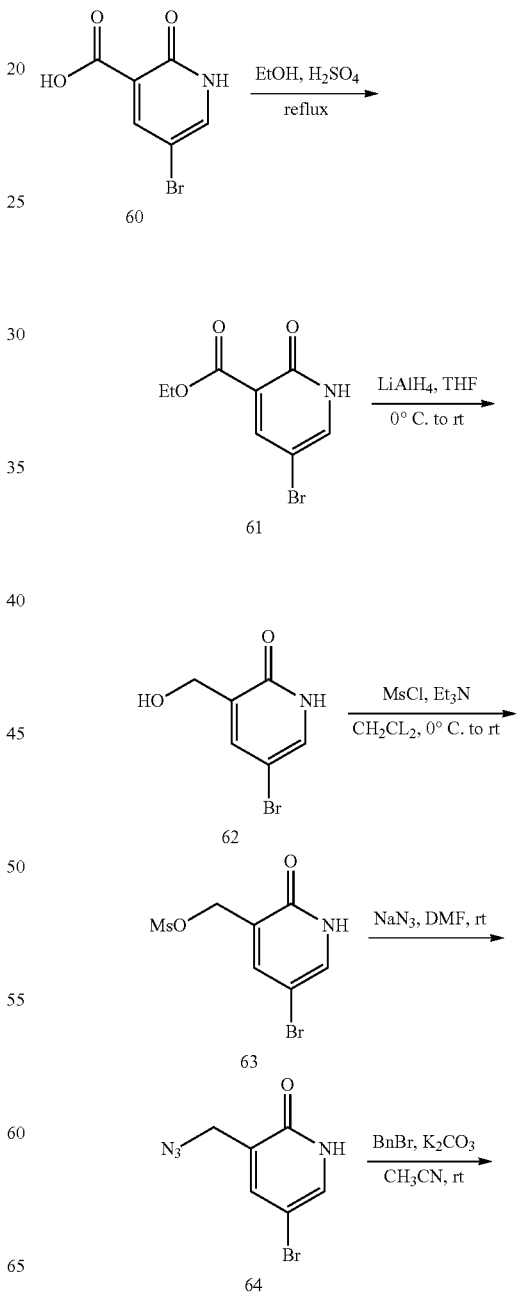

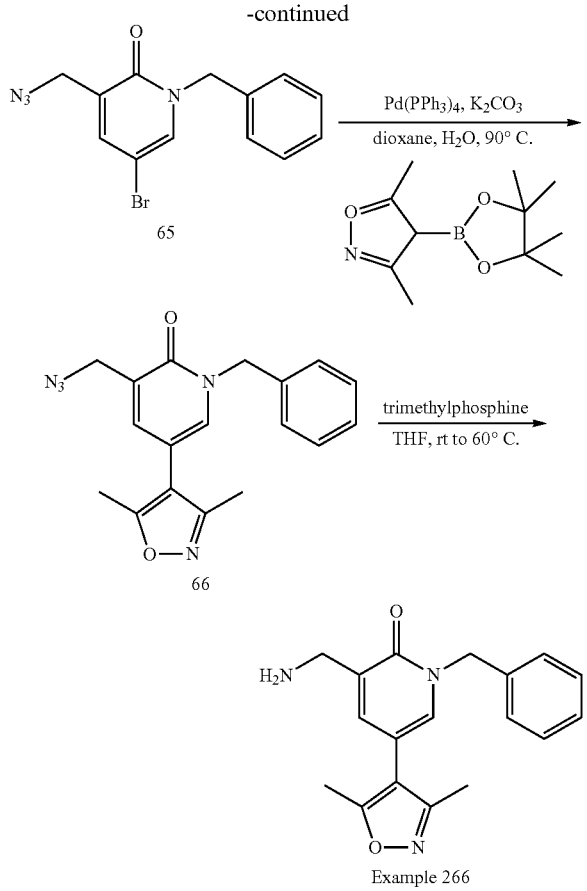

Example 266

Step 1:

A mixture of 5-bromo-2-oxo-1,2-dihydropyridine-3-carboxylic acid 60 (10 g, 45.9 mmol), $H_2SO_4$, and EtOH (225 mL) was heated at reflux for 1 hour. The solution was cooled to room temperature and concentrated. The residue was taken up in $CH_2Cl_2$ (200 mL) and washed with saturated sodium bicarbonate solution, dried over sodium sulfate and filtered. The solvent was removed and purified by silica gel chromatography (0 to 5% methanol in $CH_2Cl_2$) to provide compound 61 (8 g, 71%).

Step 2:

To a mixture of $LiAlH_4$ (300 mg, 7.93 mmol) and THF (40 mL) at 0° C. under nitrogen was slowly added a solution of ethyl 5-bromo-2-oxo-1,2-dihydropyridine-3-carboxylate 61 (1.5 g, 6.09 mmol) and THF (20 mL). After 2.5 hours, the reaction was quenched by slow addition of water. The resultant solid was removed by filtration and the filtrate was extracted with $CH_2Cl_2$ (2×100 mL). The combined extracts were dried over sodium sulfate and filtered. The solvent was removed under reduced pressure to provide compound 62 (380 mg, 28%).

Step 3:

To a suspension of 5-bromo-3-(hydroxymethyl)pyridin-2 (1H)-one 62 (350 mg, 1.72 mmol), $Et_3N$ (0.71 mL, 5.16 mmol) and $CH_2Cl_2$ (15 mL) was slowly added methanesulfonyl chloride (0.27 mL, 3.43 mmol) at 0° C. under nitrogen. The reaction mixture was allowed to warm to room temperature for 17 h and then water was added. The layers were separated and the aqueous was extracted with $CH_2Cl_2$. The organic phase was dried over sodium sulfate and filtered. The solvent was removed and the residue was purified by silica gel chromatography (eluting with 0 to 30% ethyl acetate in hexanes) to provide compound 63 (75 mg, 15%).

Step 4:

To a solution of (5-bromo-2-oxo-1,2-dihydropyridin-3-yl) methyl methanesulfonate 63 (75 mg, 0.27 mmol), and DMF (5 mL) was added sodium azide at room temperature. The mixture was stirred for 18 hours under nitrogen. The solvent was removed under reduced pressure and the residue was partitioned between water (20 mL) and ethyl acetate (20 mL). The layers were separated and the aqueous layer was extracted with ethyl acetate (20 mL). The organic layers were combined and dried over sodium sulfate and filtered. The solvent was removed under reduced pressure and the product was purified by silica gel chromatography (eluting with 0 to 70% ethyl acetate in hexanes) to provide compound 64 (34 mg, 55%).

Step 5:

To a mixture of 3-(azidomethyl)-5-bromopyridin-2(1H)-one 64 (34 mg, 0.15 mmol), $K_2CO_3$ (42 mg, 0.30 mmol) and $CH_3CN$ (5 mL) was added benzyl bromide (30 mg, 0.18 mmol) at room temperature. The reaction mixture was stirred for 18 hours and then diluted with $CH_2Cl_2$. The mixture was washed with water, dried over sodium sulfate and filtered. The solvent was removed under reduced pressure and the product was purified by silica gel chromatography (eluting with 0 to 50% ethyl acetate in hexanes) to provide compound 65 (30 mg, 63%).

Step 6:

A mixture of 3-(azidomethyl)-1-benzyl-5-bromopyridin-2(1H)-one 65 (30 mg, 0.09 mmol), 3,5-dimethyl-4-(4,4,5,5-tetramethyl-1,3,2-dioxaborolan-2-yl)-isoxazole (32 mg, 0.14 mmol), $K_2CO_3$ (25 mg, 0.18 mmol), tetrakis(triphenylphosphine)palladium(0) (12 mg, 0.01 mmol), $H_2O$ (0.5 mL) and dioxane (3 mL) was heated at 90° C. under nitrogen for 18 hours. The mixture was cooled to room temperature and adsorbed onto silica gel. The product was purified by silica gel chromatography (eluting with 0 to 50% ethyl acetate in hexanes) to provide compound 66 (9 mg, 30%).

Step 7:

To a solution of 3-(azidomethyl)-1-benzyl-5-(3,5-dimethylisoxazol-4-yl)pyridin-2(1H)-one 66 (9 mg, 0.03 mmol) and THF (1 mL) was added trimethylphosphine (1.0M in THF, 0.1 mL, 0.1 mmol) at room temperature. The mixture was heated to 60° C. for 1 hour and then concentrated. The product was purified by silica gel chromatography (eluting with 0 to 25% CMA (80% $CH_2Cl_2$, 18% methanol, 2% $NH_4OH$) in $CH_2Cl_2$) to provide Example 266 (6 mg, 67%) as a white solid: $^1H$ NMR (300 MHz, $CDCl_3$) δ 7.39-7.27 (m, 6H), 7.10 (d, J=2.5 Hz, 1H), 5.19 (s, 2H), 3.89 (s, 3H), 2.31 (s, 3H), 2.15 (s, 3H); ESI MS m/z 310 $[M+H]^+$.

Example 268

Preparation of 1-Benzyl-5-(5-oxopyrrolidin-3-yl) pyridin-2(1H)-one

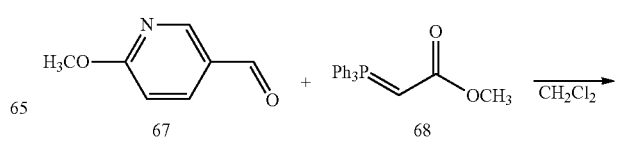

-continued

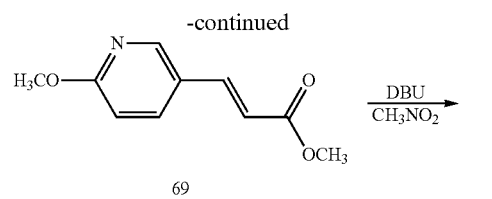

Step 2:

To a solution of 69 (280 mg, 1.45 mmol) in $CH_3NO_2$ (10 mL), DBU (0.24 mL, 1.60 mmol) was added at 0° C. The reaction mixture was stirred at 0° C. for 5 minutes, then warmed to rt for 4 h. The reaction mixture was diluted with ethyl acetate (100 mL) and washed with brine (50 mL). The organic layer was dried over sodium sulfate, filtered and concentrated. The residue was purified by chromatography (silica gel, 0-30% ethyl acetate/hexanes) to afford 70 (307 mg, 83%) as a colorless oil: $^1$H NMR (300 MHz, $CDCl_3$) δ 8.06 (d, J=2.4 Hz, 1H), 7.44 (dd, J=8.7, 2.4 Hz, 1H), 6.73 (d, J=8.7 Hz, 1H), 4.73 (dd, J=12.6, 6.9 Hz, 1H), 4.61 (dd, J=12.6, 8.1 Hz, 1H), 4.00-3.90 (m, 4H), 3.65 (s, 3H), 2.83-2.68 (m, 2H).

Step 3:

To a solution of 70 (305 mg, 1.20 mmol) in ethyl acetate (15 mL) was added $SnCl_2$ (1.08 g, 4.80 mmol) and the reaction mixture was heated to reflux for 5 h. The mixture was diluted with ethyl acetate (100 mL) and filtered. The filtrate was washed with saturated $NaHCO_3$ (100 mL). The organic layer was discarded; the aqueous layer was extracted with $CHCl_3$/i-PrOH (9/1) (4×50 mL). The combined organic layers were dried over sodium sulfate, filtered and concentrated. The residue was dissolved in MeOH (8 mL) and $K_2CO_3$ was added. The reaction mixture was heated to reflux for 2 h. The mixture was concentrated, the residue was suspended in methylene chloride (15 mL) and then filtered. The filtrate was concentrated to dryness to afford 71 (90 mg, 32%) as an off-white solid: $^1$H NMR (300 MHz, $CDCl_3$) δ 8.05 (d, J=2.4 Hz, 1H), 7.50 (dd, J=8.4, 2.4 Hz, 1H), 6.75 (d, J=8.4 Hz, 1H), 5.53 (br s, 1H), 3.93 (s, 3H), 3.81-3.62 (m, 2H), 3.36 (dd, J=8.7, 6.6 Hz, 1H), 2.73 (dd, J=16.8, 8.7 Hz, 1H), 2.43 (dd, J=16.8, 8.7 Hz, 1H).

Step 4:

A mixture of 71 (50 mg, 0.26 mmol) and benzyl bromide (0.062 mL) was heated to 120° C. for 3 h. The reaction mixture was purified by chromatography (silica gel, 0-10% methanol/methylene chloride) to afford Example 268 (15 mg, 21%) as an off-white solid: $^1$H NMR (300 MHz, $CDCl_3$) δ 7.39-7.26 (m, 6H), 7.10 (d, J=2.7 Hz, 1H), 6.67 (d, J=9.6 Hz, 1H), 5.63 (br s, 1H), 5.13 (s, 2H), 3.66 (dd, J=9.3, 9.0 Hz, 1H), 3.46-3.38 (m, 1H), 3.25 (dd, J=9.3, 7.2 Hz, 1H), 2.61 (dd, J=16.8, 9.0 Hz, 1H), 2.30 (dd, J=9.3, 8.7 Hz, 1H); ESI m/z 269 [M+H]$^+$.

Step 1:

A solution of 67 (1.37 g, 10.0 mmol) and 68 (3.34 g, 10.0 mmol) in methylene chloride (30 mL) was stirred at rt for 16 h. The reaction mixture was concentrated and the residue was purified by chromatography (silica gel, 0-30% ethyl acetate/hexanes) to afford 69 (1.75 g, 90%) as a white solid: $^1$H NMR (300 MHz, $CDCl_3$) δ 8.27 (d, J=2.4 Hz, 1H), 7.77 (dd, J=8.7, 2.4 Hz, 1H), 7.65 (d, J=15.9 Hz, 1H), 6.77 (d, J=8.7 Hz, 1H), 6.34 (d, J=15.9 Hz, 1H), 3.97 (s, 3H), 3.81 (s, 3H).

TABLE 1

Exemplary Embodiments prepared using methods described above.

| Example Number | Chemical Name | Structure | General Procedure | Analytical Data |
|---|---|---|---|---|
| 1 | 6-(3,5-dimethylisoxazol-4-yl)-2-phenethylpyridazin-3(2H)-one | 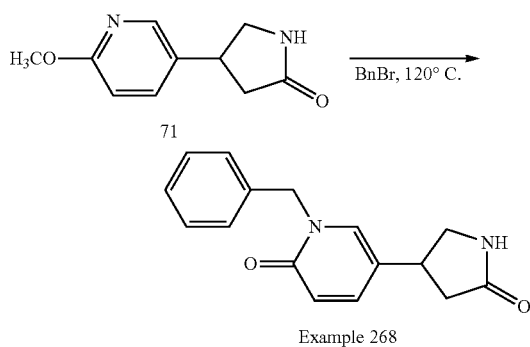 | C | 1H NMR (500 MHz, CDCl3): d 7.30-7.25 (m, 3H), 7.23-7.20 (m, 3H), 7.00 (d, J = 9.5 Hz, 1H), 4.54 (t, J = 7.5 Hz, 2H), 3.15 (t, J = 7.5 Hz, 2H), 2.41 (s, 3H), 2.27 (s, 3H). ESI MS m/z 296 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 2 | 6-(3,5-dimethylisoxazol-4-yl)-2-(pyridin-2-ylmethyl)pyridazin-3(2H)-one | 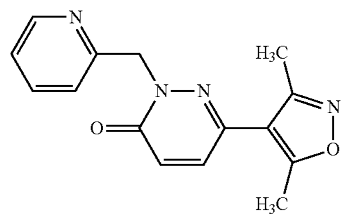 [SMILES: Cc1noc(C)c1-c1ccc(=O)n(Cc2ccccn2)n1] | C | 1H NMR (500 MHz, CDCl3): d 8.56 (d, J = 4.5 Hz, 1H), 7.66 (t, J = 7.5 Hz, 1H), 7.32 (d, J = 10 Hz, 1H), 7.27 (d, J = 7.0 Hz, 1H), 7.23-7.19 (m, 1H), 7.06 (d, J = 10 Hz, 1H), 5.52 (s, 2H), 2.45 (s, 3H), 2.28 (s, 3H). ESI MS m/z 283 [M + H]+. |
| 3 | 6-(3,5-dimethylisoxazol-4-yl)-2-(pyrimidin-2-ylmethyl)pyridazin-3(2H)-one | 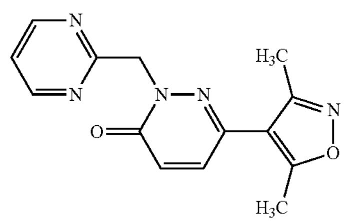 [SMILES: Cc1noc(C)c1-c1ccc(=O)n(Cc2ncccn2)n1] | C | 1H NMR (500 MHz, CDCl3): d 8.69 (d, J = 5.0 Hz, 2H), 7.36 (d, J = 9.5 Hz, 1H), 7.20 (t, J = 5.0 Hz, 1H), 7.08 (d, J = 9.5 Hz, 1H), 5.64 (s, 2H), 2.47 (s, 3H), 2.30 (s, 3H). ESI MS m/z 284 [M + H]+. |
| 4 | 5-(3,5-dimethylisoxazol-4-yl)-1-(3-(trifluoromethyl)benzyl)pyridin-2(1H)-one | 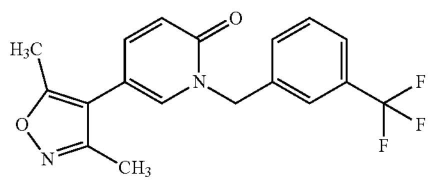 [SMILES: Cc1noc(C)c1-c1ccc(=O)n(Cc2cccc(C(F)(F)F)c2)c1] | D | 1H NMR (500 MHz, DMSO-d6): d 8.02 (d, J = 2.5 Hz, 1H), 7.76 (s, 1H), 7.68-7.52 (m, 3H), 7.50 (d, J = 3.0 Hz, 1H), 6.52 (d, J = 9.5 Hz, 1H), 5.21 (s, 2H), 2.36 (s, 3H), 2.19 (s, 3H). ESI MS m/z 349 [M + H]+. |
| 5 | 5-(3,5-dimethylisoxazol-4-yl)-1-(4-(trifluoromethoxy)benzyl)pyridin-2(1H)-one | 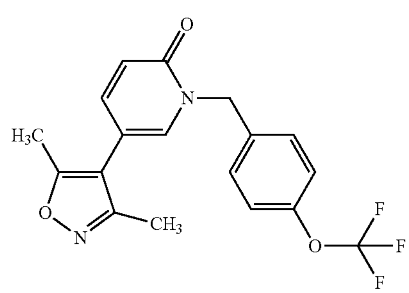 [SMILES: Cc1noc(C)c1-c1ccc(=O)n(Cc2ccc(OC(F)(F)F)cc2)c1] | D | 1H NMR (500 MHz, DMSO-d6): d 7.95 (d, J = 2.5 Hz, 1H), 7.53-7.45 (m, 3H), 7.36 (d, J = 8.0 Hz, 2H), 6.51 (d, J = 9.5 Hz, 1H), 5.21 (s, 2H), 2.36 (s, 3H), 2.19 (s, 3H). ESI MS m/z 365 [M + H]+. |
| 6 | 1-benzyl-5-(3,5-dimethylisoxazol-4-yl)pyrazin-2(1H)-one | 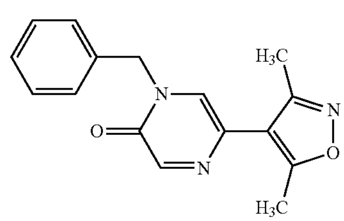 | D | 1H NMR (500 MHz, DMSO-d6): d 8.14 (d, J = 1.0 Hz, 1H), 7.95 (d, J = 1.0 Hz, 1H), 7.42-7.30 (m, 5H), 5.14 (s, 2H), 2.24 (s, 3H), 2.26 (s, 3H). ESI MS m/z 282 [M + H]+. |
| 7 | 5-(3,5-dimethylisoxazol-4-yl)-1-(4-(trifluoromethyl)benzyl)pyridin-2(1H)-one | 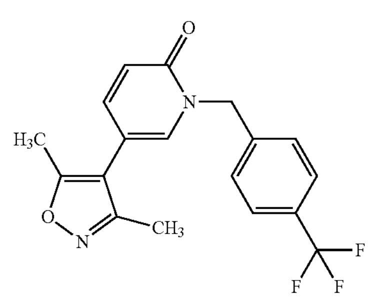 [SMILES: Cc1noc(C)c1-c1ccc(=O)n(Cc2ccc(C(F)(F)F)cc2)c1] | D | 1H NMR (500 MHz, DMSO-d6): δ 7.98 (d, J = 2.5 Hz, 1H), 7.73 (d, J = 8.0 Hz, 2H), 7.56-7.51 (m, 3H), 6.53 (d, J = 9.0 Hz, 1H), 5.23 (s, 2H), 2.37 (s, 3H), 2.20 (s, 3H). ESI MS m/z 349 [M + H]+. |

TABLE 1-continued

Exemplary Embodiments prepared using methods described above.

| Example Number | Chemical Name | Structure | General Procedure | Analytical Data |
|---|---|---|---|---|
| 8 | 1-benzyl-5-(3,5-dimethylisoxazol-4-yl)pyrimidin-2(1H)-one | 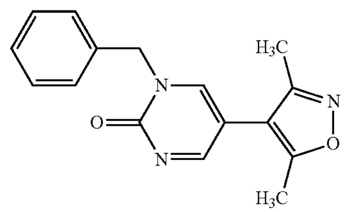 [SMILES: Cc1noc(C)c1-c1cnc(=O)n(Cc2ccccc2)c1] | D | 1H NMR (500 MHz, DMSO-d6): δ 8.64 (d, J = 3.0 Hz, 1H), 8.50 (d, J = 3.0 Hz, 1H), 7.40-7.34 (m, 5H), 5.10 (s, 2H), 2.39 (s, 3H), 2.21 (s, 3H). ESI MS m/z 282 [M + H]+. |
| 9 | 1-(4-((dimethylamino)methyl)benzyl)-5-(3,5-dimethylisoxazol-4-yl)pyridin-2(1H)-one | 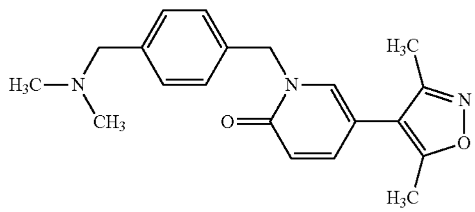 [SMILES: Cc1noc(C)c1-c1ccc(=O)n(Cc2ccc(CN(C)C)cc2)c1] | G | 1H NMR (500 MHz, DMSO-d6): δ 10.17 (br s, 1H), 7.94 (d, J = 2.5 Hz, 1H), 7.53-7.50 (m, 3H), 7.42 (d, J = 8.2 Hz, 2H), 6.52 (d, J = 9.4 Hz, 1H), 5.17 (s, 2H), 4.24 (d, J = 5.5 Hz, 2H), 2.68 (s, 3H), 2.67 (s, 3H), 2.36 (s, 3H), 2.19 (s, 3H). ESI MS m/z 338 [M + H]+. |
| 10 | 5-(3,5-dimethylisoxazol-4-yl)-1-(piperidin-4-ylmethyl)pyridin-2(1H)-one | 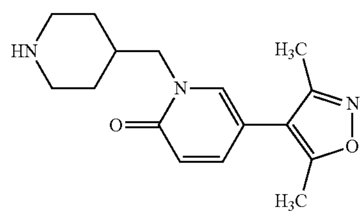 [SMILES: Cc1noc(C)c1-c1ccc(=O)n(CC2CCNCC2)c1] | G | 1H NMR (500 MHz, DMSO-d6): δ 8.69 (br d, J = 7.0 Hz, 1H), 8.42 (br s, 1H), 7.76 (d, J = 2.4 Hz, 1H), 7.49 (dd, J = 9.3, 2.5 Hz, 1H), 6.49 (d, J = 9.3 Hz, 1H), 3.86 (d, J = 7.1 Hz, 2H), 3.27-3.25 (m, 2H), 2.84-2.82 (m, 2H), 2.37 (s, 3H), 2.20 (s, 3H), 2.15-2.03 (m, 1H), 1.71-1.69 (m, 2H), 1.43-1.40 (m, 2H). ESI MS m/z 288 [M + H]+. |
| 11 | 5-(3,5-dimethylisoxazol-4-yl)-1-((3,5-dimethylisoxazol-4-yl)methyl)pyridin-2(1H)-one | 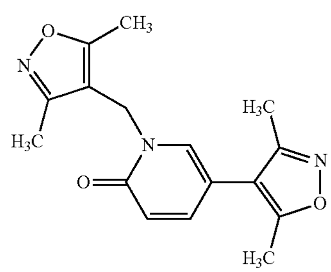 [SMILES: Cc1noc(C)c1Cn1cc(-c2c(C)noc2C)ccc1=O] | G | 1H NMR (500 MHz, CDCl3): δ 7.23 (dd, J = 9.4, 2.5 Hz, 1H), 7.04 (d, J = 2.4 Hz, 1H), 6.67 (d, J = 9.4 Hz, 1H), 4.91 (s, 2H), 2.48 (s, 3H), 2.32 (s, 3H), 2.24 (s, 3H), 2.18 (s, 3H). ESI MS m/z 300 [M + H]+. |
| 12 | 1-benzyl-5-(3,5-dimethylisoxazol-4-yl)-4-methylpyridin-2(1H)-one | 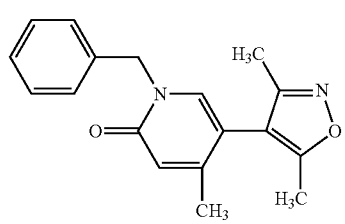 [SMILES: Cc1cc(=O)n(Cc2ccccc2)cc1-c1c(C)noc1C] | G | 1H NMR (500 MHz, CDCl3) δ 7.37-7.28 (m, 5H), 7.00 (s, 1H), 6.56 (s, 1H), 5.15 (s, 2H), 2.20 (s, 3H), 2.05 (s, 3H), 1.95 (s, 3H). ESI MS m/z 295 [M + H]+. |
| 13 | 4-((5-(3,5-dimethylisoxazol-4-yl)-2-oxopyridin-1(2H)-yl)methyl)benzamide | 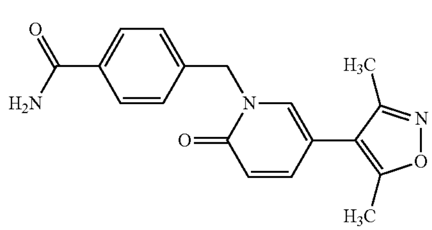 [SMILES: Cc1noc(C)c1-c1ccc(=O)n(Cc2ccc(C(N)=O)cc2)c1] | G | 1H NMR (500 MHz, DMSO-d6) δ 7.94 (d, J = 2.5 Hz, 1H), 7.93 (s, 1H), 7.84 (d, J = 8.3 Hz, 2H), 7.51 (dd, J = 9.4, 2.5 hz, 1H), 7.39 (d, J = 8.3 Hz, 2H), 7.33 (s, 1H), 6.52 (d, J = 9.4 Hz, 1H), 5.18 (s, 2H), 2.36 (s, 3H), 2.19 (s, 3H). ESI MS m/z 324 [M + H]+. |

TABLE 1-continued

Exemplary Embodiments prepared using methods described above.

| Example Number | Chemical Name | Structure | General Procedure | Analytical Data |
|---|---|---|---|---|
| 14 | 2-benzyl-6-(3,5-dimethylisoxazol-4-yl)pyridazin-3(2H)-one | 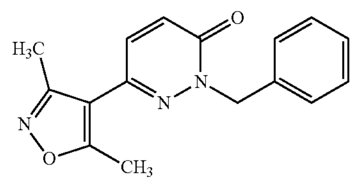 [SMILES: Cc1noc(C)c1-c1ccc(=O)n(Cc2ccccc2)n1] | A | 1H NMR (300 MHz, CDCl3) δ 7.48-7.40 (m, 2H), 7.40-7.27 (m, 4H), 7.02 (d, J = 9.6 Hz, 1H), 5.36 (s, 2H), 2.46 (s, 3H), 2.32 (s, 3H); ESI m/z 282 [M + H]+. |
| 15 | 3-((6-oxo-3-(3,4,5-trimethoxyphenyl)pyridazin-1(6H)-yl)methyl)benzonitrile | 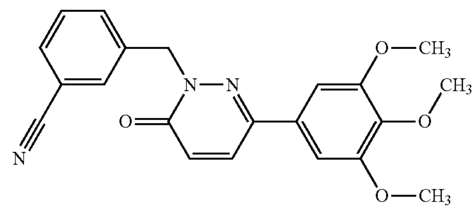 [SMILES: COc1cc(-c2ccc(=O)n(Cc3cccc(C#N)c3)n2)cc(OC)c1OC] | C | 1H NMR (300 MHz, CDCl3) δ 7.78-7.70 (m, 2H), 7.67 (d, J = 9.6 Hz, 1H), 7.63-7.57 (m, 1H), 7.46 (q, J = 7.8 Hz, 1H), 7.04 (d, J = 9.9 Hz, 1H), 6.96 (s, 2H), 5.42 (s, 2H), 3.94 (s, 6H), 3.90 (s, 3H); ESI m/z 378 [M + H]+. |
| 16 | 4-((6-oxo-3-(3,4,5-trimethoxyphenyl)pyridazin-1(6H)-yl)methyl)benzonitrile | 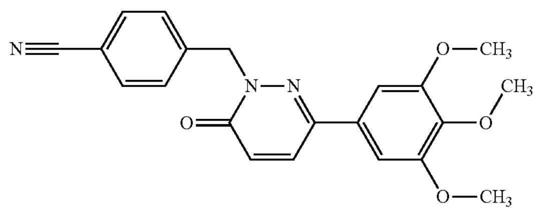 [SMILES: COc1cc(-c2ccc(=O)n(Cc3ccc(C#N)cc3)n2)cc(OC)c1OC] | C | 1H NMR (300 MHz, CDCl3) δ 7.70-7.60 (m, 3H), 7.58-7.52 (m, 2H), 7.04 (d, J = 9.9 Hz, 1H), 6.95 (s, 2H), 5.44 (s, 2H), 3.93 (s, 6H), 3.09 (s, 3H); ESI m/z 378 [M + H]+. |
| 17 | N-(3-((6-oxo-3-(3,4,5-trimethoxyphenyl)pyridazin-1(6H)-yl)methyl)phenyl)acetamide | 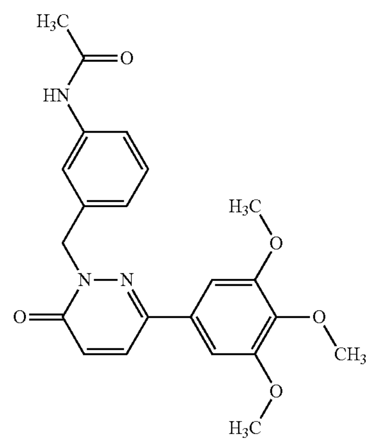 [SMILES: COc1cc(-c2ccc(=O)n(Cc3cccc(NC(C)=O)c3)n2)cc(OC)c1OC] | C | 1H NMR (300 MHz, DMSO-d6) δ 9.96 (s, 1H), 8.15 (d, J = 9.9 Hz, 1H), 7.63 (s, 1H), 7.49 (d, J = 9.3 Hz, 1H), 7.26 (t, J = 8.1 Hz, 1H), 7.16 (s, 2H), 7.09 (d, J = 9.6 Hz, 1H), 7.04 (d, J = 7.8 Hz, 1H), 5.28 (s, 2H), 3.85 (s, 6H), 3.70 (s, 3H), 2.00 (s, 3H); ESI m/z 410 [M + H]+. |
| 18 | 5-(3,5-dimethylisoxazol-4-yl)-1-(quinoxalin-6-ylmethyl)pyridin-2(1H)-one | 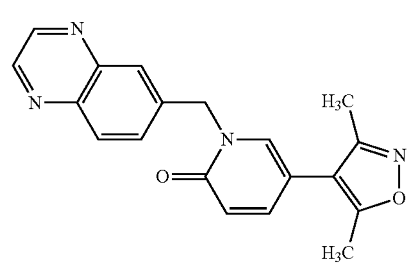 [SMILES: Cc1noc(C)c1-c1ccc(=O)n(Cc2ccc3nccnc3c2)c1] | E | 1H NMR (500 MHz, CDCl3) δ 8.86-8.85 (m, 2H); 8.15-8.11 (m, 1H), 7.96 (d, J = 1.2 Hz, 1H); 7.98 (dd, J = 9.5, 2.0 Hz, 1H); 7.29 (dd, J = 9.5, 2.5 Hz, 1H); 7.23 (d, J = 2.3 Hz, 1H); 6.75 (d, J = 9.5 Hz, 1H); 5.43 (s, 2H); 2.32 (s, 3H); 2.18 (s, 3H); ESI MS m/z 333 [M + H]+. |
| 19 | 6-(3,5-dimethylisoxazol-4-yl)-2-(1-phenylethyl)pyridazin-3(2H)-one | 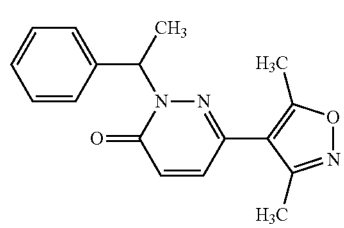 [SMILES: Cc1noc(C)c1-c1ccc(=O)n(C(C)c2ccccc2)n1] | A | 1H NMR (300 MHz, DMSO-d6) δ 7.65 (d, J = 9.6 Hz, 1H), 7.38-7.22 (m, 5H), 7.06 (d, J = 9.6 Hz, 1H), 6.27 (q, J = 7.5 Hz, 1H), 2.46 (s, 3H), 2.25 (s, 3H), 1.71 (d, J = 7.2 Hz, 3H); ESI m/z 296 [M + H]+. |

TABLE 1-continued

Exemplary Embodiments prepared using methods described above.

| Example Number | Chemical Name | Structure | General Procedure | Analytical Data |
|---|---|---|---|---|
| 20 | 2-benzyl-4-methyl-6-(5-methylisoxazol-4-yl)pyridazin-3(2H)-one | 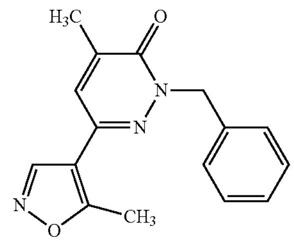 [SMILES: Cc1oncc1-c1cc(C)c(=O)n(Cc2ccccc2)n1] | A | 1H NMR (300 MHz, DMSO-d6) δ 8.98 (d, J = 0.6 Hz, 1H), 7.76 (d, J = 1.2 Hz, 1H), 7.40-7.24 (m, 5H), 5.29 (s, 2H), 2.59 (d, J = 0.3 Hz, 3H), 2.15 (d, J = 1.2 Hz, 3H); ESI m/z 282 [M + H]+. |
| 21 | 2-benzyl-6-(3,5-dimethylisoxazol-4-yl)-4-methylpyridazin-3(2H)-one | 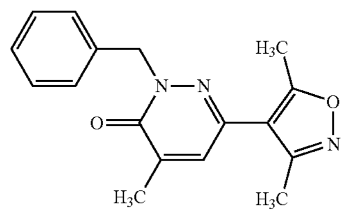 [SMILES: Cc1noc(C)c1-c1cc(C)c(=O)n(Cc2ccccc2)n1] | A | 1H NMR (300 MHz, DMSO-d6) δ 7.56 (d, J = 1.5 Hz, 1H), 7.38-7.25 (m, 5H), 5.30 (s, 2H), 2.47 (s, 3H), 2.26 (s, 3H), 2.16 (d, J = 1.2 Hz, 3H); ESI m/z 296 [M + H]+. |
| 22 | 6-(3,5-dimethylisoxazol-4-yl)-2-(3-fluorobenzyl)pyridazin-3(2H)-one | 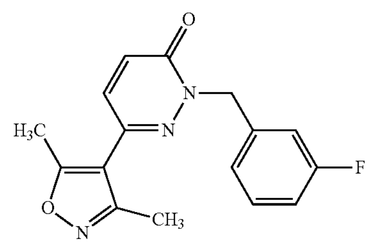 [SMILES: Cc1noc(C)c1-c1ccc(=O)n(Cc2cccc(F)c2)n1] | C | 1H NMR (300 MHz, DMSO-d6) δ 7.68 (d, J = 9.6 Hz, 1H), 7.46-7.35 (m, 1H), 7.22-7.06 (m, 4H), 5.31 (s, 2H), 2.47 (s, 3H), 2.26 (s, 3H); ESI m/z 300 [M + H]+. |
| 23 | 2-(3-chlorobenzyl)-6-(3,5-dimethylisoxazol-4-yl)pyridazin-3(2H)-one | 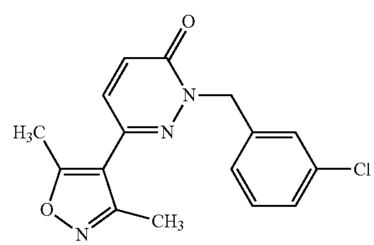 [SMILES: Cc1noc(C)c1-c1ccc(=O)n(Cc2cccc(Cl)c2)n1] | C | 1H NMR (300 MHz, DMSO-d6) δ 7.69 (d, J = 9.6 Hz, 1H), 7.46-7.28 (m, 4H), 7.11 (d, J = 9.6 Hz, 1H), 5.30 (s, 2H), 2.47 (s, 3H), 2.26 (s, 3H); ESI m/z 316 [M + H]+. |
| 24 | 2-((3-(3,5-dimethylisoxazol-4-yl)-6-oxopyridazin-1(6H)-yl)methyl)benzonitrile | 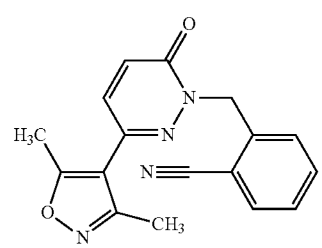 [SMILES: Cc1noc(C)c1-c1ccc(=O)n(Cc2ccccc2C#N)n1] | C | 1H NMR (300 MHz, DMSO-d6) δ 7.93-7.85 (m, 1H), 7.76-7.64 (m, 2H), 7.57-7.46 (m, 2H), 7.13 (d, J = 9.6 Hz, 1H), 5.49 (s, 2H), 2.43 (s, 3H), 2.18 (s, 3H); ESI m/z 307 [M + H]+. |
| 25 | 2-(4-chlorobenzyl)-6-(3,5-dimethylisoxazol-4-yl)pyridazin-3(2H)-one | 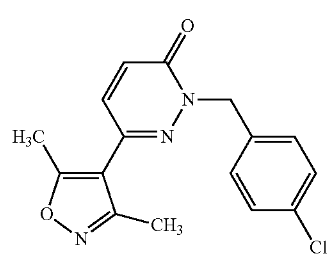 [SMILES: Cc1noc(C)c1-c1ccc(=O)n(Cc2ccc(Cl)cc2)n1] | C | 1H NMR (300 MHz, DMSO-d6) δ 7.68 (d, J = 9.6 Hz, 1H), 7.48-7.34 (m, 4H), 7.09 (d, J = 9.9 Hz, 1H), 5.29 (s, 2H), 2.47 (s, 3H), 2.26 (s, 3H); ESI m/z 316 [M + H]+. |

TABLE 1-continued

Exemplary Embodiments prepared using methods described above.

| Example Number | Chemical Name | Structure | General Procedure | Analytical Data |
|---|---|---|---|---|
| 26 | 2-(2-chlorobenzyl)-6-(3,5-dimethylisoxazol-4-yl)pyridazin-3(2H)-one | 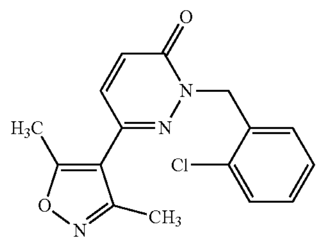 [SMILES: Cc1noc(C)c1-c1ccc(=O)n(Cc2ccccc2Cl)n1] | C | 1H NMR (300 MHz, DMSO-d6) δ 7.70 (d, J = 9.9 Hz, 1H), 7.53-7.47 (m, 1H), 7.40-7.25 (m, 3H), 7.13 (d, J = 9.6 Hz, 1H), 5.39 (s, 2H), 2.38 (s, 3H), 2.12 (s, 3H); ESI m/z 316 [M + H]+. |
| 27 | 5-(3,5-dimethylisoxazol-4-yl)-1-(2-fluorobenzyl)pyridin-2(1H)-one | 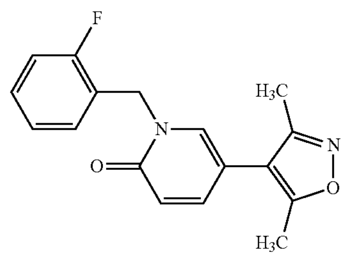 [SMILES: Cc1noc(C)c1-c1ccc(=O)n(Cc2ccccc2F)c1] | D | 1H NMR (300 MHz, DMSO-d6) δ 7.88 (d, J = 2.4 Hz, 1H), 7.54 (dd, J = 9.3 Hz, 2.7 Hz, 1H), 7.41-7.30 (m, 1H), 7.29-7.14 (m, 3H), 6.51 (d, J = 9.3 Hz, 1H), 5.18 (s, 2H), 2.20 (s, 3H), 1.99 (s, 3H); ESI m/z 299 [M + H]+. |
| 28 | 6-(3,5-dimethylisoxazol-4-yl)-2-(2-methylbenzyl)pyridazin-3(2H)-one | 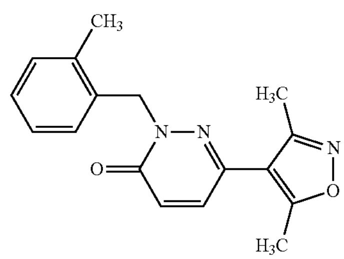 [SMILES: Cc1ccccc1Cn1nc(-c2c(C)noc2C)ccc1=O] | C | 1H NMR (300 MHz, DMSO-d6) δ 7.69 (d, J = 9.0 Hz, 1H), 7.25-7.06 (m, 5H), 5.31 (s, 2H), 2.40 (s, 3H), 2.31 (s, 3H), 2.15 (s, 3H); ESI m/z 296 [M + H]+. |
| 29 | 6-(3,5-dimethylisoxazol-4-yl)-2-(4-methylbenzyl)pyridazin-3(2H)-one | 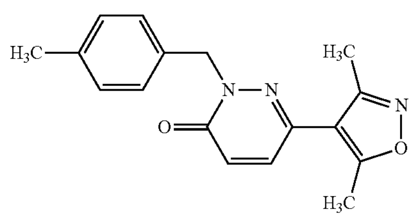 [SMILES: Cc1ccc(Cn2nc(-c3c(C)noc3C)ccc2=O)cc1] | C | 1H NMR (300 MHz, DMSO-d6) δ 7.66 (d, J = 9.6 Hz, 1H), 7.25 (d, J = 8.1 Hz, 2H), 7.15 (d, J = 7.8 Hz, 2H), 7.07 (d, J = 9.9 Hz, 1H), 5.24 (s, 2H), 2.47 (s, 3H), 2.27 (s, 3H), 2.26 (s, 3H); ESI m/z 296 [M + H]+. |
| 30 | 6-(3,5-dimethylisoxazol-4-yl)-2-(3-methylbenzyl)pyridazin-3(2H)-one | 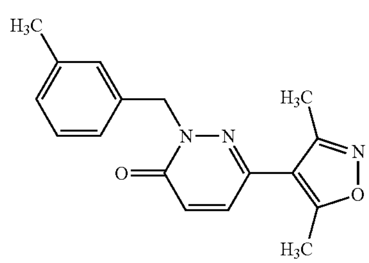 [SMILES: Cc1cccc(Cn2nc(-c3c(C)noc3C)ccc2=O)c1] | C | 1H NMR (300 MHz, DMSO-d6) ? 7.66 (d, J = 9.6 Hz, 1H), 7.28-7.04 (m, 5H), 5.25 (s, 2H), 2.47 (s, 3H), 2.28 (s, 3H), 2.26 (s, 3H); ESI m/z 296 [M + H]+. |
| 31 | 6-(3,5-dimethylisoxazol-4-yl)-2-(3-(trifluoromethyl)benzyl)pyridazin-3(2H)-one | 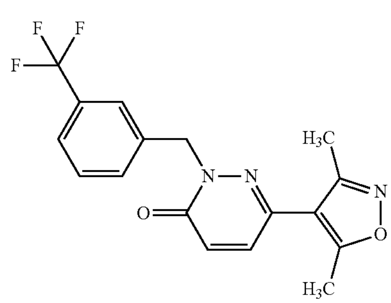 [SMILES: Cc1noc(C)c1-c1ccc(=O)n(Cc2cccc(C(F)(F)F)c2)n1] | C | 1H NMR (300 MHz, DMSO-d6) δ 7.75-7.58 (m, 5H), 7.11 (d, J = 9.6 Hz, 1H), 5.40 (s, 2H), 2.46 (s, 3H), 2.24 (s, 3H); ESI m/z 350 [M + H]+. |

TABLE 1-continued

Exemplary Embodiments prepared using methods described above.

| Example Number | Chemical Name | Structure | General Procedure | Analytical Data |
|---|---|---|---|---|
| 32 | 6-(3,5-dimethylisoxazol-4-yl)-2-(3-fluoro-5-methylbenzyl)pyridazin-3(2H)-one | 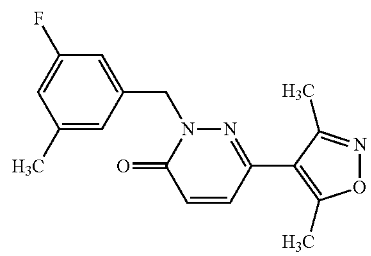 [SMILES: Cc1cc(F)cc(Cn2nc(-c3c(C)noc3C)ccc2=O)c1] | C | 1H NMR (300 MHz, DMSO-d6) δ 7.68 (d, J = 9.6 Hz, 1H), 7.10 (d, J = 9.6 Hz, 1H), 7.04-6.92 (m, 3H), 5.26 (s, 2H), 2.47 (s, 3H), 2.29 (s, 3H), 2.26 (s, 3H); ESI m/z 314 [M + H]+. |
| 33 | 6-(3,5-dimethylisoxazol-4-yl)-2-(4-methoxybenzyl)pyridazin-3(2H)-one | 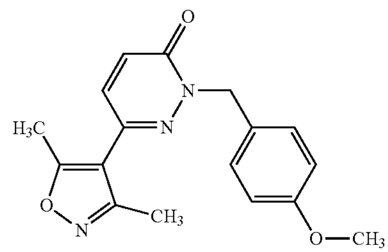 | C | 1H NMR (300 MHz, DMSO-d6) δ 7.64 (d, J = 9.6 Hz, 1H), 7.31 (d, J = 8.8 Hz, 2H), 7.06 (d, J = 9.6 Hz, 1H), 6.90 (d, J = 9.0 Hz, 2H), 5.22 (s, 2H), 3.72 (s, 3H), 2.47 (s, 3H), 2.27 (s, 3H); ESI m/z 312 [M + H]+. |
| 34 | 6-(3,5-dimethylisoxazol-4-yl)-2-(1-(2-(trifluoromethyl)phenyl)ethyl)pyridazin-3(2H)-one | 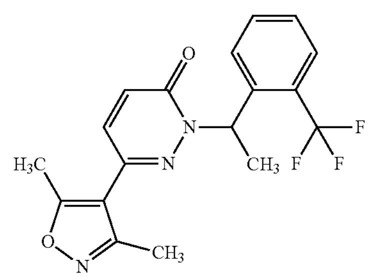 [SMILES: Cc1noc(C)c1-c1ccc(=O)n(C(C)c2ccccc2C(F)(F)F)n1] | C | 1H NMR (300 MHz, DMSO-d6) δ 7.78-7.61 (m, 4H), 7.53 (t, J = 7.5 Hz, 1H), 7.04 (d, J = 9.9 Hz, 1H), 6.41 (q, J = 6.9 Hz, 1H), 2.40 (s, 3H), 2.15 (s, 3H), 1.72 (d, J = 6.9 Hz, 3H); ESI m/z 364 [M + H]+. |
| 35 | 6-(3,5-dimethylisoxazol-4-yl)-2-(3-methoxybenzyl)pyridazin-3(2H)-one | 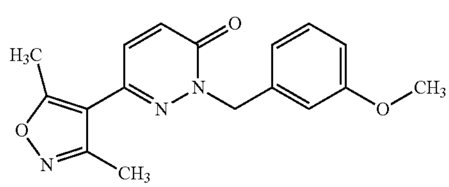 | C | 1H NMR (300 MHz, DMSO-d6) δ 7.67 (d, J = 9.6 Hz, 1H), 7.27 (t, J = 7.8 Hz, 1H), 7.09 (d, J = 9.6 Hz, 1H), 6.94-6.84 (m, 3H), 5.26 (s, 2H), 3.73 (s, 3H), 2.47 (s, 3H), 2.27 (s, 3H); ESI m/z 312 [M + H]+. |
| 36 | 6-(3,5-dimethylisoxazol-4-yl)-2-(3-(trifluoromethoxy)benzyl)pyridazin-3(2H)-one | 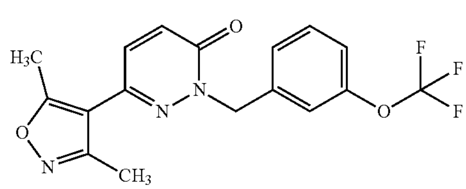 [SMILES: Cc1noc(C)c1-c1ccc(=O)n(Cc2cccc(OC(F)(F)F)c2)n1] | C | 1H NMR (300 MHz, DMSO-d6) δ 7.69 (d, J = 9.6 Hz, 1H), 7.48 (t, J = 7.8 Hz, 1H), 7.41-7.28 (m, 3H), 7.11 (d, J = 9.6 Hz, 1H), 5.35 (s, 2H), 2.46 (s, 3H), 2.24 (s, 3H); ESI m/z 366 [M + H]+. |
| 37 | 6-(3,5-dimethylisoxazol-4-yl)-2-((tetrahydro-2H-pyran-4-yl)methyl)pyridazin-3(2H)-one | 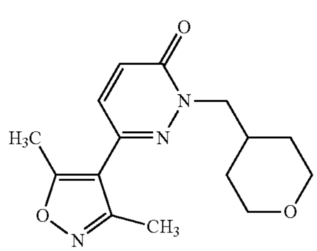 [SMILES: Cc1noc(C)c1-c1ccc(=O)n(CC2CCOCC2)n1] | C | 1H NMR (300 MHz, DMSO-d6) δ 7.65 (d, J = 9.6 Hz, 1H), 7.05 (d, J = 9.6 Hz, 1H), 4.00 (d, J = 7.5 Hz, 2H), 3.90-3.78 (m, 2H), 3.30-3.19 (m, 2H), 2.49 (s, 3H), 2.32 (s, 3H), 2.24-2.05 (m, 1H), 1.50-1.43 (m, 2H), 1.37-1.20 (m, 2H); ESI m/z 290 [M + H]+. |

TABLE 1-continued

Exemplary Embodiments prepared using methods described above.

| Example Number | Chemical Name | Structure | General Procedure | Analytical Data |
|---|---|---|---|---|
| 38 | 5-(3,5-dimethylisoxazol-4-yl)-1-(1-(2-(trifluoromethyl)phenyl)ethyl)pyridin-2(1H)-one | 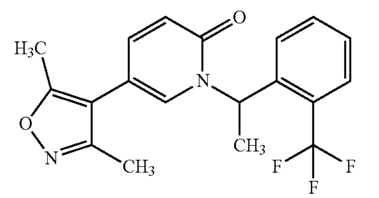 [SMILES: Cc1noc(C)c1-c1ccc(=O)n(C(C)c2ccccc2C(F)(F)F)c1] | D | 1H NMR (300 MHz, DMSO-d6) δ 7.85-7.66 (m, 3H), 7.63-7.54 (m, 1H), 7.52-7.47 (m, 2H), 6.48 (d, J = 10.2 Hz, 1H), 6.36-6.25 (s, 1H), 2.23 (s, 3H), 2.06 (s, 3H), 1.72 (d, J = 6.9 Hz, 3H); ESI m/z 363 [M + H]+. |
| 39 | 6-(3,5-dimethylisoxazol-4-yl)-2-(2-(trifluoromethoxy)benzyl)pyridazin-3(2H)-one | 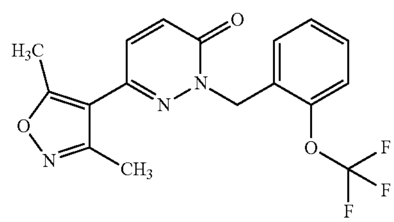 [SMILES: Cc1noc(C)c1-c1ccc(=O)n(Cc2ccccc2OC(F)(F)F)n1] | C | 1H NMR (300 MHz, DMSO-d6) δ 7.68 (d, J = 9.6 Hz, 1H), 7.53-7.33 (m, 4H), 7.12 (d, J = 9.9 Hz, 1H), 5.38 (s, 2H), 2.39 (s, 3H), 2.12 (s, 3H); ESI m/z 366 [M + H]+. |
| 40 | 5-(3,5-dimethylisoxazol-4-yl)-1-(2-(trifluoromethoxy)benzyl)pyridin-2(1H)-one | 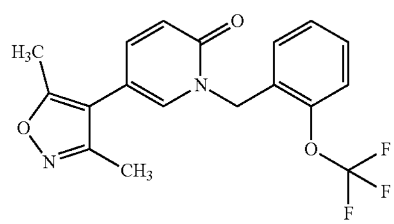 [SMILES: Cc1noc(C)c1-c1ccc(=O)n(Cc2ccccc2OC(F)(F)F)c1] | D | 1H NMR (300 MHz, DMSO-d6) δ 7.83 (d, J = 2.4 Hz, 1H), 7.56 (dd, J = 9.3 Hz, 2.7 Hz, 1H), 7.50-7.34 (m, 3H), 7.13 (d, J = 7.5 Hz, 1H), 6.54 (d, J = 9.3 Hz, 1H), 5.22 (s, 2H), 2.36 (s, 3H), 2.19 (s, 3H); ESI m/z 365 [M + H]+. |
| 41 | 5-(3,5-dimethylisoxazol-4-yl)-1-(4-methylbenzyl)pyridin-2(1H)-one | 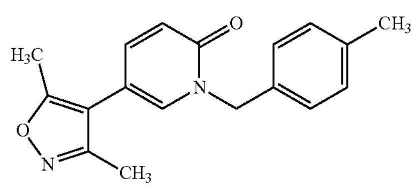 [SMILES: Cc1ccc(Cn2cc(-c3c(C)noc3C)ccc2=O)cc1] | D | 1H NMR (300 MHz, DMSO-d6) ? 7.91 (d, J = 2.4 Hz, 1H), 7.48 (dd, J = 9.5 Hz, 2.4 Hz, 1H), 7.26 (d, J = 8.1 Hz, 2H), 7.15 (d, J = 8.1 Hz, 2H), 6.49 (d, J = 9.3 Hz, 1H), 5.07 (s, 2H), 2.35 (s, 3H), 2.27 (s, 3H), 2.18 (s, 3H); ESI m/z 295 [M + H]+. |
| 42 | 5-(3,5-dimethylisoxazol-4-yl)-1-(3-fluorobenzyl)pyridin-2(1H)-one | 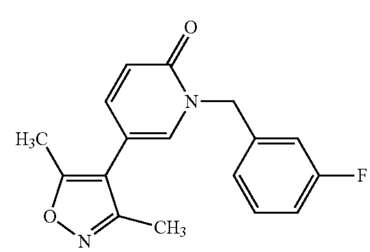 [SMILES: Cc1noc(C)c1-c1ccc(=O)n(Cc2cccc(F)c2)c1] | D | 1H NMR (300 MHz, DMSO-d6) ? 7.96 (d, J = 2.1 Hz, 1H), 7.52 (dd, J1 = 6.6 Hz, J2 = 2.7 Hz, 1H), 7.46-7.36 (m, 1H), 7.24-7.06 (m, 3H), 7.96 (d, J = 2.1 Hz, 1H), 5.14 (s, 2H), 2.36 (s, 3H), 2.19 (s, 3H); ESI m/z 299 [M + H]+. |
| 43 | 5-(3,5-dimethylisoxazol-4-yl)-1-(1-phenylpropyl)pyridin-2(1H)-one | 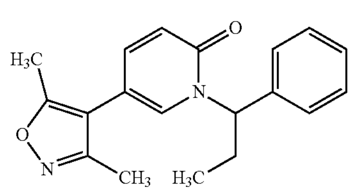 [SMILES: CCC(c1ccccc1)n1cc(-c2c(C)noc2C)ccc1=O] | D | 1H NMR (300 MHz, DMSO-d6) ? 7.71 (d, J = 2.4 Hz, 1H), 7.48-7.26 (m, 6H), 6.51 (d, J = 9.6 Hz, 1H), 6.00 (t, J = 8.1 Hz, 1H), 2.30-2.17 (m, 5H), 2.12 (s, 3H), 0.85 (t, J = 7.2 Hz, 3H); ESI m/z 309 [M + H]+. |

TABLE 1-continued

Exemplary Embodiments prepared using methods described above.

| Example Number | Chemical Name | Structure | General Procedure | Analytical Data |
|---|---|---|---|---|
| 44 | 5-(3,5-dimethylisoxazol-4-yl)-1-(pyridin-3-ylmethyl)pyridin-2(1H)-one | 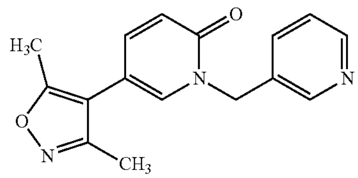 [SMILES: Cc1noc(C)c1-c1ccc(=O)n(Cc2cccnc2)c1] | D | 1H NMR (300 MHz, DMSO-d6) δ 8.63 (d, J = 1.5 Hz, 1H), 8.50 (dd, J = 4.8 Hz, 1.8 Hz, 1H), 8.02 (d, J = 2.1 Hz, 1H), 7.77 (dt, J = 7.8 Hz, 2.1 Hz, 1H), 7.52 (dd, J = 9.3 Hz, 2.7 Hz, 1H), 7.43-7.35 (m, 1H), 6.51 (d, J = 9.3 Hz, 1H), 5.16 (s, 2H), 2.37 (s, 3H), 2.20 (s, 3H); ESI m/z 282 [M + H]+. |
| 45 | 2-(cyclopropylmethyl)-6-(3,5-dimethylisoxazol-4-yl)pyridazin-3(2H)-one | 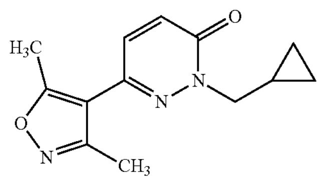 [SMILES: Cc1noc(C)c1-c1ccc(=O)n(CC2CC2)n1] | C | 1H NMR (300 MHz, DMSO-d6) δ 7.66 (d, J = 9.6 Hz, 1H), 7.05 (d, J = 9.6 Hz, 1H), 3.97 (d, J = 7.2 Hz, 2H), 2.43 (s, 3H), 2.33 (s, 3H), 1.36-1.19 (m, 1H), 0.57-0.47 (m, 2H), 0.42-0.33 (m, 2H); ESI m/z 246 [M + H]+. |
| 46 | 5-(3,5-dimethylisoxazol-4-yl)-1-((6-methylpyridin-2-yl)methyl)pyridin-2(1H)-one | 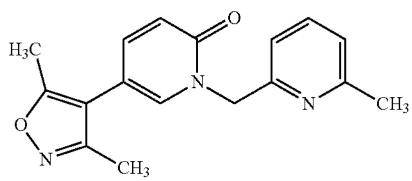 [SMILES: Cc1cccc(Cn2cc(-c3c(C)noc3C)ccc2=O)n1] | D | 1H NMR (300 MHz, DMSO-d6) δ 7.89 (d, J = 2.4 Hz, 1H), 7.66 (t, J = 9.0 Hz, 1H), 7.53 (dd, J = 9.3 Hz, 2.7 Hz, 1H), 7.17 (d, J = 8.1 Hz, 1H), 7.00 (d, J = 8.1 Hz, 1H), 6.50 (d, J = 9.3 Hz, 1H), 5.17 (s, 2H), 2.43 (s, 3H), 2.40 (s, 3H), 2.22 (s, 3H); ESI m/z 296 [M + H]+. |
| 47 | 5-(3,5-dimethylisoxazol-4-yl)-1-(quinolin-8-ylmethyl)pyridin-2(1H)-one | 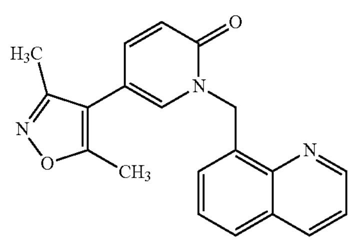 [SMILES: Cc1noc(C)c1-c1ccc(=O)n(Cc2cccc3cccnc23)c1] | D | 1H NMR (300 MHz, DMSO-d6) δ 9.01 (dd, J = 4.2 Hz, 1.8 Hz, 1H), 8.44 (dd, J = 8.2 Hz, 1.5 Hz, 1H), 8.02 (d, J = 2.3 Hz, 1H), 7.96 (dd, J = 8.7 Hz, 1.4 Hz, 1H), 7.66-7.51 (m, 3H), 7.42 (d, J = 7.3 Hz, 1H), 6.55 (d, J = 9.6 Hz, 1H), 5.75 (s, 2H), 2.33 (s, 3H), 2.17 (s, 3H); ESI m/z 332 [M + H]+. |
| 48 | 1-(cyclopropylmethyl)-5-(3,5-dimethylisoxazol-4-yl)pyridin-2(1H)-one | 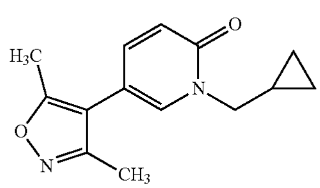 | D | 1H NMR (300 MHz, DMSO-d6) δ 7.81 (d, J = 2.4 Hz, 1H), 7.48 (dd, J = 9.6 Hz, 2.4 Hz, 1H), 6.48 (d, J = 9.6 Hz, 1H), 3.77 (d, J = 7.2 Hz, 2H), 2.38 (s, 3H), 2.21 (s, 3H), 1.32-1.18 (m, 1H), 0.57-0.35 (m, 4H); ESI m/z 245 [M + H]+. |
| 49 | 1-(cyclobutylmethyl)-5-(3,5-dimethylisoxazol-4-yl)pyridin-2(1H)-one | 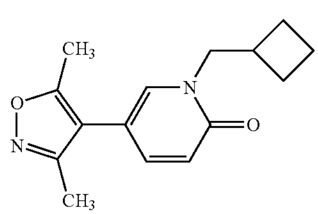 [SMILES: Cc1noc(C)c1-c1ccc(=O)n(CC2CCC2)c1] | G | 1H NMR (300 MHz, DMSO-d6) δ 7.77 (d, J = 2.1 Hz, 1H), 7.45 (dd, J = 9.3 Hz, 2.7 Hz, 1H), 6.46 (d, J = 9.0 Hz, 1H), 3.95 (d, J = 7.5 Hz, 2H), 2.77-2.64 (m, 1H), 2.36 (s, 3H), 2.19 (s, 3H), 2.01-1.71 (m, 6H); ESI m/z 259 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 50 | 1-(3-(difluoromethyl)benzyl)-5-(3,5-dimethylisoxazol-4-yl)pyridin-2(1H)-one | 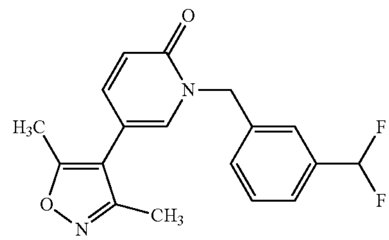 [SMILES: Cc1noc(C)c1-c1ccc(=O)n(Cc2cccc(C(F)F)c2)c1] | G | 1H NMR (300 MHz, DMSO-d6) δ 7.99 (d, J = 2.1 Hz, 1H), 7.57 (s, 1H), 7.55-7.47 (m, 4H), 7.04 (q, J = 55.8, 1H), 6.52 (d, J = 9.3 Hz, 1H), 5.19 (s, 2H), 2.36 (s, 3H), 2.19 (s, 3H); ESI m/z 331 [M + H]+. |
| 51 | 5-(3,5-dimethylisoxazol-4-yl)-1-(2-phenoxyethyl)pyridin-2(1H)-one | 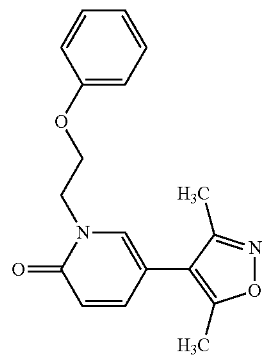 [SMILES: Cc1noc(C)c1-c1ccc(=O)n(CCOc2ccccc2)c1] | G | 1H NMR (300 MHz, DMSO-d6) δ 7.81 (d, J = 2.4 Hz, 1H), 7.50 (dd, J = 10.8 Hz, 2.4 Hz, 1H), 7.27 (q, J = 8.4, 2H), 6.97-6.87 (m, 3H), 6.50 (d, J = 9.3 Hz, 1H), 4.29 (dd, J = 14.1 Hz, 4.5 Hz, 4H), 2.37 (s, 3H), 2.20 (s, 3H); ESI m/z 311 [M + H]+. |
| 52 | 1-benzyl-5-(3,4,5-trimethoxyphenyl)pyridin-2(1H)-one | 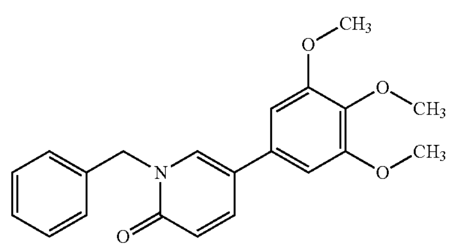 [SMILES: COc1cc(-c2ccc(=O)n(Cc3ccccc3)c2)cc(OC)c1OC] | D | 1H NMR (300 MHz, CDCl3) δ 7.58 (dd, J = 2.4, 9.6 Hz, 1H); 7.41 (d, J = 2.1 Hz, 1H); 7.33-7.37 (m, 5H); 6.72 (d, J = 9.6 Hz, 1H); 6.51 (s, 2H); 5.23 (s, 2H); 3.88 (s, 6H); 3.85 (s, 3H); ESI MS m/z 352 [M + H]+. |
| 53 | 2-((2-oxo-5-(3,4,5-trimethoxyphenyl)pyridin-1(2H)-yl)methyl)benzonitrile | 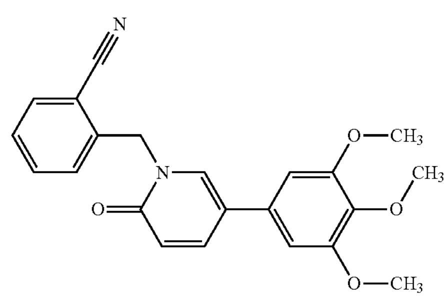 [SMILES: COc1cc(-c2ccc(=O)n(Cc3ccccc3C#N)c2)cc(OC)c1OC] | D | 1H NMR (300 MHz, CDCl3) δ 7.83 (d, J = 2.4 Hz, 1H); 7.58-7.76 (m, 4H); 7.41-7.46 (m, 1H); 6.68 (d, J = 9.6 Hz, 1H); 6.64 (s, 2H); 5.38 (s, 2H); 3.91 (s, 6H); 3.87 (s, 3H); ESI MS m/z 377 [M + H]+. |
| 54 | 2-benzyl-6-((3,4,5-trimethoxyphenyl)amino)pyridazin-3(2H)-one | 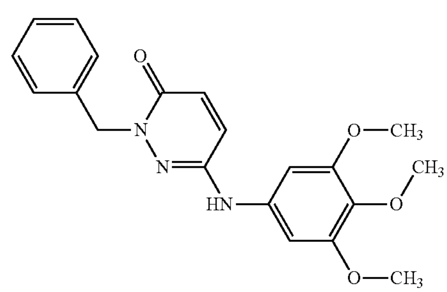 [SMILES: COc1cc(Nc2ccc(=O)n(Cc3ccccc3)n2)cc(OC)c1OC] | B | 1H NMR (300 MHz, CDCl3) δ 7.29-7.42 (m, 5H); 6.92 (s, 2H); 6.59 (s, 2H); 6.02 (s, 1H); 5.26 (s, 2H); 3.80 (s, 3H); 3.74 (s, 6H); ESI MS m/z 368 [M + H]+. |

TABLE 1-continued

Exemplary Embodiments prepared using methods described above.

| Example Number | Chemical Name | Structure | General Procedure | Analytical Data |
|---|---|---|---|---|
| 55 | 1-((5-chloropyridin-2-yl)methyl)-5-(3,5-dimethylisoxazol-4-yl)pyridin-2(1H)-one | 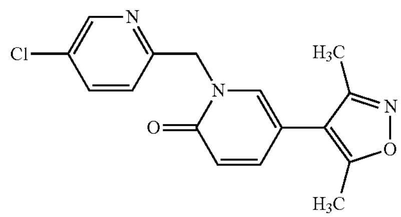 [SMILES: Cc1noc(C)c1-c1ccc(=O)n(Cc2ccc(Cl)cn2)c1] | G | 1H NMR (300 MHz, DMSO-d6) δ 8.57 (dd, J = 2.6 Hz, 0.6 Hz, 1H), 7.93 (dd, J = 8.3 Hz, 2.4 Hz, 1H), 7.88 (d, J = 5.0 Hz, 1H), 7.54 (dd, J = 9.4 Hz, 2.6 Hz, 1H), 7.35 (d, J = 8.6 Hz, 1H), 6.50 (d, J = 9.5 Hz, 1H), 5.24 (s, 2H), 2.38 (s, 3H), 2.21 (s, 3H); ESI m/z 316 [M + H]+. |
| 56 | 1-benzyl-5-(3,5-dimethylisoxazol-4-yl)pyridin-2(1H)-one | 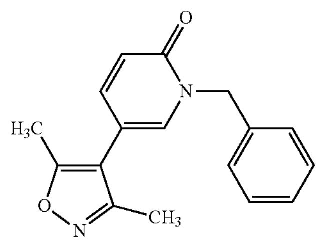 [SMILES: Cc1noc(C)c1-c1ccc(=O)n(Cc2ccccc2)c1] | D | 1H NMR (300 MHz, CDCl3) δ 7.31-7.41 (m, 5H); 7.25 (dd, J = 2.7, 9.3 Hz, 1H); 7.13 (d, J = 2.4 Hz, 1H); 6.76 (d, J = 9.3 Hz, 1H); 5.20 (s, 2H); 2.29 (s, 3H); 2.15 (s, 3H); ESI MS m/z 281 [M + H]+. |
| 57 | 1-benzyl-5-(5-methylisoxazol-4-yl)pyridin-2(1H)-one | 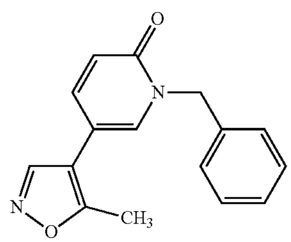 [SMILES: Cc1oncc1-c1ccc(=O)n(Cc2ccccc2)c1] | D | 1H NMR (300 MHz, CDCl3) δ 8.17 (s, 1H); 7.34-7.39 (m, 6H); 7.23 (d, J = 2.4 Hz, 1H); 6.71 (d, J = 9.3 Hz, 1H); 5.19 (s, 2H); 2.40 (s, 3H); ESI MS m/z 267 [M + H]+. |
| 58 | 1-benzyl-5-(isoxazol-4-yl)pyridin-2(1H)-one | 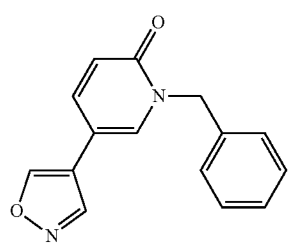 [SMILES: O=c1ccc(-c2cnoc2)cn1Cc1ccccc1] | D | 1H NMR (300 MHz, CDCl3) δ 8.50 (s, 1H); 8.34 (s, 1H); 7.32-7.44 (m, 7H); 6.72 (dd, J = 1.2, 9.0 Hz, 1H); 5.20 (s, 2H); ESI MS m/z 253 [M + H]+. |
| 59 | 1-benzyl-5-(isothiazol-4-yl)pyridin-2(1H)-one | 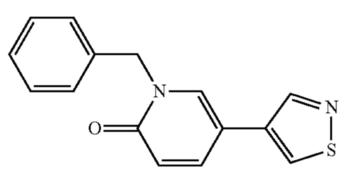 [SMILES: O=c1ccc(-c2cnsc2)cn1Cc1ccccc1] | D | 1H NMR (300 MHz, CDCl3) δ 8.54 (s, 1H); 8.50 (s, 1H); 7.57 (dd, J = 2.4, 9.3 Hz, 1H); 7.53 (d, J = 2.1 Hz, 1H); 7.33-7.40 (m, 5H); 6.76 (d, J = 9.3 Hz, 1H); 5.20 (s, 2H); ESI MS m/z 269 [M + H]+. |
| 60 | 2-benzyl-6-((3,4-dimethoxyphenyl)amino)pyridazin-3(2H)-one | 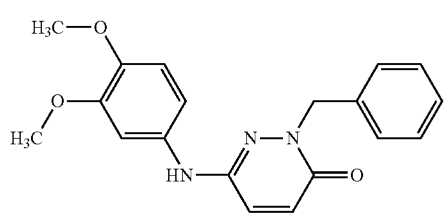 | B | 1H NMR (300 MHz, CDCl3) δ 7.41-7.44 (m, 2H); 7.28-7.36 (m, 4H); 6.91-6.98 (m, 3H); 6.76-6.82 (m, 2H); 5.24 (s, 2H); 3.87 (s, 3H); 3.77 (s, 3H); ESI MS m/z 338 [M + H]+. |

TABLE 1-continued

Exemplary Embodiments prepared using methods described above.

| Example Number | Chemical Name | Structure | General Procedure | Analytical Data |
|---|---|---|---|---|
| 61 | 2-benzyl-6-((3,5-dimethylisoxazol-4-yl)amino)pyridazin-3(2H)-one | 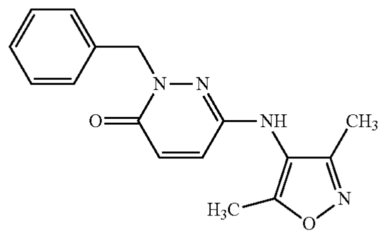 [SMILES: Cc1noc(C)c1Nc1ccc(=O)n(Cc2ccccc2)n1] | B | 1H NMR (300 MHz, CDCl3) δ 7.29-7.39 (m, 5H); 6.98-7.01 (m, 1H); 6.76-6.79 (m, 1H); 5.14 (s, 2H); 2.25 (s, 3H); 2.06 (s, 3H); ESI MS m/z 297 [M + H]+. |
| 62 | 1-benzyl-2'-hydroxy-[3,4'-bipyridin]-6(1H)-one | 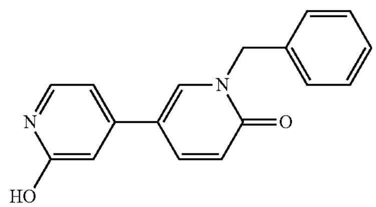 [SMILES: O=c1ccc(-c2ccnc(O)c2)cn1Cc1ccccc1] | F | 1H NMR (300 MHz, CDCl3) δ 7.56-7.62 (m, 2H); 7.33-7.40 (m, 7H); 6.73 (d, J = 9.3 Hz, 1H); 6.57 (s, 1H); 6.33 (d, J = 7.2 Hz, 1H); 5.21 (s, 2H); ESI MS m/z 279 [M + H]+. |
| 63 | 1-benzyl-5-(3,5-dimethylisoxazol-4-yl)-3-fluoropyridin-2(1H)-one | 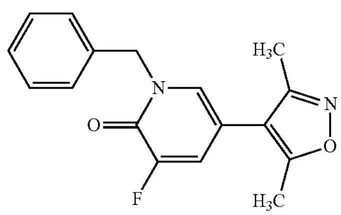 | D | 1H NMR (300 MHz, CDCl3) δ 7.33-7.40 (m, 5H); 7.01 (dd, J = 2.1, 9.6 Hz, 1H); 6.94 (d, J = 2.1 Hz, 1H); 5.23 (s, 2H); 2.29 (s, 3H); 2.15 (s, 3H); ESI MS m/z 299 [M + H]+. |
| 64 | 1-benzyl-3-chloro-5-(3,5-dimethylisoxazol-4-yl)pyridin-2(1H)-one | 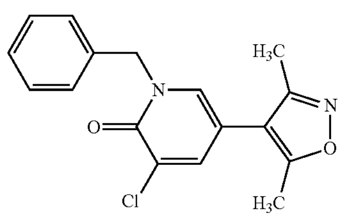 [SMILES: Cc1noc(C)c1-c1cc(Cl)c(=O)n(Cc2ccccc2)c1] | D | 1H NMR (300 MHz, CDCl3) δ 7.43 (d, J = 2.4 Hz, 1H); 7.35-7.38 (m, 5H); 7.09 (d, J = 2.4 Hz, 1H); 5.23 (s, 2H); 2.29 (s, 3H); 2.15 (s, 3H); ESI MS m/z 315 [M + H]+. |
| 65 | 1-benzyl-5-((3,4-dimethoxyphenyl)amino)pyridin-2(1H)-one | 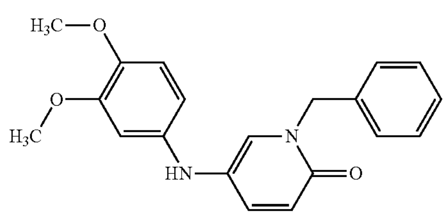 | B | 1H NMR (300 MHz, DMSO-d6) δ 7.49 (d, J = 2.7 Hz, 1H); 7.24-7.38 (m, 7H); 6.75 (d, J = 8.4 Hz, 1H); 6.45 (d, J = 9.6 Hz, 1H); 6.38 (d, J = 2.4 Hz, 1H); 6.21 (dd, J = 2.4, 8.4 Hz, 1H); 5.09 (s, 2H); 3.64 (s, 3H); 3.61 (s, 3H); ESI MS m/z 337 [M + H]+. |
| 66 | 1-benzyl-5-(3,5-dimethylisoxazol-4-yl)-3-methylpyridin-2(1H)-one | 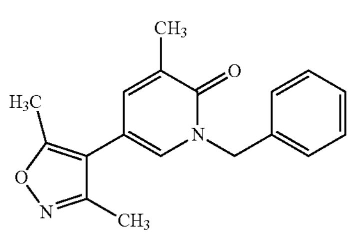 [SMILES: Cc1noc(C)c1-c1cc(C)c(=O)n(Cc2ccccc2)c1] | D | 1H NMR (300 MHz, CDCl3) δ 7.32-7.37 (m, 5H); 7.09 (dd, J = 1.2, 2.4 Hz, 1H); 7.02 (d, J = 2.1 Hz, 1H); 5.19 (s, 2H); 2.29 (s, 3H); 2.22 (s, 3H); 2.16 (s, 3H); ESI MS m/z 295 [M + H]+. |

TABLE 1-continued

Exemplary Embodiments prepared using methods described above.

| Example Number | Chemical Name | Structure | General Procedure | Analytical Data |
|---|---|---|---|---|
| 67 | 1-benzyl-3-cyclopropyl-5-(3,5-dimethylisoxazol-4-yl)pyridin-2(1H)-one | 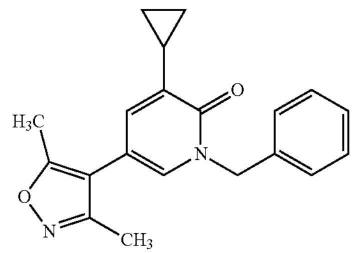 [SMILES: Cc1noc(C)c1-c1cc(C2CC2)c(=O)n(Cc2ccccc2)c1] | I | 1H NMR (300 MHz, CDCl3) δ 7.32-7.38 (m, 5H); 6.97 (d, J = 2.4 Hz, 1H); 6.72 (d, J = 2.1 Hz, 1H); 5.20 (s, 2H); 2.28 (s, 3H); 2.15-2.25 (m, 1H); 2.13 (s, 3H); 0.98-1.03 (m, 2H); 0.62-0.65 (m, 2H); ESI MS m/z 321 [M + H]+. |
| 68 | 5-(3,5-dimethylisoxazol-4-yl)-1-(4-fluorobenzoyl)pyridin-2(1H)-one | 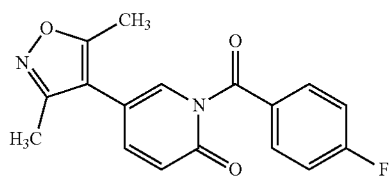 [SMILES: Cc1noc(C)c1-c1ccc(=O)n(C(=O)c2ccc(F)cc2)c1] | H | 1H NMR (300 MHz, CDCl3) δ 8.37 (d, J = 2.4 Hz, 1H); 8.25-8.30 (m, 2H); 7.76 (dd, J = 2.4, 8.4 Hz, 1H); 7.33 (d, J = 8.4 Hz, 1H); 7.19-7.24 (m, 2H); 2.46 (s, 3H); 2.31 (s, 3H); ESI MS m/z 313 [M + H]+. |
| 69 | 1-(4-chlorobenzoyl)-5-(3,5-dimethylisoxazol-4-yl)pyridin-2(1H)-one | 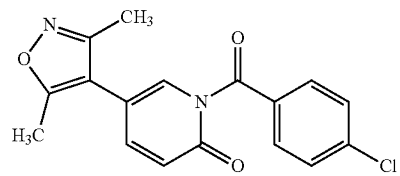 [SMILES: Cc1noc(C)c1-c1ccc(=O)n(C(=O)c2ccc(Cl)cc2)c1] | H | 1H NMR (300 MHz, CDCl3) δ 8.37 (d, J = 2.4 Hz, 1H); 8.19 (d, J = 8.7 Hz, 2H); 7.76 (dd, J = 2.4, 8.4 Hz, 1H); 7.52 (d, J = 8.7 Hz, 2H); 7.33 (d, J = 7.8 Hz, 1H); 2.46 (s, 3H); 2.31 (s, 3H); ESI MS m/z 329 [M + H]+. |
| 70 | 1-benzyl-5-(3,5-dimethylisoxazol-4-yl)-3-(4-fluorophenyl)pyridin-2(1H)-one | 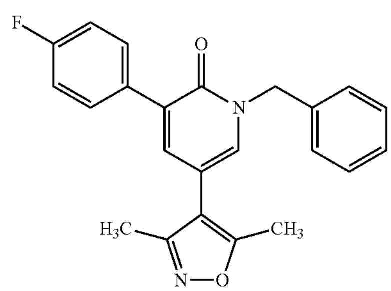 [SMILES: Cc1noc(C)c1-c1cc(-c2ccc(F)cc2)c(=O)n(Cc2ccccc2)c1] | I | 1H NMR (300 MHz, CDCl3) δ 7.67-7.72 (m, 2H); 7.36-7.40 (m, 5H); 7.34 (d, J = 2.4 Hz, 1H); 7.18 (d, J = 2.7 Hz, 1H); 7.08-7.14 (m, 2H); 5.25 (s, 2H); 2.34 (s, 3H); 2.20 (s, 3H); ESI MS m/z 375 [M + H]+. |
| 71 | N-(1-benzyl-5-(3,5-dimethylisoxazol-4-yl)-2-oxo-1,2-dihydropyridin-3-yl)acetamide | 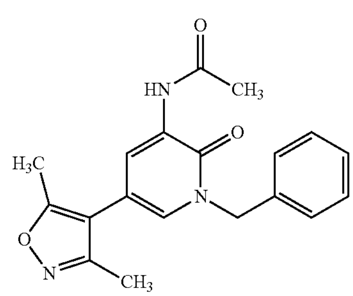 [SMILES: CC(=O)Nc1cc(-c2c(C)noc2C)cn(Cc2ccccc2)c1=O] | J | 1H NMR (300 MHz, DMSO-d6) δ 9.46 (s, 1H); 8.24 (d, J = 2.4 Hz, 1H); 7.68 (d, J = 2.4 Hz, 1H); 7.29-7.37 (m, 5H); 5.21 (s, 2H); 2.37 (s, 3H); 2.20 (s, 3H); 2.12 (s, 3H); ESI MS m/z 338 [M + H]+. |
| 72 | 1-benzyl-5-(3,5-dimethylisoxazol-4-yl)-3-(phenylamine)pyridin-2(1H)-one | 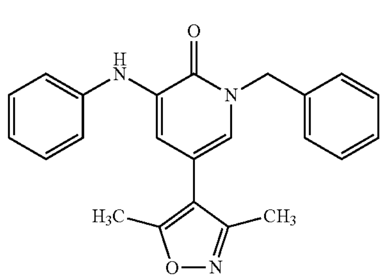 [SMILES: Cc1noc(C)c1-c1cc(Nc2ccccc2)c(=O)n(Cc2ccccc2)c1] | J | 1H NMR (300 MHz, DMSO-d6) δ 7.87 (s, 1H); 7.43-7.34 (m, 5H); 7.25-7.32 (m, 5H); 6.98 (d, J = 2.1 Hz, 1H); 6.90-6.96 (m, 1H); 5.22 (s, 2H); 2.36 (s, 3H); 2.19 (s, 3H); ESI MS m/z 372 [M + H]+. |

TABLE 1-continued

Exemplary Embodiments prepared using methods described above.

| Example Number | Chemical Name | General Procedure | Analytical Data |
|---|---|---|---|
| 73 | 3-amino-1-benzyl-5-(3,5-dimethylisoxazol-4-yl)pyridin-2(1H)-one | D | 1H NMR (300 MHz, DMSO-d6) δ 7.27-7.35 (m, 5H); 7.10 (d, J = 2.4 Hz, 1H); 6.44 (d, J = 2.1 Hz, 1H); 5.28 (s, 2H); 5.13 (s, 2H); 2.34 (s, 3H); 2.17 (s, 3H); ESI MS m/z 296 [M + H]+. |
| 74 | 1-benzyl-3-(benzylamino)-5-(3,5-dimethylisoxazol-4-yl)pyridin-2(1H)-one | D | 1H NMR (300 MHz, DMSO-d6) δ 7.21-7.36 (m, 10H); 7.07 (d, J = 2.1 Hz, 1H); 6.36 (t, J = 6.0 Hz, 1H); 5.97 (d, J = 2.1 Hz, 1H); 5.15 (s, 2H); 4.32 (d, J = 6.0 Hz, 2H); 2.17 (s, 3H); 1.98 (s, 3H); ESI MS m/z 386 [M + H]+. |
| 75 | 1-benzyl-5-(3,5-dimethylisoxazol-4-yl)-3-(methylamino)pyridin-2(1H)-one | J | 1H NMR (300 MHz, CDCl3) δ 7.29-7.36 (m, 6H); 6.55 (d, J = 2.1 Hz, 1H); 6.16 (d, J = 1.8 Hz, 1H); 5.21 (s, 2H); 2.87 (s, 3H); 2.32 (s, 3H); 2.19 (s, 3H); ESI MS m/z 310 [M + H]+. |
| 76 | 6-(3,5-dimethylisoxazol-4-yl)-2-(4-(trifluoromethoxy)benzyl)pyridazin-3(2H)-one | C | 1H NMR (500 MHz, CDCl3) δ 7.49 (d, J = 8.6 Hz, 2H), 7.28 (d, J = 9.5 Hz, 1H), 7.19 (d, J = 8.6 Hz, 2H), 7.03 (d, J = 9.5 Hz, 1H), 5.34 (s, 2H), 2.46 (s, 3H), 2.31 (s, 3H); ESI MS m/z 366 [M + H]+. |
| 77 | 6-(3,5-dimethylisoxazol-4-yl)-2-(naphthalen-2-ylmethyl)pyridazin-3(2H)-one | C | 1H NMR (500 MHz, CDCl3) δ 7.91 (s, 1H), 7.82-7.80 (m, 3H), 7.57 (dd, J = 1.7, 8.5 Hz, 1H), 7.48-7.46 (m, 2H), 7.27 (s, 1H), 7.02 (d, J = 9.6 Hz, 1H), 5.18 (s, 2H), 2.44 (s, 3H), 2.30 (s, 3H); ESI MS m/z 332 [M + H]+ |
| 78 | 5-(3,5-dimethylisoxazol-4-yl)-1-(3-methoxybenzyl)pyridin-2(1H)-one | D | 1H NMR (500 MHz, CDCl3) δ 7.32-7.27 (m, 2H), 7.16 (d, J = 2.4 Hz, 1H), 6.89-6.87 (m, 3H), 6.83 (d, J = 9.4 Hz, 1H), 5.18 (s, 2H), 3.79 (s. 3H). 2.29 (s, 3H), 2.15 (s, 3H); ESI MS m/z 311 [M + H]+ |

TABLE 1-continued

Exemplary Embodiments prepared using methods described above.

| Example Number | Chemical Name | Structure | General Procedure | Analytical Data |
|---|---|---|---|---|
| 79 | 5-(3,5-dimethylisoxazol-4-yl)-1-(thiophen-3-ylmethyl)pyridin-2(1H)-one | 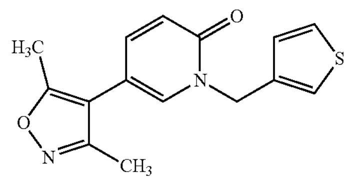 [SMILES: Cc1noc(C)c1-c1ccc(=O)n(Cc2ccsc2)c1] | D | 1H NMR (300 MHz, CDCl3) δ 7.39-7.32 (m, 3H), 7.20 (d, J = 2.1 Hz, 1H), 7.08 (dd, J = 1.3, 4.9 Hz, 1H), 6.85 (d, J = 9.2 Hz, 1H), 5.22 (s, 2H), 2.31 (s, 3H), 2.17 (s, 3H); ESI MS m/z 287 [M + H]+ |
| 80 | 1-benzyl-5-(thiazol-5-yl)pyridin-2(1H)-one | 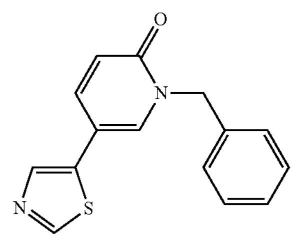 [SMILES: O=c1ccc(-c2cncs2)cn1Cc1ccccc1] | F | 1H NMR (500 MHz, CDCl3) δ 8.69 (s, 1H), 7.82 (s, 1H), 7.53 (dd, J = 2.1, 9.1 Hz, 1H), 7.50 (d, J = 2.4 Hz, 1H), 7.38-7.32 (m, 5H), 6.71 (d, J = 9.5 Hz, 1H), 5.12 (s, 2H); ESI MS m/z 269 [M + H]+ |
| 81 | 1-benzyl-5-(5-methyl-1H-imidazol-4-yl)pyridin-2(1H)-one | 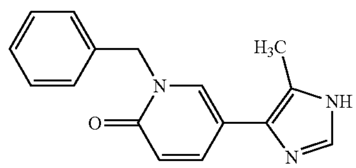 [SMILES: Cc1[nH]cnc1-c1ccc(=O)n(Cc2ccccc2)c1] | F | 1H NMR (500 MHz, CDCl3) δ 7.77-7.53 (m, 2H), 7.47 (s, 1H), 7.34-7.30 (m, 4H), 7.29-7.27 (m, 1H), 6.66 (d, J = 9.3 Hz, 1H), 5.19 (s, 2H) 2.92 (s, 3H); ESI MS m/z 266 [M + H]+ |
| 82 | N-(4-((6-oxo-3-(3,4,5-trimethoxyphenyl)pyridazin-1(6H)-yl)methyl)phenyl)acetamide | 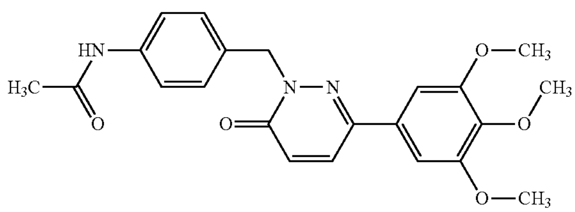 [SMILES: COc1cc(-c2ccc(=O)n(Cc3ccc(NC(C)=O)cc3)n2)cc(OC)c1OC] | C | 1H NMR (300 MHz, DMSO-d6) δ 9.96 (s, 1H), 8.13 (d, J = 9.6 Hz, 1H), 7.54 (d, J = 8.4 Hz, 2H), 7.31 (d, J = 8.4 Hz, 2H), 7.14 (s, 2H), 7.07 (d, J = 9.9 Hz, 1H), 5.25 (s, 2H), 3.84 (s, 6H), 3.69 (s, 3H), 2.02 (s, 3H); ESI-MS m/z 410 [M + H]+. |
| 83 | 2-benzyl-6-(4-hydroxy-3-methoxyphenyl)pyridazin-3(2H)-one | 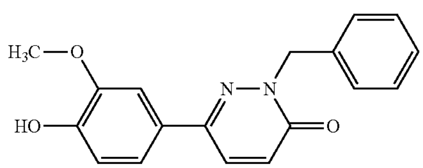 [SMILES: COc1cc(-c2ccc(=O)n(Cc3ccccc3)n2)ccc1O] | A | 1H NMR (300 MHz, DMSO-d6) δ 9.46 (s, 1H), 8.04 (d, J = 9.9 Hz, 1H), 7.41-7.29 (m, 7H), 7.04 (d, J = 9.9 Hz, 1H), 6.85 (d, J = 8.1 Hz, 1H), 5.30 (s, 2H), 3.82 (s, 3H); APCI-MS m/z 309 [M + H]+. |
| 84 | 6-(3,5-dimethylisoxazol-4-yl)-2-(2-fluorobenzyl)-4-methylpyridazin-3(2H)-one | 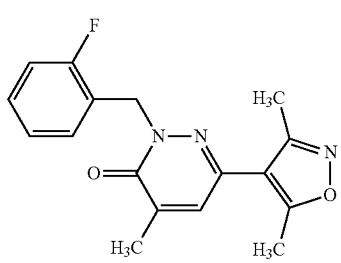 [SMILES: Cc1noc(C)c1-c1cc(C)c(=O)n(Cc2ccccc2F)n1] | A | 1H NMR (300 MHz, DMSO-d6) δ 7.57 (d, J = 1.2 Hz, 1H), 7.39-7.33 (m, 2H), 7.25-7.15 (m, 2H), 5.35 (s, 2H), 2.42 (s, 3H), 2.18 (s, 3H), 2.17 (d, J = 1.2 Hz, 3H); APCI-MS m/z 314 [M + H]+. |
| 85 | 2-(cyclopropylmethyl)-6-(3,5-dimethylisoxazol-4-yl)-4-methylpyridazin-3(2H)-one | 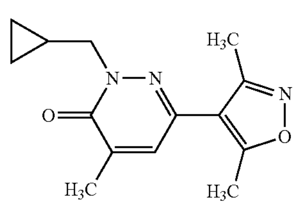 [SMILES: Cc1noc(C)c1-c1cc(C)c(=O)n(CC2CC2)n1] | A | 1H NMR (300 MHz, DMSO-d6) δ 7.55 (d, J = 1.2 Hz, 1H), 3.97 (d, J = 7.2 Hz, 2H), 2.53 (s, 3H), 2.33 (s, 3H), 2.15 (d, J = 1.2 Hz, 3H), 1.30-1.23 (m, 1H), 0.54-0.40 (m, 2H), 0.39-0.37 (m, 2H); APCI-MS m/z 260 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 86 | 2-benzyl-6-(3,5-dimethyl-1H-pyrazol-4-yl)pyridazin-3(2H)-one | 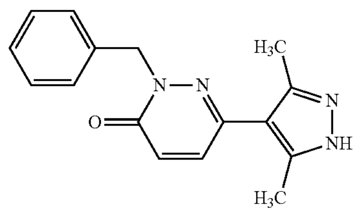 [SMILES: Cc1n[nH]c(C)c1-c1ccc(=O)n(Cc2ccccc2)n1] | A | 1H NMR (300 MHz, DMSO-d6) δ 12.48 (br. s, 1H), 7.59 (d, J = 9.6 Hz, 1H), 7.35-7.28 (m, 5H), 7.51 (d, J = 9.6 Hz, 1H), 5.26 (s, 2H), 2.25 (s, 3H), 2.19 (s, 3H); ESI-MS m/z 281 [M + H]+. |
| 87 | 6-(3,5-dimethylisoxazol-4-yl)-4-methyl-2-(pyridin-4-ylmethyl)pyridazin-3(2H)-one | 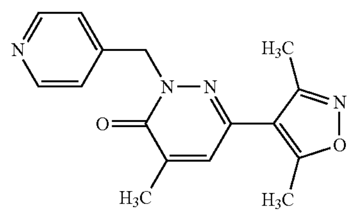 [SMILES: Cc1noc(C)c1-c1cc(C)c(=O)n(Cc2ccncc2)n1] | A | 1H NMR (500 MHz, DMSO-d6) δ 8.53 (dd, J = 7.5, 3.0 Hz, 2H), 7.61 (d, J = 2.0 Hz, 1H), 7.28 (dd, J = 7.5, 3.0 Hz, 2H), 5.34 (s, 2H), 2.47 (s, 3H), 2.25 (s, 3H), 2.17 (d, J = 2.0 Hz, 3H); ESI-MS m/z 297 [M + H]+. |
| 88 | 2-(cyclobutylmethyl)-6-(3,5-dimethylisoxazol-4-yl)pyridazin-3(2H)-one | 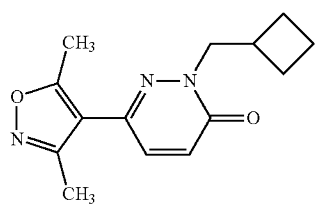 [SMILES: Cc1noc(C)c1-c1ccc(=O)n(CC2CCC2)n1] | C | 1H NMR (500 MHz, CDCl3) δ 7.26 (d, J = 9.5 Hz, 1H), 6.99 (d, J = 9.51H), 4.24 (d, J = 7.5 Hz, 2H), 2.94-2.88 (m, 1H), 2.53 (s, 3H), 2.38 (s, 3H), 2.10-2.04 (m, 2H), 1.96-1.84 (m, 4H); ESI-MS m/z 260 [M + H]+. |
| 89 | 4-((3-(3,5-dimethylisoxazol-4-yl)-6-oxopyridazin-1(6H)-yl)methyl)-N-methylbenzamide | 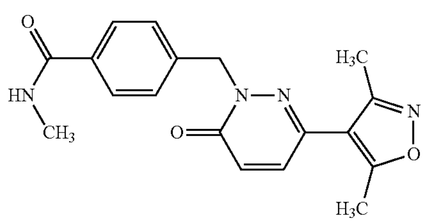 [SMILES: CNC(=O)c1ccc(Cn2nc(-c3c(C)noc3C)ccc2=O)cc1] | C | 1H NMR (500 MHz, DMSO-d6) δ 8.39 (q, J = 4.5 Hz, 1H), 7.80 (d, J = 8.5 Hz, 2H), 7.68 (d, J = 9.5 Hz, 1H), 7.41 (d, J = 8.5 Hz, 2H), 7.10 (d, J = 9.5 Hz, 1H), 5.34 (s, 2H), 2.76 (d, J = 4.5 Hz, 3H), 2.46 (s, 3H), 2.25 (s, 3H); ESI-MS m/z 339 [M + H]+. |
| 90 | 2-(2,6-difluorobenzyl)-6-(3,5-dimethylisoxazol-4-yl)pyridazin-3(2H)-one | 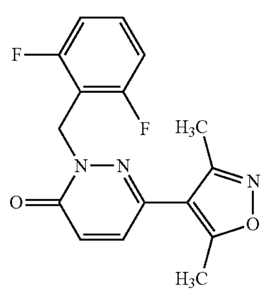 [SMILES: Cc1noc(C)c1-c1ccc(=O)n(Cc2c(F)cccc2F)n1] | C | 1H NMR (300 MHz, DMSO-d6) δ 7.65 (d, J = 9.9 Hz, 1H), 7.50-7.42 (m, 1H), 7.17-7.12 (m, 2H), 7.08 (d, J = 9.6 Hz, 1H), 5.37 (s, 2H), 2.35 (s, 3H), 2.07 (s, 3H); ESI-MS m/z 318 [M + H]+. |
| 91 | 6-(3,5-dimethylisoxazol-4-yl)-2-(4-(trifluoromethyl)benzyl)pyridazin-3(2H)-one | 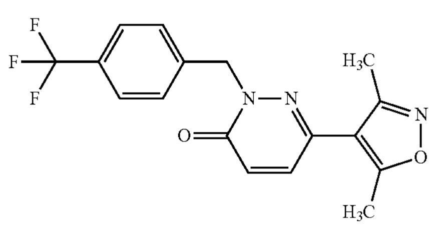 [SMILES: Cc1noc(C)c1-c1ccc(=O)n(Cc2ccc(C(F)(F)F)cc2)n1] | C | 1H NMR (300 MHz, DMSO-d6) δ 7.73 (d, J = 8.1 Hz, 2H), 7.70 (d, J = 9.6 Hz, 1H), 7.56 (d, J = 8.1 Hz, 2H), 7.12 (d, J = 9.6 Hz, 1H), 5.40 (s, 2H), 2.47 (s, 3H), 2.25 (s, 3H); ESI-MS m/z 350 [M + H]+. |

TABLE 1-continued

Exemplary Embodiments prepared using methods described above.

| Example Number | Chemical Name | Structure | General Procedure | Analytical Data |
|---|---|---|---|---|
| 92 | 6-(3,5-dimethylisoxazol-4-yl)-2-(2,4,6-trifluorobenzyl)pyridazin-3(2H)-one | 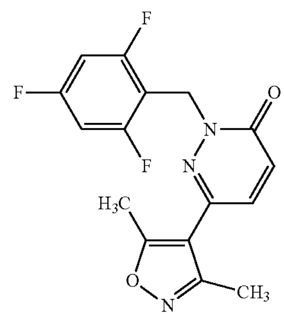 [SMILES: Cc1noc(C)c1-c1ccc(=O)n(Cc2c(F)cc(F)cc2F)n1] | C | 1H NMR (300 MHz, DMSO-d6) δ 7.65 (d, J = 9.6 Hz, 1H), 7.30-7.22 (m, 2H), 7.08 (d, J = 9.9 Hz, 1H), 5.33 (s, 2H), 2.38 (s, 3H), 2.12 (s, 3H); ESI-MS m/z 336 [M + H]+. |
| 93 | 6-(3,5-dimethylisoxazol-4-yl)-2-(2-fluorobenzyl)pyridazin-3(2H)-one | 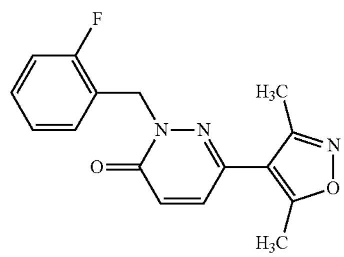 [SMILES: Cc1noc(C)c1-c1ccc(=O)n(Cc2ccccc2F)n1] | C | 1H NMR (500 MHz, DMSO-d6) δ 7.67 (d, J = 9.5 Hz, 1H), 7.39-7.35 (m, 2H), 7.24-7.17 (m, 2H), 7.09 (d, J = 10.0 Hz, 1H), 5.35 (s, 2H), 2.42 (s, 3H), 2.18 (s, 3H); ESI-MS m/z 300 [M + H]+. |
| 94 | 6-(3,5-dimethylisoxazol-4-yl)-2-(2-(trifluoromethyl)benzyl)pyridazin-3(2H)-one | 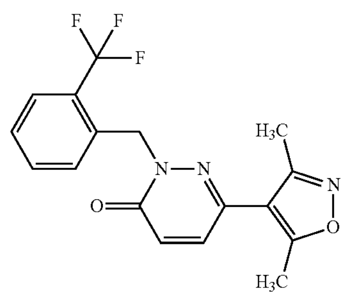 [SMILES: Cc1noc(C)c1-c1ccc(=O)n(Cc2ccccc2C(F)(F)F)n1] | C | 1H NMR (500 MHz, DMSO-d6) δ 7.79 (d, J = 7.5 Hz, 1H), 7.72 (d, J = 9.5 Hz, 1H), 7.66 (t, J = 7.5 Hz, 1H), 7.54 (t, J = 7.5 Hz, 1H), 7.28 (d, J = 7.5 Hz, 1H), 7.15 (d, J = 9.5 Hz, 1H), 5.49 (s, 2H), 2.39 (s, 3H), 2.11 (s, 3H); ESI-MS m/z 350 [M + H]+. |
| 95 | 6-(3,5-dimethylisoxazol-4-yl)-2-(1-(2-fluorophenyl)ethyl)pyridazin-3(2H)-one | 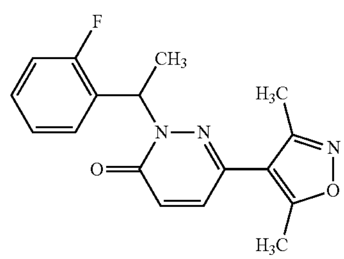 [SMILES: Cc1noc(C)c1-c1ccc(=O)n(C(C)c2ccccc2F)n1] | C | 1H NMR (500 MHz, DMSO-d6) δ 7.65 (d, J = 9.5 Hz, 1H), 7.43 (td, J = 7.5, 1.5 Hz, 1H), 7.37-7.34 (m, 1H), 7.23-7.16 (m, 2H), 7.06 (d, J = 9.5 Hz, 1H), 6.42 (q, J = 7.0 Hz, 1H), 2.49 (s, 3H), 2.14 (s, 3H), 1.70 (d, J = 7.0 Hz, 3H); ESI-MS m/z 314 [M + H]+. |
| 96 | 2-(2-chloro-6-fluorobenzyl)-6-(3,5-dimethylisoxazol-4-yl)pyridazin-3(2H)-one | 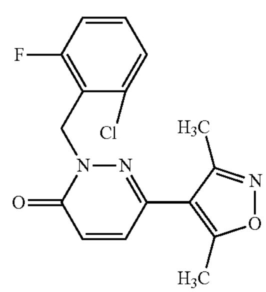 [SMILES: Cc1noc(C)c1-c1ccc(=O)n(Cc2c(F)cccc2Cl)n1] | C | 1H NMR (300 MHz, DMSO-d6) δ 7.65 (d, J = 9.6 Hz, 1H), 7.48-7.38 (m, 2H), 7.33-7.27 (m, 1H), 7.10 (d, J = 9.6 Hz, 1H), 5.43 (s, 2H), 2.29 (s, 3H), 1.97 (s, 3H); ESI-MS m/z 334 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 97 | 6-(3,5-dimethylisoxazol-4-yl)-2-(isoxazol-4-ylmethyl)pyridazin-3(2H)-one | 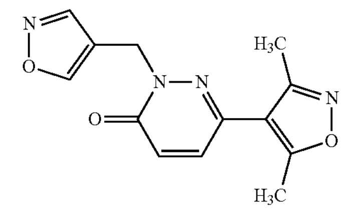 [SMILES: Cc1noc(C)c1-c1ccc(=O)n(Cc2cnoc2)n1] | C | 1H NMR (300 MHz, DMSO-d6) δ 9.03 (s, 1H), 8.63 (s, 1H), 7.67 (d, J = 9.9 Hz, 1H), 7.09 (d, J = 9.6 Hz, 1H), 5.20 (s, 2H), 2.50 (s, 3H), 2.23 (s, 3H); ESI-MS m/z 273 [M + H]+. |
| 98 | 5-(5-amino-3-methylisoxazol-4-yl)-1-benzylpyridin-2(1H)-one | 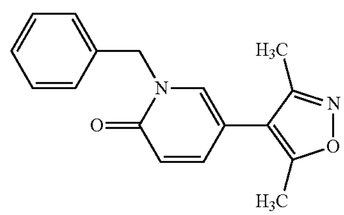 | F | 1H NMR (300 MHz, DMSO-d6) δ 7.70 (d, J = 2.4 Hz, 1H), 7.41-7.27 (m, 6H), 6.68 (br. s, 2H), 6.45 (d, J = 9.3 Hz, 1H), 5.11 (s, 2H), 2.01 (s, 3H); ESI-MS m/z 282 [M + H]+. |
| 99 | 2-benzyl-6-((5,6-dimethoxypyridin-2-yl)amino)pyridazin-3(2H)-one | 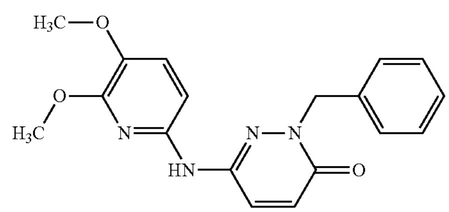 [SMILES: COc1ccc(Nc2ccc(=O)n(Cc3ccccc3)n2)nc1OC] | B | 1H NMR (300 MHz, DMSO-d6) δ 9.26 (s, 1H), 7.52 (d, J = 9.9 Hz, 1H), 7.36-7.25 (m, 7H), 6.93 (d, J = 9.9 Hz, 1H), 5.15 (s, 2H), 3.84 (s, 3H), 3.72 (s, 3H); ESI-MS m/z 339 [M + H]+. |
| 100 | 2-benzyl-6-(3,4-dimethoxyphenoxy)pyridazin-3(2H)-one | 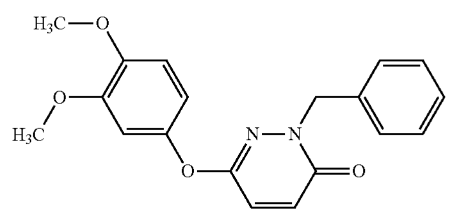 [SMILES: COc1ccc(Oc2ccc(=O)n(Cc3ccccc3)n2)cc1OC] | No general procedure | 1H NMR (300 MHz, DMSO-d6) δ 7.38 (d, J = 9.6 Hz, 1H), 7.32-7.20 (m, 5H), 7.09 (d, J = 9.6 Hz, 1H), 6.93 (d, J = 8.7 Hz, 1H), 6.83 (d, J = 2.7 Hz, 1H), 6.67 (dd, J = 8.7, 2.7 Hz, 1H), 5.03 (s, 2H), 3.74 (s, 3H), 3.66 (s, 3H); ESI-MS m/z 339 [M + H]+. |
| 101 | 5-(3,5-dimethylisoxazol-4-yl)-1-(1-(4-fluorophenyl)ethyl)pyridin-2(1H)-one | 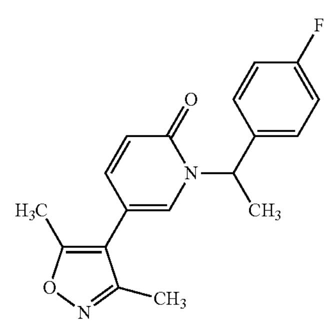 [SMILES: Cc1noc(C)c1-c1ccc(=O)n(C(C)c2ccc(F)cc2)c1] | E | 1H NMR (300 MHz, DMSO-d6) δ 7.65 (d, J = 2.1 Hz, 1H), 7.48-7.41 (m, 3H), 7.23-7.17 (m, 2H), 6.51 (d, J = 9.3 Hz, 1H), 6.20 (q, J = 7.2 Hz, 1H), 2.27 (s, 3H), 2.11 (s, 3H), 1.73 (d, J = 7.2 Hz, 3H); ESI-MS m/z 313 [M + H]+. |
| 102 | 6-(3,5-dimethylisoxazol-4-yl)-2-(quinolin-8-ylmethyl)pyridazin-3(2H)-one | 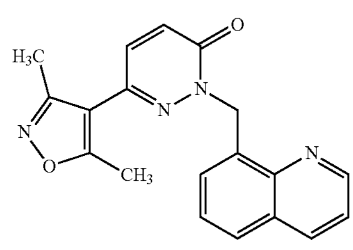 [SMILES: Cc1noc(C)c1-c1ccc(=O)n(Cc2cccc3cccnc23)n1] | C | 1H NMR (300 MHz, DMSO-d6) δ 8.96 (dd, J = 4.2, 1.8 Hz, 1H), 8.43 (dd, J = 8.4, 1.8 Hz, 1H), 7.96 (dd, J = 8.1, 1.2 Hz, 1H), 7.71 (d, J = 9.6 Hz, 1H), 7.63-7.55 (m, 2H), 7.43 (dd, J = 6.9, 1.2 Hz, 1H), 7.15 (d, J = 9.9 Hz, 1H), 5.94 (s, 2H), 2.33 (s, 3H), 2.03 (s, 3H); ESI-MS m/z 333 [M + H]+. |

TABLE 1-continued

Exemplary Embodiments prepared using methods described above.

| Example Number | Chemical Name | General Procedure | Analytical Data |
|---|---|---|---|
| 103 | 1-(1-(2-chlorophenyl)ethyl)-5-(3,5-dimethylisoxazol-4-yl)pyridin-2(1H)-one | D | 1H NMR (300 MHz, DMSO-d6) δ 7.57-7.36 (m, 5H), 7.34 (d, J = 2.1 Hz, 1H), 6.50 (d, J = 9.3 Hz, 1H), 6.22 (q, J = 6.9 Hz, 1H), 2.20 (s, 3H), 2.02 (s, 3H), 1.70 (d, J = 6.9 Hz, 3H); ESI-MS m/z 329 [M + H]+. |
| 104 | 5-(3,5-dimethylisoxazol-4-yl)-1-(1-(3-fluorophenyl)ethyl)pyridin-2(1H)-one | E | 1H NMR (300 MHz, DMSO-d6) δ 7.70 (d, J = 2.4 Hz, 1H), 7.47 (dd, J = 9.3, 2.4 Hz, 1H), 7.40 (dd, J = 7.8, 6.0 Hz, 1H), 7.26-7.12 (m, 3H), 6.52 (d, J = 9.3 Hz, 1H), 6.20 (q, J = 7.2 Hz, 1H), 2.29 (s, 3H), 2.12 (s, 3H), 1.75 (d, J = 7.2 Hz, 3H); ESI-MS m/z 313 [M + H]+. |
| 105 | 1-(1-(4-chlorophenyl)ethyl)-5-(3,5-dimethylisoxazol-4-yl)pyridin-2(1H)-one | D | 1H NMR (300 MHz, DMSO-d6) δ 7.67 (d, J = 2.1 Hz, 1H), 7.47 (dd, J = 9.3, 2.4 Hz, 1H), 7.43-7.37 (m, 4H), 6.51 (d, J = 9.3 Hz, 1H), 6.18 (q, J = 7.2 Hz, 1H), 2.29 (s, 3H), 2.12 (s, 3H), 1.74 (d, J = 7.2 Hz, 3H); ESI-MS m/z 329 [M + H]+. |
| 106 | 5-(3,5-dimethylisoxazol-4-yl)-1-(2-phenylpropan-2-yl)pyridin-2(1H)-one | E | 1H NMR (300 MHz, DMSO-d6) δ 7.85 (d, J = 2.1 Hz, 1H), 7.49 (dd, J = 9.3, 2.4 Hz, 1H), 7.31-7.26 (m, 2H), 7.20-7.13 (m, 3H), 6.31 (d, J = 9.3 Hz, 1H), 2.42 (s, 3H), 2.24 (s, 3H), 1.87 (s, 6H); ESI-MS m/z 309 [M + H]+. |
| 107 | 6-(3,5-dimethylisoxazol-4-yl)-2-(thiophen-3-ylmethyl)pyridazin-3(2H)-one | C | 1H NMR (300 MHz, DMSO-d6) δ 7.66 (d, J = 9.6 Hz, 1H), 7.51 (dd, J = 4.8, 3.0 Hz, 1H), 7.47 (dd, J = 3.0, 1.5 Hz, 1H), 7.10 (dd, J = 4.8, 1.2 Hz, 1H), 7.08 (d, J = 9.6 Hz, 1H), 5.28 (s, 2H), 2.48 (s, 3H), 2.27 (s, 3H); ESI-MS m/z 288 [M + H]+. |
| 108 | (R)-6-(3,5-dimethylisoxazol-4-yl)-2-(1-phenylethyl)pyridazin-3(2H)-one | K | 1H NMR (300 MHz, DMSO-d6) δ 7.65 (d, J = 9.6 Hz, 1H), 7.35-7.27 (m, 5H), 7.06 (d, J = 9.6 Hz, 1H), 6.27 (q, J = 7.2 Hz, 1H), 2.46 (s, 3H), 2.24 (s, 3H), 1.71 (d, J = 7.2 Hz, 3H); ESI-MS m/z 296 [M + H]+; Chiralcel OD (10% EtOH in heptane, 0.8 mL/min): tR = 22.95 min. |

TABLE 1-continued

Exemplary Embodiments prepared using methods described above.

| Example Number | Chemical Name | Structure | General Procedure | Analytical Data |
|---|---|---|---|---|
| 109 | (S)-6-(3,5-dimethylisoxazol-4-yl)-2-(1-phenylethyl)pyridazin-3(2H)-one | 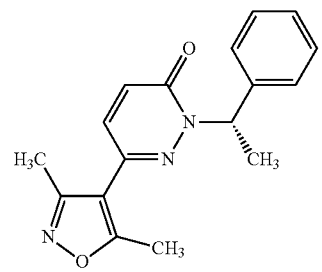 [SMILES: Cc1noc(C)c1-c1ccc(=O)n([C@@H](C)c2ccccc2)n1] | K | 1H NMR (300 MHz, DMSO-d6) δ 7.65 (d, J = 9.6 Hz, 1H), 7.35-7.27 (m, 5H), 7.06 (d, J = 9.6 Hz, 1H), 6.27 (q, J = 7.2 Hz, 1H), 2.46 (s, 3H), 2.24 (s, 3H), 1.71 (d, J = 7.2 Hz, 3H); ESI-MS m/z 296 [M + H]+; Chiralcel OD (10% EtOH in heptane, 0.8 mL/min): tR = 24.82 min. |
| 110 | (S)-5-(3,5-dimethylisoxazol-4-yl)-1-(1-(4-fluorophenyl)ethyl)pyridin-2(1H)-one | 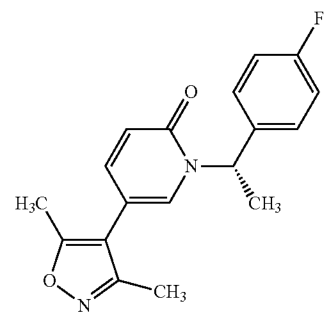 | K | 1H NMR (300 MHz, DMSO-d6) δ 7.65 (d, J = 2.1 Hz, 1H), 7.48-7.41 (m, 3H), 7.23-7.17 (m, 2H), 6.51 (d, J = 9.3 Hz, 1H), 6.20 (q, J = 7.2 Hz, 1H), 2.27 (s, 3H), 2.11 (s, 3H), 1.73 (d, J = 7.2 Hz, 3H); ESI-MS m/z 313 [M + H]+; Chiralcel OD (10% EtOH in heptane, 0.8 mL/min): tR = 11.07 min. |
| 111 | (R)-5-(3,5-dimethylisoxazol-4-yl)-1-(1-(4-fluorophenyl)ethyl)pyridin-2(1H)-one | 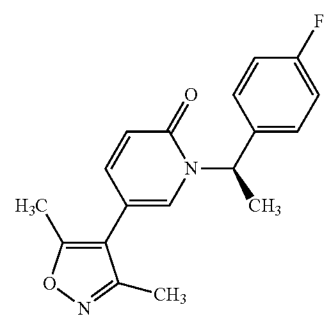 [SMILES: Cc1noc(C)c1-c1ccc(=O)n([C@H](C)c2ccc(F)cc2)c1] | K | 1H NMR (300 MHz, DMSO-d6) δ 7.65 (d, J = 2.1 Hz, 1H), 7.48-7.41 (m, 3H), 7.23-7.17 (m, 2H), 6.51 (d, J = 9.3 Hz, 1H), 6.20 (q, J = 7.2 Hz, 1H), 2.27 (s, 3H), 2.11 (s, 3H), 1.73 (d, J = 7.2 Hz, 3H); ESI-MS m/z 313 [M + H]+; Chiralcel OD (10% EtOH in heptane, 0.8 mL/min): tR = 18.19 min. |
| 112 | 5-(3,5-dimethylisoxazol-4-yl)-1-(1-(pyridin-2-yl)ethyl)pyridin-2(1H)-one | 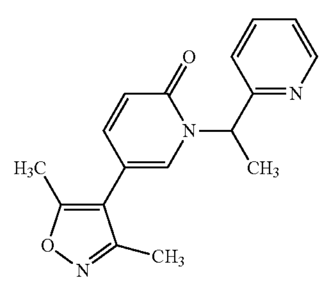 [SMILES: Cc1noc(C)c1-c1ccc(=O)n(C(C)c2ccccn2)c1] | D | 1H NMR (300 MHz, DMSO-d6) δ 8.56 (dd, J = 3.9, 0.9 Hz, 1H), 7.82 (td, J = 7.5, 1.8 Hz, 1H), 7.74 (d, J = 2.4 Hz, 1H), 7.49 (dd, J = 9.3, 2.7 Hz, 1H), 7.40 (d, J = 7.8 Hz, 1H), 7.35-7.31 (m, 1H), 6.49 (d, J = 9.0 Hz, 1H), 6.23 (q, J = 7.2 Hz, 1H), 2.33 (s, 3H), 2.16 (s, 3H), 1.74 (d, J = 7.2 Hz, 3H); ESI-MS m/z 296 [M + H]+. |
| 113 | 1-(1-(3-chlorophenyl)ethyl)-5-(3,5-dimethylisoxazol-4-yl)pyridin-2(1H)-one | 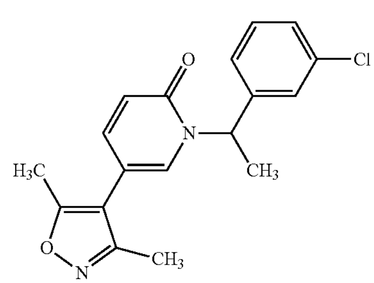 [SMILES: Cc1noc(C)c1-c1ccc(=O)n(C(C)c2cccc(Cl)c2)c1] | E | 1H NMR (300 MHz, DMSO-d6) δ 7.75 (d, J = 2.4 Hz, 1H), 7.50-7.30 (m, 5H), 6.52 (d, J = 9.3 Hz, 1H), 6.18 (q, J = 7.2 Hz, 1H), 2.30 (s, 3H), 2.13 (s, 3H), 1.75 (d, J = 7.2 Hz, 3H); ESI-MS m/z 329 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 114 | 1-benzyl-6-chloro-5-(3,5-dimethylisoxazol-4-yl)pyridin-2(1H)-one | 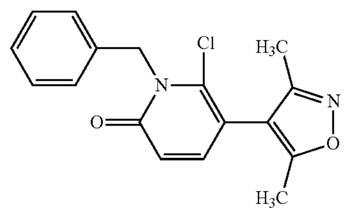 [SMILES: Cc1noc(C)c1-c1ccc(=O)n(Cc2ccccc2)c1Cl] | D | 1H NMR (300 MHz, DMSO-d6) δ 7.84 (d, J = 8.4 Hz, 1H), 7.52-7.49 (m, 2H), 7.44-7.39 (m, 3H), 7.02 (d, J = 8.4 Hz, 1H), 5.36 (s, 2H), 2.28 (s, 3H), 2.10 (s, 3H); ESI-MS m/z 315 [M + H]+. |
| 115 | 1-benzyl-5-(3,5-dimethylisoxazol-4-yl)-6-methylpyridin-2(1H)-one | 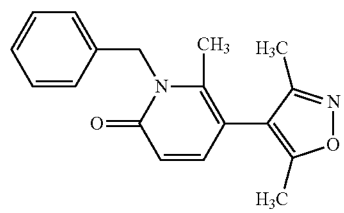 [SMILES: Cc1noc(C)c1-c1ccc(=O)n(Cc2ccccc2)c1C] | D | 1H NMR (300 MHz, DMSO-d6) δ 7.54 (d, J = 8.4 Hz, 1H), 7.51-7.48 (m, 2H), 7.43-7.34 (m, 3H), 6.78 (d, J = 8.4 Hz, 1H), 5.36 (s, 2H), 2.23 (s, 3H), 2.22 (s, 3H), 2.04 (s, 3H); ESI-MS m/z 295 [M + H]+. |
| 116 | 2-(4-(methylsulfonyl)benzyl)-6-(3,4,5-trimethoxyphenyl)pyridazin-3(2H)-one | 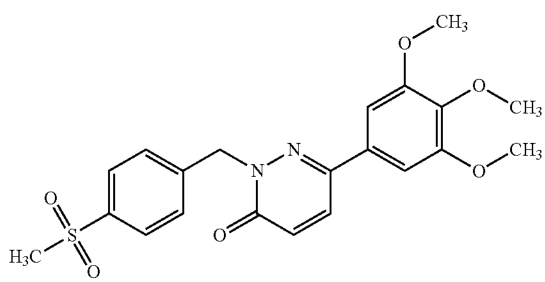 | C | 1H NMR (500 MHz, CDCl3): δ 7.92 (d, J = 8.5 Hz, 2H), 7.67 (d, J = 10.0 Hz, 1H), 7.64 (d, J = 8.5 Hz, 2H), 7.0 (d, J = 9.5 Hz, 1H), 6.96 (s, 2H), 5.48 (s, 2H), 3.96 (s, 6H), 3.90 (s, 3H), 3.02 (s, 3H). ESI MS m/z 431 [M + H]+. |
| 117 | 2-(4-methoxybenzyl)-6-(3,4,5-trimethoxyphenyl)pyridazin-3(2H)-one | 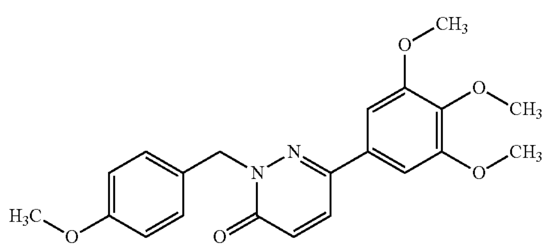 | No general procedure | 1H NMR (500 MHz, CDCl3): δ 7.60 (d, J = 9.5 Hz, 1H), 7.44 (d, J = 8.5 Hz, 2H), 7.0 (d, J = 9.5 Hz, 1H), 6.96 (s, 2H), 6.86 (d, J = 8.5 Hz, 2H), 5.34 (s, 2H), 3.92 (s, 6H), 3.89 (s, 3H), 3.78 (s, 3H). ESI MS m/z 383 [M + H]+. |
| 118 | 2-((6-oxo-3-(3,4,5-trimethoxyphenyl)pyridazin-1(6H)-yl)methyl)benzonitrile | 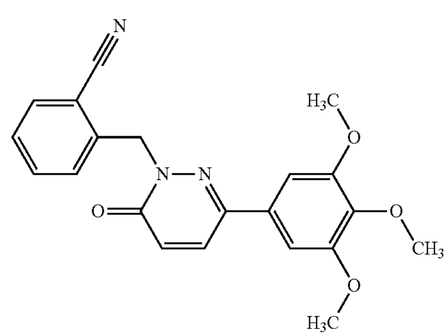 [SMILES: COc1cc(-c2ccc(=O)n(Cc3ccccc3C#N)n2)cc(OC)c1OC] | C | 1H NMR (500 MHz, CDCl3): δ 7.70-7.66 (m, 2H), 7.58-7.55 (m, 1H), 7.43-7.39 (m, 1H), 7.08 (s, 2H), 7.04 (d, J = 9.5 Hz, 2H), 5.65 (s, 2H), 3.93 (s, 6H), 3.89 (s, 3H). ESI MS m/z 378 [M + H]+. |

TABLE 1-continued

Exemplary Embodiments prepared using methods described above.

| Example Number | Chemical Name | Structure | General Procedure | Analytical Data |
|---|---|---|---|---|
| 119 | 2-(3-methoxybenzyl)-6-(3,4,5-trimethoxyphenyl)pyridazin-3(2H)-one | 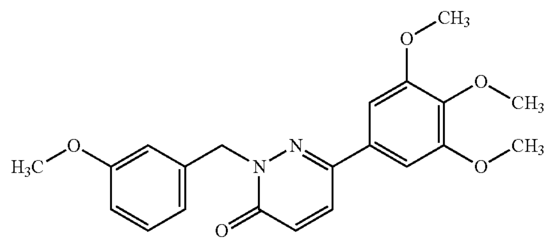 | C | 1H NMR (500 MHz, CDCl3): δ 7.62 (d, J = 9.5 Hz, 1H), 7.26-7.23 (m, 1H), 7.05-7.04 (m, 1H), 7.03-7.00 (m, 2H), 6.97 (s, 2H), 6.83-6.82 (m, 1H), 5.37 (s, 2H), 3.92 (s, 6H), 3.89 (s, 3H), 3.79 (s, 3H). ESI MS m/z 383 [M + H]+. |
| 120 | 2-(4-(tert-butyl)benzyl)-6-(3,4,5-trimethoxyphenyl)pyridazin-3(2H)-one | 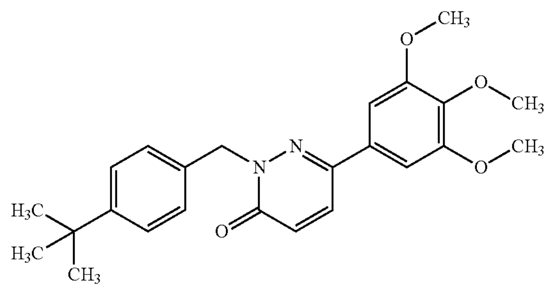 [SMILES: COc1cc(-c2ccc(=O)n(Cc3ccc(C(C)(C)C)cc3)n2)cc(OC)c1OC] | C | 1H NMR (500 MHz, CDCl3): δ 7.61 (d, J = 9.5 Hz, 1H), 7.41 (d, J = 8.5 Hz, 2H), 7.35 (d, J = 8.5 Hz, 2H), 7.0 (d, J = 9.5 Hz, 1H), 6.98 (s, 2H), 5.38 (s, 2H), 3.92 (s, 6H), 3.89 (s, 3H), 1.29 (s, 9H). ESI MS m/z 409 [M + H]+. |
| 121 | 5-(3,5-dimethylisoxazol-4-yl)-1-(2-methylbenzyl)pyridin-2(1H)-one | 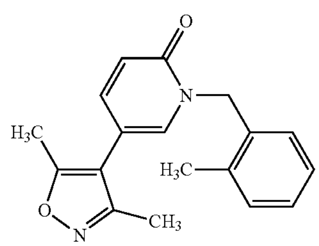 [SMILES: Cc1ccccc1Cn1cc(-c2c(C)noc2C)ccc1=O] | D | 1H NMR (500 MHz, CDCl3): δ 7.28-7.21 (m, 2H), 7.15-7.14 (m, 2H), 7.11-7.11 (m, 2H), 6.69 (d, J = 9.5 Hz, 1H), 5.14 (s, 2H), 2.34 (s, 3H), 2.28 (s, 3H), 2.15 (s, 3H). ESI MS m/z 295 [M + H]+. |
| 122 | 5-(3,5-dimethylisoxazol-4-yl)-1-(3-methylbenzyl)pyridin-2(1H)-one | 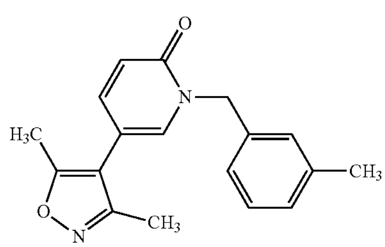 | D | 1H NMR (500 MHz, CDCl3): δ 7.29-7.21 (m, 4H), 7.13-7.11 (m, 1H), 6.90 (d, J = 2.5 Hz, 1H), 6.71 (d, J = 9.5 Hz, 1H), 5.18 (s, 2H), 2.28 (s, 3H), 2.22 (s, 3H), 2.09 (s, 3H). ESI MS m/z 295 [M + H]+. |
| 123 | 5-(3,5-dimethylisoxazol-4-yl)-1-(2-(trifluoromethyl)benzyl)pyridin-2(1H)-one | 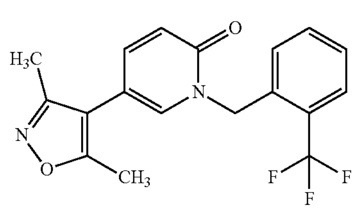 [SMILES: Cc1noc(C)c1-c1ccc(=O)n(Cc2ccccc2C(F)(F)F)c1] | D | 1H NMR (500 MHz, DMSO-d6): δ 7.84 (d, J = 2.5 Hz, 1H), 7.80 (d, J = 7.7 Hz, 1H), 7.64 (t, J = 7.7 Hz, 1H), 7.61 (dd, J = 2.6, 9.4 Hz, 1H), 7.51 (t, J = 7.7 Hz, 1H), 6.92 (d, J = 7.8 Hz, 1H), 6.58 (d, J = 9.4 Hz, 1H), 5.35 (s, 2H), 2.37 (s, 3H), 2.20 (s, 3H). ESI MS m/z 349 [M + H]+. |
| 124 | 5-(3,5-dimethylisoxazol-4-yl)-1-(1-(2-fluorophenyl)ethyl)pyridin-2(1H)-one | 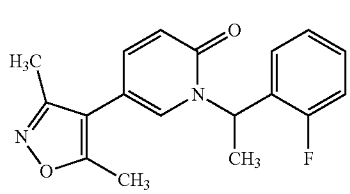 [SMILES: Cc1noc(C)c1-c1ccc(=O)n(C(C)c2ccccc2F)c1] | D | 1H NMR (500 MHz, DMSO-d6): ? 7.60-7.35 (m, 4H), 7.30-7.15 (m, 2H), 6.49 (d, J = 9.4 Hz, 1H), 6.28 (q, J = 7.0 Hz, 1H), 2.24 (s, 3H), 2.06 (s, 3H), 1.71 (d, J = 7.0 Hz, 3H). ESI MS m/z 313 [M + H]+. |

TABLE 1-continued

Exemplary Embodiments prepared using methods described above.

| Example Number | Chemical Name | Structure | General Procedure | Analytical Data |
|---|---|---|---|---|
| 125 | 5-(3,5-dimethylisoxazol-4-yl)-1-(1-phenylethyl)pyridin-2(1H)-one | 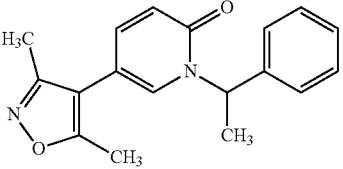 | D | 1H NMR (500 MHz, DMSO-d6): ? 7.60 (d, J = 2.4 Hz, 1H), 7.45 (dd, J = 2.5, 9.4 Hz, 1H), 7.40-7.35 (m, 4H), 7.34-7.27 (m, 1H), 6.51 (d, J = 9.4 Hz, 1H), 6.22 (q, J = 7.0 Hz, 1H), 2.25 (s, 3H), 2.09 (s, 3H), 1.74 (d, J = 7.0 Hz, 3H). ESI MS m/z 295 [M + H]+. |
| 126 | 1-(3-chlorobenzyl)-5-(3,5-dimethylisoxazol-4-yl)pyridin-2(1H)-one | 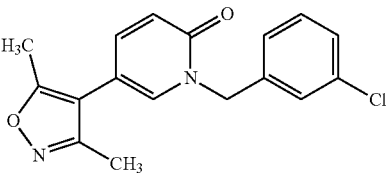 | D | 1H NMR (500 MHz, DMSO-d6): ? 7.96 (s, 1H), 7.66-7.28 (m, 5H), 6.52 (d, J = 9.4 Hz, 1H), 5.13 (s, 2H), 2.36 (s, 3H), 2.19 (s, 3H). ESI MS m/z 315 [M + H]+. |
| 127 | 1-(2-chlorobenzyl)-5-(3,5-dimethylisoxazol-4-yl)pyridin-2(1H)-one | 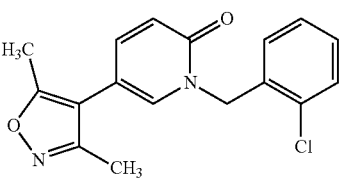 [SMILES: Cc1noc(C)c1-c1ccc(=O)n(Cc2ccccc2Cl)c1] | D | 1H NMR (500 MHz, DMSO-d6): δ 7.81 (d, J = 2.5 Hz, 1H), 7.57 (dd, J = 2.5, 9.4 Hz, 1H), 7.54-7.49 (m, 1H), 7.37-7.30 (m, 2H), 6.99-6.93 (m, 1H), 6.56 (d, J = 9.4 Hz, 1H), 5.21 (s, 2H), 2.36 (s, 3H), 2.19 (s, 3H). ESI MS m/z 315 [M + H]+. |
| 128 | 1-(4-chlorobenzyl)-5-(3,5-dimethylisoxazol-4-yl)pyridin-2(1H)-one | 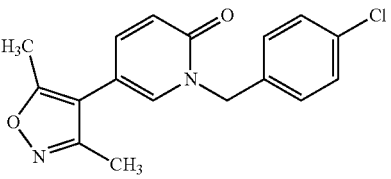 [SMILES: Cc1noc(C)c1-c1ccc(=O)n(Cc2ccc(Cl)cc2)c1] | D | 1H NMR (500 MHz, DMSO-d6): δ 7.94 (d, J = 2.5 Hz, 1H), 7.50 (dd, J = 2.5, 9.4 Hz, 1H), 7.41 (q, J = 10.1 Hz, 4H), 6.51 (d, J = 9.4 Hz, 1H), 5.12 (s, 2H), 2.36 (s, 3H), 2.19 (s, 3H). ESI MS m/z 315 [M + H]+. |
| 129 | 5-(3,5-dimethylisoxazol-4-yl)-1-(pyridin-4-ylmethyl)pyridin-2(1H)-one | 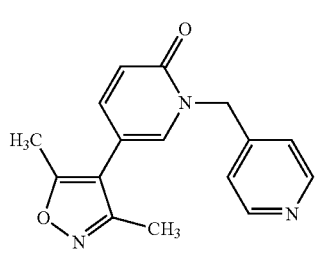 | D | 1H NMR (500 MHz, DMSO-d6): δ 8.53 (s, 1H), 7.93 (s, 2H), 7.55 (d, J = 9.4 Hz, 1H), 7.24 (s, 2H), 6.54 (d, J = 9.4 Hz, 1H), 5.17 (s, 2H), 2.37 (s, 3H), 2.20 (s, 3H). ESI MS m/z 282 [M + H]+. |
| 130 | 5-(3,5-dimethylisoxazol-4-yl)-1-(4-methoxybenzyl)pyridin-2(1H)-one | 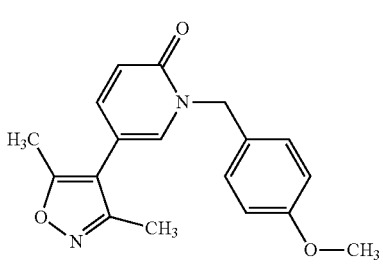 | D | 1H NMR (500 MHz, DMSO-d6): δ 7.90 (s, 1H), 7.46 (d, J = 9.4 Hz, 1H), 7.34 (d, J = 8.2 Hz, 2H), 6.90 (d, J = 8.2 Hz, 2H), 6.48 (d, J = 9.4 Hz, 1H), 5.04 (s, 2H), 3.72 (s, 3H), 2.34 (s, 3H), 2.18 (s, 3H). ESI MS m/z 311 [M + H]+. |

TABLE 1-continued

Exemplary Embodiments prepared using methods described above.

| Example Number | Chemical Name | Structure | General Procedure | Analytical Data |
|---|---|---|---|---|
| 131 | 1-(3,4-dimethoxybenzyl)-5-(3,5-dimethylisoxazol-4-yl)pyridin-2(1H)-one | 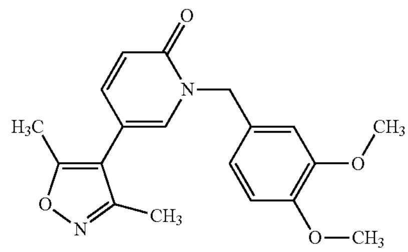 | D | 1H NMR (500 MHz, DMSO-d6): δ 7.90 (s, 1H), 7.46 (d, J = 9.4 Hz, 1H), 7.08 (s, 1H), 6.91 (s, 2H), 6.49 (d, J = 9.4 Hz, 1H), 5.04 (s, 2H), 3.72 (s, 6H), 2.34 (s, 3H), 2.18 (s, 3H). ESI MS m/z 341 [M + H]+. |
| 132 | 5-(3,5-dimethylisoxazol-4-yl)-1-(4-fluorobenzyl)pyridin-2(1H)-one | 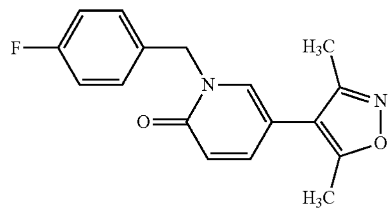 [SMILES: Cc1noc(C)c1-c1ccc(=O)n(Cc2ccc(F)cc2)c1] | D | 1H NMR (500 MHz, DMSO-d6): δ 7.94 (d, J = 2.5 Hz, 1H), 7.49 (dd, J = 2.5, 9.4 Hz, 1H), 7.46-7.40 (m, 2H), 7.22-7.15 (m, 2H), 6.50 (d, J = 9.4 Hz, 1H), 5.11 (s, 2H), 2.35 (s, 3H), 2.18 (s, 3H). ESI MS m/z 299 [M + H]+. |
| 133 | (S)-5-(3,5-dimethylisoxazol-4-yl)-1-(1-phenylethyl)pyridin-2(1H)-one | 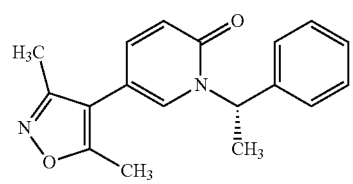 [SMILES: Cc1noc(C)c1-c1ccc(=O)n([C@@H](C)c2ccccc2)c1] | K | 1H NMR (500 MHz, DMSO-d6): δ 7.60 (d, J = 2.4 Hz, 1H), 7.45 (dd, J = 2.5, 9.4 Hz, 1H), 7.40-7.35 (m, 4H), 7.34-7.27 (m, 1H), 6.51 (d, J = 9.4 Hz, 1H), 6.22 (q, J = 7.0 Hz, 1H), 2.26 (s, 3H), 2.09 (s, 3H), 1.74 (d, J = 7.0 Hz, 3H). ESI MS m/z 295 [M + H]+. |
| 134 | (R)-5-(3,5-dimethylisoxazol-4-yl)-1-(1-phenylethyl)pyridin-2(1H)-one | 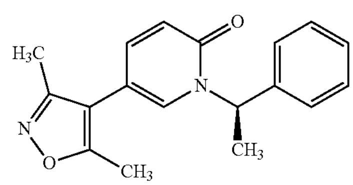 [SMILES: Cc1noc(C)c1-c1ccc(=O)n([C@H](C)c2ccccc2)c1] | K | 1H NMR (500 MHz, DMSO-d6): δ 7.60 (d, J = 2.4 Hz, 1H), 7.45 (dd, J = 2.5, 9.4 Hz, 1H), 7.40-7.35 (m, 4H), 7.34-7.27 (m, 1H), 6.51 (d, J = 9.4 Hz, 1H), 6.22 (q, J = 7.0 Hz, 1H), 2.26 (s, 3H), 2.09 (s, 3H), 1.74 (d, J = 7.0 Hz, 3H). ESI MS m/z 295 [M + H]+. |
| 135 | 2-((5-(3,5-dimethylisoxazol-4-yl)-2-oxopyridin-1(2H)-yl)methyl)benzonitrile | 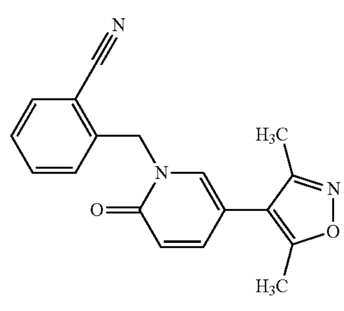 [SMILES: Cc1noc(C)c1-c1ccc(=O)n(Cc2ccccc2C#N)c1] | D | 1H NMR (500 MHz, DMSO-d6): δ 7.92 (d, J = 2.5 Hz, 1H), 7.88 (dd, J = 1.0, 7.7 Hz, 1H), 7.68 (td, J = 1.2, 7. Hz, 1H), 7.58 (dd, J = 2.5, 9.4 Hz, 1H), 7.50 (t, J = 7.6 Hz, 1H), 7.18 (d, J = 7.9 Hz, 1H), 6.54 (d, J = 9.4 Hz, 1H), 5.33 (s, 2H), 2.39 (s, 3H), 2.22 (s, 3H). ESI MS m/z 306 [M + H]+. |
| 136 | 1-(2,4-dichlorobenzyl)-5-(3,5-dimethylisoxazol-4-yl)pyridin-2(1H)-one | 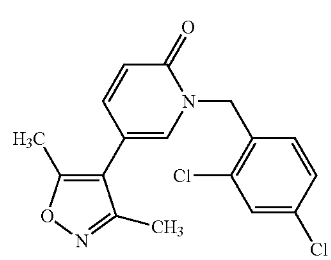 [SMILES: Cc1noc(C)c1-c1ccc(=O)n(Cc2ccc(Cl)cc2Cl)c1] | D | 1H NMR (500 MHz, DMSO-d6): δ 7.83 (d, J = 2.5 Hz, 1H), 7.69 (d, J = 2.2 Hz, 1H), 7.57 (dd, J = 2.5, 9.4 Hz, 1H), 7.42 (dd, J = 2.2, 9.4 Hz, 1H), 7.00 (d, J = 9.4 Hz, 1H), 6.56 (d, J = 9.4 Hz, 1H), 5.18 (s, 2H), 2.36 (s, 3H), 2.19 (s, 3H). ESI MS m/z 349 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 137 | 4-((5-(3,5-dimethylisoxazol-4-yl)-2-oxopyridin-1(2H)-yl)methyl)benzonitrile | 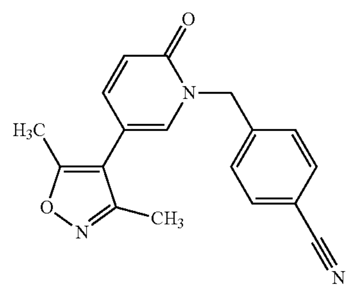 [SMILES: Cc1noc(C)c1-c1ccc(=O)n(Cc2ccc(C#N)cc2)c1] | D | 1H NMR (500 MHz, DMSO-d6): δ 7.96 (s, 1H), 7.83 (d, J = 9.4 Hz, 2H), 7.53 (dd, J = 2.5, 9.4 Hz, 1H), 7.50 (d, J = 9.4 Hz, 2H), 6.53 (d, J = 9.4 Hz, 1H), 5.22 (s, 2H), 2.37 (s, 3H), 2.20 (s, 3H). ESI MS m/z 306 [M + H]+. |
| 138 | 1-(2,4-difluorobenzyl)-5-(3,5-dimethylisoxazol-4-yl)pyridin-2(1H)-one | 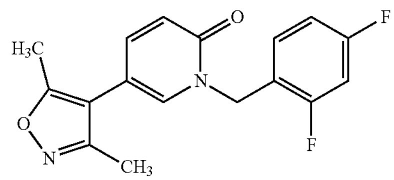 | D | 1H NMR (500 MHz, DMSO-d6): δ 7.86 (d, J = 2.5 Hz, 1H), 7.52 (dd, J = 2.5, 9.4 Hz, 1H), 7.36-7.24 (m, 2H), 7.11-7.05 (m, 1H), 6.50 (d, J = 9.4 Hz, 1H), 5.14 (s, 2H), 2.36 (s, 3H), 2.19 (s, 3H). ESI MS m/z 317 [M + H]+. |
| 139 | 1-(4-chloro-2-fluorobenzyl)-5-(3,5-dimethylisoxazol-4-yl)pyridin-2(1H)-one | 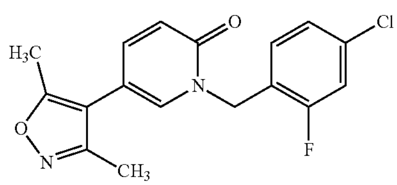 [SMILES: Cc1noc(C)c1-c1ccc(=O)n(Cc2ccc(Cl)cc2F)c1] | D | 1H NMR (500 MHz, DMSO-d6): δ 7.88 (d, J = 2.5 Hz, 1H), 7.53 (dd, J = 2.5, 9.4 Hz, 1H), 7.47 (dd, J = 2.1, 10.1 Hz, 1H), 7.32-7.22 (m, 2H), 6.51 (d, J = 9.4 Hz, 1H), 5.15 (s, 2H), 2.37 (s, 3H), 2.20 (s, 3H). ESI MS m/z 333 [M + H]+. |
| 140 | 1-(2-chloro-4-fluorobenzyl)-5-(3,5-dimethylisoxazol-4-yl)pyridin-2(1H)-one | 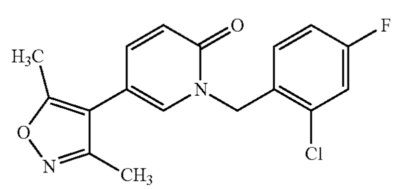 [SMILES: Cc1noc(C)c1-c1ccc(=O)n(Cc2ccc(F)cc2Cl)c1] | D | 1H NMR (500 MHz, DMSO-d6): δ 7.81 (d, J = 2.4 Hz, 1H), 7.57 (dd, J = 2.7, 9.4 Hz, 1H), 7.52 (dd, = 2.7, 8.7 Hz, 1H), 7.22 (td, J = 2.7, 8.6 Hz, 1H), 7.08 (dd, J = 6.1, 8.7 Hz, 1H), 6.55 (d, J = 9.3 Hz, 1H), 5.17 (s, 2H), 2.36 (s, 3H), 2.19 (s, 3H). ESI MS m/z 333 [M + H]+. |
| 141 | 1-(4-chloro-3-fluorobenzyl)-5-(3,5-dimethylisoxazol-4-yl)pyridin-2(1H)-one | 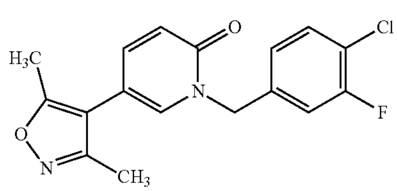 [SMILES: Cc1noc(C)c1-c1ccc(=O)n(Cc2ccc(Cl)c(F)c2)c1] | D | 1H NMR (500 MHz, DMSO-d6): δ 7.95 (d, J = 2.5 Hz, 1H), 7.58 (t, J = 8.1 Hz, 1H), 7.52 (dd, J = 2.6, 9.3 Hz, 1H), 7.43 (dd, J = 1.9, 10.3 Hz, 1H), 7.22 (dd, J = 1.5, 8.3 Hz, 1H), 6.52 (d, J = 9.4 Hz, 1H), 5.13 (s, 2H), 2.37 (s, 3H), 2.20 (s, 3H). ESI MS m/z 333 [M + H]+. |
| 142 | 5-(3,5-dimethylisoxazol-4-yl)-1-(3,4,5-trifluorobenzyl)pyridin-2(1H)-one | 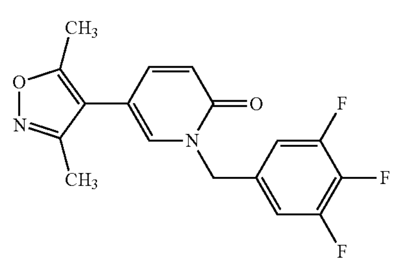 [SMILES: Cc1noc(C)c1-c1ccc(=O)n(Cc2cc(F)c(F)c(F)c2)c1] | D | 1H NMR (500 MHz, DMSO-d6): δ 7.94 (d, J = 2.5 Hz, 1H), 7.52 (dd, J = 2.5, 9.4 Hz, 1H), 7.38-7.30 (m, 2H), 6.52 (d, J = 9.4 Hz, 1H), 5.10 (s, 2H), 2.37 (s, 3H), 2.20 (s, 3H). ESI MS m/z 335 [M + H]+. |

TABLE 1-continued

Exemplary Embodiments prepared using methods described above.

| Example Number | Chemical Name | Structure | General Procedure | Analytical Data |
|---|---|---|---|---|
| 143 | 2-((1H-benzo[d]imidazol-5-yl)methyl)-6-(3,5-dimethylisoxazol-4-yl)pyridazin-3(2H)-one | 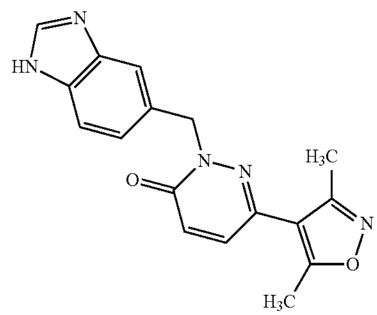 [SMILES: Cc1noc(C)c1-c1ccc(=O)n(Cc2ccc3[nH]cnc3c2)n1] | L | 1H NMR (500 MHz, DMSO-d6): δ 8.19 (s, 1H), 7.65 (d, J = 9.6 Hz, 1H), 7.60 (s, 1H), 7.55 (d, J = 8.3 Hz, 1H), 7.24 (dd, J = 1.4, 8.3 Hz, 1H), 7.07 (d, J = 9.7 Hz, 1H), 5.39 (s, 2H), 2.47 (s, 3H), 2.27 (s, 3H). ESI MS m/z 322 [M + H]+. |
| 144 | 6-(3,5-dimethylisoxazol-4-yl)-2-(3,4,5-trifluorobenzyl)pyridazin-3(2H)-one | 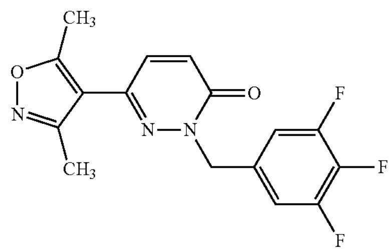 [SMILES: Cc1noc(C)c1-c1ccc(=O)n(Cc2cc(F)c(F)c(F)c2)n1] | C | 1H NMR (500 MHz, DMSO-d6): δ 7.68 (d, J = 9.6 Hz, 1H), 7.35-7.27 (m, 2H), 7.10 (d, J = 9.7 Hz, 1H), 5.29 (s, 2H), 2.48 (s, 3H), 2.27 (s, 3H). ESI MS m/z 336 [M + H]+. |
| 145 | 5-(3,5-dimethylisoxazol-4-yl)-1-(4-(methylsulfonyl)benzyl)pyridin-2(1H)-one | 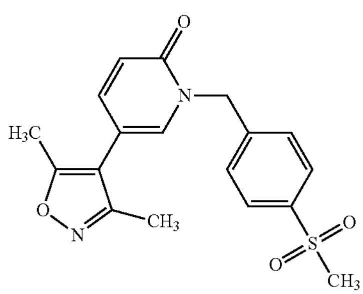 [SMILES: Cc1noc(C)c1-c1ccc(=O)n(Cc2ccc(S(C)(=O)=O)cc2)c1] | D | 1H NMR (500 MHz, DMSO-d6): δ 7.98 (d, J = 2.4 Hz, 1H), 7.91 (d, J = 8.5 Hz, 2H), 7.58 (d, J = 8.5 Hz, 2H), 7.54 (dd, J = 2.6, 9.4 Hz, 1H), 6.53 (d, J = 9.5 Hz, 1H), 5.24 (s, 2H), 3.19 (s, 3H), 2.37 (s, 3H), 2.21 (s, 3H). ESI MS m/z 359 [M + H]+. |
| 146 | 1-((1H-benzo[d]imidazol-5-yl)methyl)-5-(3,5-dimethylisoxazol-4-yl)pyridin-2(1H)-one | 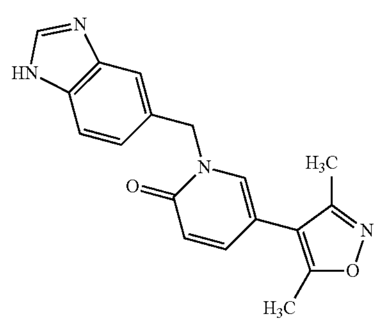 [SMILES: Cc1noc(C)c1-c1ccc(=O)n(Cc2ccc3[nH]cnc3c2)c1] | L | 1H NMR (500 MHz, DMSO-d6): δ 8.19 (s, 1H), 7.96 (d, J = 2.5 Hz, 1H), 7.62 (s, 1H), 7.55 (d, J = 8.3 Hz, 1H), 7.47 (dd, J = 2.6, 9.3 Hz, 1H), 7.27 (dd, J = 1.6, 8.3 Hz, 1H), 6.54 (d, J = 9.3 Hz, 1H), 5.23 (s, 2H), 2.34 (s, 3H), 2.17 (s, 3H). ESI MS m/z 321 [M + H]+. |
| 147 | 1-(3-chloro-4-fluorobenzyl)-5-(3,5-dimethylisoxazol-4-yl)pyridin-2(1H)-one | 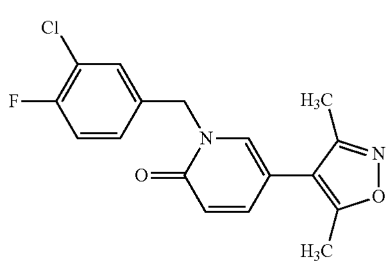 [SMILES: Cc1noc(C)c1-c1ccc(=O)n(Cc2ccc(F)c(Cl)c2)c1] | D | 1H NMR (500 MHz, DMSO-d6): δ 7.97 (d, J = 2.4 Hz, 1H), 7.65 (d, J = 7.7 Hz, 1H), 7.51 (dd, J = 2.4, 9.3 Hz, 1H), 7.44-7.38 (m, 2H), 6.51 (d, J = 9.4 Hz, 1H), 5.10 (s, 2H), 2.36 (s, 3H), 2.20 (s, 3H). ESI MS m/z 333 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 148 | 1-((1H-indazol-5-yl)methyl)-5-(3,5-dimethylisoxazol-4-yl)pyridin-2(1H)-one | 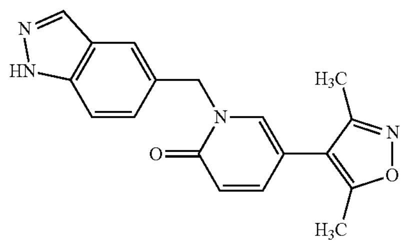 [SMILES: Cc1noc(C)c1-c1ccc(=O)n(Cc2ccc3[nH]ncc3c2)c1] | L | 1H NMR (500 MHz, DMSO-d6): δ 13.06 (s, 1H), 8.06 (s, 1H), 7.95 (d, J = 2.4 Hz, 1H), 7.78 (s, 1H), 7.55-7.40 (m, 3H), 6.51 (d, J = 9.3 Hz, 1H), 5.22 (s, 2H), 2.34 (s, 3H), 2.17 (s, 3H). ESI MS m/z 321 [M + H]+. |
| 149 | 1-((1H-indol-4-yl)methyl)-5-(3,5-dimethylisoxazol-4-yl)pyridin-2(1H)-one | 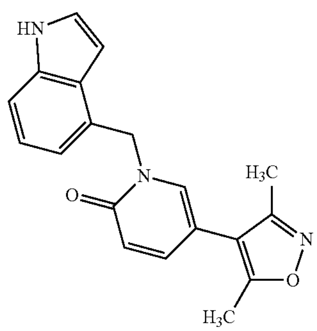 [SMILES: Cc1noc(C)c1-c1ccc(=O)n(Cc2cccc3[nH]ccc23)c1] | L | 1H NMR (500 MHz, DMSO-d6): δ 11.21 (s, 1H), 7.72 (d, J = 2.5 Hz, 1H), 7.48 (dd, J = 2.5, 9.3 Hz, 1H), 7.39-7.33 (m, 2H), 7.05 (t, J = 7.4 Hz, 1H), 6.87 (d, J = 7.0 Hz, 1H), 6.63-6.58 (m, 1H), 6.53 (d, J = 9.4 Hz, 1H), 5.40 (s, 2H), 2.25 (s, 3H), 2.09 (s, 3H). ESI MS m/z 320 [M + H]+. |
| 150 | 1-((4-chlorophenyl)sulfonyl)-5-(3,5-dimethylisoxazol-4-yl)pyridin-2(1H)-one | 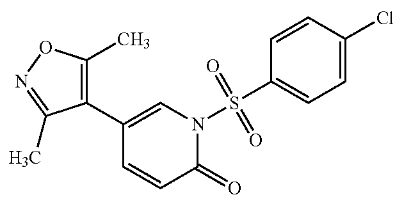 [SMILES: Cc1noc(C)c1-c1ccc(=O)n(S(=O)(=O)c2ccc(Cl)cc2)c1] | H | 1H NMR (300 MHz, CDCl3) δ 8.16 (dd, J = 2.4, 0.6 Hz, 1H), 8.02 (dt, J = 6.9, 2.4 Hz, 2H), 7.69 (dd, J = 8.4, 2.7 Hz, 1H), 7.57 (dt, J = 6.6, 2.4 Hz, 2H), 7.21 (dd, J = 8.4, 0.6 Hz, 1H), 2.41 (s, 3H), 2.26 (s, 3H); ESI-MS m/z 365 [M + H]+. |
| 151 | 5-(3-amino-5-methylisoxazol-4-yl)-1-benzylpyridin-2(1H)-one | 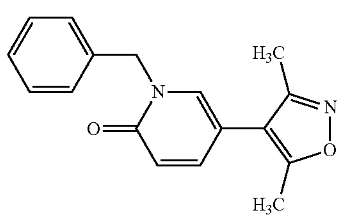 | no general procedure | 1H NMR (300 MHz, DMSO-d6) δ 7.81 (d, J = 2.1 Hz, 1H), 7.42 (dd, J = 2.7, 9.3 Hz, 1H), 7.28-7.36 (m, 5H), 5.49 (d, J = 9.3 Hz, 1H), 5.43 (s, 2H), 5.13 (s, 2H), 2.21 (s, 3H). ESI MS m/z 282 [M + H]+. |
| 152 | 3-amino-1-(4-chlorobenzyl)-5-(3,5-dimethylisoxazol-4-yl)pyridin-2(1H)-one | 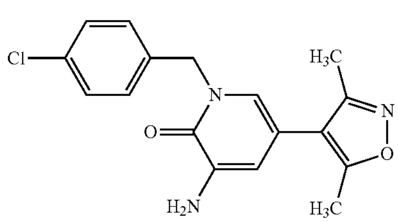 [SMILES: Cc1noc(C)c1-c1cc(N)c(=O)n(Cc2ccc(Cl)cc2)c1] | N | 1H NMR (300 MHz, DMSO-d6) δ 7.42 (d, J = 9.0 Hz, 2H), 7.37 (d, J = 9.0 Hz, 2H), 7.13 (d, J = 2.1 Hz, 1H), 6.45 (d, J = 2.1 Hz, 1H), 5.29 (s, 2H), 5.12 (s, 2H), 2.35 (s, 3H), 2.18 (s, 3H); ESI MS m/z 330 [M + H]+. |

TABLE 1-continued

Exemplary Embodiments prepared using methods described above.

| Example Number | Chemical Name | Structure | General Procedure | Analytical Data |
|---|---|---|---|---|
| 153 | 1-benzyl-5-(3,5-dimethylisoxazol-4-yl)-3-(4-methylpiperazin-1-yl)pyridin-2(1H)-one, hydrochloride | 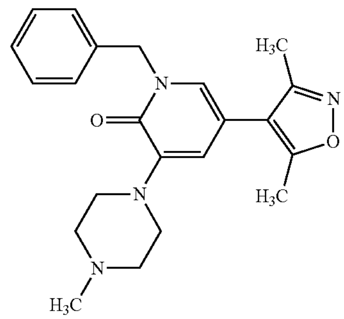 [SMILES: Cc1noc(C)c1-c1cc(N2CCN(C)CC2)c(=O)n(Cc2ccccc2)c1] | J | 1H NMR (500 MHz, DMSO-d6) δ 10.65 (br s, 1H), 7.64 (d, J = 2.2 Hz, 1H), 7.36-7.33 (m, 4H), 7.31-7.26 (m, 1H), 6.81 (d, J = 2.2 Hz, 1H), 5.16 (s, 2H), 3.88 (d, J = 13.0 Hz, 2H), 3.45 (d, J = 11.7 Hz, 2H), 3.17-3.11 (m, 2H), 2.92 (t, J = 12.0 Hz, 2H), 2.80 (s, 3H), 2.37 (s, 3H), 2.20 (s, 3H); ESI m/z 379 [M + H]+. |
| 154 | 1-benzyl-5-(3,5-dimethylisoxazol-4-yl)-4-methoxypyridin-2(1H)-one | 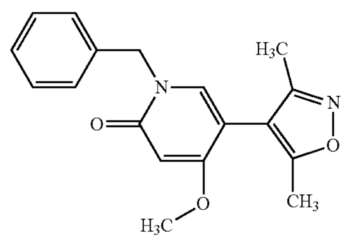 [SMILES: COc1cc(=O)n(Cc2ccccc2)cc1-c1c(C)noc1C] | G | 1H NMR (500 MHz, CDCl3) δ 7.36-7.29 (m, 5H), 6.95 (s, 1H), 6.04 (s, 1H), 5.13 (s, 2H), 3.77 (s, 3H), 2.19 (s, 3H), 2.07 (s, 3H); ESI m/z 311 [M + H]+. |
| 155 | 1-(3,4-dichlorobenzyl)-5-(3,5-dimethylisoxazol-4-yl)pyridin-2(1H)-one | 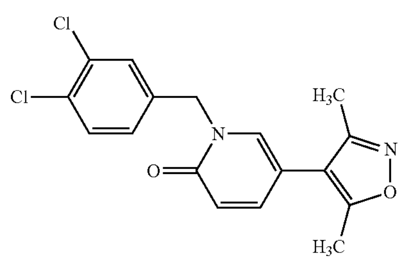 [SMILES: Cc1noc(C)c1-c1ccc(=O)n(Cc2ccc(Cl)c(Cl)c2)c1] | D | 1H NMR (500 MHz, DMSO-d6): δ 7.97 (d, J = 2.4 Hz, 1H), 7.67 (d, J = 2.0 Hz, 1H), 7.63 (d, J = 8.4 Hz, 1H), 7.51 (dd, J = 2.6, 9.4 Hz, 1H), 7.35 (dd, J = 2.2, 8.4 Hz, 1H), 6.51 (d, J = 9.4 Hz, 1H), 5.12 (s, 2H), 2.37 (s, 3H), 2.20 (s, 3H). ESI MS m/z 349 [M + H]+. |
| 156 | 1-benzyl-5-(3,5-dimethylisoxazol-4-yl)-3-((4-fluorophenyl)amino)pyridin-2(1H)-one | 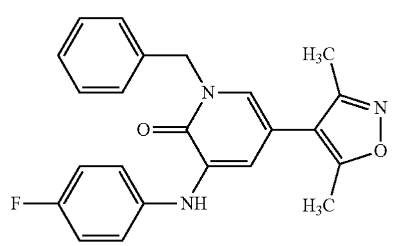 [SMILES: Cc1noc(C)c1-c1cc(Nc2ccc(F)cc2)c(=O)n(Cc2ccccc2)c1] | J | 1H NMR (500 MHz, CDCl3) δ 7.35-7.33 (m, 5H), 7.15-7.12 (m, 2H), 7.05-7.02 (m, 3H), 6.68 (d, J = 2.1 Hz, 1H), 6.62 (d, J = 2.1 Hz, 1H), 5.25 (s, 2H) 2.28 (s, 3H), 2.15 (s, 3H); ESI MS m/z 390 [M + H]+. |
| 157 | 1-benzyl-5-(3,5-dimethylisoxazol-4-yl)-3-((3-fluorophenyl)amino)pyridin-2(1H)-one | 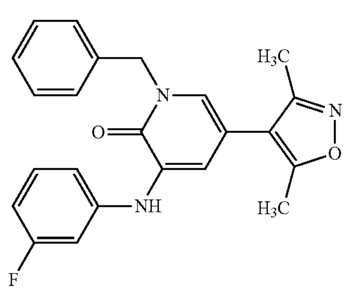 [SMILES: Cc1noc(C)c1-c1cc(Nc2cccc(F)c2)c(=O)n(Cc2ccccc2)c1] | J | 1H NMR (500 MHz, CDCl3) δ 7.40-7.26 (m, 6H), 6.92-6.87 (m, 3H), 6.73-6.67 (m, 2H), 5.25 (s, 2H) 2.31 (s, 3H), 2.18 (s, 3H). ESI MS m/z 390 [M + H]+. |

TABLE 1-continued

Exemplary Embodiments prepared using methods described above.

| Example Number | Chemical Name | Structure | General Procedure | Analytical Data |
|---|---|---|---|---|
| 158 | 1-benzyl-5-(3-(hydroxymethyl)-5-methylisoxazol-4-yl)pyridin-2(1H)-one | 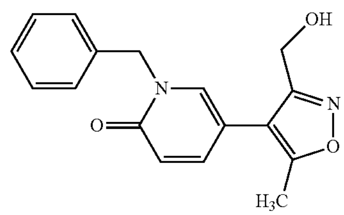 [SMILES: Cc1onc(CO)c1-c1ccc(=O)n(Cc2ccccc2)c1] | F | 1H NMR (500 MHz, DMSO-d6): δ 7.96 (d, J = 2.4 Hz, 1H), 7.59 (dd, J = 2.6, 9.4 Hz, 1H), 7.39-7.33 (m, 4H), 7.32-7.25 (m, 1H), 6.50 (d, J = 9.4 Hz, 1H), 5.47 (t, J = 5.6 Hz, 1H), 5.13 (s, 2H), 4.46 (d, J = 5.6 Hz, 1H), 2.39 (s, 3H). ESI MS m/z 297 [M + H]+. |
| 159 | 1-(4-chlorobenzyl)-5-(3-(hydroxymethyl)-5-methylisoxazol-4-yl)pyridin-2(1H)-one | 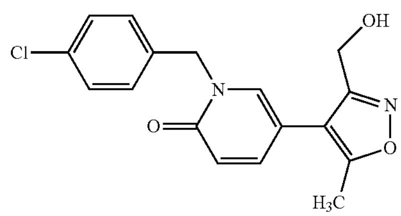 [SMILES: Cc1onc(CO)c1-c1ccc(=O)n(Cc2ccc(Cl)cc2)c1] | F | 1H NMR (500 MHz, DMSO-d6): δ 7.97 (d, J = 2.4 Hz, 1H), 7.60 (dd, J = 2.6, 9.4 Hz, 1H), 7.45-7.35 (m, 4H), 6.50 (d, J = 9.4 Hz, 1H), 5.46 (t, J = 5.5 Hz, 1H), 5.11 (s, 2H), 4.47 (d, J = 5.6 Hz, 1H), 2.39 (s, 3H). ESI MS m/z 331 [M + H]+. |
| 160 | 1-benzyl-5-(3-methylisothiazol-4-yl)pyridin-2(1H)-one | 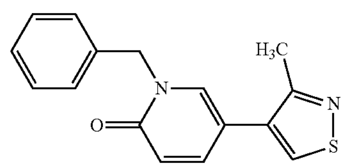 [SMILES: Cc1nscc1-c1ccc(=O)n(Cc2ccccc2)c1] | F | 1H NMR (300 MHz, DMSO-d6) δ 8.93 (s, 1H), 8.04 (d, J = 2.1 Hz, 1H), 7.37 (dd, J = 9.3, 2.7 Hz, 1H), 7.37-7.25 (m, 5H), 6.51 (d, J = 9.3 Hz, 1H), 5.14 (s, 2H), 2.44 (s, 3H); ESI MS m/z 283 [M + H]+. |
| 161 | 1-benzyl-5-(3,5-dimethylisoxazol-4-yl)-3-(piperazin-1-yl)pyridin-2(1H)-one, hydrochloride | 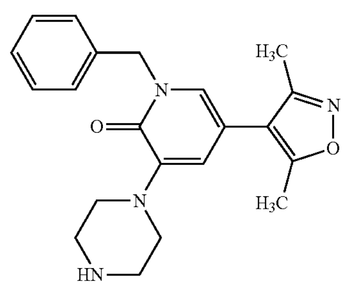 [SMILES: Cc1noc(C)c1-c1cc(N2CCNCC2)c(=O)n(Cc2ccccc2)c1] | M | 1H NMR (500 MHz, DMSO-d6) δ 8.96 (br s, 2H), 7.65 (d, J = 2.2 Hz, 1H), 7.35-7.28 (m, 5H), 6.80 (d, J = 2.2 Hz, 1H), 5.15 (s, 2H), 3.37-3.28 (m, 4H), 3.24-3.14 (m, 4H), 2.37 (s, 3H), 2.20 (s, 3H); ESI m/z 365 [M + H]+. |
| 162 | 5-(3,5-dimethylisoxazol-4-yl)-1-(2-methoxybenzyl)pyridin-2(1H)-one | 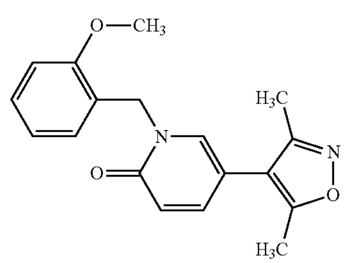 [SMILES: COc1ccccc1Cn1cc(-c2c(C)noc2C)ccc1=O] | G | 1H NMR (300 MHz, DMSO-d6) δ 7.74 (d, J = 2.4 Hz, 1H), 7.51 (dd, J = 9.4 Hz, 2.6 Hz, 1H), 7.34-7.25 (m, 1H), 7.04 (d, J = 8.0 Hz, 1H), 7.01-6.87 (m, 2H), 6.51 (d, J = 9.3 Hz, 1H), 5.07 (s, 2H), 3.84 (s, 3H), 2.35 (s, 3H), 2.18 (s, 3H); ESI m/z 311 [M + H]+. |
| 163 | 5-(3,5-dimethylisoxazol-4-yl)-1-(pyrimidin-2-ylmethyl)pyridin-2(1H)-one | 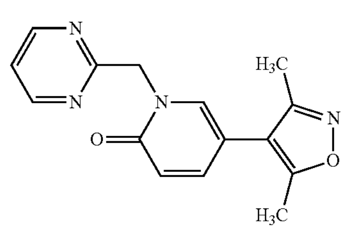 [SMILES: Cc1noc(C)c1-c1ccc(=O)n(Cc2ncccn2)c1] | G | 1H NMR (300 MHz, DMSO-d6) δ 8.77 (d, J = 4.8 Hz, 2H), 7.90 (d, J = 2.1 Hz, 1H), 7.56 (dd, J = 9.4 Hz, 2.6 Hz, 1H), 7.43 (q, J = 4.8 Hz, 1H), 6.50 (d, J = 9.6 Hz, 1H), 5.35 (s, 2H), 2.39 (s, 3H), 2.22 (s, 3H); ESI m/z 283 [M + H]+. |

TABLE 1-continued

Exemplary Embodiments prepared using methods described above.

| Example Number | Chemical Name | Structure | General Procedure | Analytical Data |
|---|---|---|---|---|
| 164 | 2-benzyl-4-(2-hydroxy-3,4-dimethoxyphenyl)phthalazin-1(2H)-one | 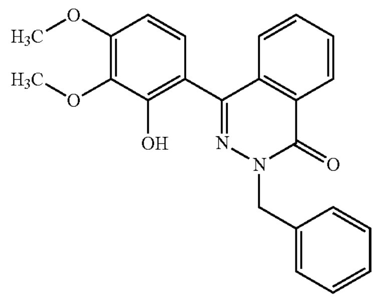 [SMILES: COc1ccc(-c2nn(Cc3ccccc3)c(=O)c3ccccc23)c(O)c1OC] | No general procedure | 1H NMR (400 MHz, CDCl3) δ 8.49 (d, J = 7.4 Hz, 1H), 7.76-7.66 (m, 2H), 7.49 (d, J = 7.4 Hz, 2H), 7.41 (d, J = 7.8 Hz, 1H), 7.34-7.28 (m, 2H), 7.27-7.22 (m, 1H), 7.04 (d, J = 8.6 Hz, 1H), 6.80 (d, J = 8.6 Hz, 1H), 5.47 (s, 2H), 3.94 (s, 6H), 3.64 (s, 3H). |
| 165 | 2-benzyl-4-(4-hydroxy-3-methoxyphenyl)phthalazin-1(2H)-one | 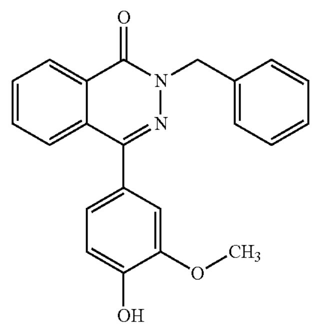 [SMILES: COc1cc(-c2nn(Cc3ccccc3)c(=O)c3ccccc23)ccc1O] | No general procedure | 1H NMR (400 MHz, CDCl3) δ 8.54-8.52 (m, 1H), 7.79-7.71 (m, 3H), 7.52 (d, J = 7.2 Hz, 2H), 7.34-7.25 (m, 4H), 7.11-7.04 (m, 2H), 5.82 (s, 1H), 5.47 (s, 2H), 3.93 (s, 3H); ESI MS m/z 359 [M + 1]+. |
| 166 | 2-benzyl-4-(3,4-dimethoxyphenyl)isoquinolin-1(2H)-one | 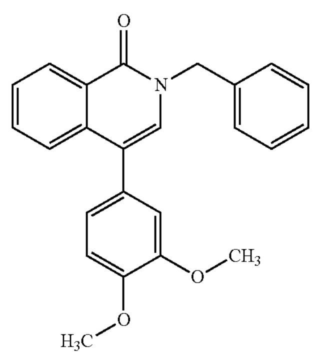 [SMILES: COc1ccc(-c2cn(Cc3ccccc3)c(=O)c3ccccc23)cc1OC] | No general procedure | 1H NMR (400 MHz, CDCl3): δ 8.57 (d, J = 7.81 Hz, 1H), 7.47-7.66 (m, 3H), 7.24-7.42 (m, 5H), 7.06 (s, 1H), 6.85-6.98 (m, 3H), 5.27 (s, 2H), 3.93 (s, 3H), 3.87 (s, 3H). ESI MS m/z 372 [M + H]+. |
| 167 | 2-benzyl-4-(3,5-dimethylisoxazol-4-yl)isoquinolin-1(2H)-one | 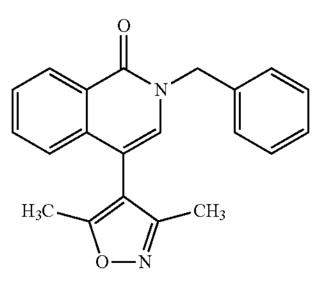 [SMILES: Cc1noc(C)c1-c1cn(Cc2ccccc2)c(=O)c2ccccc12] | No general procedure | 1H NMR (400 MHz, CDCl3) δ 8.56 (d, J = 7.8 Hz, 1H), 7.60-7.68 (m, 1H), 7.51-7.60 (m, 1H), 7.29-7.39 (m, 5H), 7.19 (d, J = 7.8 Hz, 1H), 6.97 (s, 1H), 5.18-5.33 (m, 2H), 2.23 (s, 3H), 2.06 (s, 3H); ESI MS m/z 331 [M + H]+. |

TABLE 1-continued

Exemplary Embodiments prepared using methods described above.

| Example Number | Chemical Name | Structure | General Procedure | Analytical Data |
|---|---|---|---|---|
| 168 | 2-benzyl-4-(3,4,5-trimethoxyphenyl)isoquinolin-1(2H)-one | 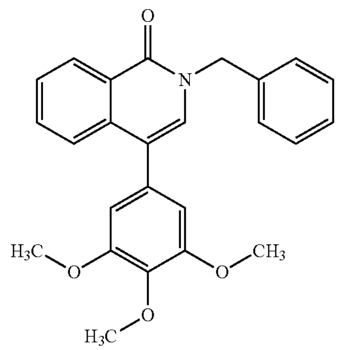 [SMILES: COc1cc(-c2cn(Cc3ccccc3)c(=O)c3ccccc23)cc(OC)c1OC] | No general procedure | 1H NMR (400 MHz, CDCl3) δ 8.57 (d, J = 7.8 Hz, 1H), 7.49-7.66 (m, 3H), 7.28-7.41 (m, 5H), 7.08 (s, 1H), 6.57 (s, 2H), 5.28 (s, 2H), 3.91 (s, 3H), 3.85 (s, 6H); ESI MS m/z 402 [M + H]+. |
| 169 | 2-benzyl-4-(4-hydroxy-3-methoxyphenyl)isoquinolin-1(2H)-one | 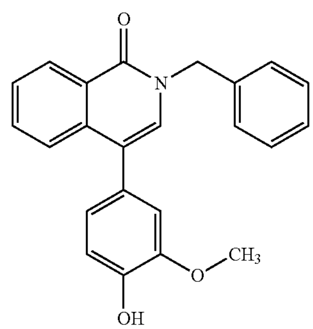 [SMILES: COc1cc(-c2cn(Cc3ccccc3)c(=O)c3ccccc23)ccc1O] | No general procedure | 1H NMR (400 MHz, CDCl3) δ 8.56 (d, J = 8.2 Hz, 1H), 7.58-7.65 (m, 1H), 7.50-7.57 (m, 2H), 7.28-7.40 (m, 5H), 7.05 (s, 1H), 6.99 (d, J = 8.6 Hz, 1H), 6.84-6.89 (m, 2H), 5.70 (s, 1H), 5.27 (s, 2H), 3.89 (s, 3H); ESI MS m/z 358 [M + H]+. |
| 170 | 2-benzyl-4-(3,5-dimethylisoxazol-4-yl)phthalazin-1(2H)-one | 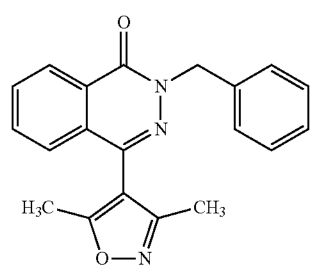 [SMILES: Cc1noc(C)c1-c1nn(Cc2ccccc2)c(=O)c2ccccc12] | No general procedure | 1H NMR (400 MHz, CDCl3) δ 8.55-8.53 (m, 1H), 7.83-7.76 (m, 2H), 7.48 (d, J = 7.2 Hz, 2H), 7.44-7.42 (m, 1H), 7.35-7.26 (m, 3H), 5.45 (s, 2H), 2.31 (s, 3H), 2.15 (s, 3H). |
| 171 | 2-benzyl-4-((3,4,5-trimethoxyphenyl)amino)phthalazin-1(2H)-one | 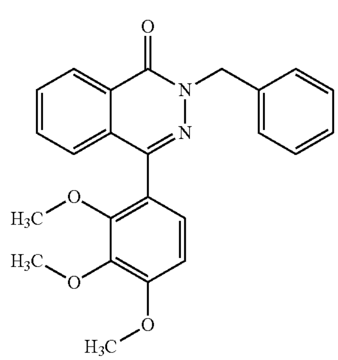 | No general procedure | 1H NMR (400 MHz, CDCl3) δ 8.57-8.55 (m, 1H), 7.84-7.76 (m, 3H), 7.41 (d, J = 6.8 Hz, 2H), 7.32-7.22 (m, 3H), 6.69 (s, 2H), 6.40 (s, 1H), 5.38 (s, 2H), 3.81 (s, 3H), 3.70 (s, 6H); ESI MS m/z 418 [M + 1]+. |

TABLE 1-continued

Exemplary Embodiments prepared using methods described above.

| Example Number | Chemical Name | Structure | General Procedure | Analytical Data |
|---|---|---|---|---|
| 172 | 2-benzyl-4-((3,4,5-trimethoxyphenyl)amino)isoquinolin-1(2H)-one | 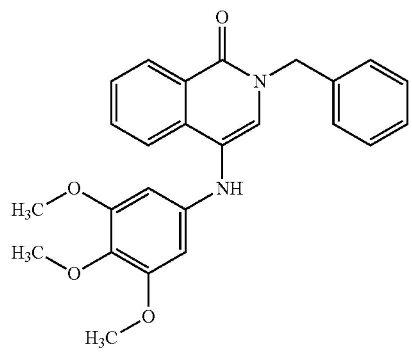 [SMILES: COc1cc(Nc2cn(Cc3ccccc3)c(=O)c3ccccc23)cc(OC)c1OC] | No general procedure | 1H NMR (400 MHz, CDCl3) δ 8.53 (d, J = 8.2 Hz, 1H), 7.61-7.68 (m, 2H), 7.54 (ddd, J = 8.2, 5.6, 2.7 Hz, 1H), 7.27-7.35 (m, 5H), 7.17 (s, 1H), 5.85 (s, 2H), 5.23 (s, 2H), 5.10 (s, 1H), 3.75 (s, 3H), 3.65 (s, 6H); ESI MS m/z 417 [M + H]+. |
| 173 | 6-benzyl-8-(3,5-dimethylisoxazol-4-yl)-1,6-naphthyridin-5(6H)-one | 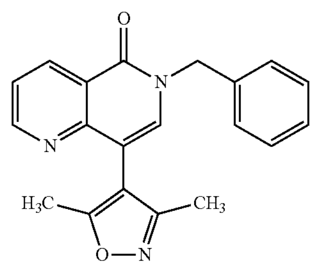 [SMILES: Cc1noc(C)c1-c1cn(Cc2ccccc2)c(=O)c2cccnc12] | No general procedure | 1H NMR (400 MHz, CDCl3) δ 8.92 (dd, J = 4.5, 1.9 Hz, 1H), 8.78 (dd, J = 8.0, 1.9 Hz, 1H), 7.47 (dd, J = 8.0, 4.5 Hz, 1H), 7.30-7.41 (m, 5H), 7.20 (s, 1H), 5.27 (s, 2H), 2.25 (s, 3H), 2.11 (s, 3H); ESI MS m/z 332 [M + H]+. |
| 174 | 7-benzyl-5-(3,5-dimethylisoxazol-4-yl)-1,7-naphthyridin-8(7H)-one | 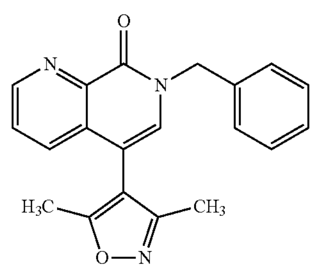 [SMILES: Cc1noc(C)c1-c1cn(Cc2ccccc2)c(=O)c2ncccc12] | No general procedure | 1H NMR (400 MHz, CDCl3): δ 8.92-9.00 (m, 1H), 7.52-7.60 (m, 2H), 7.29-7.42 (m, 5H), 7.04 (s, 1H), 5.26-5.43 (m, 2H), 2.22 (s, 3H), 2.04 (s, 3H); ESI MS m/z 332.0 [M + H]+. |
| 175 | 2-benzyl-4-(3,5-dimethylisoxazol-4-yl)-2,7-naphthyridin-1(2H)-one | 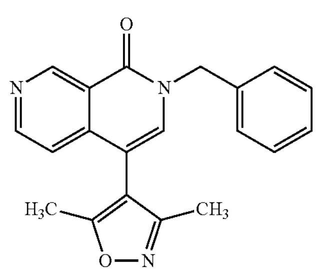 [SMILES: Cc1noc(C)c1-c1cn(Cc2ccccc2)c(=O)c2cnccc12] | No general procedure | 1H NMR (400 MHz, CDCl3) δ 9.73 (s, 1H), 8.75 (d, J = 5.4 Hz, 1H), 7.31-7.41 (m, 5H), 7.16 (s, 1H), 7.02 (d, J = 5.4 Hz, 1H), 5.26 (s, 2H), 2.23 (s, 3H), 2.06 (s, 3H); ESI MS m/z 332 [M + H]+. |
| 176 | 2-benzyl-4-(3,5-dimethylisoxazol-4-yl)-2,6-naphthyridin-1(2H)-one | 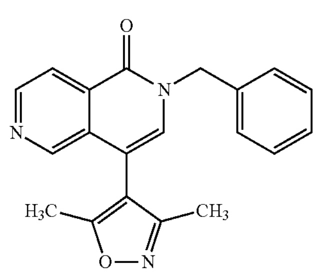 [SMILES: Cc1noc(C)c1-c1cn(Cc2ccccc2)c(=O)c2ccncc12] | No general procedure | 1H NMR (400 MHz, CDCl3) δ 8.78 (d, J = 5.4 Hz, 1H), 8.65 (s, 1H), 8.30 (d, J = 5.4 Hz, 1H), 7.30-7.40 (m, 5H), 7.04 (s, 1H), 5.26 (s, 2H), 2.26 (s, 3H), 2.09 (s, 3H); ESI MS m/z 332 [M + H]+. |

TABLE 1-continued

Exemplary Embodiments prepared using methods described above.

| Example Number | Chemical Name | Structure | General Procedure | Analytical Data |
|---|---|---|---|---|
| 177 | 2-benzyl-4-(2,3,4-trimethoxyphenyl)phthalazin-1(2H)-one | 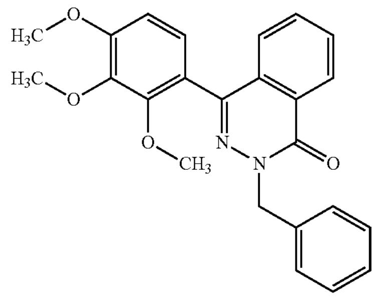 | No general procedure | 1H NMR (400 MHz, CDCl3) δ 8.51 (d, J = 7.5 Hz, 1H), 7.79-7.69 (m, 2H), 7.63 (d, J = 7.5 Hz, 2H), 7.51 (d, J = 7.6 Hz, 2H), 7.36-7.30 (m, 1H), 7.30-7.24 (m, 1H), 7.10 (d, J = 8.6 Hz, 1H), 6.74 (s, 1H), 6.63 (d, J = 8.6 Hz, 1H), 5.47 (s, 2H), 3.97 (s, 3H), 3.94 (s, 3H); ESI MS m/z 389 [M + H]+. |
| 178 | 6-(4-hydroxyphenyl)-2-(1-phenylethyl)pyridazin-3(2H)-one | 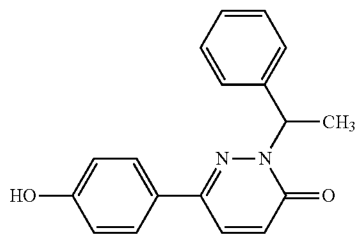 [SMILES: CC(c1ccccc1)n1nc(-c2ccc(O)cc2)ccc1=O] | A | 1H NMR (300 MHz, DMSO-d6) δ 9.85 (s, 1H), 7.96 (d, J = 9.9 Hz, 1H), 7.74 (d, J = 8.7 Hz, 2H), 7.44-7.19 (m, 5H), 6.99 (d, J = 9.9 Hz, 1H), 6.84 (d, J = 8.7 Hz, 2H), 6.24 (q, J = 8.1 Hz, 1H), 1.75 (d, J = 7.2 Hz, 3H); ESI m/z 293 [M + H]+. |
| 179 | 2-benzyl-6-(4-methyl-3-oxopiperazin-1-yl)pyridazin-3(2H)-one | 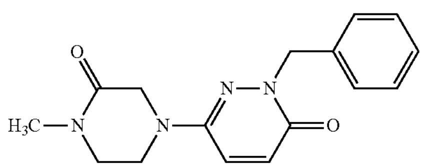 [SMILES: CN1CCN(c2ccc(=O)n(Cc3ccccc3)n2)CC1=O] | B | 1H NMR (300 MHz, CDCl3) δ 7.42-7.45 (m, 2H); 7.27-7.35 (m, 3H); 7.04 (d, J = 9.9 Hz, 1H); 6.92 (d, J = 9.9 Hz, 1H); 5.19 (s, 2H); 3.93 (s, 2H); 3.52-3.56 (m, 2H); 3.40-3.43 (m, 2H); 3.01 (s, 3H); ESI MS m/z 299 [M + H]+. |
| 180 | 3-amino-5-(3,5-dimethylisoxazol-4-yl)-1-(4-fluorobenzyl)pyridin-2(1H)-one | 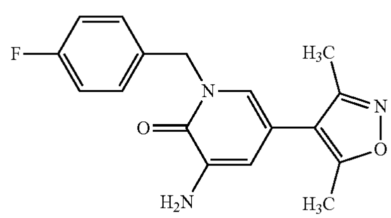 [SMILES: Cc1noc(C)c1-c1cc(N)c(=O)n(Cc2ccc(F)cc2)c1] | N | 1H NMR (300 MHz, DMSO-d6) δ 7.45-7.40 (m, 2H), 7.21-7.15 (m, 2H), 7.13 (d, J = 2.4 Hz, 1H), 6.44 (d, J = 2.4 Hz, 1H), 5.29 (s, 2H), 5.11 (s, 2H), 2.35 (s, 3H), 2.18 (s, 3H); ESI m/z 314 [M + H]+ |
| 181 | 3-chloro-5-(3,5-dimethylisoxazol-4-yl)-1-(4-fluorobenzyl)pyridin-2(1H)-one | 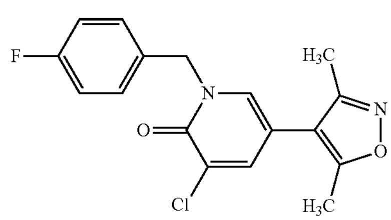 [SMILES: Cc1noc(C)c1-c1cc(Cl)c(=O)n(Cc2ccc(F)cc2)c1] | D | 1H NMR (300 MHz, DMSO-d6) δ 8.04 (s, 1H), 8.03 (s, 1H), 7.49-7.45 (m, 2H), 7.23-7.16 (m, 2H), 5.17 (s, 2H), 3.37 (s, 3H), 2.20 (s, 3H); ESI m/z 333 [M + H]+. |
| 182 | 5-(3,5-dimethylisoxazol-4-yl)-1-(4-fluorobenzyl)-3-(phenylamino)pyridin-2(1H)-one | 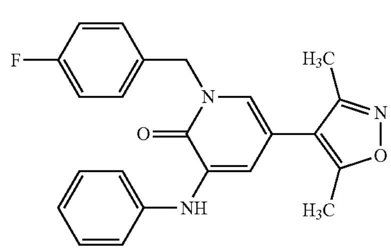 [SMILES: Cc1noc(C)c1-c1cc(Nc2ccccc2)c(=O)n(Cc2ccc(F)cc2)c1] | J | 1H NMR (300 MHz, DMSO-d6) δ 7.87 (s, 1H), 7.51-7.46 (m, 2H), 7.40 (d, J = 2.1 Hz, 1H), 7.28-7.27 (m, 4H), 7.23-7.17 (m, 2H), 6.97 (d, J = 2.1 Hz, 1H), 6.95-6.93 (m, 1H), 5.19 (s, 2H), 2.19 (s, 3H), 1.99 (s, 3H); ESI m/z 390 [C23H2OFN3O2 + H]+. |

TABLE 1-continued

Exemplary Embodiments prepared using methods described above.

| Example Number | Chemical Name | Structure | General Procedure | Analytical Data |
| --- | --- | --- | --- | --- |
| 183 | 3-(azetidin-1-yl)-1-benzyl-5-(3,5-dimethylisoxazol-4-yl)pyridin-2(1H)-one | 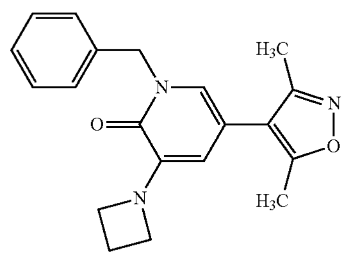 [SMILES: Cc1noc(C)c1-c1cc(N2CCC2)c(=O)n(Cc2ccccc2)c1] | No general procedure | 1H NMR (500 MHz, DMSO-d6) δ 7.25-7.38 (m, 5H), 7.21 (d, J = 2.2 Hz, 1H), 6.07 (d, J = 2.2 Hz, 1H), 5.07 (s, 2H), 3.89 (t, J = 7.2 Hz, 4H), 2.34 (s, 3H), 2.18 (t, J = 7.2 Hz, 2H), 2.17 (s, 3H); ESI m/z 336 [M + H]+. |
| 184 | 1-benzyl-5-(3,5-dimethylisoxazol-4-yl)-3-((1-methyl-1H-pyrazol-3-yl)amino)pyridin-2(1H)-one | 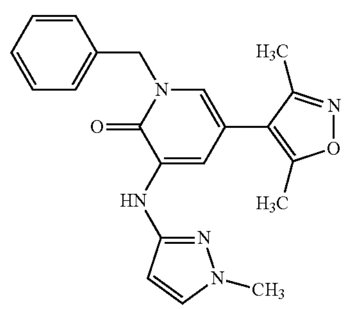 [SMILES: Cc1noc(C)c1-c1cc(Nc2ccn(C)n2)c(=O)n(Cc2ccccc2)c1] | J | 1H NMR (500 MHz, CDCl3): δ 7.82 (d, J = 2.0 Hz, 1H), 7.46 (s, 1H), 7.37-7.26 (m, 5H), 7.21 (d, J = 1.5 Hz, 1H), 6.63 (d, J = 1.5 Hz, 1H), 5.83 (d, J = 2.0 Hz, 1H), 5.25 (s, 2H), 3.80 (s, 3H), 2.34 (s, 3H), 2.23 (s, 3H). ESI MS m/z 376 [M + H]+. |
| 185 | 3-(1-benzyl-5-(3,5-dimethylisoxazol-4-yl)-2-oxo-1,2-dihydropyridin-3-yl)benzamide | 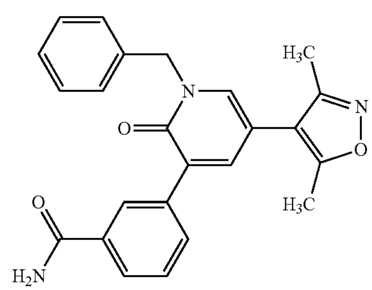 [SMILES: Cc1noc(C)c1-c1cc(-c2cccc(C(N)=O)c2)c(=O)n(Cc2ccccc2)c1] | I | 1H NMR (300 MHz, DMSO-d6) δ 8.13-8.12 (m, 1H), 8.05 (d, J = 2.7 Hz, 1H), 7.98 (s, 1H), 7.92-7.88 (m, 1H), 7.83-7.79 (m, 1H), 7.75 (d, J = 2.4 Hz, 1H), 7.49-7.27 (m, 7H), 5.24 (s, 2H), 2.41 (s, 3H), 2.24 (s, 3H); ESI MS m/z 400 [M + H]+. |
| 186 | 1-benzyl-5-(3,5-dimethylisoxazol-4-yl)-3-(ethylamino)pyridin-2(1H)-one | 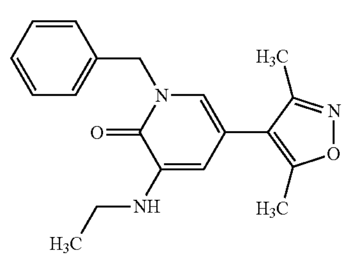 [SMILES: CCNc1cc(-c2c(C)noc2C)cn(Cc2ccccc2)c1=O] | J | 1H NMR (300 MHz, DMSO-d6) δ 7.35-7.26 (m, 5H), 7.08 (d, J = 2.1 Hz, 1H), 6.14 (d, J = 2.4 Hz, 1H), 5.49 (t, J = 6.0 Hz, 1H), 5.14 (s, 2H), 3.11-3.02 (m, 2H), 2.36 (s, 3H), 2.19 (s, 3H), 1.15 (t, J = 7.2 Hz, 3H); ESI MS m/z 324 [M + H]+. |
| 187 | 1-benzyl-5-(3-(methoxymethyl)-5-methylisoxazol-4-yl)pyridin-2(1H)-one | 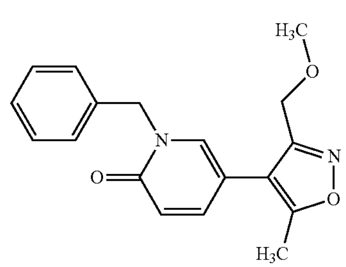 [SMILES: COCc1noc(C)c1-c1ccc(=O)n(Cc2ccccc2)c1] | D | 1H NMR (300 MHz, DMSO-d6) δ 7.91 (d, J = 2.4 Hz, 1H), 7.53 (dd, J = 9.3, 2.4 Hz, 1H), 7.39-7.27 (m, 5H), 6.52 (d, J = 9.3 Hz, 1H), 5.14 (s, 2H), 4.41 (s, 2H), 3.18 (s, 3H), 2.40 (s, 3H); ESI m/z 311 [M + H]+. |

TABLE 1-continued

Exemplary Embodiments prepared using methods described above.

| Example Number | Chemical Name | Structure | General Procedure | Analytical Data |
|---|---|---|---|---|
| 188 | 1-(4-chlorobenzyl)-5-(3,5-dimethylisoxazol-4-yl)-3-(phenylamino)pyridin-2(1H)-one | 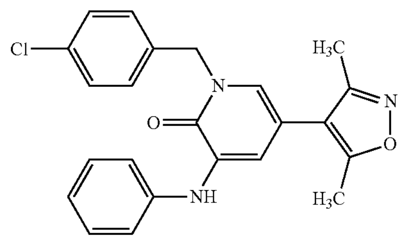 [SMILES: Cc1noc(C)c1-c1cc(Nc2ccccc2)c(=O)n(Cc2ccc(Cl)cc2)c1] | J | 1H NMR (300 MHz, DMSO-d6) δ 7.87 (s, 1H), 7.44 (s, 4H), 7.40 (d, J = 2.1 Hz, 1H), 7.29-7.27 (m, 4H), 6.98 (d, J = 2.1 Hz, 1H), 6.95-6.91 (m, 1H), 5.20 (s, 2H), 2.37 (s, 3H), 2.19 (s, 3H); ESI m/z 406 [M + H]+. |
| 189 | 3-amino-1-benzyl-5-(3-(hydroxymethyl)-5-methylisoxazol-4-yl)pyridin-2(1H)-one | 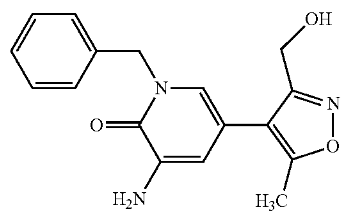 [SMILES: Cc1onc(CO)c1-c1cc(N)c(=O)n(Cc2ccccc2)c1] | No general procedure | 1H NMR (500 MHz, DMSO-d6) δ 7.25-7.37 (m, 5H), 7.18 (d, J = 2.2 Hz, 1H), 6.57 (d, J = 2.2 Hz, 1H), 5.42 (t, J = 5.6 Hz, 1H), 5.25 (s, 2H), 5.12 (s, 2H), 4.44 (d, J = 5.6 Hz, 2H), 2.37 (s, 3H); ESI m/z 312 [M + H]+ |
| 190 | 1-benzyl-5-(3,5-dimethylisoxazol-4-yl)-3-morpholinopyridin-2(1H)-one | 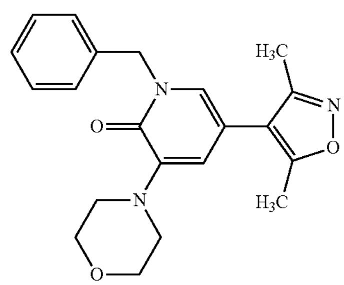 [SMILES: Cc1noc(C)c1-c1cc(N2CCOCC2)c(=O)n(Cc2ccccc2)c1] | M | 1H NMR (300 MHz, CDCl3) δ 7.37-7.31 (m, 5H), 6.91 (br s, 1H), 6.71 (br s, 1H), 5.19 (s, 2H), 3.96-3.93 (m, 4H), 3.27 (s, 4H), 2.31 (s, 3H), 2.18 (s, 3H); ESI m/z 366 [M + H]+. |
| 191 | 1-benzyl-3-(benzyloxy)-5-(3,5-dimethylisoxazol-4-yl)pyridin-2(1H)-one | 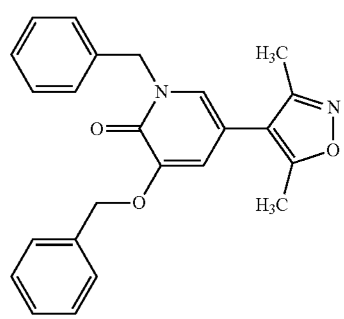 [SMILES: Cc1noc(C)c1-c1cc(OCc2ccccc2)c(=O)n(Cc2ccccc2)c1] | N | 1H NMR (300 MHz, DMSO-d6) δ 7.52 (d, J = 2.1 Hz, 1H), 7.45-7.32 (m, 10H), 6.91 (d, J = 2.1 Hz, 1H), 5.15 (s, 2H), 5.07 (s, 2H), 2.31 (s, 3H), 2.14 (s, 3H); ESI m/z 387 [C24H22N2O3 + H]+. |
| 192 | 1-benzyl-5-(3,5-dimethylisoxazol-4-yl)-3-(isopropylamino)pyridin-2(1H)-one | 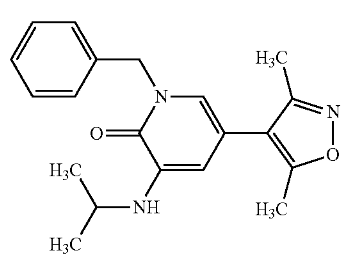 [SMILES: Cc1noc(C)c1-c1cc(NC(C)C)c(=O)n(Cc2ccccc2)c1] | J | 1H NMR (300 MHz, DMSO-d6) δ 7.38-7.26 (m, 5H), 7.09 (d, J = 2.1 Hz, 1H), 6.18 (d, J = 2.1 Hz, 1H), 5.17 (d, J = 8.4 Hz, 1H), 5.14 (s, 2H), 3.57-3.30 (m, 1H), 2.36 (s, 3H), 2.20 (s, 3H), 1.14 (d, J = 6.3 Hz, 6H); ESI MS m/z 338 [M + H]+. |

TABLE 1-continued

Exemplary Embodiments prepared using methods described above.

| Example Number | Chemical Name | Structure | General Procedure | Analytical Data |
|---|---|---|---|---|
| 193 | 1-benzyl-5-(3,5-dimethylisoxazol-4-yl)-3-(pyridin-2-ylamino)pyridin-2(1H)-one | 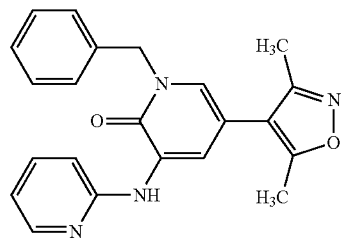 | J | 1H NMR (300 MHz, DMSO-d6) δ 8.71 (s, 1H), 8.65 (d, J = 2.1 Hz, 1H), 8.20 (dd, J = 5.1, 1.2 Hz, 1H), 7.62-7.56 (m, 1H), 7.49 (d, J = 2.1 Hz, 1H), 7.43-7.26 (m, 6H), 6.83-6.79 (m, 1H), 5.24 (s, 2H), 2.42 (s, 3H), 2.25 (s, 3H); ESI MS m/z 373 [M + H]+. |
| 194 | 1-benzyl-5-(3,5-dimethylisoxazol-4-yl)-3-(pyridin-3-ylamino)pyridin-2(1H)-one | 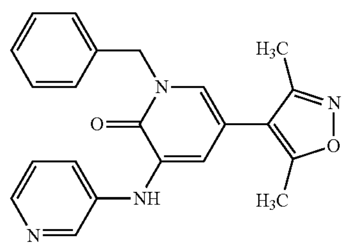 | J | 1H NMR (300 MHz, DMSO-d6) δ 8.55 (d, J = 2.7 Hz, 1H), 8.12 (s, 1H), 8.10 (d, J = 1.5 Hz, 1H), 7.68-7.65 (m, 1H), 7.45-7.26 (m, 7H), 7.02 (d, J = 2.1 Hz, 1H), 5.22 (s, 2H), 2.36 (s, 3H), 2.19 (s, 3H); ESI MS m/z 373 [M + H]+. |
| 195 | 1-benzyl-5-(3,5-dimethylisoxazol-4-yl)-3-(pyridin-4-ylamino)pyridin-2(1H)-one | 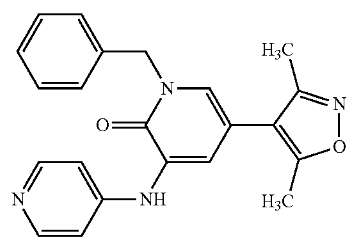 [SMILES: Cc1noc(C)c1-c1cc(Nc2ccncc2)c(=O)n(Cc2ccccc2)c1] | J | 1H NMR (300 MHz, DMSO-d6) δ 8.46 (s, 1H), 8.24 (dd, J = 1.5, 4.8 Hz, 2H), 7.60 (d, J = 2.1 Hz, 1H), 7.43-7.30 (m, 6H), 7.15 (dd, J = 1.5, 4.8 Hz, 2H), 5.22 (s, 2H), 2.39 (s, 3H), 2.23 (s, 3H); ESI MS m/z 373 [M + H]+. |
| 196 | 1-benzyl-5-(3,5-dimethylisothiazol-4-yl)pyridin-2(1H)-one | 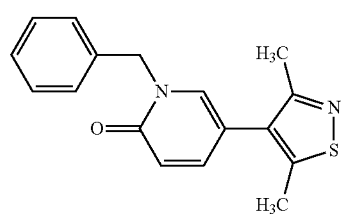 | F | 1H NMR (300 MHz, DMSO-d6) δ 7.92 (d, J = 2.1 Hz, 1H), 7.47 (dd, J = 9.3, 2.4 Hz, 1H), 7.36-7.29 (m, 5H), 6.52 (d, J = 9.3 Hz, 1H), 5.14 (s, 2H), 2.39 (s, 3H), 2.29 (s, 3H); ESI m/z 297 [M + H]+. |
| 197 | 1-(4-chlorobenzyl)-5-(3,5-dimethyl-4H-1,2,4-triazol-4-yl)pyridin-2(1H)-one | 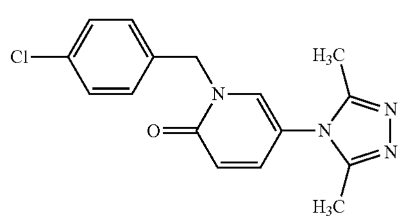 [SMILES: Cc1nnc(C)n1-c1ccc(=O)n(Cc2ccc(Cl)cc2)c1] | No general procedure | 1H NMR (300 MHz, DMSO-d6) δ 8.30 (d, J = 2.7 Hz, 1H), 7.58 (dd, J = 9.6, 2.4 Hz, 1H), 7.45-7.36 (m, 4H), 6.55 (d, J = 9.6 Hz, 1H), 5.08 (s, 2H), 2.19 (s, 6H); ESI m/z 315 [M + H]+. |
| 198 | 1-benzyl-5-(3,5-dimethylisoxazol-4-yl)-2-oxo-1,2-dihydropyridine-3-carbonitrile | 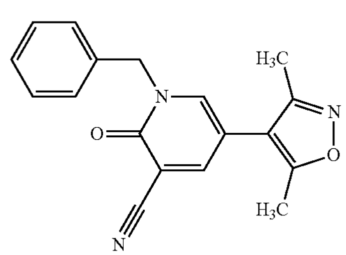 [SMILES: Cc1noc(C)c1-c1cc(C#N)c(=O)n(Cc2ccccc2)c1] | No general procedure | 1H NMR (300 MHz, CDCl3) d 7.68 (d, J = 2.6 Hz, 1H), 7.45-7.33 (m, 6H), 5.21 (s, 2H), 2.28 (s, 3H), 2.13 (s, 3H); ESI MS m/z 306 [M + H]+ |

TABLE 1-continued

Exemplary Embodiments prepared using methods described above.

| Example Number | Chemical Name | Structure | General Procedure | Analytical Data |
|---|---|---|---|---|
| 199 | methyl 4-(1-(4-chlorobenzyl)-6-oxo-1,6-dihydropyridin-3-yl)-5-methylisoxazole-3-carboxylate | 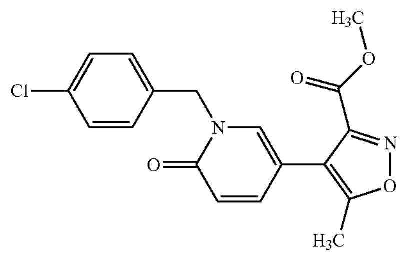 [SMILES: COC(=O)c1noc(C)c1-c1ccc(=O)n(Cc2ccc(Cl)cc2)c1] | No general procedure | 1H NMR (500 MHz, DMSO-d6) δ 7.99 (d, J = 2.3 Hz, 1H), 7.50 (dd, J = 2.5, 9.3 Hz, 1H), 7.33-7.47 (m, 4H), 6.47 (d, J = 9.3 Hz, 1H), 5.09 (s, 2H), 3.79 (s, 3H), 2.44 (s, 3H); ESI m/z 359 [M + H]+. |
| 200 | N-(1-benzyl-5-(3,5-dimethylisoxazol-4-yl)-2-oxo-1,2-dihydropyridin-3-yl)methanesulfonamide | 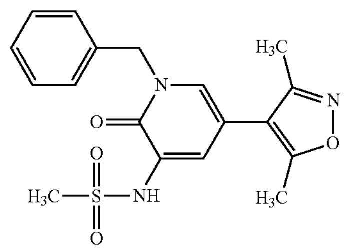 [SMILES: Cc1noc(C)c1-c1cc(NS(C)(=O)=O)c(=O)n(Cc2ccccc2)c1] | No general procedure | 1H NMR (500 MHz, DMSO-d6): δ 9.02 (s, 1H), 7.78 (d, J = 3.5 Hz, 1H), 7.38-7.26 (m, 6H), 5.20 (s, 2H), 3.30 (s, 3H), 2.42 (s, 3H), 2.20 (s, 3H). ESI MS m/z 374 [M + H]+. |
| 201 | 2-benzyl-6-(((3,5-dimethylisoxazol-4-yl)methyl)amino)pyridazin-3(2H)-one | 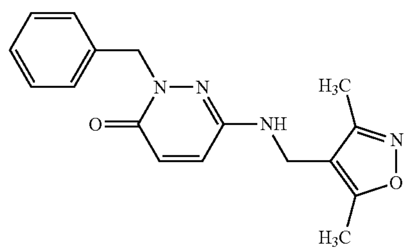 [SMILES: Cc1noc(C)c1CNc1ccc(=O)n(Cc2ccccc2)n1] | No general procedure | 1H NMR (300 MHz, DMSO-d6) δ 7.41-7.38 (m, 2H), 7.35-7.27 (m, 3H), 6.86 (d, J = 16.0 Hz, 1H), 6.69 (d, J = 16.0 Hz, 1H), 5.20 (s, 2H), 4.09 (s, 2H), 2.34 (s, 3H), 2.23 (s, 3H); ESI m/z 311 [M + H]+. |
| 202 | 4-(1-(4-chlorobenzyl)-6-oxo-1,6-dihydropyridin-3-yl)-5-methylisoxazole-3-carboxamide | 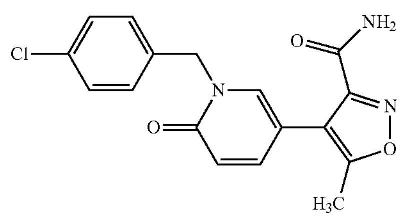 [SMILES: Cc1onc(C(N)=O)c1-c1ccc(=O)n(Cc2ccc(Cl)cc2)c1] | No general procedure | 1H NMR (500 MHz, DMSO-d6) δ 8.13 (s, 1H), 7.95 (d, J = 2.3 Hz, 1H), 7.82 (s, 1H), 7.45 (dd, J = 2.5, 9.3 Hz, 1H), 7.34-7.44 (m, 4H), 6.45 (d, J = 9.3 Hz, 1H), 5.09 (s, 2H), 2.42 (s, 3H); ESI m/z 344 [M + H]+. |
| 203 | 3-amino-1-(4-chloro-3-fluorobenzyl)-5-(3,5-dimethylisoxazol-4-yl)pyridin-2(1H)-one | 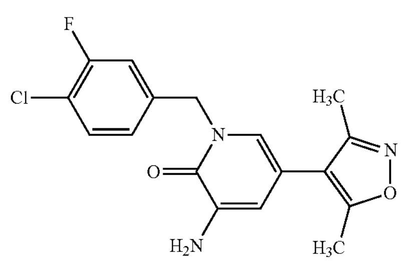 | D | 1H NMR (300 MHz, CDCl3) δ 7.40-7.35 (m, 1H), 7.11 (d, J = 9.6 Hz, 1H), 7.06 (d, J = 8.2 Hz, 1H), 6.57 (d, J = 2.1 Hz, 1H), 6.40 (d, J = 2.1 Hz, 1H), 5.15 (s, 2H), 4.38 (s, 2H), 2.33 (s, 3H), 2.20 (s, 3H); ESI m/z 348 [M + H]+; |
| 204 | 1-benzyl-5-(3,5-dimethylisoxazol-4-yl)-3-(1H-imidazol-1-yl)pyridin-2(1H)-one | 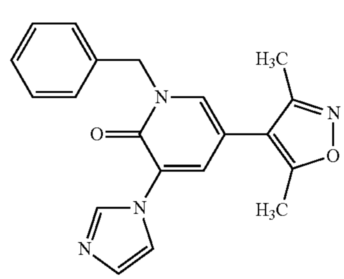 [SMILES: Cc1noc(C)c1-c1cc(-n2ccnc2)c(=O)n(Cc2ccccc2)c1] | J | 1H NMR (300 MHz, CDCl3) δ 8.16 (s, 1H), 7.45-7.37 (m, 6H), 7.28 (d, J = 2.4 Hz, 1H), 7.19 (s, 1H), 7.18 (d, J = 2.4 Hz, 1H), 5.28 (s, 2H), 2.33 (s, 3H), 2.19 (s, 3H); ESI m/z 347 [M + H]+. |

TABLE 1-continued

Exemplary Embodiments prepared using methods described above.

| Example Number | Chemical Name | Structure | General Procedure | Analytical Data |
|---|---|---|---|---|
| 205 | 3-amino-1-(4-chlorobenzyl)-5-(3-(hydroxymethyl)-5-methylisoxazol-4-yl)pyridin-2(1H)-one | 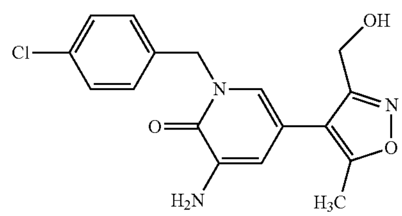 [SMILES: Cc1onc(CO)c1-c1cc(N)c(=O)n(Cc2ccc(Cl)cc2)c1] | No general procedure | 1H NMR (500 MHz, DMSO-d6) δ 7.32-7.45 (m, 4H), 7.19 (d, J = 2.2 Hz, 1H), 6.57 (d, J = 2.2 Hz, 1H), 5.43 (t, J = 5.6 Hz, 1H), 5.27 (s, 2H), 5.11 (s, 2H), 4.44 (d, J = 5.6 Hz, 2H), 2.38 (s, 3H); ESI m/z 346 [M + H]+. |
| 206 | 3-amino-1-(4-chloro-2-fluorobenzyl)-5-(3,5-dimethylisoxazol-4-yl)pyridin-2(1H)-one | 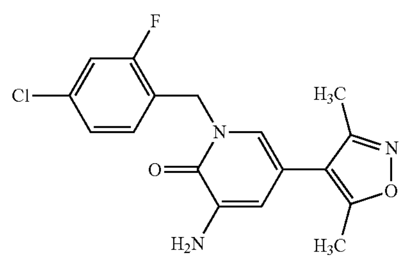 [SMILES: Cc1noc(C)c1-c1cc(N)c(=O)n(Cc2ccc(Cl)cc2F)c1] | N | 1H NMR (300 MHz, CDCl3) δ 7.51-7.46 (m, 1H), 7.16-7.10 (m, 2H), 6.72-6.71 (m, 1H), 6.38 (d, J = 2.1 Hz, 1H), 5.16 (s, 2H), 4.32 (s, 2H), 2.35 (s, 3H), 2.21 (s, 3H); ESI m/z 348 [M + H]+. |
| 207 | 3-amino-1-(2-chloro-4-fluorobenzyl)-5-(3,5-dimethylisoxazol-4-yl)pyridin-2(1H)-one | 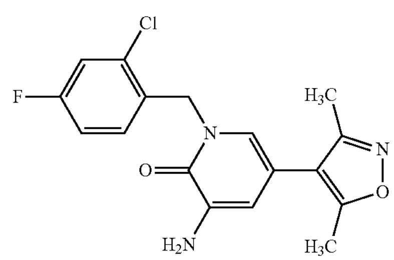 [SMILES: Cc1noc(C)c1-c1cc(N)c(=O)n(Cc2ccc(F)cc2Cl)c1] | N | 1H NMR (300 MHz, CDCl3) δ 7.40 (dd, J = 8.6, 6.0 Hz, 1H), 7.17 (dd, J = 8.3, 2.6 Hz, 1H), 7.02-6.97 (m, 1H), 6.67 (d, J = 2.2 Hz, 1H), 6.41 (d, J = 2.2 Hz, 1H), 5.27 (s, 2H), 4.36 (br s, 2H), 2.33 (s, 3H), 2.19 (s, 3H); ESI m/z 348 [M + H]+; |
| 208 | 1-benzyl-3-(cyclopentylamino)-5-(3,5-dimethylisoxazol-4-yl)pyridin-2(1H)-one | 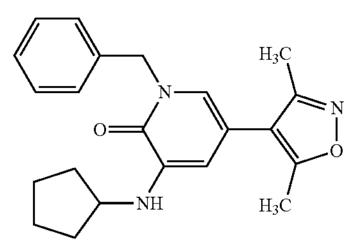 [SMILES: Cc1noc(C)c1-c1cc(NC2CCCC2)c(=O)n(Cc2ccccc2)c1] | J | 1H NMR (300 MHz, DMSO-d6) δ 7.38-7.26 (m, 5H), 7.10 (d, J = 2.1 Hz, 1H), 6.17 (d, J = 1.8 Hz, 1H), 5.29 (d, J = 6.6 Hz, 1H), 5.13 (s, 2H), 3.71-3.65 (m, 1H), 2.36 (s, 3H), 2.20 (s, 3H), 1.96-1.88 (m, 2H), 1.67-1.45 (m, 6H); ESI MS m/z 364 [M + H]+. |
| 209 | 1-benzyl-5-(3,5-dimethylisoxazol-4-yl)-3-hydroxypyridin-2(1H)-one | 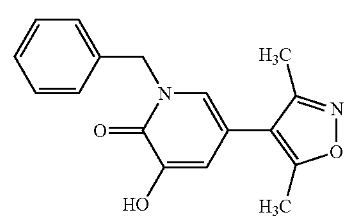 [SMILES: Cc1noc(C)c1-c1cc(O)c(=O)n(Cc2ccccc2)c1] | N | 1H NMR (300 MHz, DMSO-d6) δ 9.37 (s, 1H), 7.39 (d, J = 2.1 Hz, 1H), 7.37-7.27 (m, 5H), 6.77 (d, J = 2.1 Hz, 1H), 5.17 (s, 2H), 2.35 (s, 3H), 2.18 (s, 3H); ESI m/z 297 [C17H16N2O3 + H]+. |
| 210 | 1-benzyl-5-(3,5-dimethylisoxazol-4-yl)-3-methoxypyridin-2(1H)-one | 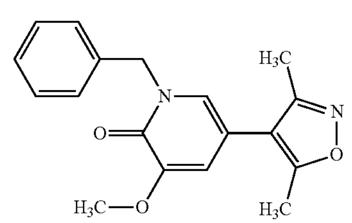 [SMILES: COc1cc(-c2c(C)noc2C)cn(Cc2ccccc2)c1=O] | N | 1H NMR (300 MHz, CDCls) δ 7.33-7.24 (m, 5H), 6.75 (s, 1H), 6.45 (s, 1H), 5.22 (s, 2H), 3.85 (s, 3H), 2.30 (s, 3H), 2.17 (s, 3H); ESI m/z 311 [C18H18N2O3 + H]+. |

TABLE 1-continued

Exemplary Embodiments prepared using methods described above.

| Example Number | Chemical Name | Structure | General Procedure | Analytical Data |
|---|---|---|---|---|
| 211 | 3-amino-1-(3,4-difluorobenzyl)-5-(3,5-dimethylisoxazol-4-yl)pyridin-2(1H)-one | 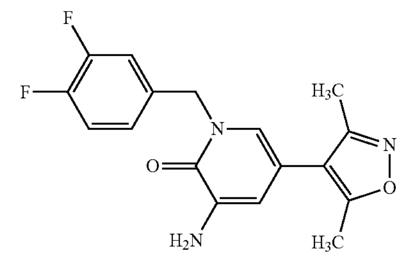 [SMILES: Cc1noc(C)c1-c1cc(N)c(=O)n(Cc2ccc(F)c(F)c2)c1] | N | 1H NMR (500 MHz, DMSO-d6): δ 7.50-7.32 (m, 2H), 7.24-7.14 (m, 1H), 7.08 (d, J = 2.5 Hz, 1H), 6.46 (d, J = 3.5 Hz, 1H), 5.31 (s, 2H), 5.10 (s, 2H), 2.35 (s, 3H), 2.18 (s, 3H). ESI MS m/z 332 [M + H]+. |
| 212 | 3-amino-1-(3-chloro-4-fluorobenzyl)-5-(3,5-dimethylisoxazol-4-yl)pyridin-2(1H)-one | 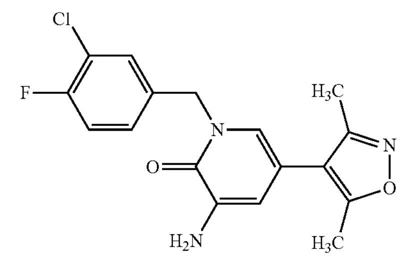 [SMILES: Cc1noc(C)c1-c1cc(N)c(=O)n(Cc2ccc(F)c(Cl)c2)c1] | N | 1H NMR (500 MHz, DMSO-d6): δ 7.62 (d, J = 3.5 Hz, 1H), 7.45-7.38 (m, 2H), 7.17 (d, J = 3.5 Hz, 1H), 6.44 (d, J = 3.5 Hz, 1H), 5.31 (s, 2H), 5.10 (s, 2H), 2.40 (s, 3H), 2.18 (s, 3H). ESI MS m/z 348 [M + H]+. |
| 213 | 3-amino-1-(3,4-dichlorobenzyl)-5-(3,5-dimethylisoxazol-4-yl)pyridin-2(1H)-one | 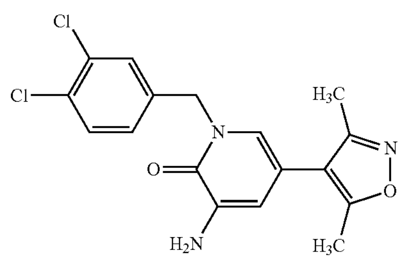 [SMILES: Cc1noc(C)c1-c1cc(N)c(=O)n(Cc2ccc(Cl)c(Cl)c2)c1] | N | 1H NMR (500 MHz, DMSO-d6): δ 7.66-7.62 (m, 1H), 7.61 (s, 1H), 7.34 (dd, J = 13, 3.5 Hz, 1H), 7.17 (d, J = 3.5 Hz, 1H), 6.45 (d, J = 3.5 Hz, 1H), 5.31 (s, 2H), 5.12 (s, 2H), 2.36 (s, 3H), 2.19 (s, 3H). ESI MS m/z 365 [M + H]+. |
| 214 | 1-benzyl-5-(5-(hydroxymethyl)-3-methylisoxazol-4-yl)pyridin-2(1H)-one | 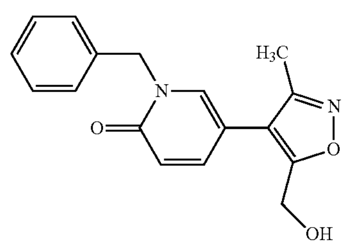 [SMILES: Cc1noc(CO)c1-c1ccc(=O)n(Cc2ccccc2)c1] | F | 1H NMR (300 MHz, DMSO-d6) δ 7.94 (d, J = 2.4 Hz, 1H), 7.54 (dd, J = 9.3, 2.4 Hz, 1H), 7.36-7.29 (m, 5H), 6.52 (d, J = 9.3 Hz, 1H), 5.62 (d, J = 6.0 Hz, 1H), 5.13 (s, 2H), 4.47 (d, J = 6.0 Hz, 2H), 2.23 (s, 3H); ESI m/z 297 [M + H]+. |
| 215 | 3-amino-5-(3,5-dimethylisoxazol-4-yl)-1-(thiazol-2-ylmethyl)pyridin-2(1H)-one | 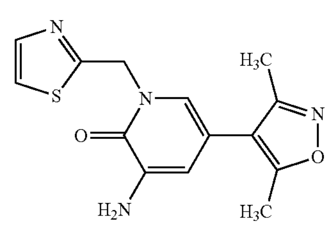 [SMILES: Cc1noc(C)c1-c1cc(N)c(=O)n(Cc2nccs2)c1] | N | 1H NMR (300 MHz, DMSO-d6) δ 7.77 (d, J = 3.3 Hz, 1H), 7.69 (d, J = 3.3 Hz, 1H), 7.14 (d, J = 2.1 Hz, 1H), 6.47 (d, J = 2.1 Hz, 1H), 5.45 (s, 2H), 5.34 (s, 2H), 2.37 (s, 3H), 2.19 (s, 3H); ESI m/z 303 [M + H]+. |
| 216 | 4-((3-amino-5-(3,5-dimethylisoxazol-4-yl)-2-oxopyridin-1(2H)-yl)methyl)benzonitrile | 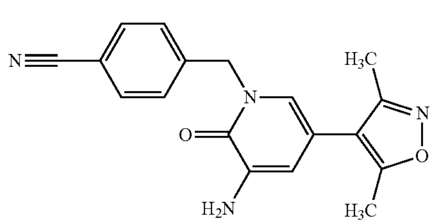 [SMILES: Cc1noc(C)c1-c1cc(N)c(=O)n(Cc2ccc(C#N)cc2)c1] | N | 1H NMR (300 MHz, DMSO-d6) δ 7.83 (d, J = 8.4 Hz, 2H), 7.48 (d, J = 8.4 Hz, 2H), 7.15 (d, J = 2.4 Hz, 1H), 6.47 (d, J = 2.1 Hz, 1H), 5.31 (s, 2H), 5.22 (s, 2H), 2.36 (s, 3H), 2.19 (s, 3H); ESI m/z 321 [C18H16N4O2 + H]+. |

TABLE 1-continued

Exemplary Embodiments prepared using methods described above.

| Example Number | Chemical Name | Structure | General Procedure | Analytical Data |
|---|---|---|---|---|
| 217 | 1-benzyl-5-(3,5-dimethylisoxazol-4-yl)-3-((3,5-dimethylisoxazol-4-yl)amino)pyridin-2(1H)-one | 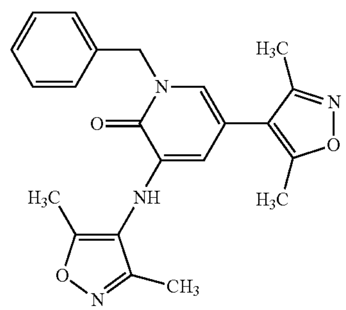 [SMILES: Cc1noc(C)c1Nc1cc(-c2c(C)noc2C)cn(Cc2ccccc2)c1=O] | M | 1H NMR (300 MHz, DMSO-d6) δ 7.45-7.30 (m, 5H), 7.26 (d, J = 2.1 Hz, 1H), 7.20 (s, 1H), 6.91 (d, J = 2.1 Hz, 1H), 5.19 (s, 2H), 2.29 (s, 3H), 2.22 (s, 3H), 2.11 (s, 3H), 2.04 (s, 3H); ESI m/z 391 [M + H]+; |
| 218 | 5-(3,5-dimethylisoxazol-4-yl)-1-(4-vinylbenzyl)pyridin-2(1H)-one | 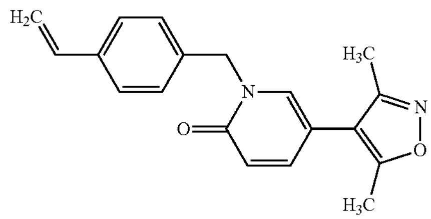 [SMILES: C=Cc1ccc(Cn2cc(-c3c(C)noc3C)ccc2=O)cc1] | No general procedure | 1H NMR (500 MHz, DMSO-d6) δ 7.94 (d, J = 2.4 Hz, 1H), 7.50 (dd, J = 2.5, 9.3 Hz, 1H), 7.30-7.50 (m, 4H), 6.71 (dd, J = 10.9, 17.6 Hz, 1H), 6.51 (d, J = 9.3 Hz, 1H), 5.81 (dd, J = 0.7, 17.6 Hz, 1H), 5.25 (dd, J = 0.63, 10.9 Hz, 1H), 5.11 (s, 2H), 2.35 (s, 3H), 2.18 (s, 3H); ESI m/z 307 [M + H]+. |
| 219 | 3-amino-5-(3,5-dimethylisoxazol-4-yl)-1-(thiophen-3-ylmethyl)pyridin-2(1H)-one | 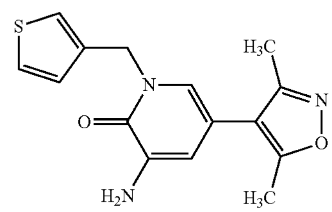 [SMILES: Cc1noc(C)c1-c1cc(N)c(=O)n(Cc2ccsc2)c1] | N | 1H NMR (300 MHz, DMSO-d6) δ 7.50 (d, J = 4.9 Hz, 1H), 7.45 (d, J = 1.2 Hz, 1H), 7.14 (dd, J = 4.9, 1.2 Hz, 1H), 7.10 (d, J = 2.3 Hz, 1H), 6.43 (d, J = 2.3 Hz, 1H), 5.28 (s, 2H), 5.11 (s, 2H), 2.34 (s, 3H), 2.17 (s, 3H); ESI m/z 302 [M + H]+; |
| 220 | 3-amino-5-(3,5-dimethylisoxazol-4-yl)-1-(4-methoxybenzyl)pyridin-2(1H)-one | 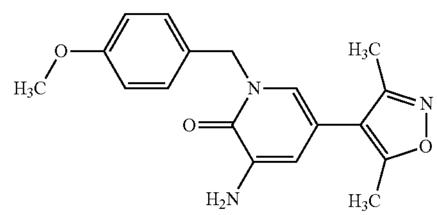 [SMILES: COc1ccc(Cn2cc(-c3c(C)noc3C)cc(N)c2=O)cc1] | N | 1H NMR (300 MHz, DMSO-d6) δ 7.34 (d, J = 8.7 Hz, 2H), 7.09 (d, J = 2.4 Hz, 1H), 6.89 (d, J = 8.4 Hz, 2H), 6.42 (d, J = 2.4 Hz, 1H), 5.26 (s, 2H), 5.05 (s, 2H), 3.72 (s, 3H), 2.34 (s, 3H), 2.17 (s, 3H); ESI m/z 326 [C18H19N3O3 + H]+. |
| 221 | 1-benzyl-5-(3,5-dimethylisoxazol-4-yl)-3-(pyridazin-3-ylamino)pyridin-2(1H)-one | 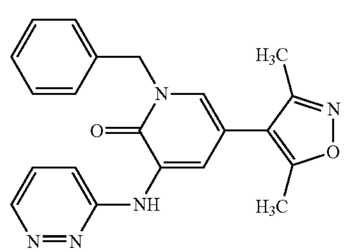 [SMILES: Cc1noc(C)c1-c1cc(Nc2cccnn2)c(=O)n(Cc2ccccc2)c1] | J | 1H NMR (300 MHz, DMSO-d6) δ 9.02 (s, 1H), 8.74 (d, J = 2.4 Hz, 1H), 8.71 (d, J = 1.2 Hz, 1H), 7.63-7.49 (m, 2H), 7.48-7.30 (m, 6H), 5.26 (s, 2H), 2.41 (s, 3H), 2.24 (s, 3H); ESI m/z 374 [C21H19N5O2 + H]+. |
| 222 | 3-amino-1-((5-chlorothiophen-2-yl)methyl)-5-(3,5-dimethylisoxazol-4-yl)pyridin-2(1H)-one | 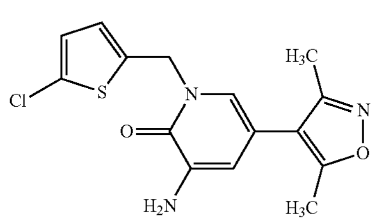 [SMILES: Cc1noc(C)c1-c1cc(N)c(=O)n(Cc2ccc(Cl)s2)c1] | N | 1H NMR (300 MHz, DMSO-d6) δ 7.15 (d, J = 2.1 Hz, 1H), 7.09 (d, J = 3.9 Hz, 1H), 6.99 (d, J = 3.6 Hz, 1H), 6.44 (d, J = 2.1 Hz, 1H), 5.39 (s, 2H ), 5.19 (s, 2H), 2.36 (s, 3H), 2.18 (s, 3H); ESI m/z 336 [M + H]+. |

TABLE 1-continued

Exemplary Embodiments prepared using methods described above.

| Example Number | Chemical Name | Structure | General Procedure | Analytical Data |
| --- | --- | --- | --- | --- |
| 223 | 1-benzyl-5-(3,5-dimethylisoxazol-4-yl)-3-((5-fluoropyridin-3-yl)amino)pyridin-2(1H)-one | 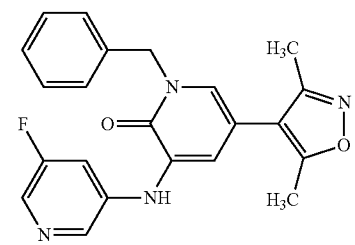 [SMILES: Cc1noc(C)c1-c1cc(Nc2cncc(F)c2)c(=O)n(Cc2ccccc2)c1] | J | 1H NMR (300 MHz, DMSO-d6) δ 8.42 (s, 1H), 8.40 (s, 1H), 8.05 (d, J = 2.4 Hz, 1H), 7.56-7.50 (m, 3H), 7.44-7.30 (m, 5H), 7.21 (d, J = 2.1 Hz, 1H), 5.23 (s, 2H), 2.38 (s, 3H), 2.21 (s, 3H); ESI m/z 391 [M + H]+. |
| 224 | 3-amino-5-(3,5-dimethylisoxazol-4-yl)-1-methylpyridin-2(1H)-one | 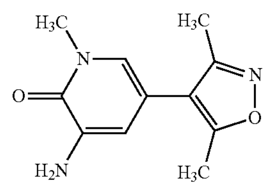 [SMILES: Cc1noc(C)c1-c1cc(N)c(=O)n(C)c1] | No general procedure | 1H NMR (500 MHz, DMSO-d6) δ 6.97 (d, J = 2.2 Hz, 1H), 6.42 (d, J = 2.2 Hz, 1H), 5.22 (s, 2H), 3.47 (s, 3H), 2.35 (s, 3H), 2.18 (s, 3H); ESI m/z 220 [M + H]+. |
| 225 | 4-(1-(4-chlorobenzyl)-6-oxo-1,6-dihydropyridin-3-yl)-5-methylisoxazole-3-carboxylic acid | 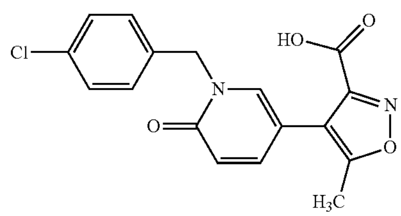 [SMILES: Cc1onc(C(=O)O)c1-c1ccc(=O)n(Cc2ccc(Cl)cc2)c1] | No general procedure | 1H NMR (500 MHz, CD3OD) δ 7.84 (d, J = 2.4 Hz, 1H), 7.56 (dd, J = 2.4, 9.3 Hz, 1H), 7.35 (s, 4H), 6.60 (d, J = 9.3 Hz, 1H), 5.19 (s, 2H), 2.40 (s, 3H); ESI m/z 345 [M + H]+. |
| 226 | 3-amino-5-(3,5-dimethylisoxazol-4-yl)-1-(4-(trifluoromethoxy)benzyl)pyridin-2(1H)-one | 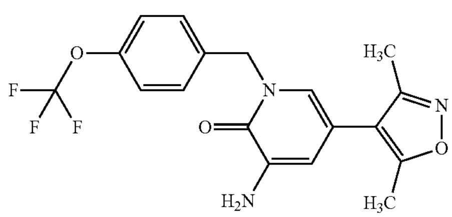 [SMILES: Cc1noc(C)c1-c1cc(N)c(=O)n(Cc2ccc(OC(F)(F)F)cc2)c1] | N | 1H NMR (300 MHz, CDCl3) δ 7.36 (d, J = 8.2 Hz, 2H), 7.20 (d, J = 8.2 Hz, 2H), 6.58 (d, J = 2.1 Hz, 1H), 6.40 (d, J = 2.1 Hz, 1H), 5.21 (s, 2H), 4.38 (s, 2H), 2.31 (s, 3H), 2.18 (s, 3H); ESI MS m/z 380 [M + H]+ |
| 227 | 3-amino-1-(2-chlorobenzyl)-5-(3,5-dimethylisoxazol-4-yl)pyridin-2(1H)-one | 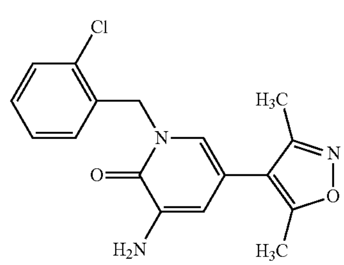 [SMILES: Cc1noc(C)c1-c1cc(N)c(=O)n(Cc2ccccc2Cl)c1] | N | 1H NMR (300 MHz, CDCl3) δ 7.55-7.38 (m, 2H), 7.32-7.23 (m, 2H), 6.64 (d, J = 2.1 Hz, 1H), 6.41 (d, J = 2.1 Hz, 1H), 4.37 (s, 2H), 2.31 (s, 3H), 2.18 (s, 3H); ESI MS m/z 330 [M + H]+ |
| 228 | 3-amino-5-(3,5-dimethylisoxazol-4-yl)-1-(4-(trifluoromethyl)benzyl)pyridin-2(1H)-one | 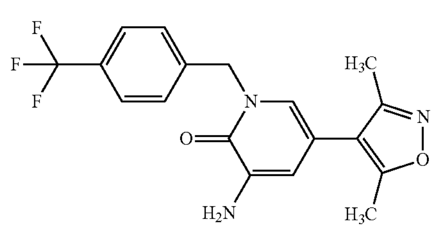 [SMILES: Cc1noc(C)c1-c1cc(N)c(=O)n(Cc2ccc(C(F)(F)F)cc2)c1] | N | 1H NMR (500 MHz, DMSO-d6) δ 7.72 (d, J = 8.5 Hz, 2H), 7.52 (d, J = 8.0 Hz, 2H), 7.14 (d, J = 2.5 Hz, 1H), 6.46 (d, J = 2.5 Hz, 1H), 5.29 (s, 2H), 5.23 (s, 2H), 2.35 (s, 3H), 2.18 (s, 3H); ESI m/z 364 [M + H]+. |

TABLE 1-continued

Exemplary Embodiments prepared using methods described above.

| Example Number | Chemical Name | Structure | General Procedure | Analytical Data |
|---|---|---|---|---|
| 229 | 1-benzyl-5-(3,5-dimethylisoxazol-4-yl)-2-oxo-1,2-dihydropyridine-3-carboxylic acid | 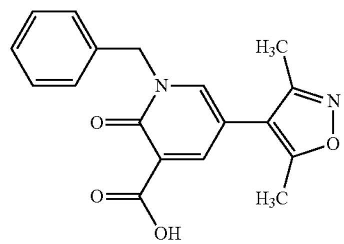 [SMILES: Cc1noc(C)c1-c1cc(C(=O)O)c(=O)n(Cc2ccccc2)c1] | No general procedure | 1H NMR (500 MHz, CDCl3) δ 8.41 (s, 1H), 7.49-7.39 (m, 4H), 7.36-7.33 (m, 2H), 5.28 (s, 2H), 2.32 (s, 3H), 2.15 (s, 3H); ESI MS m/z 325 [M + H]+ |
| 230 | 1-benzyl-5-(3,5-dimethylisoxazol-4-yl)-2-oxo-1,2-dihydropyridine-3-carboxamide | 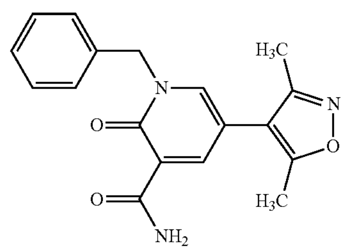 [SMILES: Cc1noc(C)c1-c1cc(C(N)=O)c(=O)n(Cc2ccccc2)c1] | No general procedure | 1H NMR (500 MHz, CDCl3) δ 9.55 (s, 1H), 8.45 (d, J = 2.7 Hz, 1H), 7.44-7.30 (m, 6H), 5.75 (s, 1H), 5.26 (s, 2H), 2.30 (s, 3H), 2.15 (s, 3H); ESI MS m/z 324 [M + H]+ |
| 231 | 1-benzyl-5-(3,5-dimethylisoxazol-4-yl)-3-((5-methoxypyridin-3-yl)amino)pyridin-2(1H)-one | 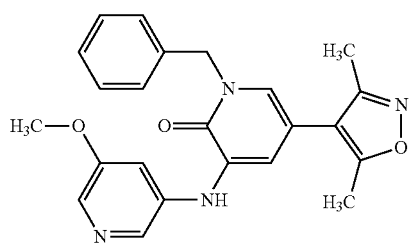 [SMILES: COc1cncc(Nc2cc(-c3c(C)noc3C)cn(Cc3ccccc3)c2=O)c1] | J | 1H NMR (300 MHz, DMSO-d6) δ 8.17 (d, J = 2.1 Hz, 1H), 8.09 (s, 1H), 7.85 (d, J = 2.4 Hz, 1H), 7.46 (d, J = 2.1 Hz, 1H), 7.44-7.26 (m, 6H), 7.09 (dd, J = 2.1, 2.1 Hz, 1H), 5.22 (s, 2H), 3.78 (s, 3H), 2.38 (s, 3H), 2.21 (s, 3H); ESI m/z 403 [M + H]+. |
| 232 | 5-((1-benzyl-5-(3,5-dimethylisoxazol-4-yl)-2-oxo-1,2-dihydropyridin-3-yl)amino)picolinonitrile | 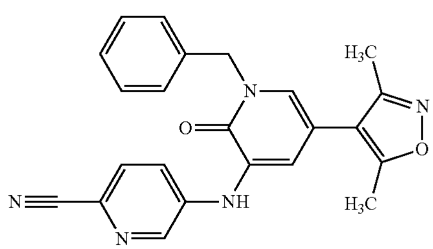 [SMILES: Cc1noc(C)c1-c1cc(Nc2ccc(C#N)nc2)c(=O)n(Cc2ccccc2)c1] | J | 1H NMR (300 MHz, DMSO-d6) δ 8.85 (s, 1H), 8.58 (d, J = 2.4 Hz, 1H), 7.79 (d, J = 8.4 Hz, 1H), 7.67-7.60 (m, 2H), 7.43-7.28 (m, 6H), 5.23 (s, 2H), 2.38 (s, 3H), 2.22 (s, 3H); ESI m/z 398 [M + H]+. |
| 233 | 4-amino-2-(4-chlorobenzyl)-6-(3,5-dimethylisoxazol-4-yl)pyridazin-3(2H)-one | 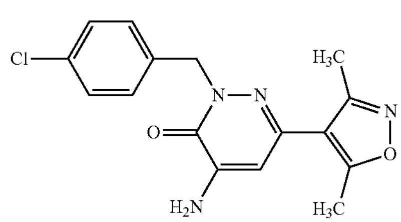 [SMILES: Cc1noc(C)c1-c1cc(N)c(=O)n(Cc2ccc(Cl)cc2)n1] | N | 1H NMR (300 MHz, DMSO-d6) δ 7.42-7.33 (m, 4H), 6.63 (s, 2H), 6.42 (s, 1H), 5.24 (s, 2H), 2.44 (s, 3H), 2.23 (s, 3H); ESI m/z 331 [M + H]+. |
| 234 | 1-benzyl-5-(3,5-dimethylisoxazol-4-yl)-3-((6-methoxypyridin-3-yl)amino)pyridin-2(1H)-one | 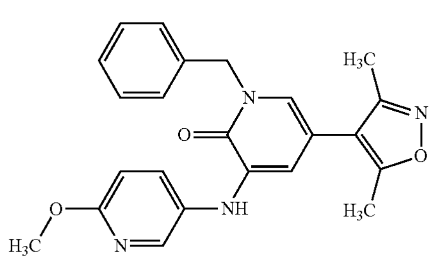 [SMILES: COc1ccc(Nc2cc(-c3c(C)noc3C)cn(Cc3ccccc3)c2=O)cn1] | J | 1H NMR (300 MHz, DMSO-d6) δ 8.10 (d, J = 2.7 Hz, 1H), 7.80 (s, 1H), 7.67 (dd, J = 9.2, 2.7 Hz, 1H), 7.44-7.28 (m, 6H), 6.78 (d, J = 8.7 Hz, 1H), 6.64 (s, 1H), 5.21 (s, 2H), 3.81 (s, 3H), 2.33 (s, 3H), 2.15 (s, 3H); ESI m/z 403 [C23H22N4O3 + H]+. |

TABLE 1-continued

Exemplary Embodiments prepared using methods described above.

| Example Number | Chemical Name | Structure | General Procedure | Analytical Data |
|---|---|---|---|---|
| 235 | 1-benzyl-5-(3,5-dimethylisoxazol-4-yl)-3-(pyrazin-2-ylamino)pyridin-2(1H)-one | 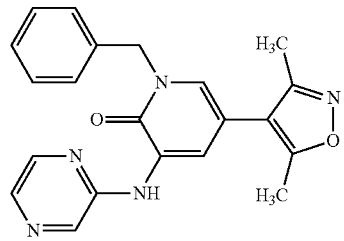 [SMILES: Cc1noc(C)c1-c1cc(Nc2cnccn2)c(=O)n(Cc2ccccc2)c1] | J | 1H NMR (300 MHz, DMSO-d6) δ 9.23 (s, 1H), 8.68 (d, J = 1.2 Hz, 1H), 8.55 (d, J = 2.1 Hz, 1H), 8.19-8.17 (m, 1H), 7.98 (d, J = 2.7 Hz, 1H), 7.58 (d, J = 2.4 Hz, 1H), 7.40-7.33 (m, 5H), 5.25 (s, 2H), 2.41 (s, 3H), 2.24 (s, 3H); ESI m/z 374 [C21H19N5O2 + H]+. |
| 236 | 1-benzyl-5-(3,5-dimethylisoxazol-4-yl)-3-(pyrimidin-5-ylamino)pyridin-2(1H)-one | 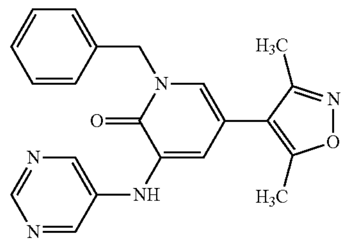 [SMILES: Cc1noc(C)c1-c1cc(Nc2cncnc2)c(=O)n(Cc2ccccc2)c1] | J | 1H NMR (300 MHz, DMSO-d6) δ 8.73 (s, 2H), 8.70 (s, 1H), 8.33 (s, 1H), 7.52 (d, J = 2.1 Hz, 1H), 7.43-7.28 (m, 5H), 7.17 (d, J = 2.1 Hz, 1H), 5.23 (s, 2H), 2.37 (s, 3H), 2.20 (s, 3H); ESI m/z 374 [C21H19N5O2 + H]+. |
| 237 | 3-amino-1-(4-(azetidin-1-yl)benzyl)-5-(3,5-dimethylisoxazol-4-yl)pyridin-2(1H)-one | 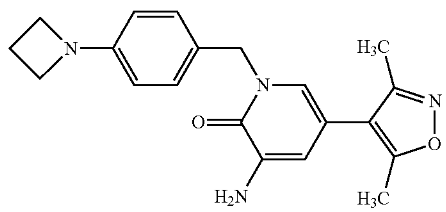 [SMILES: Cc1noc(C)c1-c1cc(N)c(=O)n(Cc2ccc(N3CCC3)cc2)c1] | No general procedure | 1H NMR (500 MHz, DMSO-d6) δ 7.23 (d, J = 8.5 Hz, 2H), 7.04 (d, J = 2.2 Hz, 1H), 6.04 (d, J = 2.2 Hz, 1H), 6.35 (d, J = 8.5 Hz, 2H), 5.23 (s, 2H), 4.98 (s, 2H), 3.74 (t, J = 7.1 Hz, 4H), 2.33 (s, 3H), 2.26 (quintet, J = 7.1 Hz, 2H), 2.16 (s, 3H); ESI m/z 351 [M + H]+. |
| 238 | 3-amino-5-(3,5-dimethylisoxazol-4-yl)-1-(4-morpholinobenzyl)pyridin-2(1H)-one | 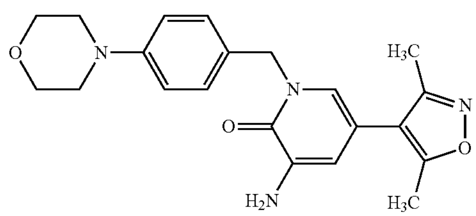 [SMILES: Cc1noc(C)c1-c1cc(N)c(=O)n(Cc2ccc(N3CCOCC3)cc2)c1] | No general procedure | 1H NMR (500 MHz, DMSO-d6) δ 7.27 (d, J = 8.7 Hz, 2H), 7.07 (d, J = 2.2 Hz, 1H), 6.89 (d, J = 8.7 Hz, 2H), 6.41 (d, J = 2.2 Hz, 1H), 5.24 (s, 2H), 5.01 (s, 2H), 3.70 (t, J = 4.8 Hz, 4H), 3.06 (t, J = 4.8 Hz, 4H), 2.33 (s, 3H), 2.16 (s, 3H); ESI m/z 381 [M + H]+. |
| 239 | 1-benzyl-5-(3,5-dimethylisoxazol-4-yl)-3-(pyrrolidin-3-ylamino)pyridin-2(1H)-one | 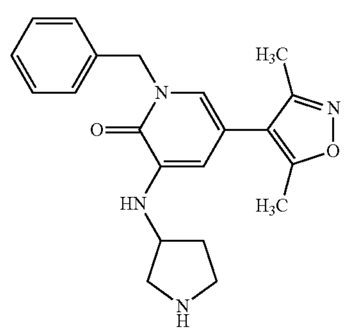 [SMILES: Cc1noc(C)c1-c1cc(NC2CCNC2)c(=O)n(Cc2ccccc2)c1] | M | 1H NMR (500 MHz, DMSO-d6) δ 9.12 (br s, 1H), 8.85 (br s, 1H), 7.38-7.33 (m, 4H), 7.30-7.28 (m, 1H), 7.21 (d, J = 2.0 Hz, 1H), 6.28 (d, J = 2.0 Hz, 1H), 5.16-5.15 (m, 2H), 4.13-4.05 (m, 1H), 3.41-3.34 (m, 1H), 3.34-3.26 (m, 1H), 2.21-2.19 (m, 2H), 2.37 (s, 3H), 2.21 (s, 3H), 2.20-2.13 (m, 1H), 2.00-1.92 (m, 1H); ESI m/z 365 [M + H]+; |
| 240 | 3-amino-5-(3,5-dimethylisoxazol-4-yl)-1-((3-methylisoxazol-5-yl)methyl)pyridin-2(1H)-one | 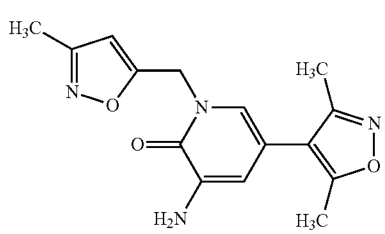 [SMILES: Cc1cc(Cn2cc(-c3c(C)noc3C)cc(N)c2=O)on1] | N | 1H NMR (500 MHz, DMSO-d6) δ 7.07 (d, J = 2.0 Hz, 1H), 6.46 (d, J = 2.0 Hz, 1H), 6.23 (s, 1H), 5.31 (s, 2H), 5.26 (s, 2H), 2.37 (s, 3H), 2.19 (s, 6H); ESI m/z 301 [M + H]+. |

TABLE 1-continued

Exemplary Embodiments prepared using methods described above.

| Example Number | Chemical Name | Structure | General Procedure | Analytical Data |
|---|---|---|---|---|
| 241 | 3-amino-1-(4-bromobenzyl)-5-(3,5-dimethylisoxazol-4-yl)pyridin-2(1H)-one | 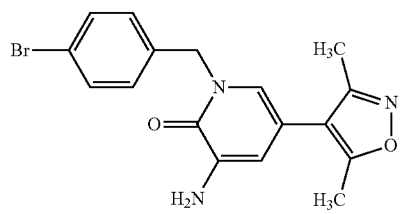 [SMILES: Cc1noc(C)c1-c1cc(N)c(=O)n(Cc2ccc(Br)cc2)c1] | No general procedure | 1H NMR (500 MHz, DMSO-d6) δ 7.54 (d, J = 8.4 Hz, 2H), 7.31 (d, J = 8.4 Hz, 2H), 7.11 (d, J = 2.2 Hz, 1H), 6.45 (d, J = 2.2 Hz, 1H), 5.27 (s, 2H), 5.10 (s, 2H), 2.34 (s, 3H), 2.17 (s, 3H); ESI m/z 374 [M + H]+. |
| 242 | 3-amino-5-(3,5-dimethylisoxazol-4-yl)-1-(4-isopropylbenzyl)pyridin-2(1H)-one | 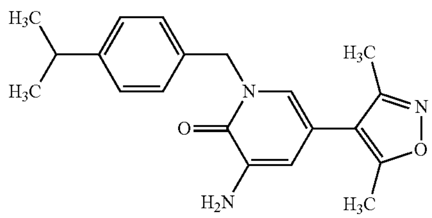 [SMILES: Cc1noc(C)c1-c1cc(N)c(=O)n(Cc2ccc(C(C)C)cc2)c1] | No general procedure | 1H NMR (500 MHz, DMSO-d6) δ 7.27 (d, J = 8.1 Hz, 2H), 7.20 (d, J = 8.1 Hz, 2H), 7.08 (d, J = 2.2 Hz, 1H), 6.43 (d, J = 2.2 Hz, 1H), 5.25 (s, 2H), 5.08 (s, 2H), 2.84 (octet, J = 6.9 Hz, 1H), 2.34 (s, 3H), 2.17 (s, 3H), 1.17 (d, J = 6.9 Hz, 6H); ESI m/z 338 [M + H]+. |
| 243 | 1-(4-chlorobenzyl)-5-(3,5-dimethylisoxazol-4-yl)-3-((2,2,2-trifluoroethyl)amino)pyridin-2(1H)-one | 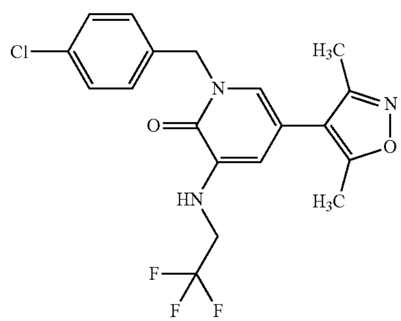 [SMILES: Cc1noc(C)c1-c1cc(NCC(F)(F)F)c(=O)n(Cc2ccc(Cl)cc2)c1] | No general procedure | 1H NMR (500 MHz, DMSO-d6) δ 7.36-7.45 (m, 4H), 7.23 (d, J = 2.1 Hz, 1H), 6.55 (d, J = 1.7 Hz, 1H), 6.11 (t, J = 7.1 Hz, 1H), 5.14 (s, 2H), 3.93-4.04 (m, 2H), 2.35 (s, 3H), 2.18 (s, 3H); ESI m/z 412 [M + H]+. |
| 244 | 3-amino-5-(3,5-dimethylisoxazol-4-yl)-1-((6-methylpyridin-2-yl)methyl)pyridin-2(1H)-one | 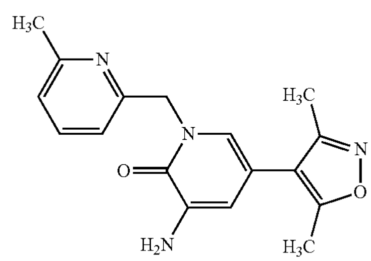 [SMILES: Cc1cccc(Cn2cc(-c3c(C)noc3C)cc(N)c2=O)n1] | N | 1H NMR (500 MHz, CDCl3) δ 7.55 (t, J = 7.7 Hz, 1H), 7.14 (d, J = 7.7 Hz, 1H), 7.08 (d, J = 7.7 Hz, 1H), 6.87 (d, J = 2.1 Hz, 1H), 6.40 (d, J = 2.1 Hz, 1H), 5.26 (s, 2H), 4.31 (s, 2H), 2.51 (s, 3H), 2.35 (s, 3H), 2.21 (s, 3H); ESI MS m/z 311 [M + H]+ |
| 245 | 1-benzyl-5-(3,5-dimethylisoxazol-4-yl)-3-((6-methylpyridin-3-yl)amino)pyridin-2(1H)-one | 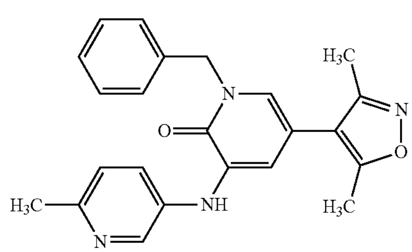 [SMILES: Cc1ccc(Nc2cc(-c3c(C)noc3C)cn(Cc3ccccc3)c2=O)cn1] | J | 1H NMR (300 MHz, DMSO-d6) δ 8.41 (d, J = 2.7 Hz, 1H), 7.91 (s, 1H), 7.58 (dd, J = 8.3 Hz, 3.0 Hz, 1H), 7.40-7.35 (m, 6H), 7.15 (d, J = 8.4 Hz, 1H), 6.89 (d, J = 2.1 Hz, 1H), 5.22 (s, 2H), 2.37 (d, J = 11.1 Hz, 6H), 2.18 (s, 3H); ESI m/z 387 [C23H22N4O2 + H]+. |
| 246 | 1-benzyl-5-(3,5-dimethylisoxazol-4-yl)-3-((5-methylpyridin-3-yl)amino)pyridin-2(1H)-one | 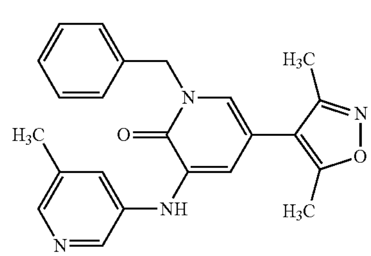 [SMILES: Cc1cncc(Nc2cc(-c3c(C)noc3C)cn(Cc3ccccc3)c2=O)c1] | J | 1H NMR (300 MHz, DMSO-d6) δ 8.34 (d, J = 2.4 Hz, 1H), 8.02 (s, 1H), 7.96 (s, 1H), 7.50-7.30 (m, 7H), 7.04 (d, J = 2.1 Hz, 1H), 5.22 (s, 2H), 2.38 (s, 3H), 2.24 (s, 3H), 2.21 (s, 3H); ESI m/z 387 [M + H]+. |

TABLE 1-continued

Exemplary Embodiments prepared using methods described above.

| Example Number | Chemical Name | Structure | General Procedure | Analytical Data |
|---|---|---|---|---|
| 247 | 1-((1H-indol-4-yl)methyl)-3-amino-5-(3,5-dimethylisoxazol-4-yl)pyridin-2(1H)-one | 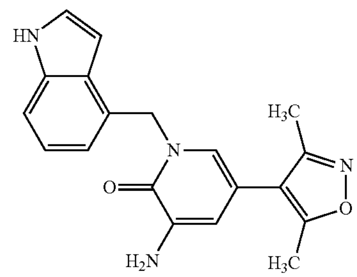 [SMILES: Cc1noc(C)c1-c1cc(N)c(=O)n(Cc2cccc3[nH]ccc23)c1] | No general procedure | 1H NMR (500 MHz, DMSO-d6) δ 11.17 (s, 1H), 7.31-7.36 (m, 2H), 7.03 (t, J = 7.3 Hz, 1H), 6.63 (d, J = 2.3 Hz, 1H), 6.87 (d, J = 7.0 Hz, 1H), 6.59-6.62 (m, 1H), 6.43 (d, J = 2.3 Hz, 1H), 5.40 (s, 2H), 5.28 (s, 2H), 2.25 (s, 3H), 2.08 (s, 3H); ESI m/z 335 [M + H]+. |
| 248 | 2-benzyl-6-(3,5-dimethylisoxazol-4-yl)-4-(pyridin-3-ylamino)pyridazin-3(2H)-one | 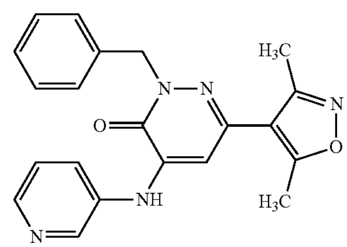 [SMILES: Cc1noc(C)c1-c1cc(Nc2cccnc2)c(=O)n(Cc2ccccc2)n1] | J | 1H NMR (300 MHz, DMSO-d6) δ 9.13 (s, 1H), 8.66 (d, J = 2.4 Hz, 1H), 8.32 (dd, J = 4.8, 1.5 Hz, 1H), 7.86 (dd, J = 8.1, 1.5 Hz, 1H), 7.42-7.30 (m, 6H), 6.81 (s, 1H), 5.35 (s, 2H), 2.43 (s, 3H), 2.23 (s, 3H); ESI m/z 374 [M + H]+. |
| 249 | 4-(1-benzyl-6-oxo-1,6-dihydropyridin-3-yl)-N-methoxy-N,5-dimethylisoxazole-3-carboxamide | 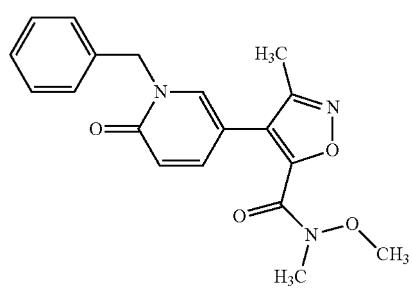 [SMILES: CON(C)C(=O)c1onc(C)c1-c1ccc(=O)n(Cc2ccccc2)c1] | F | 1H NMR (500 MHz, CDCl3) δ 7.38-7.35 (m, 1H), 7.33-7.30 (m, 6H), 6.76 (d, J = 9.3 Hz, 1H), 5.16 (s, 2H), 3.66 (s, 3H), 3.21 (s, 3H), 2.39 (s, 3H); ESI m/z 354 [M + H]+; |
| 250 | 4-amino-2-benzyl-6-(3,5-dimethylisoxazol-4-yl)pyridazin-3(2H)-one | 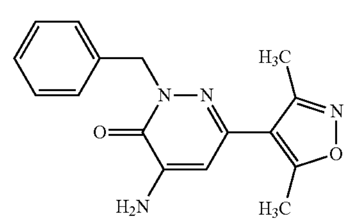 [SMILES: Cc1noc(C)c1-c1cc(N)c(=O)n(Cc2ccccc2)n1] | N | 1H NMR (300 MHz, DMSO-d6) δ 7.34-7.26 (m, 5H), 6.62 (s, 2H), 6.41 (s, 1H), 5.25 (s, 2H), 2.43 (s, 3H), 2.23 (s, 3H); ESI m/z 297 [M + H]+. |
| 251 | 3-amino-5-(3,5-dimethylisoxazol-4-yl)-1-((2,5-dimethylthiophen-3-yl)methyl)pyridin-2(1H)-one | 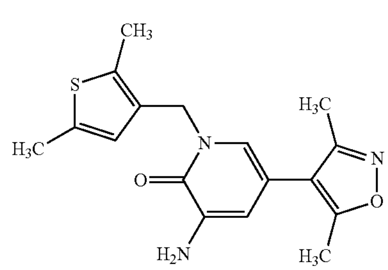 [SMILES: Cc1cc(Cn2cc(-c3c(C)noc3C)cc(N)c2=O)c(C)s1] | N | 1H NMR (300 MHz, DMSO-d6) δ 6.99 (d, J = 2.1 Hz, 1H), 6.62 (s, 1H), 6.42 (d, J = 2.1 Hz, 1H), 5.28 (s, 2H), 4.94 (s, 2H), 2.43 (s, 3H), 2.35 (s, 3H), 2.30 (s, 3H), 2.17 (s, 3H); ESI m/z 330 [M + H]+. |

TABLE 1-continued

Exemplary Embodiments prepared using methods described above.

| Example Number | Chemical Name | Structure | General Procedure | Analytical Data |
|---|---|---|---|---|
| 252 | 3-amino-1-((5-chloropyridin-3-yl)methyl)-5-(3,5-dimethylisoxazol-4-yl)pyridin-2(1H)-one | 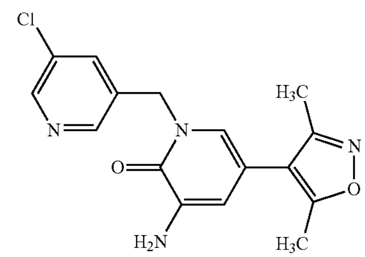 [SMILES: Cc1noc(C)c1-c1cc(N)c(=O)n(Cc2cncc(Cl)c2)c1] | N | 1H NMR (500 MHz, DMSO-d6) δ 8.57 (d, J = 1.5 Hz, 1H), 8.56 (d, J = 2.0 Hz, 1H), 7.92 (s, 1H), 7.21 (d, J = 2.0 Hz, 1H), 6.46 (d, J = 2.0 Hz, 1H), 5.32 (s, 2H), 5.16 (s, 2H), 2.36 (s, 3H), 2.19 (s, 3H); ESI m/z 331 [M + H]+. |
| 253 | 3-amino-1-((3-chloropyridin-4-yl)methyl)-5-(3,5-dimethylisoxazol-4-yl)pyridin-2(1H)-one | 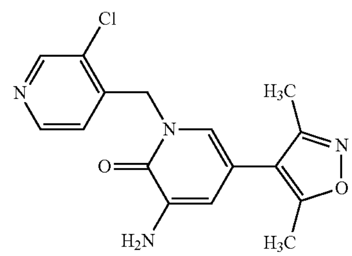 [SMILES: Cc1noc(C)c1-c1cc(N)c(=O)n(Cc2ccncc2Cl)c1] | N | 1H NMR (500 MHz, DMSO-d6) δ 8.41 (d, J = 1.5 Hz, 1H), 7.96 (dd, J = 8.0, 1.0 Hz, 1H), 7.36 (dd, J = 8.0, 7.5 Hz, 1H), 7.02 (d, J = 2.0 Hz, 1H), 6.50 (d, J = 2.5 Hz, 1H), 5.36 (s, 2H), 5.17 (s, 2H), 2.36 (s, 3H), 2.19 (s, 3H); ESI m/z 331 [M + H]+. |
| 254 | 3-amino-1-((3-chloropyridin-2-yl)methyl)-5-(3,5-dimethylisoxazol-4-yl)pyridin-2(1H)-one | 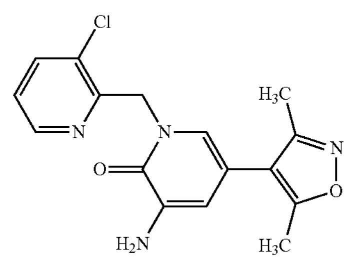 | N | 1H NMR (500 MHz, DMSO-d6) δ 8.65 (s, 1H), 8.46 (d, J = 5.0 Hz, 1H), 7.09 (d, J = 2.5 Hz, 1H), 6.82 (d, J = 2.5 Hz, 1H), 6.54 (d, J = 2.5 Hz, 1H), 5.34 (s, 2H), 5.24 (s, 2H), 2.37 (s, 3H), 2.20 (s, 3H); ESI m/z 331 [M + H]+. |
| 255 | 3-amino-1-((5-chloropyridin-2-yl)methyl)-5-(3,5-dimethylisoxazol-4-yl)pyridin-2(1H)-one | 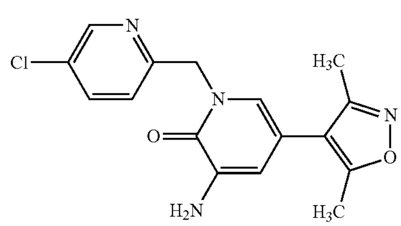 [SMILES: Cc1noc(C)c1-c1cc(N)c(=O)n(Cc2ccc(Cl)cn2)c1] | N | 1H NMR (500 MHz, CD3OD) δ 8.52 (d, J = 2.3 Hz, 1H), 7.84 (dd, 8.4, 2.5 Hz, 1H), 7.36 (d, J = 8.4 Hz, 1H), 7.09 (d, J = 2.2 Hz, 1H), 6.66 (d, J = 2.2 Hz, 1H), 5.33 (s, 2H), 2.41 (s, 3H), 2.25 (s, 3H); ESI MS m/z 331 [M + H]+ |
| 256 | 3-amino-1-(benzo[d][1,3]dioxol-5-ylmethyl)-5-(3,5-dimethylisoxazol-4-yl)pyridin-2(1H)-one | 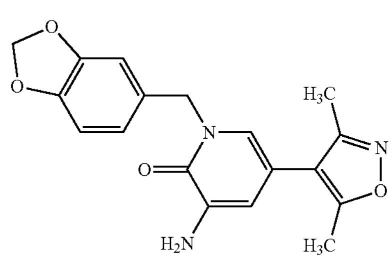 [SMILES: Cc1noc(C)c1-c1cc(N)c(=O)n(Cc2ccc3c(c2)OCO3)c1] | N | 1H NMR (500 MHz, CD3OD) δ 6.98 (d, J = 2.2 Hz, 1H), 6.91-6.89 (m, 1H), 6.89-6.85 (m, 1H), 6.79 (d, J = 7.9 Hz, 1H), 6.61 (d, J = 2.2 Hz, 1H), 5.92 (s, 2H), 5.15 (s, 2H), 2.35 (s, 3H), 2.20 (s, 3H); ESI MS m/z 340 [M + H]+ |

TABLE 1-continued

Exemplary Embodiments prepared using methods described above.

| Example Number | Chemical Name | Structure | General Procedure | Analytical Data |
|---|---|---|---|---|
| 257 | 3-amino-1-(benzo[d][1,3]dioxol-4-ylmethyl)-5-(3,5-dimethylisoxazol-4-yl)pyridin-2(1H)-one | 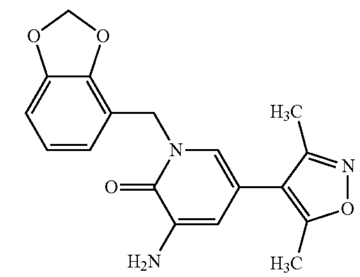 [SMILES: Cc1noc(C)c1-c1cc(N)c(=O)n(Cc2cccc3c2OCO3)c1] | N | 1H NMR (500 MHz, CD3OD) δ 6.99 (d, J = 2.2 Hz, 1H), 6.83-6.80 (m, 3H), 6.62 (d, J = 2.2 Hz, 5.98 (s, 2H), 5.22 (s, 2H), 2.37 (s, 3H), 2.21 (s, 3H); ESI MS m/z 340 [M + H]+ |
| 258 | 3-amino-5-(3,5-dimethylisoxazol-4-yl)-1-((6-methylpyridin-3-yl)methyl)pyridin-2(1H)-one | 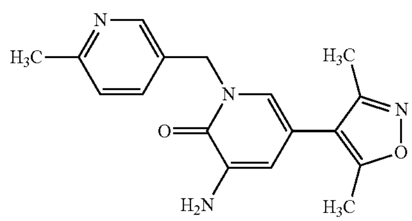 [SMILES: Cc1ccc(Cn2cc(-c3c(C)noc3C)cc(N)c2=O)cn1] | N | 1H NMR (500 MHz, DMSOd6) δ 8.46 (d, J = 2.0 Hz, 1H), 7.75 (dd, J = 8.1, 2.3 Hz, 1H), 7.31 (d, J = 8.1 Hz, 1H), 7.10 (d, J = 8.0 Hz, 1H), 6.62 (d, J = 2.2 Hz, 1H), 5.25 (s, 2H), 2.53 (s, 3H), 2.37 (s, 3H), 2.22 (s, 3H); ESI MS m/z 311 [M + H]+ |
| 259 | methyl 4-(1-(4-chlorobenzyl)-6-oxo-1,6-dihydropyridin-3-yl)-3-methylisoxazole-5-carboxylate | 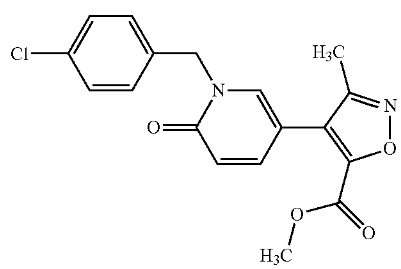 [SMILES: COC(=O)c1onc(C)c1-c1ccc(=O)n(Cc2ccc(Cl)cc2)c1] | F | 1H NMR (300 MHz, DMSO-d6) δ 8.15 (d, J = 2.4 Hz, 1H), 7.59 (dd, J = 9.6, 2.4 Hz, 1H), 7.46-7.37 (m, 4H), 6.50 (d, J = 9.6 Hz, 1H), 5.10 (s, 2H), 3.78 (s, 3H), 2.29 (s, 3H); ESI m/z 359 [M + H]+. |
| 260 | 4-(1-(4-chlorobenzyl)-6-oxo-1,6-dihydropyridin-3-yl)-3-methylisoxazole-5-carboxylic acid | 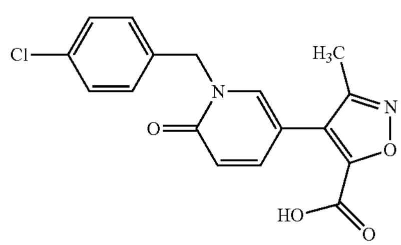 [SMILES: Cc1noc(C(=O)O)c1-c1ccc(=O)n(Cc2ccc(Cl)cc2)c1] | F | 1H NMR (300 MHz, DMSO-d6) δ 8.00 (d, J = 2.1 Hz, 1H), 7.58 (dd, J = 9.3, 2.7 Hz, 1H), 7.40 (s, 4H), 6.39 (d, J = 9.3 Hz, 1H), 5.09 (s, 2H), 2.17 (s, 3H); ESI m/z 345 [M + H]+. |
| 261 | 4-((3-amino-5-(3,5-dimethylisoxazol-4-yl)-2-oxopyridin-1(2H)-yl)methyl)-3-fluorobenzonitrile | 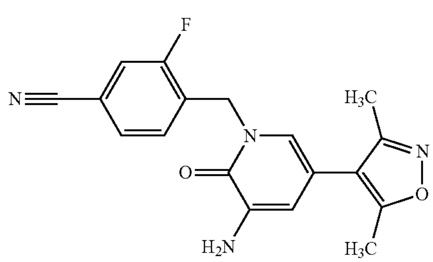 [SMILES: Cc1noc(C)c1-c1cc(N)c(=O)n(Cc2ccc(C#N)cc2F)c1] | N | 1H NMR (500 MHz, DMSO-d6) δ 7.88 (dd, J = 5.0, 1.5 Hz, 1H), 7.68 (dd, J = 8.0, 1.5 Hz, 1H), 7.28 (t, J = 8.0 Hz, 1H), 7.09 (d, J = 2.0 Hz, 1H), 6.49 (d, J = 2.5 Hz, 1H), 5.30 (s, 2H), 5.24 (s, 2H), 2.36 (s, 3H), 2.19 (s, 3H); ESI m/z 339 [M + H]+. |
| 262 | 4-((3-amino-5-(3,5-dimethylisoxazol-4-yl)-2-oxopyridin-1(2H)-yl)methyl)-2-fluorobenzonitrile | 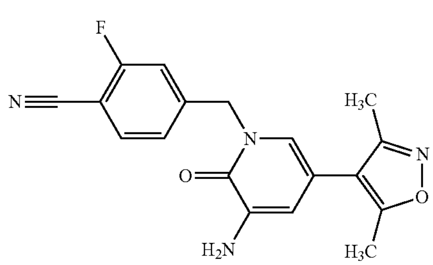 [SMILES: Cc1noc(C)c1-c1cc(N)c(=O)n(Cc2ccc(C#N)c(F)c2)c1] | N | 1H NMR (500 MHz, DMSO-d6): δ 7.91 (dd, J = 8, 7 Hz, 1H), 7.45 (dd, J = 15, 1 Hz, 1H), 7.30 (dd, J = 8, 1.5 Hz, 1H), 7.14 (d, J = 2 Hz, 1H), 6.47 (d, J = 2 Hz, 1H), 5.32 (s, 2H), 5.22 (s, 2H), 2.36 (s, 3H), 2.19 (s, 3H). ESI MS m/z 339 [M + H]+. |

TABLE 1-continued

Exemplary Embodiments prepared using methods described above.

| Example Number | Chemical Name | Structure | General Procedure | Analytical Data |
|---|---|---|---|---|
| 263 | 3-amino-5-(3,5-dimethylisoxazol-4-yl)-1-(1-phenylethyl)pyridin-2(1H)-one | 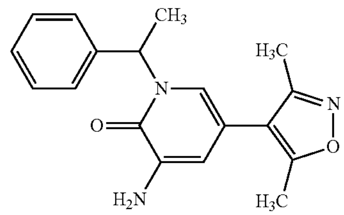 [SMILES: Cc1noc(C)c1-c1cc(N)c(=O)n(C(C)c2ccccc2)c1] | N | 1H NMR (300 MHz, DMSO-d6) δ 7.37-7.35 (m, 4H), 7.33-7.27 (m, 1H), 6.80 (d, J = 2.1 Hz, 1H), 6.42 (d, J = 2.1 Hz, 1H), 6.28 (q, J = 7.2 Hz, 1H), 5.30 (s, 2H), 2.26 (s, 3H), 2.09 (s, 3H), 1.72 (d, J = 7.2 Hz, 3H); ESI m/z 310 [M + H]+. |
| 264 | 5-((3-amino-5-(3,5-dimethylisoxazol-4-yl)-2-oxopyridin-1(2H)-yl)methyl)thiophene-2-carbonitrile | 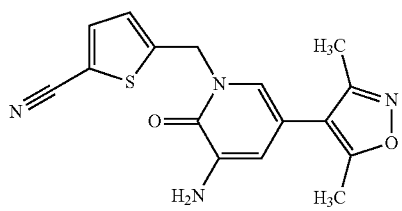 [SMILES: Cc1noc(C)c1-c1cc(N)c(=O)n(Cc2ccc(C#N)s2)c1] | N | 1H NMR (300 MHz, DMSO-d6) δ 7.84 (d, J = 3.6 Hz, 1H), 7.35 (d, J = 3.9 Hz, 1H), 7.20 (d, J = 2.1 Hz, 1H), 6.45 (d, J = 2.1 Hz, 1H), 5.40-5.30 (m, 4H), 2.36 (s, 3H), 2.19 (s, 3H); ESI m/z 327 [M + H]+. |
| 265 | 4-(1-(4-chlorobenzyl)-6-oxo-1,6-dihydropyridin-3-yl)-N,3-dimethylisoxazole-5-carboxamide | 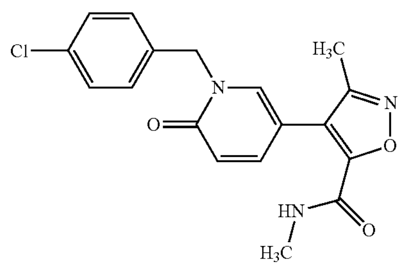 [SMILES: CNC(=O)c1onc(C)c1-c1ccc(=O)n(Cc2ccc(Cl)cc2)c1] | F | 1H NMR (300 MHz, DMSO-d6) δ 8.83 (q, J = 4.5 Hz, 1H), 8.07 (d, J = 2.4 Hz, 1H), 7.54 (dd, J = 9.3, 2.4 Hz, 1H), 7.44-7.38 (m, 4H), 6.45 (d, J = 9.6 Hz, 1H), 5.10 (s, 2H), 2.73 (d, J = 4.5 Hz, 3H), 2.27 (s, 3H); ESI m/z 358 [M + H]+. |
| 266 | 3-(aminomethyl)-1-benzyl-5-(3,5-dimethylisoxazol-4-yl)pyridin-2(1H)-one | 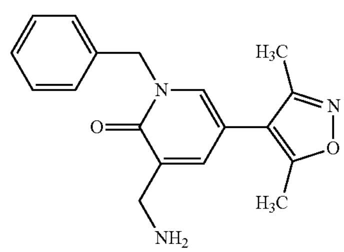 [SMILES: Cc1noc(C)c1-c1cc(CN)c(=O)n(Cc2ccccc2)c1] | No general procedure | 1H NMR (300 MHz, CDCl3) δ 7.39-7.27 (m, 5H), 7.24 (s, 1H), 7.10 (d, J = 2.5 Hz, 1H), 5.19 (s, 2H), 3.89 (s, 2H), 3.17 (s, 2H), 2.31 (s, 3H), 2.15 (s, 3H); ESI MS m/z 310 [M + H]+ |
| 267 | 3-amino-5-(3,5-dimethylisoxazol-4-yl)-1-(4-iodobenzyl)pyridin-2(1H)-one | 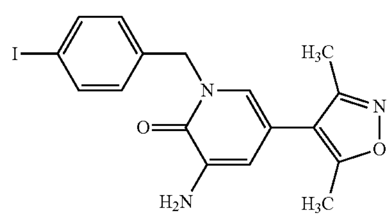 [SMILES: Cc1noc(C)c1-c1cc(N)c(=O)n(Cc2ccc(I)cc2)c1] | O | 1H NMR (300 MHz, DMSO-d6) δ 7.70 (d, J = 8.1 Hz, 2H), 7.16 (d, J = 8.1 Hz, 2H), 7.11 (d, J = 2.1 Hz, 1H), 6.44 (d, J = 2.4 Hz, 1H), 5.29 (s, 2H), 5.08 (s, 2H), 2.35 (s, 3H), 2.18 (s, 3H); ESI m/z 422 [M + H]+. |
| 268 | 1-benzyl-5-(5-oxopyrrolidin-3-yl)pyridin-2(1H)-one | 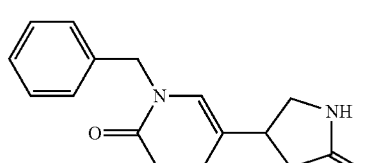 | No general procedure | 1H NMR (300 MHz, CDCl3) δ 7.39-7.26 (m, 6H), 7.10 (d, J = 2.7 Hz, 1H), 6.67 (d, J = 9.6 Hz, 1H), 5.63 (br.s, 1H), 5.13 (s, 2H), 3.66 (dd, J = 9.3, 9.0 Hz, 1H), 3.46-3.38 (m, 1H), 3.25 (dd, J = 9.3, 7.2 Hz, 1H), 2.61 (dd, J = 16.8, 9.0 Hz, 1H), 2.30 (dd, J = 9.3, 8.7 Hz, 1H); ESI m/z 269 [M + H]+. |

TABLE 1-continued

Exemplary Embodiments prepared using methods described above.

| Example Number | Chemical Name | Structure | General Procedure | Analytical Data |
|---|---|---|---|---|
| 269 | 4-(1-(3-amino-5-(3,5-dimethylisoxazol-4-yl)-2-oxopyridin-1(2H)-yl)ethyl)benzonitrile | 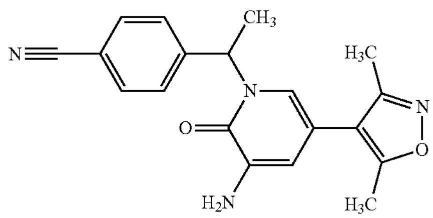 [SMILES: Cc1noc(C)c1-c1cc(N)c(=O)n(C(C)c2ccc(C#N)cc2)c1] | N | 1H NMR (300 MHz, DMSO-d6) δ 7.84 (d, J = 8.4 Hz, 2H), 7.51 (d, J = 8.4 Hz, 2H), 6.91 (d, J = 2.1 Hz, 1H), 6.44 (d, J = 2.1 Hz, 1H), 6.25 (q, J = 6.9 Hz, 1H), 5.32 (s, 2H), 2.30 (s, 3H), 2.13 (s, 3H), 1.76 (d, J = 7.2 Hz, 3H); ESI m/z 335 [M + H]+. |
| 270 | 1-((1H-indol-3-yl)methyl)-3-amino-5-(3,5-dimethylisoxazol-4-yl)pyridin-2(1H)-one | 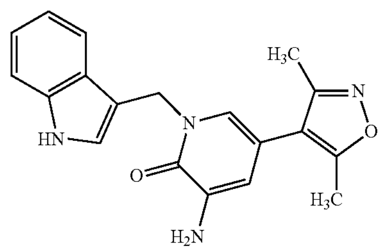 [SMILES: Cc1noc(C)c1-c1cc(N)c(=O)n(Cc2c[nH]c3ccccc23)c1] | P | 1H NMR (500 MHz, DMSO-d6) δ 11.07 (s, 1H), 7.77 (d, J = 7.9 Hz, 1H), 7.51 (d, J = 2.4 Hz, 1H), 7.35 (d, J = 8.1 Hz, 1H), 7.07 (t, J = 7.9 Hz, 1H), 7.04 (d, J = 2.2 Hz, 1H), 6.97 (t, J = 7.9 Hz, 1H), 6.37 (d, J = 2.2 Hz, 1H), 5.26 (s, 4H), 2.26 (s, 3H), 2.09 (s, 3H); ESI m/z 335 [M + H]+. |
| 271 | 3-amino-5-(3,5-dimethylisoxazol-4-yl)-1-((3-methyl-1H-indol-4-yl)methyl)pyridin-2(1H)-one | 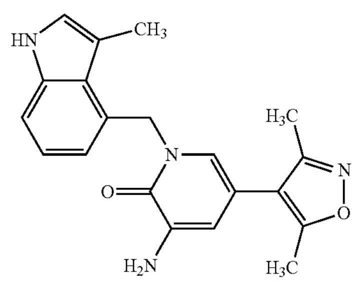 [SMILES: Cc1noc(C)c1-c1cc(N)c(=O)n(Cc2cccc3[nH]cc(C)c23)c1] | P | 1H NMR (500 MHz, DMSO-d6) δ 10.85 (s, 1H), 7.26 (d, J = 7.8 Hz, 1H), 7.12-7.95 (m, 1H), 6.97 (t, J = 7.4 Hz, 1H), 6.69 (d, J = 2.5 Hz, 1H), 6.50 (d, J = 2.5 Hz, 1H), 6.44 (d, J = 7.8 Hz, 1H), 5.58 (s, 2H), 5.28 (s, 2H), 2.37 (d, J = 0.5 Hz, 3H), 2.22 (s, 3H), 2.05 (s, 3H); ESI m/z 349 [M + H]+. |
| 272 | 5-((3-amino-5-(3,5-dimethylisoxazol-4-yl)-2-oxopyridin-1(2H)-yl)methyl)-2-bromobenzonitrile | 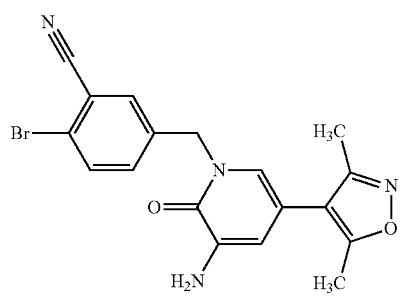 [SMILES: Cc1noc(C)c1-c1cc(N)c(=O)n(Cc2ccc(Br)c(C#N)c2)c1] | P | 1H NMR (500 MHz, DMSO-d6): δ 7.95 (d, J = 2.0 Hz, 1H), 7.87 (d, J = 8.5 Hz, 1H), 7.60-7.58 (m, 1H), 7.16 (d, J = 2.0 Hz, 1H), 6.45 (d, J = 2.0 Hz, 1H), 5.31 (s, 2H), 5.13 (s, 2H), 2.36 (s, 3H), 2.18 (s, 3H); ESI m/z 399 [M + H]+. |
| 273 | 4-((3-amino-5-(3,5-dimethylisoxazol-4-yl)-2-oxopyridin-1(2H)-yl)methyl)-2-bromobenzonitrile | 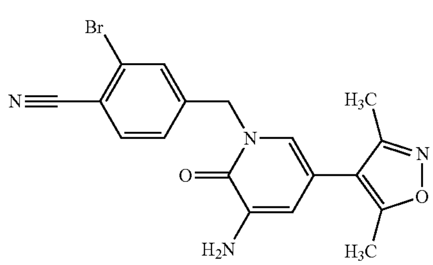 [SMILES: Cc1noc(C)c1-c1cc(N)c(=O)n(Cc2ccc(C#N)c(Br)c2)c1] | P | 1H NMR (500 MHz, DMSO-d6): δ 7.93 (d, J = 8.0 Hz, 1H), 7.84 (d, J = 1.5 Hz, 1H), 7.48-7.46 (m, 1H), 7.16 (d, J = 2.5 Hz, 1H), 6.47 (d, J = 2.5 Hz, 1H), 5.31 (s, 2H), 5.20 (s, 2H), 2.36 (s, 3H), 2.19 (s, 3H); ESI m/z 399 [M + H]+. |

TABLE 1-continued

Exemplary Embodiments prepared using methods described above.

| Example Number | Chemical Name | Structure | General Procedure | Analytical Data |
|---|---|---|---|---|
| 274 | 3-amino-5-(3,5-dimethylisoxazol-4-yl)-1-(quinolin-5-ylmethyl)pyridin-2(1H)-one | 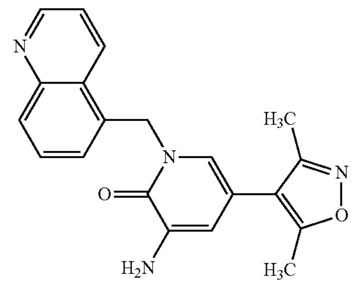 [SMILES: Cc1noc(C)c1-c1cc(N)c(=O)n(Cc2cccc3ncccc23)c1] | P | 1H NMR (500 MHz, DMSO-d6) δ 8.95 (dd, J = 4.1, 1.4 Hz, 1H), 8.74 (d, J = 8.1 Hz, 1H), 7.98 (d, J = 8.4 Hz, 1H), 7.72 (t, J = 7.8 Hz, 1H), 7.62 (dd, J = 8.5, 4.2 Hz, 1H), 7.31 (d, J = 6.8 Hz, 1H), 7.02 (d, J = 2.2 Hz, 1H), 6.49 (d, J = 2.2 Hz, 1H), 5.66 (s, 2H), 5.36 (s, 2H), 2.28 (s, 3H), 2.12 (s, 3H); ESI m/z 347 [M + H]+. |

Example 164

2-Benzyl-4-(2-hydroxy-3,4-dimethoxyphenyl)phthalazin-1(2H)-one

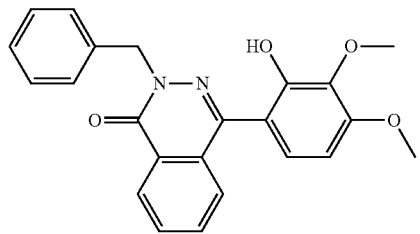 [SMILES: COc1ccc(-c2nn(Cc3ccccc3)c(=O)c3ccccc23)c(O)c1OC]

1,2,3-trimethoxybenzene (2.0 g, 11.9 mmol) was slowly added to a suspension of aluminum chloride (1.6 g, 11.9 mmol) in dichloromethane (50 mL) at 0° C. After the addition was complete phthalic anhydride (1.76 g, 11.9 mmol) was added. The resulting solution heated to reflux and stirred overnight. After that time, the reaction was cooled to rt, concentrated under reduced pressure and cautiously quenched with ice-water. The resulting mixture was extracted with dichloromethane (3×100 mL). The organic phase was dried and concentrated under reduced pressure. The resulting material was combined with N-benzylhydrazine hydrochloride (0.68 g, 3.5 mmol) and potassium acetate (1.62 g, 16.5 mmol) in ethanol (100 mL). The mixture was heated to reflux for 18 h. After that time, the reaction was cooled to rt, concentrated under reduced pressure and diluted with dichloromethane (200 mL). The organic phase was washed with saturated NaHCO$_3$, then water, dried over Na$_2$SO$_4$ and concentrated under reduced pressure. The product was purified by flash column chromatography (silica gel, hexanes/ethyl acetate) to give 2-benzyl-4-(2,3,4-trimethoxyphenyl)phthalazin-1(2H)-one (0.37 g, 28%) as a colorless solid: mp 144-145° C.; $^1$H NMR (400 M Hz, CDCl$_3$) δ 8.49 (d, J=7.4 Hz, 1H), 7.76-7.66 (m, 2H), 7.49 (d, J=7.4 Hz, 2H), 7.41 (d, J=7.8 Hz, 1H), 7.34-7.28 (m, 2H), 7.27-7.22 (m, 1H), 7.04 (d, J=8.6 Hz, 1H), 6.80 (d, J=8.6 Hz, 1H), 5.47 (s, 2H), 3.94 (s, 6H), 3.64 (s, 3H); ESI MS m/z 389.1 [M+H]$^+$.

Example 165

2-Benzyl-4-(4-hydroxy-3-methoxyphenyl)-2H-phthalazin-1-one

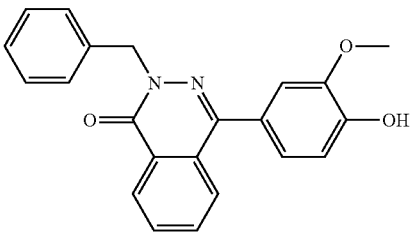 [SMILES: COc1cc(-c2nn(Cc3ccccc3)c(=O)c3ccccc23)ccc1O]

Sodium hydride (60% suspension in mineral oil, 0.92 g, 22.8 mmol) was added in one portion to a stirred suspension of 4-chloro-2H-phthalazin-1-one (3.74 g, 20.7 mmol) in anhydrous DMF (80 mL). The reaction was stirred for 15 min and then cooled to 10° C. Benzyl bromide (4.25 g, 24.8 mmol) was added drop wise and the reaction mixture was then stirred for 21 h at rt. After that time the reaction was diluted with ethyl acetate (200 mL), washed with water (5×80 mL) then brine (80 mL), dried over MgSO$_4$ and concentrated under reduced pressure. The resulting pale yellow solid was suspended in hexanes (80 mL) and stirred for 3 h. After that time, the precipitate was collected by filtration, washed with hexanes and dried to give 2-benzyl-4-chloro-2H-phthalazin-1-one (5.05 g, 90%) as white solid: $^1$H NMR (400 MHz, CDCl$_3$) δ 8.45 (d, J=7.6 Hz, 1H), 7.98 (d, J=8.8 Hz, 1H), 7.97-7.83 (m, 2H), 7.50 (d, J=6.8 Hz, 2H), 7.36-7.7.29 (m, 3H), 5.37 (s, 2H).

A mixture of 2-benzyl-4-chloro-2H-phthalazin-1-one (1.35 g, 5 mmol), 2-methoxy-4-(4,4,5,5-tetramethyl-[1,3,2]dioxaborolan-2-yl)phenol (1.50 g, 6 mmol), Pd(PPh$_3$)$_4$ (0.87 g, 0.75 mmol) and Na$_2$CO$_3$ (2.12 g, 20 mmol) in toluene (25 mL), ethanol (12.5 mL) and water (12.5 mL) was degassed and then heated to reflux with stirring for 19 h. After that time, the reaction was cooled to rt and diluted with ethyl acetate (150 mL) and water (100 mL). The organic phase was separated, washed with water (2×30 mL) then brine (50 mL), dried over MgSO$_4$ and concentrated under reduced pressure. The residue was triturated with hexanes (100 mL) to give a yellow solid. The product was purified by flash column chromatography (silica gel, 70:30 hexanes/ethyl acetate) followed by recrystallization from CHCl₃/hexanes to give 2-benzyl-4-(4-hydroxy-3-methoxyphenyl)phthalazin-1(2H)-one (0.135 g, 7.5%) as a white solid: mp 197-200° C.; ¹H NMR (400 MHz, CDCl₃) δ 8.54-8.52 (m, 1H), 7.79-7.71 (m, 3H), 7.52 (d, J=7.2 Hz, 2H), 7.34-7.25 (m, 4H), 7.11-7.04 (m, 2H), 5.82 (s, 1H), 5.47 (s, 2H), 3.93 (s, 3H); ESI MS m/z 359 [M+1]⁺.

Example 166

2-Benzyl-4-(3,4-dimethoxyphenyl)isoquinolin-1(2H)-one

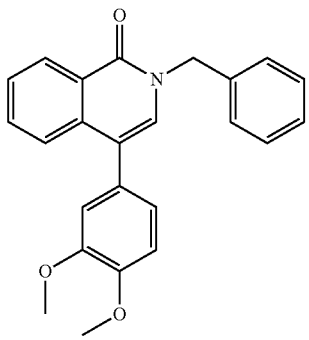 [SMILES: COc1ccc(-c2cn(Cc3ccccc3)c(=O)c3ccccc23)cc1OC]

A mixture of 2-benzyl-4-bromoisoquinolin-1(2H)-one (0.377 g, 1.20 mmol), 2-(3,4-dimethoxyphenyl)-4,4,5,5-tetramethyl-1,3-dioxolane (0.380 g, 1.44 mmol) and Na₂CO₃ (0.382 g, 3.60 mmol) was degassed under nitrogen. Toluene (20 mL), ethanol (20 mL) and water (2 mL) were then added. The reaction mixture was degassed again and Pd(PPh₃)₄ (0.139 g, 0.12 mmol) was added. The reaction was stirred at 90° C. for 16 h under nitrogen. After that time, the mixture was cooled to rt and concentrated under reduced pressure. The residue was diluted with water (50 mL) and extracted with ethyl acetate (2×100 mL). The organic phase was washed with water, brine, dried over Na₂SO₄ and concentrated under reduced pressure. The product was purified by flash column chromatography (silica gel, 70:30 hexanes/ethyl acetate to 60:40 hexanes/ethyl acetate) to give 2-benzyl-4-(3,4-dimethoxyphenyl)isoquinolin-1(2H)-one (0.385 g, 86%) as a pale yellow solid: mp 174-176° C.; ¹H NMR (400 MHz, CDCl₃): δ 8.57 (d, J=7.81 Hz, 1H), 7.47-7.66 (m, 3H), 7.24-7.42 (m, 5H), 7.06 (s, 1H), 6.85-6.98 (m, 3H), 5.27 (s, 2H), 3.93 (s, 3H), 3.87 (s, 3H). ESI MS m/z 372 [M+H]⁺.

Example 167

2-Benzyl-4-(3,5-dimethylisoxazol-4-yl)isoquinolin-1(2H)-one

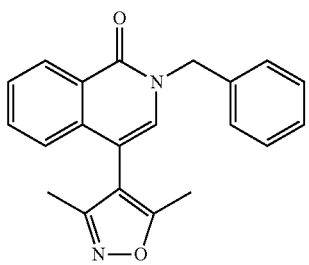 [SMILES: Cc1noc(C)c1-c1cn(Cc2ccccc2)c(=O)c2ccccc12]

Sodium hydride (60% dispersion in mineral oil, 0.656 g, 16.4 mmol) was carefully added to a solution of 4-bromoisoquinolin-1(2H)-one (3.5 g, 15.6 mmol) in anhydrous DMF (60 mL) cooled to 0° C. The reaction was stirred at 0° C. for 30 min, then benzyl bromide (8.02 g, 46.9 mmol) was added slowly. The reaction was allowed to warm to rt and stirred for 17 h. After that time the reaction was diluted with water (200 mL) and extracted with ethyl acetate (3×200 mL). The organic phase was washed with water, brine, dried over Na₂SO₄ and concentrated under reduced pressure. The product was purified by flash column chromatography (silica gel, 90:10 hexanes/ethyl acetate to 75:25 hexanes/ethyl acetate) to give 2-benzyl-4-bromoisoquinolin-1(2H)-one (4.55 g, 93%) as a white solid: ¹H NMR (400 MHz, CDCl₃) δ 8.49 (d, J=7.4 Hz, 1H), 7.79-7.84 (m, 1H), 7.71-7.79 (m, 1H), 7.53-7.60 (m, 1H), 7.29-7.38 (m, 6H), 5.21 (s, 2H); ESI MS m/z 314 [M+H]⁺ and 316 [M+H]⁺.

A mixture of 2-benzyl-4-bromoisoquinolin-1(2H)-one (0.320 g, 1.02 mmol), 3,5-dimethyl-4-(4,4,5,5-tetramethyl-1,3,2-dioxaborolan-2-yl)isoxazole (0.341 g, 1.53 mmol) and Na₂CO₃ (0.324 g, 3.06 mmol) in toluene (20 mL), ethanol (10 mL) and water (3 mL) was degassed under nitrogen. Pd(PPh₃)₄ (0.118 g, 0.10 mmol) was then added and the reaction was stirred at 100° C. for 17 h under nitrogen. After that time, the mixture was cooled to rt and concentrated under reduced pressure. The residue was dissolved in ethyl acetate (100 mL) and washed with water, brine, dried over Na₂SO₄ and concentrated under reduced pressure. The product was purified by flash column chromatography (silica gel, 90:10 hexanes/ethyl acetate to 75:25 hexanes/ethyl acetate) to give 2-benzyl-4-(3,5-dimethylisoxazol-4-yl)isoquinolin-1(2H)-one (0.140 g, 42%) as an off white solid: mp 139-141° C.; ¹H NMR (400 MHz, CDCl₃) δ 8.56 (d, J=7.8 Hz, 1H), 7.60-7.68 (m, 1H), 7.51-7.60 (m, 1H), 7.29-7.39 (m, 5H), 7.19 (d, J=7.8 Hz, 1H), 6.97 (s, 1H), 5.18-5.33 (m, 2H), 2.23 (s, 3H), 2.06 (s, 3H); ESI MS m/z 331 [M+H]⁺.

Example 168

2-Benzyl-4-(3,4,5-trimethoxyphenyl)isoquinolin-1(2H)-one

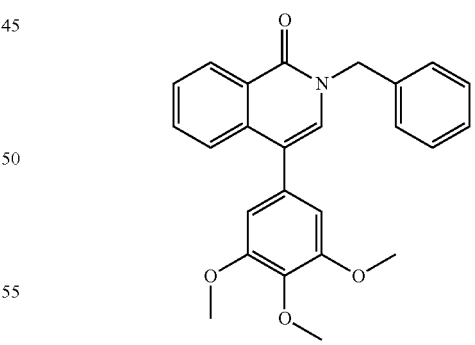

A mixture of 2-benzyl-4-bromoisoquinolin-1(2H)-one (0.420 g, 1.34 mmol), 4,4,5,5-tetramethyl-2-(3,4,5-trimethoxyphenyl)-1,3,2-dioxaborolane (0.511 g, 1.74 mmol) and Na₂CO₃ (0.425 g, 4.01 mmol) in toluene (20 mL), ethanol (10 mL) and water (3 mL) was degassed under nitrogen. Pd(PPh₃)₄ (0.154 g, 0.13 mmol) was then added and the reaction mixture was stirred at 100° C. for 17 h under nitrogen. After that time, the mixture was cooled to rt and concentrated under reduced pressure. The residue was dissolved in ethyl acetate (100 mL) and washed with water, brine, dried over Na$_2$SO$_4$ and concentrated under reduced pressure. The product was purified by flash column chromatography (silica gel, 90:10 hexanes/ethyl acetate to 75:25 hexanes/ethyl acetate) to give 2-benzyl-4-(3,4,5-trimethoxyphenyl)isoquinolin-1(2H)-one (0.298 g, 55%) as an off white solid: mp 166-168° C.; $^1$H NMR (400 MHz, CDCl$_3$) δ 8.57 (d, J=7.8 Hz, 1H), 7.49-7.66 (m, 3H), 7.28-7.41 (m, 5H), 7.08 (s, 1H), 6.57 (s, 2H), 5.28 (s, 2H), 3.91 (s, 3H), 3.85 (s, 6H); ESI MS m/z 402 [M+H]$^+$.

Example 169

2-Benzyl-4-(4-hydroxy-3-methoxyphenyl)isoquinolin-1(2H)-one

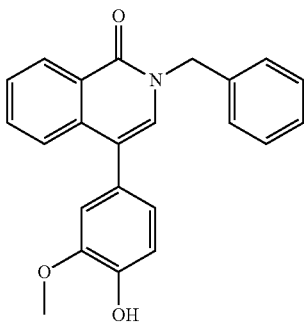 [SMILES: COc1cc(-c2cn(Cc3ccccc3)c(=O)c3ccccc23)ccc1O]

A mixture of 2-benzyl-4-bromoisoquinolin-1(2H)-one (0.50 g, 1.59 mmol), 2-methoxy-4-(4,4,5,5-tetramethyl-1,3-dioxolan-2-yl)phenol (0.477 g, 1.90 mmol) and Na$_2$CO$_3$ (0.843 g, 7.95 mmol) in toluene (30 mL), ethanol (30 mL) and water (5 mL) was degassed under nitrogen. Pd(PPh$_3$)$_4$ (0.183 g, 0.157 mmol) was added and the reaction was stirred at 90° C. for 16 h under nitrogen. After that time, the mixture was cooled to rt and diluted with ethyl acetate (250 mL). The organic phase was separated, washed with water and brine, dried over Na$_2$SO$_4$ and concentrated under reduced pressure. The product was purified by flash column chromatography (silica gel, 70:30 hexanes/ethyl acetate) to give 2-benzyl-4-(4-hydroxy-3-methoxyphenyl)isoquinolin-1(2H)-one (0.253 g, 45%) as a white solid: mp 165-167° C.; $^1$H NMR (400 MHz, CDCl$_3$) δ 8.56 (d, J=8.2 Hz, 1H), 7.58-7.65 (m, 1H), 7.50-7.57 (m, 2H), 7.28-7.40 (m, 5H), 7.05 (s, 1H), 6.99 (d, J=8.6 Hz, 1H), 6.84-6.89 (m, 2H), 5.70 (s, 1H), 5.27 (s, 2H), 3.89 (s, 3H); ESI MS m/z 358 [M+H]$^+$.

Example 170

2-Benzyl-4-(3,5-dimethylisoxazol-4-yl)-2H-phthalazin-1-one

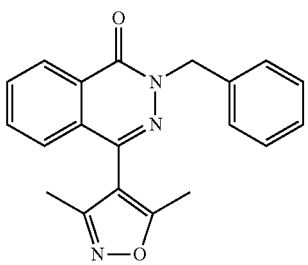 [SMILES: Cc1noc(C)c1-c1nn(Cc2ccccc2)c(=O)c2ccccc12]

A mixture of 2-benzyl-4-chloro-2H-phthalazin-1-one (1.35 g, 5 mmol), 3,5-dimethyl-4-(4,4,5,5-tetramethyl-[1,3,2]dioxaborolan-2-yl)isoxazole (1.34 g, 6 mmol), Pd(PPh$_3$)$_4$ (0.58 g, 0.5 mmol) and Na$_2$CO$_3$ (1.59 g, 15 mmol) in toluene (25 mL), ethanol (12.5 mL) and water (12.5 mL) was degassed and heated to reflux with stirring for 18 h. After that time, the mixture was cooled to rt and diluted with ethyl acetate (80 mL). The organic phase was separated, washed with water and brine, dried over MgSO$_4$ and concentrated under reduced pressure. The resulting semi-solid was triturated with hexanes to give a yellow solid. The product was purified by flash column chromatography (silica gel, 80:20 hexanes/ethyl acetate) followed by recrystallization from CHCl$_3$/hexanes to give 2-benzyl-4-(3,5-dimethylisoxazol-4-yl)phthalazin-1(2H)-one (0.39 g, 23%) as a white solid: mp 186-188° C.; $^1$H NMR (400 MHz, CDCl$_3$) δ 8.55-8.53 (m, 1H), 7.83-7.76 (m, 2H), 7.48 (d, J=7.2 Hz, 2H), 7.44-7.42 (m, 1H), 7.35-7.26 (m, 3H), 5.45 (s, 2H), 2.31 (s, 3H), 2.15 (s, 3H).

Example 171

2-Benzyl-4-(3,4,5-trimethoxyphenylamino)-2H-phthalazin-1-one

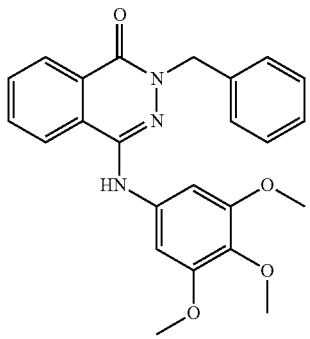 [SMILES: COc1cc(Nc2nn(Cc3ccccc3)c(=O)c3ccccc23)cc(OC)c1OC]

A mixture of 2-benzyl-4-chloro-2H-phthalazin-1-one (1.35 g, 5 mmol), 3,4,5-trimethoxyaniline (1.10 g, 6 mmol), bis(dibenzylideneacetone)palladium(II) (0.46 g, 0.5 mmol), 2,2'-bis(diphenylphosphino)-1,1'-binapthyl (0.62 g, 1 mmol) and potassium tert-butoxide (0.84 g, 7.5 mmol) in anhydrous toluene (20 mL) was degassed and heated to reflux with stirring for 19 h. After that time, the mixture was cooled to rt and quenched with saturated aqueous NH$_4$Cl (20 mL). Ethyl acetate (20 mL) and water (20 mL) were added and the organic phase was separated, washed with brine (20 mL), dried over MgSO$_4$ and concentrated under reduced pressure. The product was purified by flash column chromatography (silica gel, 60:40 hexanes/ethyl acetate) followed by recrystallization from CHCl$_3$/hexanes to give 2-benzyl-4-((3,4,5-trimethoxyphenyl)amino)phthalazin-1(2H)-one (0.598 g, 29%) as a white solid: mp 206-207° C.; $^1$H NMR (400 MHz, CDCl$_3$) δ 8.57-8.55 (m, 1H), 7.84-7.76 (m, 3H), 7.41 (d, J=6.8 Hz, 2H), 7.32-7.22 (m, 3H), 6.69 (s, 2H), 6.40 (s, 1H), 5.38 (s, 2H), 3.81 (s, 3H), 3.70 (s, 6H); ESI MS m/z 418 [M+1]$^+$.

Example 172

2-Benzyl-4-((3,4,5-trimethoxyphenyl)amino)isoquinolin-1(2H)-one

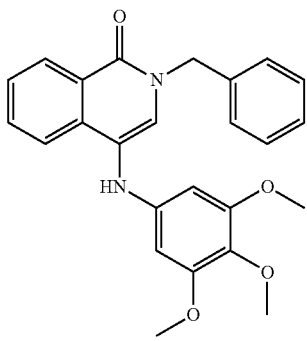 [SMILES: COc1cc(Nc2cn(Cc3ccccc3)c(=O)c3ccccc23)cc(OC)c1OC]

A mixture of 2-benzyl-4-bromoisoquinolin-1(2H)-one (0.500 g, 1.59 mmol) and 3,4,5-trimethoxyaniline (0.349 g, 1.91 mmol) in dry toluene (30 mL) was degassed under nitrogen. $Pd_2(dba)_3$ (0.218 g, 0.24 mmol) and BINAP (0.297 g, 0.48 mmol) were added and the mixture was degassed again. Sodium tert-butoxide (0.306 g, 3.18 mmol) was then added and the reaction was stirred at 100° C. for 17 h under nitrogen. After that time, the reaction mixture was cooled to rt, diluted with water (20 mL) and extracted with ethyl acetate (3×20 mL). The organic phase was washed with brine, dried over $Na_2SO_4$ and concentrated under reduced pressure. The product was purified by flash column chromatography (silica gel, 25:75 hexanes/ethyl acetate to 50:50 hexanes/ethyl acetate) followed by trituration with methanol to give 2-benzyl-4-((3,4,5-trimethoxyphenyl)amino)isoquinolin-1(2H)-one (0.183 g, 28%) as a light brown solid: mp 162-164° C.; $^1$H NMR (400 MHz, $CDCl_3$) δ 8.53 (d, J=8.2 Hz, 1H), 7.61-7.68 (m, 2H), 7.54 (ddd, J=8.2, 5.6, 2.7 Hz, 1H), 7.27-7.35 (m, 5H), 7.17 (s, 1H), 5.85 (s, 2H), 5.23 (s, 2H), 5.10 (s, 1H), 3.75 (s, 3H), 3.65 (s, 6H); ESI MS m/z 417 $[M+H]^+$.

Example 173

6-Benzyl-8-(3,5-dimethylisoxazol-4-yl)-1,6-naphthyridin-5(6H)-one

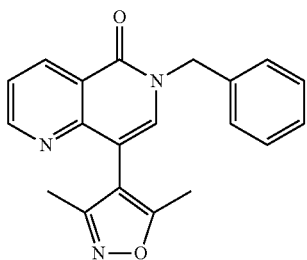 [SMILES: Cc1noc(C)c1-c1cn(Cc2ccccc2)c(=O)c2cccnc12]

To a solution of 8-bromo-1,6-naphthyridin-5(6H)-one (0.225 g, 1.0 mmol) in anhydrous DMF (6 mL) was added sodium hydride (60% dispersion in mineral oil, 0.052 g, 1.3 mmol) at 0° C. The resulting mixture was stirred at 0° C. for 45 min and then benzyl bromide (0.205 g, 1.2 mmol) was added slowly. The reaction mixture was stirred at 0° C. for 2 h, then allowed to warm to rt and stirred for 17 h. After that time, saturated $NH_4Cl$ solution (5 mL) and water (5 mL) were added and the mixture was extracted with ethyl acetate (2×25 mL). The organic phase was washed with brine, dried over $Na_2SO_4$, filtered and concentrated under reduced pressure. The product was purified by flash column chromatography (silica gel, 99:1 dichloromethane/methanol to 97:3 dichloromethane/methanol) to give 6-benzyl-8-bromo-1,6-naphthyridin-5(6H)-one (0.270 g, 86%) as an off-white solid: $^1$H NMR (400 MHz, $CDCl_3$) δ 9.04 (dd, J=4.5, 1.8 Hz, 1H), 8.71-8.77 (m, 1H), 7.65 (s, 1H), 7.50 (dd, J=8.0, 4.5 Hz, 1H), 7.30-7.41 (m, 5H), 5.22 (s, 2H); ESI MS m/z 315 $[M+H]^+$ and 317 $[M+H]^+$.

A mixture of 6-benzyl-8-bromo-1,6-naphthyridin-5(6H)-one (0.260 g, 0.82 mmol), (3,5-dimethylisoxazol-4-yl)boronic acid (0.174 g, 1.24 mmol) and $Na_2CO_3$ (0.262 g, 2.47 mmol) in toluene (25 mL), ethanol (15 mL) and water (5 mL) was degassed. $Pd(PPh_3)_4$ (0.095 g, 0.08 mmol) was then added and the reaction heated at 95° C. for 17 h. After that time the reaction was cooled to rt and concentrated under reduced pressure. The residue was dissolved in ethyl acetate (100 mL), washed with water and brine, dried over $Na_2SO_4$, filtered and concentrated under reduced pressure. The product was purified by flash column chromatography (silica gel, 99:1 ethyl acetate/methanol) to give 6-benzyl-8-(3,5-dimethylisoxazol-4-yl)-1,6-naphthyridin-5(6H)-one (0.180 g, 66%) as a white solid: mp 192-195° C.; $^1$H NMR (400 MHz, $CDCl_3$) δ 8.92 (dd, J=4.5, 1.9 Hz, 1H), 8.78 (dd, J=8.0, 1.9 Hz, 1H), 7.47 (dd, J=8.0, 4.5 Hz, 1H), 7.30-7.41 (m, 5H), 7.20 (s, 1H), 5.27 (s, 2H), 2.25 (s, 3H), 2.11 (s, 3H); ESI MS m/z 332 $[M+H]^+$.

Example 174

7-Benzyl-5-(3,5-dimethylisoxazol-4-yl)-1,7-naphthyridin-8(7H)-one

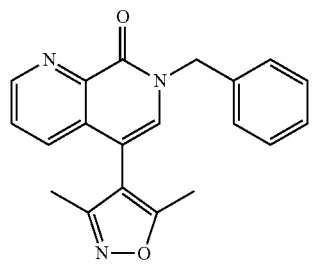 [SMILES: Cc1noc(C)c1-c1cn(Cc2ccccc2)c(=O)c2ncccc12]

To a suspension of 5-bromo-1,7-naphthyridin-8(7H)-one (0.50 g, 2.22 mmol) in anhydrous DMF (60 mL) was added benzyl bromide (0.34 mL, 2.88 mmol) and $Cs_2CO_3$ (0.94 g, 2.88 mmol). The reaction was stirred at rt for 16 h. After that time the reaction was concentrated under reduced pressure, diluted with water (50 mL) and extracted with ethyl acetate (100 mL). The organic phase was washed with water then brine, dried over $Na_2SO_4$, filtered and concentrated under reduced pressure. The product was purified by flash column chromatography (silica gel, 98:2 dichloromethane/methanol) to give 7-benzyl-5-bromo-1,7-naphthyridin-8(7H)-one (0.584 g, 83%) as a brown solid: $^1$H NMR (400 MHz, $CDCl_3$) δ 8.93 (dd, J=4.4, 1.5 Hz, 1H), 8.16 (dd, J=8.2, 1.5 Hz, 1H), 7.66 (dd, J=8.2, 4.4 Hz, 1H), 7.42 (s, 1H), 7.28-7.41 (m, 5H), 5.28 (s, 2H); ESI MS m/z 314.9 $[M+H]^+$ and 316.9 $[M+H]^+$.

A mixture of 7-benzyl-5-bromo-1,7-naphthyridin-8(7H)-one (0.574 g, 1.82 mmol), (3,5-dimethylisoxazol-4-yl)boronic acid (0.385 g, 2.73 mmol) and Na$_2$CO$_3$ (0.579 g, 5.46 mmol) was degassed under nitrogen. Then toluene (30 mL), ethanol (30 mL) and water (3 mL) were added. The reaction mixture was degassed again and Pd(PPh$_3$)$_4$ (0.210 g, 0.12 mmol) was added and degassing procedure was repeated. The reaction was stirred at 90° C. for 6 h under nitrogen. After that time the reaction was cooled to rt, concentrated under reduced pressure, diluted with water (50 mL) and extracted with ethyl acetate (2×100 mL). The organic phase was washed with water then brine, dried over Na$_2$SO$_4$, and concentrated under reduced pressure. The product was purified by flash column chromatography (silica gel, dichloromethane to 97:3 dichloromethane/methanol) to give 7-benzyl-5-(3,5-dimethylisoxazol-4-yl)-1,7-naphthyridin-8 (7H)-one (0.341 g, 56%) as a tan solid: mp 168-170° C.; $^1$H NMR (400 MHz, CDCl$_3$): δ 8.92-9.00 (m, 1H), 7.52-7.60 (m, 2H), 7.29-7.42 (m, 5H), 7.04 (s, 1H), 5.26-5.43 (m, 2H), 2.22 (s, 3H), 2.04 (s, 3H); ESI MS m/z 332.0 [M+H]$^+$.

Example 175

2-Benzyl-4-(3,5-dimethylisoxazol-4-yl)-2,7-naphthyridin-1(2H)-one

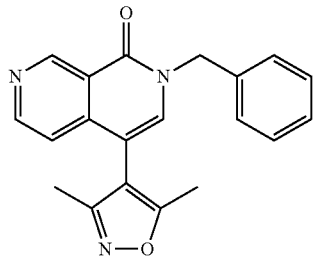 [SMILES: Cc1noc(C)c1-c1cn(Cc2ccccc2)c(=O)c2cnccc12]

To a solution of 4-iodo-2,7-naphthyridin-1(2H)-one (0.544 g, 2.0 mmol) in anhydrous DMF (10 mL) was added sodium hydride (60% dispersion in mineral oil, 0.104 g, 2.6 mmol) at 0° C. The resulting mixture was stirred at 0° C. for 30 min and then benzyl bromide (0.410 g, 2.4 mmol) was added slowly. The reaction was stirred at 0° C. for 2 h, then allowed to warm to rt and stirred for 17 h. Saturated NH$_4$Cl solution (5 mL) and water (5 mL) were added and the mixture was extracted with ethyl acetate (2×25 mL). The organic phase was washed with brine, dried over Na$_2$SO$_4$, filtered and concentrated under reduced pressure. The product was purified by flash column chromatography (silica gel, 99:1 dichloromethane/methanol to 97:3 dichloromethane/methanol) to give 2-benzyl-4-iodo-2,7-naphthyridin-1(2H)-one (0.540 g, 75%) as an off-white solid: $^1$H NMR (400 MHz, CDCl3) δ 9.56 (s, 1H), 8.84 (d, J=5.5 Hz, 1H), 7.68 (s, 1H), 7.45 (d, J=5.5 Hz, 1H), 7.30-7.41 (m, 5H), 5.19 (s, 2H); ESI MS m/z 363 [M+H]$^+$.

A mixture of 2-benzyl-4-iodo-2,7-naphthyridin-1(2H)-one (0.540 g, 1.49 mmol), (3,5-dimethylisoxazol-4-yl)boronic acid (0.315 g, 2.24 mmol) and Na$_2$SO$_4$ (0.474 g, 4.47 mmol) in toluene (25 mL), ethanol (25 mL) and water (4 mL) was degassed. Pd(PPh$_3$)$_4$ (0.172 g, 0.15 mmol) was then added and the reaction mixture was heated at 95° C. for 6 h. After that time the reaction was cooled to rt, concentrated under reduced pressure and diluted with ethyl acetate (100 mL). The organic phase was washed with water then brine, dried over Na$_2$SO$_4$, and concentrated under reduced pressure. The product was purified by flash column chromatography (silica gel, dichloromethane to 99:1 ethyl acetate/methanol) to give 2-benzyl-4-(3,5-dimethylisoxazol-4-yl)-2,7-naphthyridin-1(2H)-one (0.260 g, 54%) as an off-white solid: mp 174-177° C.; $^1$H NMR (400 MHz, CDCl$_3$) δ 9.73 (s, 1H), 8.75 (d, J=5.4 Hz, 1H), 7.31-7.41 (m, 5H), 7.16 (s, 1H), 7.02 (d, J=5.4 Hz, 1H), 5.26 (s, 2H), 2.23 (s, 3H), 2.06 (s, 3H); ESI MS m/z 332 [M+H]$^+$.

Example 176

2-Benzyl-4-(3,5-dimethylisoxazol-4-yl)-2,6-naphthyridin-1(2H)-one

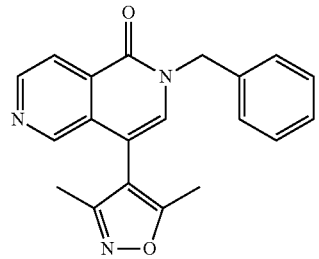 [SMILES: Cc1noc(C)c1-c1cn(Cc2ccccc2)c(=O)c2ccncc12]

Benzyl bromide (0.057 g, 0.34 mmol) was added to a mixture of 4-iodo-2,6-naphthyridin-1(2H)-one trifluoroacetate (0.100 g, 0.26 mmol) and Cs$_2$CO$_3$ (0.253 g, 0.78 mmol) in anhydrous DMF (10 mL) cooled to 0° C. The reaction was stirred at 0° C. for 30 min, then allowed to warm to rt and stirred for 17 h. After that time the reaction was concentrated under reduced pressure, diluted with water (10 mL), and extracted with ethyl acetate (2×25 mL). The organic phase was washed with brine, dried over Na$_2$SO$_4$, filtered and concentrated under reduced pressure. The product was purified by flash column chromatography (silica gel, 99:1 dichloromethane/methanol to 97:3 dichloromethane/methanol) to give 2-benzyl-4-iodo-2,6-naphthyridin-1(2H)-one (0.070 g, 74%) as an off-white solid: $^1$H NMR (400 MHz, CDCl$_3$) δ 9.04 (s, 1H), 8.78 (d, J=5.3 Hz, 1H), 8.14 (d, J=5.3 Hz, 1H), 7.57 (s, 1H), 7.31-7.40 (m, 5H), 5.20 (s, 2H); ESI MS m/z 363 [M+H]$^+$.

A mixture of 2-benzyl-4-iodo-2,6-naphthyridin-1(2H)-one (0.070 g, 0.19 mmol), (3,5-dimethylisoxazol-4-yl)boronic acid (0.041 g, 0.29 mmol) and Na$_2$CO$_3$ (0.062 g, 0.58 mmol) in toluene (15 mL), ethanol (15 mL) and water (2 mL) was degassed. Pd(PPh$_3$)$_4$ (0.022 g, 0.19 μmol) was then added and the reaction was heated at 95° C. for 17 h. After that time the reaction was cooled to rt, concentrated under reduced pressure and diluted with ethyl acetate (30 mL). The organic phase was washed with water then brine, dried over Na$_2$SO$_4$, filtered and concentrated under reduced pressure. The product was purified by flash column chromatography (silica gel, 99:1 dichloromethane/methanol) followed by trituration with diethyl ether to give 2-benzyl-4-(3,5-dimethylisoxazol-4-yl)-2,6-naphthyridin-1(2H)-one (0.020 g, 32%) as an off-white solid: mp 159-161° C.; 1H NMR (400 MHz, CDCl$_3$) δ 8.78 (d, J=5.4 Hz, 1H), 8.65 (s, 1H), 8.30 (d, J=5.4 Hz, 1H), 7.30-7.40 (m, 5H), 7.04 (s, 1H), 5.26 (s, 2H), 2.26 (s, 3H), 2.09 (s, 3H); ESI MS m/z 332 [M+H]$^+$.

Example 177

2-Benzyl-4-(2,3,4-trimethoxyphenyl)phthalazin-1(2H)-one

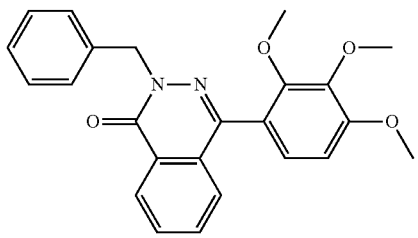 [SMILES: COc1ccc(-c2nn(Cc3ccccc3)c(=O)c3ccccc23)c(OC)c1OC]

Example 177 was isolated as a byproduct from the procedure described for Example 164. Continued elution during the purification process provided 2-benzyl-4-(2-hydroxy-3,4-dimethoxyphenyl)phthalazin-1(2H)-one (0.37 g, 28%) as a colorless solid: mp 155-156° C.; $^1$H NMR (400 MHz, CDCl$_3$) δ 8.51 (d, J=7.5 Hz, 1H), 7.79-7.69 (m, 2H), 7.63 (d, J=7.5 Hz, 2H), 7.51 (d, J=7.6 Hz, 2H), 7.36-7.30 (m, 1H), 7.30-7.24 (m, 1H), 7.10 (d, J=8.6 Hz, 1H), 6.74 (s, 1H), 6.63 (d, J=8.6 Hz, 1H), 5.47 (s, 2H), 3.97 (s, 3H), 3.94 (s, 3H); ESI MS m/z 389 [M+H]$^+$.

Example 275

Inhibition of Tetra-Acetylated Histone H4 Binding Individual BET Bromodomains Proteins were cloned and overexpressed with a N-terminal 6× His tag, then purified by nickel affinity followed by size exclusion chromatography. Briefly, *E. coli* BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein is pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Time Resolved Fluorescence Resonance Energy Transfer (TR-FRET) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Final buffer concentrations were 30 mM HEPES pH 7.4, 30 mM NaCl, 0.3 mM CHAPS, 20 mM phosphate pH 7.0, 320 mM KF, 0.08% BSA). After a 2-h incubation at room temperature, the fluorescence by FRET was measured at 665 and 620 nm by a SynergyH4 plate reader (Biotek). Illustrative results with the first bromodomain of Brd4 and the second bromodomain of Brd2 are shown below. The binding inhibitory activity was shown by a decrease in 665 nm fluorescence relative to 620 nm. IC$_{50}$ values were determined from a dose response curve.

Compounds with an IC$_{50}$ value less than 30 μM were deemed to be active.

TABLE 2

Inhibition of Tetra-acetylated Histone H4 Binding to Brd4 bromodomain 1 (BRD4(1) and Brd 3 bromodomain 2 (BRD2(2) as Measured by FRET

| Example Number | FRET activity (IC50 <30 μM) BRD2(2)-BRD4(1) | | Example Number | FRET activity (IC50 <30 μM) BRD2(2)-BRD4(1) | | Example Number | FRET activity (IC50 <30 μM) BRD2(2)-BRD4(1) | |
|---|---|---|---|---|---|---|---|---|
| 1 | Active | Active | 2 | Active | Active | 3 | Active | Not Active |
| 4 | Active | Active | 5 | Active | Active | 6 | Active | Active |
| 7 | Active | Active | 8 | Active | Active | 9 | Active | Active |
| 10 | Active | Active | 11 | Active | Active | 12 | Active | Active |
| 13 | Active | Active | 14 | Active | Active | 15 | Active | Active |
| 16 | Active | Active | 17 | Active | Active | 18 | Active | Active |
| 19 | Active | Active | 20 | Active | Not Active | 21 | Active | Active |
| 22 | Active | Active | 23 | Active | Active | 24 | Active | Active |
| 25 | Active | Active | 26 | Active | Active | 27 | Active | Active |
| 28 | Active | Active | 29 | Active | Active | 30 | Active | Active |
| 31 | Active | Active | 32 | Active | Not Active | 33 | Active | Active |
| 34 | Active | Active | 35 | Active | Active | 36 | Active | Active |
| 37 | Active | Active | 38 | Active | Active | 39 | Active | Active |
| 40 | Active | Active | 41 | Active | Active | 42 | Active | Active |
| 43 | Active | Active | 44 | Active | Active | 45 | Active | Active |
| 46 | Active | Active | 47 | Active | Active | 48 | Active | Active |
| 49 | Active | Active | 50 | Active | Active | 51 | Active | Active |
| 52 | Active | Active | 53 | Active | Active | 54 | Active | Active |
| 55 | Active | Active | 56 | Active | Active | 57 | Active | Active |
| 58 | Active | Not Active | 59 | Active | Not Active | 60 | Active | Active |
| 61 | Active | Active | 62 | Active | Not Active | 63 | Active | Active |
| 64 | Active | Active | 65 | Active | Active | 66 | Active | Active |
| 67 | Active | Active | 68 | Active | Active | 69 | Active | Active |
| 70 | Active | Active | 71 | Active | Active | 72 | Active | Active |

TABLE 2-continued

Inhibition of Tetra-acetylated Histone H4 Binding to Brd4 bromodomain 1
(BRD4(1) and Brd 3 bromodomain 2 (BRD2(2) as Measured by FRET

| Example Number | FRET activity (IC50 <30 μM) BRD2(2)-BRD4(1) | | Example Number | FRET activity (IC50 <30 μM) BRD2(2)-BRD4(1) | | Example Number | FRET activity (IC50 <30 μM) BRD2(2)-BRD4(1) | |
|---|---|---|---|---|---|---|---|---|
| 73 | Active | Active | 74 | Active | Active | 75 | Active | Active |
| 76 | Active | Active | 77 | Active | Active | 78 | Active | Active |
| 79 | Active | Active | 80 | Active | Not Active | 81 | Active | Not Active |
| 82 | Active | Active | 83 | Active | Active | 84 | Active | Active |
| 85 | Active | Active | 86 | Active | Active | 87 | Active | Active |
| 88 | Active | Active | 89 | Active | Active | 90 | Active | Active |
| 91 | Active | Active | 92 | Active | Active | 93 | Active | Active |
| 94 | Active | Active | 95 | Active | Active | 96 | Active | Active |
| 97 | Not Active | Active | 98 | Active | Active | 99 | Active | Active |
| 100 | Active | Not Active | 101 | Active | Active | 102 | Active | Active |
| 103 | Active | Active | 104 | Active | Active | 105 | Active | Active |
| 106 | Active | Active | 107 | Active | Active | 108 | Active | Active |
| 109 | Active | Active | 110 | Active | Active | 111 | Active | Active |
| 112 | Active | Active | 113 | Active | Active | 114 | Active | Active |
| 115 | Active | Active | 116 | Active | Active | 117 | Active | Active |
| 118 | Active | Active | 119 | Active | Active | 120 | Active | Active |
| 121 | Active | Active | 122 | Active | Active | 123 | Active | Active |
| 124 | Active | Active | 125 | Active | Active | 126 | Active | Active |
| 127 | Active | Active | 128 | Active | Active | 129 | Active | Active |
| 130 | Active | Active | 131 | Active | Active | 132 | Active | Active |
| 133 | Active | Active | 134 | Active | Active | 135 | Active | Active |
| 136 | Active | Active | 137 | Active | Active | 138 | Active | Active |
| 139 | Active | Active | 140 | Active | Active | 141 | Active | Active |
| 142 | Active | Active | 143 | Active | Active | 144 | Active | Active |
| 145 | Active | Active | 146 | Active | Active | 147 | Active | Active |
| 148 | Active | Active | 149 | Active | Active | 150 | Not Active | Active |
| 151 | Active | Active | 152 | Not Tested | Active | 153 | Not Tested | Active |
| 154 | Not Tested | Active | 155 | Not Tested | Active | 156 | Not Tested | Active |
| 157 | Not Tested | Active | 158 | Not Tested | Active | 159 | Not Tested | Active |
| 160 | Not Tested | Active | 161 | Not Tested | Not Active | 162 | Active | Active |
| 163 | Active | Active | 164 | Active | Active | 165 | Active | Active |
| 166 | Not Active | Active | 167 | Active | Active | 168 | Active | Not Active |
| 169 | Active | Active | 170 | Active | Not Active | 171 | Active | Active |
| 172 | Active | Active | 173 | Active | Active | 174 | Active | Active |
| 175 | Active | Active | 176 | Active | Active | 177 | Active | Active |
| 178 | Not Tested | Active | 179 | Not Tested | Active | 180 | Not Tested | Active |
| 181 | Not Tested | Active | 182 | Not Tested | Active | 183 | Not Tested | Active |
| 184 | Not Tested | Active | 185 | Not Tested | Active | 186 | Not Tested | Active |
| 187 | Not Tested | Active | 188 | Not Tested | Active | 189 | Not Tested | Active |
| 190 | Not Tested | Active | 191 | Not Tested | Active | 192 | Not Tested | Active |
| 193 | Not Tested | Not Active | 194 | Not Tested | Active | 195 | Not Tested | Active |
| 196 | Not Tested | Active | 197 | Not Tested | Not Active | 198 | Not Tested | Active |
| 199 | Not Tested | Active | 200 | Not Tested | Not Active | 201 | Not Tested | Not Active |
| 202 | Not Tested | Active | 203 | Not Tested | Active | 204 | Not Tested | Active |
| 205 | Not Tested | Active | 206 | Not Tested | Active | 207 | Not Tested | Active |
| 208 | Not Tested | Active | 209 | Not Tested | Active | 210 | Not Tested | Active |
| 211 | Not Tested | Active | 212 | Not Tested | Active | 213 | Not Tested | Active |
| 214 | Not Tested | Active | 214 | Not Tested | Active | 215 | Not Tested | Active |
| 216 | Not Tested | Active | 217 | Not Tested | Active | 218 | Not Tested | Active |

TABLE 2-continued

Inhibition of Tetra-acetylated Histone H4 Binding to Brd4 bromodomain 1
(BRD4(1) and Brd 3 bromodomain 2 (BRD2(2) as Measured by FRET

| Example Number | FRET activity (IC50 <30 μM) BRD2(2)-BRD4(1) | | Example Number | FRET activity (IC50 <30 μM) BRD2(2)-BRD4(1) | | Example Number | FRET activity (IC50 <30 μM) BRD2(2)-BRD4(1) | |
|---|---|---|---|---|---|---|---|---|
| 219 | Not Tested | Active | 220 | Not Tested | Active | 221 | Not Tested | Active |
| 222 | Not Tested | Active | 223 | Not Tested | Active | 224 | Not Tested | Active |
| 225 | Not Tested | Not Active | 226 | Not Tested | Active | 227 | Not Tested | Active |
| 228 | Not Tested | Active | 229 | Not Tested | Active | 230 | Not Tested | Active |
| 231 | Not Tested | Active | 232 | Not Tested | Active | 233 | Not Tested | Active |
| 234 | Not Tested | Active | 235 | Not Tested | Active | 236 | Not Tested | Active |
| 237 | Not Tested | Active | 238 | Not Tested | Active | 239 | Not Tested | Active |
| 240 | Not Tested | Active | 241 | Not Tested | Active | 242 | Not Tested | Active |
| 243 | Not Tested | Active | 244 | Not Tested | Active | 245 | Not Tested | Active |
| 246 | Not Tested | Active | 247 | Not Tested | Active | 248 | Not Tested | Active |
| 249 | Not Tested | Not Active | 250 | Not Tested | Active | 251 | Not Tested | Active |
| 252 | Not Tested | Active | 253 | Not Tested | Active | 254 | Not Tested | Active |
| 255 | Not Tested | Active | 256 | Not Tested | Active | 257 | Not Tested | Active |
| 258 | Not Tested | Active | 259 | Not Tested | Not Active | 260 | Not Tested | Not Active |
| 261 | Not Tested | Active | 262 | Not Tested | Active | 263 | Not Tested | Active |
| 264 | Not Tested | Active | 265 | Not Tested | Not Active | 266 | Not Tested | Not Active |
| 267 | Not Tested | Active | 268 | Not Tested | Not Active | 269 | Not Tested | Not Active |
| 270 | Not Tested | Active | 271 | Not Tested | Active | 272 | Not Tested | Active |
| 273 | Not Tested | Active | 274 | Not Tested | Active | — | — | — |

Example 276

Inhibition of c-Myc Expression in Cancer Cell Lines

MV4-11 cells (2.5×10$^4$ cells) were plated in 96 well U-bottom plates with test compound or DMSO (0.1%), and incubated for 3 h at 37° C. Cells were then harvested by centrifugation, lysed, and mRNA was isolated using the mRNA catcher plus kit (Invitrogen). Reverse transcription of the mRNA and duplex amplification of the c-myc and cyclophilin cDNAs was performed using the RNA Ultrasense kit (Invitrogen) and a ViiA7 real-time PCR machine (Applied Biosystems). IC$_{50}$ values were determined from a dose response curve.

Compounds with an IC$_{50}$ value less than 30 μM were deemed to be active.

TABLE 3

Inhibition of c-myc Activity in Human AML MV4-11 cells

| Example Number | c-myc activity (IC50 <30 μM) | Example Number | c-myc activity (IC50 <30 μM) | Example Number | c-myc activity (IC50 <30 μM) | Example Number | c-myc activity (IC50 <30 μM) |
|---|---|---|---|---|---|---|---|
| 1 | Not Active | 2 | Not Active | 4 | Active | 5 | Active |
| 13 | Not Active | 14 | Not Active | 15 | Not Active | 16 | Not Active |
| 17 | Active | 19 | Active | 21 | Active | 22 | Not Active |
| 24 | Not Active | 25 | Active | 28 | Active | 29 | Active |
| 30 | Not Active | 34 | Active | 42 | Active | 43 | Active |
| 47 | Active | 49 | Active | 50 | Active | 51 | Not Active |
| 52 | Not Active | 53 | Not Active | 54 | Active | 55 | Active |
| 56 | Active | 60 | Not Active | 63 | Active | 64 | Active |
| 65 | Active | 66 | Active | 70 | Active | 71 | Active |
| 72 | Active | 73 | Active | 75 | Active | 78 | Active |
| 79 | Active | 82 | Not Active | 83 | Not Active | 84 | Not Active |

TABLE 3-continued

Inhibition of c-myc Activity in Human AML MV4-11 cells

| Example Number | c-myc activity (IC50 <30 μM) | Example Number | c-myc activity (IC50 <30 μM) | Example Number | c-myc activity (IC50 <30 μM) | Example Number | c-myc activity (IC50 <30 μM) |
|---|---|---|---|---|---|---|---|
| 90 | Not Active | 91 | Not Active | 93 | Not Active | 94 | Not Active |
| 95 | Not Active | 96 | Active | 98 | Not Active | 99 | Active |
| 101 | Active | 104 | Active | 105 | Active | 107 | Not Active |
| 108 | Active | 109 | Active | 113 | Active | 117 | Not Active |
| 118 | Not Active | 119 | Not Active | 120 | Not Active | 121 | Active |
| 122 | Active | 123 | Active | 124 | Active | 125 | Active |
| 126 | Active | 127 | Active | 128 | Active | 132 | Active |
| 133 | Active | 134 | Active | 135 | Active | 136 | Active |
| 137 | Active | 142 | Active | 146 | Active | 147 | Active |
| 148 | Active | 149 | Active | 151 | Not Active | 162 | Active |
| 164 | Not Active | 165 | Active | 167 | Not Active | 168 | Not Active |
| 169 | Active | 171 | Active | 172 | Not Active | 179 | Active |
| 180 | Active | 181 | Active | 182 | Active | 183 | Active |
| 184 | Active | 185 | Active | 186 | Active | 187 | Not Active |
| 188 | Not Active | 189 | Active | 190 | Active | 191 | Active |
| 192 | Active | 193 | Not Active | 194 | Active | 198 | Not Active |
| 203 | Active | 205 | Active | 206 | Active | 207 | Active |
| 208 | Active | 209 | Active | 210 | Active | 211 | Active |
| 212 | Active | 213 | Active | 215 | Active | 216 | Active |
| 219 | Active | 220 | Active | 222 | Active | 223 | Active |
| 226 | Active | 227 | Active | 228 | Active | 230 | Active |
| 231 | Active | 233 | Active | 237 | Active | 238 | Active |
| 240 | Active | 241 | Active | 242 | Active | 247 | Active |
| 251 | Active | 252 | Active | 254 | Active | 255 | Active |
| 256 | Active | 261 | Active | 262 | Active | 263 | Active |
| 264 | Active | 267 | Active | 270 | Active | 271 | Active |
| 272 | Active | 273 | Active | 274 | Active | — | — |

Example 277

Inhibition of Cell Proliferation in Cancer Cell Lines

MV4-11 cells: 96-well plates were seeded with $5 \times 10^4$ cells per well of exponentially growing human AML MV-4-11 (CRL-9591) cells and immediately treated with two-fold dilutions of test compounds, ranging from 30 μM to 0.2 μM. Triplicate wells were used for each concentration, as well as a media only and three DMSO control wells. The cells and compounds were incubated at 37° C., 5% $CO_2$ for 72 h before adding 20 μL of the CellTiter Aqueous One Solution (Promega) to each well and incubating at 37° C., 5% $CO_2$ for an additional 3-4 h. The absorbance was taken at 490 nm in a spectrophotometer and the percentage of proliferation relative to DMSO-treated cells was calculated after correction from the blank well. $IC_{50}$ were calculated using the GraphPad Prism software.

Compounds with an $IC_{50}$ value less than 30 μM were deemed to be active.

TABLE 4

Inhibition of Cell Proliferation in Human AML MV-4-11 cells

| Example Number | Cell Proliferation activity (IC50 <30 μM) | Example Number | Cell Proliferation activity (IC50 <30 μM) | Example Number | Cell Proliferation activity (IC50 <30 μM) | Example Number | Cell Proliferation activity (IC50 <30 μM) |
|---|---|---|---|---|---|---|---|
| 1 | Not Active | 2 | Not Active | 4 | Active | 5 | Active |
| 6 | Active | 7 | Active | 13 | Not Active | 14 | Active |
| 15 | Not Active | 17 | Not Active | 19 | Active | 21 | Not Active |
| 22 | Not Active | 24 | Active | 25 | Active | 26 | Active |
| 27 | Active | 28 | Active | 29 | Active | 30 | Active |
| 34 | Active | 42 | Active | 43 | Active | 47 | Active |
| 49 | Active | 50 | Active | 51 | Not Active | 52 | Not Active |
| 53 | Active | 54 | Active | 55 | Active | 56 | Active |
| 60 | Not Active | 63 | Active | 64 | Active | 65 | Active |
| 66 | Active | 70 | Active | 73 | Active | 75 | Active |
| 78 | Active | 82 | Not Active | 83 | Active | 84 | Not Active |
| 87 | Not Active | 90 | Not Active | 91 | Active | 93 | Active |
| 94 | Active | 95 | Not Active | 96 | Active | 98 | Active |
| 99 | Not Active | 101 | Active | 104 | Active | 105 | Active |
| 107 | Active | 108 | Active | 109 | Active | 113 | Active |
| 117 | Not Active | 118 | Active | 119 | Active | 120 | Active |
| 122 | Active | 123 | Active | 124 | Active | 125 | Active |
| 126 | Active | 127 | Active | 128 | Active | 132 | Active |
| 133 | Not Active | 134 | Active | 136 | Active | 137 | Active |
| 142 | Active | 146 | Not Active | 147 | Active | 148 | Active |
| 149 | Active | 151 | Active | 162 | Active | 164 | Active |

TABLE 4-continued

Inhibition of Cell Proliferation in Human AML MV-4-11 cells

| Example Number | Cell Proliferation activity (IC50 <30 μM) | Example Number | Cell Proliferation activity (IC50 <30 μM) | Example Number | Cell Proliferation activity (IC50 <30 μM) | Example Number | Cell Proliferation activity (IC50 <30 μM) |
|---|---|---|---|---|---|---|---|
| 165 | Active | 167 | Active | 168 | Active | 169 | Active |
| 171 | Active | 172 | Active | 179 | Active | 180 | Active |
| 181 | Not Active | 182 | Not Active | 183 | Active | 184 | Active |
| 185 | Active | 186 | Active | 187 | Not Active | 188 | Not Active |
| 189 | Active | 190 | Active | 191 | Active | 192 | Active |
| 193 | Active | 194 | Active | 198 | Not Active | 203 | Active |
| 205 | Active | 206 | Active | 207 | Active | 208 | Active |
| 209 | Active | 210 | Active | 211 | Active | 212 | Active |
| 213 | Active | 215 | Active | 216 | Active | 219 | Active |
| 220 | Active | 222 | Active | 223 | Active | 226 | Active |
| 227 | Active | 228 | Active | 230 | Active | 231 | Active |
| 233 | Active | 237 | Active | 238 | Active | 240 | Active |
| 241 | Active | 242 | Active | 246 | Active | 247 | Active |
| 250 | Active | 251 | Active | 252 | Active | 254 | Active |
| 255 | Active | 256 | Active | 261 | Active | 262 | Active |
| 263 | Active | 264 | Active | 267 | Active | 270 | Active |
| 271 | Active | 272 | Active | 273 | Active | 274 | Active |

Example 278

Inhibition of hIL-6 mRNA Transcription

In this example, hIL-6 mRNA in tissue culture cells was quantitated to measure the transcriptional inhibition of hIL-6 when treated with a compound of the present disclosure.

A human leukemic monocyte lymphoma cell line (U937) was plated ($3.2 \times 10^4$ cells per well) in a 96-well plate in 100 μL RPMI-1640 containing 10% FBS and penicillin/streptomycin, and differentiated into macrophages for 3 days in 60 ng/mL PMA (phorbol-13-myristate-12-acetate) at 37° C. in 5% $CO_2$ prior to the addition of the compound of interest. The cells were pretreated for 1 h with the test compound prior to stimulation with 1 ug/mL lipopolysaccharide from *Escherichia coli*. The cells were incubated at 37° C. for 3 h before the cells were harvested. At time of harvest, the spent media was removed from the cells and the cells were rinsed in 2004 PBS. Cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hIL-6 to an internal control, prior to determining the fold induction of each unknown sample, relative to the control.

Compounds with an $IC_{50}$ value less than 30 μM were deemed to be active.

TABLE 5

Inhibition of hIL-6 mRNA Transcription

| Example Number | IL-6 activity (IC50 <30 μM) | Example Number | IL-6 activity (IC50 <30 μM) | Example Number | IL-6 activity (IC50 <30 μM) | Example Number | IL-6 activity (IC50 <30 μM) |
|---|---|---|---|---|---|---|---|
| 1 | Not Active | 4 | Active | 5 | Active | 6 | Active |
| 7 | Active | 13 | Active | 14 | Active | 15 | Active |
| 17 | Active | 19 | Active | 21 | Active | 24 | Not Active |
| 25 | Active | 26 | Active | 27 | Active | 28 | Active |
| 29 | Active | 30 | Active | 34 | Active | 38 | Active |
| 39 | Active | 42 | Active | 43 | Active | 44 | Not Active |
| 46 | Active | 47 | Active | 49 | Active | 50 | Active |
| 51 | Active | 52 | Active | 53 | Active | 54 | Active |
| 55 | Active | 56 | Active | 60 | Active | 63 | Active |
| 64 | Active | 65 | Active | 66 | Active | 70 | Active |
| 72 | Active | 73 | Active | 75 | Active | 78 | Active |
| 79 | Active | 82 | Active | 83 | Active | 84 | Active |
| 87 | Not Active | 89 | Not Active | 91 | Not Active | 93 | Not Active |
| 94 | Not Active | 95 | Active | 96 | Active | 98 | Active |
| 99 | Active | 101 | Active | 102 | Active | 103 | Not Active |
| 104 | Active | 105 | Active | 107 | Active | 108 | Active |
| 109 | Active | 111 | Active | 112 | Not Active | 113 | Active |
| 117 | Active | 118 | Active | 119 | Active | 120 | Not Active |
| 121 | Active | 122 | Active | 123 | Active | 124 | Active |
| 125 | Active | 126 | Active | 127 | Active | 128 | Active |

TABLE 5-continued

Inhibition of hIL-6 mRNA Transcription

| Example Number | IL-6 activity (IC50 <30 μM) | Example Number | IL-6 activity (IC50 <30 μM) | Example Number | IL-6 activity (IC50 <30 μM) | Example Number | IL-6 activity (IC50 <30 μM) |
|---|---|---|---|---|---|---|---|
| 129 | Active | 130 | Active | 131 | Active | 132 | Active |
| 133 | Not Active | 134 | Active | 136 | Active | 137 | Active |
| 138 | Active | 139 | Active | 141 | Active | 142 | Active |
| 146 | Active | 147 | Active | 148 | Active | 149 | Active |
| 151 | Active | 162 | Active | 164 | Not Active | 165 | Active |
| 167 | Active | 168 | Not Active | 169 | Active | 171 | Active |
| 172 | Active | 179 | Active | 180 | Active | 181 | Not Active |
| 182 | Active | 185 | Not Active | 186 | Active | 187 | Not Active |
| 188 | Active | 189 | Active | 190 | Not Active | 191 | Not Active |
| 192 | Active | 193 | Active | 194 | Active | 198 | Not Active |
| 203 | Active | 205 | Active | 206 | Active | 207 | Active |
| 208 | Active | 209 | Active | 210 | Active | 211 | Active |
| 212 | Active | 213 | Active | 214 | Active | 215 | Active |
| 216 | Active | 217 | Not Active | 218 | Active | 219 | Active |
| 220 | Active | 221 | Not Active | 222 | Active | 223 | Active |
| 226 | Active | 227 | Active | 228 | Active | 230 | Active |
| 231 | Active | 233 | Active | 237 | Active | 238 | Active |
| 240 | Active | 241 | Active | 242 | Active | 244 | Active |
| 247 | Active | 250 | Active | 251 | Active | 252 | Active |
| 254 | Active | 256 | Active | 258 | Active | 263 | Active |
| 264 | Active | 267 | Active | 270 | Active | 271 | Active |
| 272 | Active | 273 | Active | 274 | Active | — | — |

Example 279

Inhibition of IL-17 mRNA Transcription

In this example, hIL-17 mRNA in human peripheral blood mononuclear cells was quantitated to measure the transcriptional inhibition of hIL-17 when treated with a compound of the invention.

Human peripheral blood mononuclear cells were plated ($2.0 \times 10^5$ cells per well) in a 96-well plate in 45 μL OpTimizer T Cell expansion media containing 20 ng/ml IL-2 and penicillin/streptomycin. The cells were treated with the test compound (45 μL at 2× concentration), and then the cells were incubated at 37° C. for 1 h before addition of 10× stock OKT3 antibody at 10 ug/ml in media. Cells were incubated at 37° C. for 3 h before the cells were harvested. At time of harvest, cells were centrifuged (800 rpm, 5 min). Spent media was removed and cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hIL-17 to an internal control, prior to determining the fold induction of each unknown sample, relative to the control.

Compounds with an $IC_{50}$ value less than 30 μM were deemed to be active.

TABLE 6

Inhibition of hIL-17 mRNA Transcription

| Example | IL-17 activity (IC50 <30 μM) |
|---|---|
| Example 128 | Active |
| Example 180 | Active |
| Example 219 | Active |
| Example 241 | Active |
| Example 247 | Active |
| Example 271 | Active |

Example 280

Inhibition of hVCAM mRNA Transcription

In this example, hVCAMmRNA in tissue culture cells is quantitated to measure the transcriptional inhibition of hVCAM when treated with a compound of the present disclosure.

Human umbilical vein endothelial cells (HUVECs) are plated in a 96-well plate ($4.0 \times 10^3$ cells/well) in 100 μL EGM media and incubated for 24 h prior to the addition of the compound of interest. The cells are pretreated for 1 h with the test compound prior to stimulation with tumor necrosis factor-α. The cells are incubated for an additional 24 h before the cells are harvested. At time of harvest, the spent media is removed from the HUVECs and rinsed in 200 μL PBS. Cell lysis solution (70 μl) is then added the cells in each well and incubated for ~5-10 min at room temperature, to allow for complete cell lysis and detachment. mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 μL) is then added to each well. mRNA is then eluted by incubating the mRNA Catcher PLUS plate with elution buffer for 5 min at 68° C. and then immediately placing the plate on ice.

The eluted mRNA so isolated is then used in a one-step quantitative real-time PCR reaction, using components of the Ultra Sense Kit together with Applied Biosystems primer-probe mixes. Real-time PCR data was analyzed, normalizing the Ct values for hVCAM to an internal control, prior to determining the fold induction of each unknown sample, relative to the control.

Compounds with an $IC_{50}$ value less than 30 μM are deemed to be active.

Example 281

Inhibition of hMCP-1 mRNA Transcription

In this example, hMCP-1 mRNA in human peripheral blood mononuclear cells was quantitated to measure the transcriptional inhibition of hMCP-1 when treated with a compound of the present disclosure.

Human Peripheral Blood Mononuclear Cells were plated ($1.0 \times 10^5$ cells per well) in a 96-well plate in 45 μL RPMI-1640 containing 10% FBS and penicillin/streptomycin. The cells were treated with the test compound (45 μL at 2× concentration), and then the cells were incubated at 37° C. for 3 h before the cells were harvested. At time of harvest, cells were transferred to V-bottom plates and centrifuged (800 rpm, 5 min). Spent media was removed and cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hMCP-1 to an internal control, prior to determining the fold induction of each unknown sample, relative to the control.

Compounds with an $IC_{50}$ value less than 30 μM were deemed to be active.

TABLE 7

Inhibition of hMCP-1 mRNA Transcription

| Example | MCP-1 activity (IC50 <30 μM) | Example | MCP-1 activity (IC50 <30 μM) |
|---|---|---|---|
| 27 | Active | 56 | Active |
| 73 | Active | 128 | Active |
| 134 | Active | — | — |

Example 282

Up-Regulation of hApoA-1 mRNA Transcription

In this example, ApoA-I mRNA in tissue culture cells was quantitated to measure the transcriptional up-regulation of ApoA-I when treated with a compound of the present disclosure.

Huh7 cells ($2.5 \times 10^5$ per well) were plated in a 96-well plate using 100 μL DMEM per well, (Gibco DMEM supplemented with penicillin/streptomycin and 10% FBS), 24 h before the addition of the compound of interest. After 48 h treatment, the spent media was removed from the Huh-7 cells and placed on ice (for immediate use) or at −80° C. (for future use) with the "LDH cytotoxicity assay Kit II" from Abcam. The cells remaining in the plate were rinsed with 100 μl. PBS.

Then 85 μL of cell lysis solution was added to each well and incubated for 5-10 min at room temperature, to allow for complete cell lysis and detachment. mRNA was then prepared using the "mRNA Catcher PLUS plate" from Life Technologies, according to the protocol supplied. After the last wash, as much wash buffer as possible was aspirated without allowing the wells to dry. Elution Buffer (E3, 80 μL) was then added to each well. mRNA was then eluted by incubating the mRNA Catcher PLUS plate with Elution Buffer for 5 min at 68° C., and then 1 min at 4° C. Catcher plates with mRNA eluted were kept on ice for use or stored at −80° C.

The eluted mRNA isolated was then used in a one-step real-time PCR reaction, using components of the Ultra Sense Kit together with Life Technologies primer-probe mixes. Real-time PCR data was analyzed, using the Ct values, to determine the fold induction of each unknown sample, relative to the control (that is, relative to the control for each independent DMSO concentration).

Compounds with an $EC_{170}$ value less than 30 μM were deemed to be active.

TABLE 8

Up-regulation of hApoA-1 mRNA Transcription.

| Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) |
|---|---|---|---|---|---|---|---|
| 5 | Active | 6 | Active | 7 | Active | 13 | Active |
| 14 | Active | 16 | Active | 17 | Active | 19 | Active |
| 43 | Active | 47 | Active | 49 | Active | 50 | Active |
| 51 | Active | 52 | Active | 53 | Active | 54 | Active |
| 55 | Active | 56 | Active | 60 | Active | 66 | Active |
| 72 | Active | 73 | Active | 75 | Active | 82 | Active |
| 83 | Active | 99 | Active | 104 | Active | 105 | Active |
| 108 | Active | 109 | Active | 111 | Active | 112 | Active |
| 117 | Active | 118 | Active | 119 | Active | 125 | Active |
| 128 | Active | 132 | Active | 134 | Active | 146 | Active |
| 147 | Active | 148 | Active | 149 | Active | 155 | Active |
| 157 | Active | 158 | Active | 160 | Active | 162 | Active |

TABLE 8-continued

Up-regulation of hApoA-1 mRNA Transcription.

| Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) | Example Number | ApoA-1 activity ($EC_{170}$ <30 μM) |
|---|---|---|---|---|---|---|---|
| 179 | Active | 180 | Active | 181 | Active | 182 | Active |
| 183 | Active | 184 | Active | 185 | Active | 186 | Active |
| 189 | Active | 190 | Active | 191 | Active | 192 | Active |
| 193 | Active | 194 | Active | 198 | Active | 203 | Active |
| 205 | Active | 206 | Active | 207 | Active | 208 | Active |
| 209 | Active | 210 | Active | 211 | Active | 212 | Active |
| 213 | Active | 214 | Active | 215 | Active | 216 | Active |
| 217 | Active | 218 | Active | 219 | Active | 220 | Active |
| 222 | Active | 223 | Active | 226 | Active | 227 | Active |
| 228 | Active | 230 | Active | 233 | Active | 241 | Active |

Example 283

In Vivo Efficacy in Athymic Nude Mouse Strain of an Acute Myeloid Leukemia Xenograft Model Using MV4-11 Cells MV4-11 cells (ATCC) are grown under standard cell culture conditions and (NCr) nu/nu fisol strain of female mice age 6-7 weeks were injected with $5 \times 10^6$ cells/animal in 100 μL PBS+100 μL Matrigel in the lower left abdominal flank. By approximately day 18-21 after MV4-11 cells injection, mice are randomized based on tumor volume (L×W×H)/2) of average ~100-300 mm³. Mice are dosed orally with compound at 5 to 120 mg/kg b.i.d and or 30 mg/kg q.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Examples 284

In Vivo Efficacy in Athymic Nude Mouse Strain of an Acute Myeloid Leukemia Xenograft Model Using OCI-3 AML Cells OCI-3 AML cells (DMSZ) are grown under standard cell culture conditions and (NCr) nu/nu fisol strain of female mice age 6-7 weeks are injected with $10 \times 10^6$ cells/animal in 100 μL PBS+100 μL Matrigel in the lower left abdominal flank. By approximately day 18-21 after OCI-3 AML cells injection, mice are randomized based on tumor volume (L×W×H)/2) of average ~300 mm³. Mice are dosed orally with compound at 30 mg/kg b.i.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Example 285

In Vivo Efficacy in Athymic Nude Mouse Strain of Multiple Myeloma Xenograft Model Using MM1.s Cells MM1.s cells (ATCC) were grown under standard cell culture conditions and SCID-Beige strain of female mice age 6-7 weeks were injected with $10 \times 10^6$ cells/animal in 100 μl PBS+100 μL Matrigel in the lower left abdominal flank. By approximately day 21 after MM1.s cells injection, mice were randomized based on tumor volume (L×W×H)/2) of average ~120 mm³. Mice were dosed orally with compound at 25 to 90 mg/kg b.i.d in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 9

In vivo efficacy in athymic nude mouse strain of multiple myeloma xenograft model using MM1.s cells

| Example | In vivo activity |
|---|---|
| Example 152 | Active |

Example 286

In Vivo Efficacy in Mouse Endotoxemia Model Assay

Sub lethal doses of Endotoxin (*E. Coli* bacterial lipopolysaccharide) were administered to animals to produce a generalized inflammatory response which was monitored by increases in secreted cytokines. Compounds were administered to C57/Bl6 mice orally at 75 mg/kg dose to evaluate inhibition in IL-6 and IL-17 cytokines post 4-h challenge with lipopolysaccharide (LPS) at 0.5 mg/kg dose intraperitoneally.

TABLE 10

In Vivo Efficacy in Mouse Endotoxemia Model Assay.

| Example | In vivo activity |
|---|---|
| Example 128 | Active |
| Example 56 | Active |

Example 287

In Vivo Efficacy in Rat Collagen-Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen was administered to female Lewis strain of rats on Day 1 and 7 of study and dosed with compounds from Day 11 to Day 17. Test compounds were evaluated to assess the potential to inhibit the inflammation (including paw swelling), cartilage destruction and bone resorption in arthritic rats, using a model in which the treatment is administered after the disease has been established.

TABLE 11

In Vivo Efficacy in Rat Collagen-Induced Arthritis.

| Example | In vivo activity |
|---|---|
| Example 128 | Active |

Example 288

In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

This study may be conducted to assess the potential anti-inflammatory effect of test compounds to inhibit the inflammation and clinical EAE scores of a 28 day preventative mouse model. In this model, EAE is induced by $MOG_{35-55}$/CFA immunization and pertussis toxin injection in female C57Bl/6 mice.

In view of the preceding disclosure and examples, the invention includes at least the following exemplary embodiments:

1. A compound of Formula I:

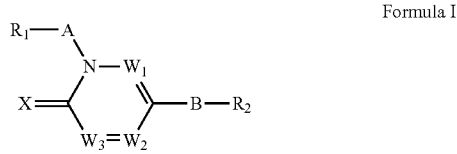

Formula I or a stereoisomer, tautomer, pharmaceutically acceptable salt, or hydrate thereof,
wherein:
$W_1$ is selected from N and $CR_5$;
$W_2$ is selected from N and $CR_4$;
$W_3$ is selected from N and $CR_3$;
each W may be the same or different from each other;
$R_1$ is selected from a carbocycles or heterocycles;
$R_2$ is selected from a 5- or 6-membered monocyclic carbocycle or a 5- or 6-membered monocyclic heterocycle;
$R_3$, $R_4$, and $R_5$ are each independently selected from hydrogen, alkyl, —OH, —$NH_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN;
$R_3$ and $R_4$ may be connected to form an optionally substituted 5-, 6-, or 7-membered carbocycle or heterocycle;
$R_4$ may be connected to B or $R_2$ to form a carbocycle or heterocycle;
X is selected from O and S;
A is selected from —$CR_xR_y$—, C=O, —$C(O)CR_xR_y$—, —$CR_xR_yCR_zR_v$—, —$SO_2$—, —$CR_xR_yCR_zR_vO$—, —$CR_xR_yCR_zR_vN$—, —$CR_xR_yCR_zR_vS$—, and —$CR_xR_yCR_zR_vCR_QR_R$—;
$R_x$, $R_y$, $R_z$, $R_v$, $R_Q$, and $R_R$ are each independently selected from hydrogen, alkyl($C_1$-$C_8$), halogen, —OH, —$CF_3$, amino, alkoxy ($C_1$-$C_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;
B is selected from —$(CR_aR_b)_n$—, —$(CR_aR_bCR_cR_d)$—, —O—, —$OCR_aR_b$—, —$CR_aR_bO$—, —NH—, —$NHCR_aR_b$-, —$CR_aR_bNH$—, —S—, —$SCR_aR_b$—, —$CR_aR_bS$—, —S(O)—, —$S(O)CR_aR_b$—, —$CR_aR_bS(O)$—, —$SO_2$—, —$SO_2CR_aR_b$—, and —$CR_aR_bSO_2$—;
n is selected from 0 and 1, meaning if n=0 then B is absent and $R_2$ is connected directly to the center ring;
$R_a$, $R_b$, $R_c$, and $R_d$ are each independently selected from hydrogen, alkyl($C_1$-$C_3$), and alkoxy($C_1$-$C_3$).

2. A compound of Formula II:

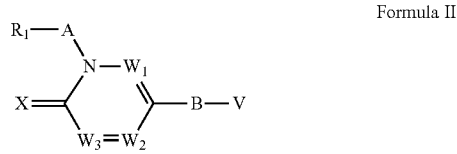

Formula II or a stereoisomer, tautomer, pharmaceutical acceptable salt, or hydrate thereof,
wherein:
$W_1$ is selected from N and $CR_5$;
$W_2$ is selected from N and $CR_4$;
$W_3$ is selected from N and $CR_3$, with the proviso that if $W_3$ is N then neither $R_5$ nor $R_4$ is —OH;
each W may be the same or different from each other;
$R_1$ is a carbocycle or heterocycle;
V is selected from a 5-membered monocyclic carbocycle or monocyclic heterocycle, where the heterocycle is connected to the rest of the molecule via a carbon-carbon bond,
with the proviso that V cannot be unsubstituted thiophene, cyclopentyl, cyclopentenyl, ribofuranosyl, or furan,
$R_3$, $R_4$, and $R_5$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN,
$R_3$ and $R_4$ may be connected to form an optionally substituted 5-, 6-, or 7-membered carbocycle or heterocycle;
$R_4$ may be connected to B or V to form a carbocycle or heterocycle;
X is selected from O and S;
A is selected from —$CR_xR_y$—, C=O, —C(O)$CR_xR_y$—, —$CR_xR_yCR_zR_v$—, —SO$_2$—, —$CR_xR_yCR_zR_vO$—, —$CR_xR_yCR_zR_vN$—, —$CR_xR_yCR_zR_vS$—, and —$CR_xR_yCR_zR_vCR_QR_R$—,
with the proviso that $R_x$ and $R_y$ cannot both be an unsubstituted phenyl ring,
and with the proviso that if A is —CH$_2$CH$_2$CH$_2$— and $W_3$ is N then $R_4$ is not —OH,
and with the proviso that if A is —CH$_2$CH$_2$O— or —CH$_2$C(O)NH— then V is not a substituted

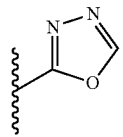 [SMILES: *c1nnco1]

or a substituted

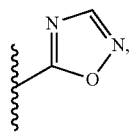

and with the proviso that if A is —CH$_2$CH$_2$O— then $R_1$ is not

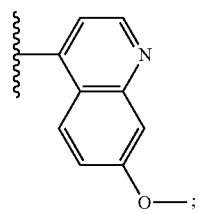 [SMILES: *c1ccnc2cc(OC)ccc12]

$R_x$, $R_y$, $R_z$, $R_v$, $R_Q$ and $R_R$ are each independently selected from hydrogen, alkyl($C_1$-$C_8$), halogen, —OH, —CF$_3$, amino, alkoxy ($C_1$-$C_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;
B is selected from —$(CR_aR_b)_n$—, —$(CR_aR_bCR_cR_d)$—, —O—, —$OCR_aR_b$—, —$CR_aR_bO$—, —NH—, —$NHCR_aR_b$—, —$CR_aR_bNH$—, —S—, —$SCR_aR_b$—, —$CR_aR_bS$—, —S(O)—, —$S(O)CR_aR_b$—, —$CR_aR_bS(O)$—, —SO$_2$—, —$SO_2CR_aR_b$—, and —$CR_aR_bSO_2$—;
n is selected from 0 and 1, meaning if n=0 then B is absent; and wherein
$R_a$, $R_b$, $R_c$, and $R_d$ are each independently selected from hydrogen, alkyl($C_1$-$C_3$), and alkoxy($C_1$-$C_3$).
3. The compound according to embodiment 2, wherein if $W_1$=$CR_5$ and V is an optionally substituted

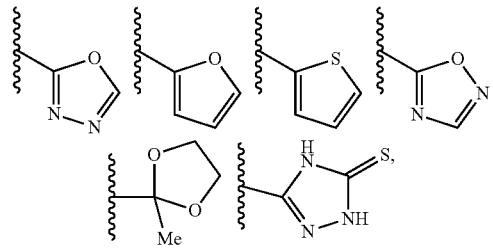

then at least one of $R_3$ and $R_4$ are not hydrogen.
4. The compound according to embodiment 2, wherein if $W_3$=N, then $R_4$ is not hydrogen.
5. The compound according to embodiment 2, wherein if $W_1$=$CR_5$ and V is

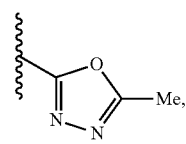 [SMILES: *c1nnc(C)o1]

then $R_1$ is not

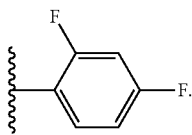 [SMILES: *c1ccc(F)cc1F]

6. The compound according to embodiment 2, wherein if $W_1$=$CR_5$ and V is

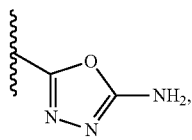 [SMILES: *c1nnc(N)o1]

then $R_1$ is not

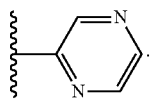

7. The compound according to embodiment 2, wherein if $W_1$=N and V is an optionally substituted

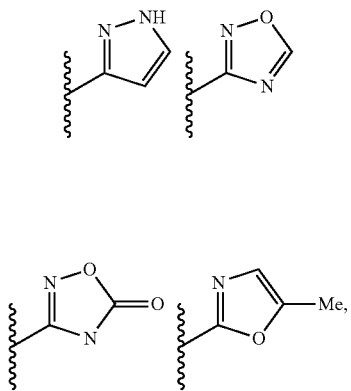

then at least one of $R_3$ and $R_4$ are not hydrogen.

8. The compound according to embodiment 2, wherein if $W_3$=N, then $R_4$ is not hydrogen.

9. The compound according to embodiment 2, wherein if $W_1$=N and V is an optionally substituted

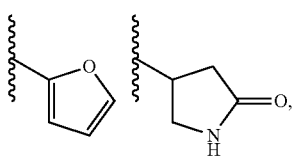

then $R_1$-A is not

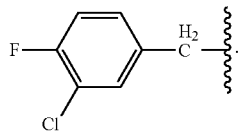

10. The compound according to embodiment 2, wherein if $W_1$=N and V is

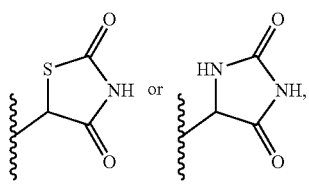 [SMILES: *C1SC(=O)NC1=O ; *C1NC(=O)NC1=O]

then $R_3$ and $R_4$ cannot be connected to form

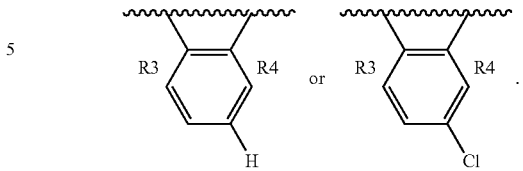

11. The compound according to embodiment 2, wherein if $R_5$ is —COOMe then V is not a substituted thiophene.

12. The compound according to embodiment 2, wherein if $R_5$ is methyl then $R_2$ is not

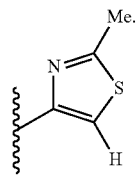 [SMILES: *c1csc(C)n1]

13. The compound according to embodiment 2, wherein if B is present then neither $R_4$ nor $R_5$ is hydroxyl.

14. The compound according to embodiment 2, wherein $R_x$ and $R_y$ cannot both be an unsubstituted phenyl ring.

15. The compound according to any one of embodiments 2 to 14, wherein V is selected from an optionally substituted 5-membered monocyclic heterocycle selected from

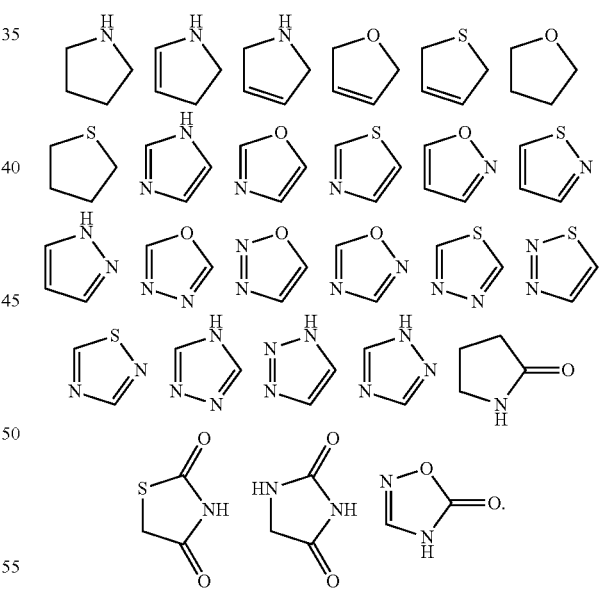

16. The compound according to any one of embodiments 2 to 14, wherein V is optionally substituted with hydrogen, alkyl ($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu—$NMe_2$, NMeEt, —$NEt_2$, —NEtBu), —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et, —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and thio-oxo.

17. The compound according to any one of embodiments 2 to 14, wherein V is selected from an optionally substituted 5-membered monocyclic heterocycle containing one oxygen and one or two nitrogens, where the heterocycle is connected to the rest of the molecule via a carbon-carbon bond.

18. The compound according to any one of embodiments 2 to 14, wherein V is an optionally substituted isoxazole.

19. The compound according to any one of embodiments 2 to 14, wherein V is

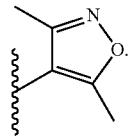

20. The compound according to any one of embodiments 2 to 14, wherein W$_1$ is CR$_5$.

21. The compound according to any one of embodiments 2 to 14, wherein W$_2$ is CR$_4$.

22. The compound according to any one of embodiments 2 to 14, wherein X is oxygen.

23. The compound according to any one of embodiments 2 to 14, wherein n=0, meaning B is absent.

24. The compound according to any one of embodiments 2 to 14, wherein A is selected from C=O and —CR$_x$R$_y$—.

25. The compound according to any one of embodiments 2 to 14, wherein R$_1$ is selected from an optionally substituted 3-, 4-, 5-, and 6-membered carbocycle or heterocycle.

26. The compound according to embodiment 25, wherein the carbocycle or heterocycle is selected from cyclopropyl, phenyl, pyridyl, thiophene, cyclobutyl, piperidine, piperazine, cyclopentyl, and cyclohexyl.

27. The compound according to embodiment 25, wherein R$_1$ is selected from an optionally substituted 5- and 6-membered carbocycle or heterocycle.

28. The compound according to embodiment 27, wherein the carbocycle or heterocycle is selected from phenyl, pyridyl, thiophene, and cyclopentyl.

29. The compound according to embodiment 28, wherein R$_1$ is selected from an optionally substituted phenyl or pyridyl ring.

30. The compound according to any one of embodiments 2 to 14, wherein R$_3$, R$_4$, and R$_5$ are each independently selected from hydrogen, alkyl (C$_1$-C$_8$), —OH, —NH$_2$, thioalkyl (C$_1$-C$_8$), alkoxy(C$_1$-C$_8$) (such as methoxy, ethoxy, —OPr, -OiPr), ketone(C$_1$-C$_8$), ester, carboxylic acid, urea, carbamate, carbonate, amino, amide, halogen (such as F, Cl, Br), carbocycle (such as cyclopropyl, cyclopentyl, phenyl), alkenyl(C$_1$-C$_8$), alkynyl (C$_1$-C$_8$), heterocycle, sulfone, sulfoxide, sulfide, sulfonamide, and —CN, any of which may be optionally substituted.

31. The compound according to any one of embodiments 2 to 14, wherein R$_5$ is selected from hydrogen, methyl, —CF$_3$, Ethyl, propyl, isopropyl, methoxy, ethoxy, propoxy, —NHMe, —NHEthyl, —NHAc, NH$_2$, and —CN.

32. The compound according to any one of embodiments 2 to 14, wherein R$_3$ is selected from hydrogen, —CN, —NH$_2$, amino (such as —NHMe, —NHethyl, —NHcyclopropyl, —NHPh, —NHBn, —NMe$_2$, —NHpyridyl, —NHcyclopentyl), amido (such as —NHAc, —NHC(O)Et, —NHC(O)Pr, —NHC(O)phenyl, —C(O)NHMe, —C(O)NH$_2$, —C(O)NHEt, —C(O)NMe$_2$), sulfone, Sulfoxide, sulfonamide (such as —SO$_2$NH$_2$, —NHSO$_2$Me), carbocycle (phenyl, cyclopropyl, cyclobutyl, cyclopentyl), and heterocycle, any of which may be optionally substituted.

33. The compound according to any one of embodiments 2 to 14, wherein R$_3$ is selected from hydrogen, —NH$_2$, amino (such as —NHMe, —NHEt, —NHcyclopropyl, —NHPh, —NHBn, —NMe$_2$, —NHpyridyl, —NHcyclopentyl), and —NHheterocycle or heterocycle selected from

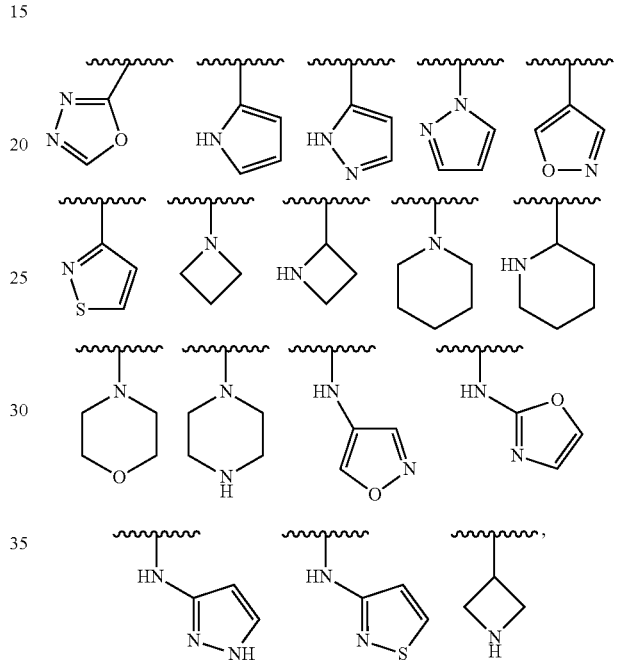

any of which may be optionally substituted with groups independently selected from hydrogen, alkyl (C$_1$-C$_3$), —OH, —NH$_2$, thioalkyl (C$_1$-C$_3$), alkoxy (C$_1$-C$_3$), ketone (C$_1$-C$_3$), ester, carboxylic acid, urea, carbamate, carbonate, amino, amide, and halogen.

34. The compound according to embodiment 33, wherein R$_3$ is selected from hydrogen, —NH$_2$, and amino.

35. The compound according to any one of embodiments 2 to 14, wherein R$_3$ and R$_4$ are connected to form an optionally substituted 5-, 6-, or 7-membered carbocycle or heterocycle selected

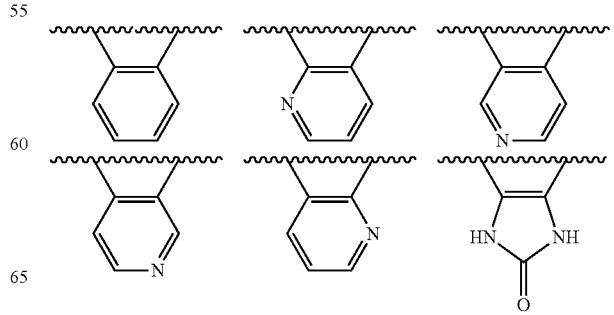

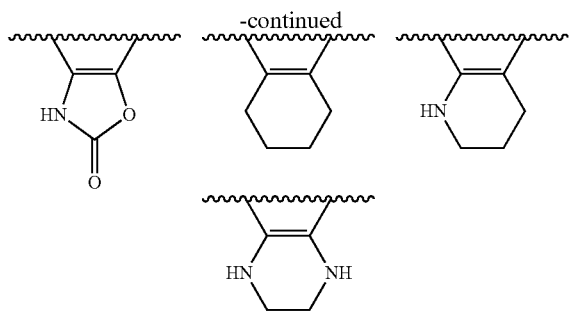

from

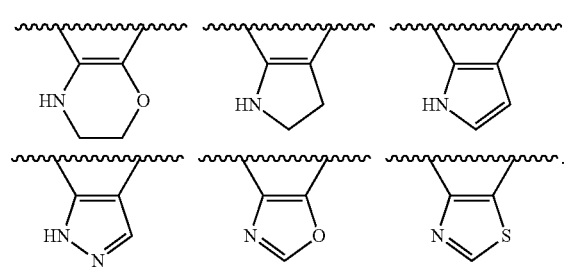

36. The compound according to any one of embodiments 2 to 14, wherein $R_x$ and $R_y$ are selected from hydrogen, alkyl($C_1$-$C_3$); halogen (such as F and Cl), —$CF_3$, amino (such as —NHMe, —NHEt, —NHiPr), alkoxy (such as —OMe, OEt, OPr), —CN.

37. The compound according to any one of embodiments 2 to 14, wherein $R_a$, $R_b$, $R_c$, and $R_d$ are independently selected from hydrogen, methyl, methoxy, and —$CF_3$.

38. The compound according to any one of embodiments 2 to 14, wherein B is selected from —$(CR_aR_b)_n$—, —O—, —NH—, —S—, —S(O)—, —$SO_2$—, where n is 0 or 1, meaning if n=0 then B is absent.

39. The compound according to any one of embodiments 2 to 14, wherein the compound of Formula II is selected from:
6-(3,5-Dimethylisoxazol-4-yl)-2-phenethylpyridazin-3 (2H)-one (Example 1);
6-(3,5-Dimethylisoxazol-4-yl)-2-(pyridin-2-ylmethyl) pyridazin-3(2H)-one (Example 2);
6-(3,5-Dimethylisoxazol-4-yl)-2-(pyrimidin-2-ylmethyl) pyridazin-3(2H)-one (Example 3);
5-(3,5-Dimethylisoxazol-4-yl)-1-(3-(trifluoromethyl)benzyl)pyridin-2(1H)-one (Example 4);
5-(3,5-Dimethylisoxazol-4-yl)-1-(4-(trifluoromethoxy)benzyl)pyridin-2(1H)-one (Example 5);
1-Benzyl-5-(3,5-dimethylisoxazol-4-yl)pyrazin-2(1H)-one (Example 6);
5-(3,5-Dimethylisoxazol-4-yl)-1-(4-(trifluoromethyl)benzyl)pyridin-2(1H)-one (Example 7);
1-Benzyl-5-(3,5-dimethylisoxazol-4-yl)pyrimidin-2(1H)-one (Example 8);
1-(4-((Dimethylamino)methyl)benzyl)-5-(3,5-dimethylisoxazol-4-yl)pyridin-2(1H)-one hydrochloric acid (Example 9);
5-(3,5-Dimethylisoxazol-4-yl)-1-(piperidin-4-ylmethyl)pyridin-2(1H)-one hydrochloric acid (Example 10);
5-(3,5-Dimethylisoxazol-4-yl)-1-((3,5-dimethylisoxazol-4-yl)methyl)pyridin-2(1H)-one (Example 11);
1-Benzyl-5-(3,5-dimethylisoxazol-4-yl)-4-methylpyridin-2 (1H)-one (Example 12);
4-((5-(3,5-Dimethylisoxazol-4-yl)-2-oxopyridin-1(2H)-yl) methyl)benzamide (Example 13);
2-Benzyl-6-(3,5-dimethylisoxazol-4-yl)pyridazin-3(2H)-one (Example 14);
5-(3,5-Dimethylisoxazol-4-yl)-1-(quinoxalin-6-ylmethyl) pyridin-2(1H)-one (Example 18);
6-(3,5-Dimethylisoxazol-4-yl)-2-(1-phenylethyl)pyridazin-3(2H)-one (Example 19);
2-Benzyl-4-methyl-6-(5-methylisoxazol-4-yl)pyridazin-3 (2H)-one (Example 20);
2-Benzyl-6-(3,5-dimethylisoxazol-4-yl)-4-methylpyridazin-3(2H)-one (example 21);
6-(3,5-Dimethylisoxazol-4-yl)-2-(3-fluorobenzyl) pyridazin-3(2H)-one (Example 22);
2-(3-Chlorobenzyl)-6-(3,5-dimethylisoxazol-4-yl) pyridazin-3(2H)-one (Example 23);
2-((3-(3,5-Dimethylisoxazol-4-yl)-6-oxopyridazin-1(6H)-yl)methyl)benzonitrile (Example 24);
2-(4-Chlorobenzyl)-6-(3,5-dimethylisoxazol-4-yl) pyridazin-3(2H)-one (Example 25);
2-(2-Chlorobenzyl)-6-(3,5-dimethylisoxazol-4-yl) pyridazin-3(2H)-one (Example 26);
5-(3,5-Dimethylisoxazol-4-yl)-1-(2-fluorobenzyl)pyridin-2 (1H)-one (Example 27);
6-(3,5-Dimethylisoxazol-4-yl)-2-(2-methylbenzyl) pyridazin-3(2H)-one (Example 28);
6-(3,5-Dimethylisoxazol-4-yl)-2-(4-methylbenzyl) pyridazin-3(2H)-one (Example 29);
6-(3,5-Dimethylisoxazol-4-yl)-2-(3-methylbenzyl) pyridazin-3(2H)-one (Example 30);
6-(3,5-Dimethylisoxazol-4-yl)-2-(3-(trifluoromethyl)benzyl)pyridazin-3(2H)-one (Example 31);
6-(3,5-Dimethylisoxazol-4-yl)-2-(3-fluoro-5-methylbenzyl) pyridazin-3(2H)-one (Example 32);
6-(3,5-Dimethylisoxazol-4-yl)-2-(4-methoxybenzyl) pyridazin-3(2H)-one (Example 33);
6-(3,5-Dimethylisoxazol-4-yl)-2-(1-(2-(trifluoromethyl) phenyl)ethyl)pyridazin-3(2H)-one (Example 34);
6-(3,5-Dimethylisoxazol-4-yl)-2-(3-methoxybenzyl) pyridazin-3(2H)-one (Example 35);
6-(3,5-Dimethylisoxazol-4-yl)-2-(3-(trifluoromethoxy)benzyl)pyridazin-3(2H)-one (Example 36);
6-(3,5-Dimethylisoxazol-4-yl)-2-((tetrahydro-2H-pyran-4-yl)methyl)pyridazin-3(2H)-one (Example 37);
5-(3,5-Dimethylisoxazol-4-yl)-1-(1-(2-(trifluoromethyl) phenyl)ethyl)pyridin-2(1H)-one (Example 38);
6-(3,5-Dimethylisoxazol-4-yl)-2-(2-(trifluoromethoxy)benzyl)pyridazin-3(2H)-one (Example 39);
5-(3,5-Dimethylisoxazol-4-yl)-1-(2-(trifluoromethoxy)benzyl)pyridin-2(1H)-one (Example 40);
5-(3,5-Dimethylisoxazol-4-yl)-1-(4-methylbenzyl)pyridin-2 (1H)-one (Example 41);
5-(3,5-Dimethylisoxazol-4-yl)-1-(3-fluorobenzyl)pyridin-2 (1H)-one (Example 42);
5-(3,5-Dimethylisoxazol-4-yl)-1-(1-phenylpropyl)pyridin-2 (1H)-one (Example 43);
5-(3,5-Dimethylisoxazol-4-yl)-1-(pyridin-3-ylmethyl)pyridin-2(1H)-one (Example 44);
2-(Cyclopropylmethyl)-6-(3,5-dimethylisoxazol-4-yl) pyridazin-3(2H)-one (Example 45);
5-(3,5-Dimethylisoxazol-4-yl)-1-((6-methylpyridin-2-yl) methyl)pyridin-2(1H)-one (Example 46);
5-(3,5-Dimethylisoxazol-4-yl)-1-(quinolin-8-ylmethyl)pyridin-2(1H)-one (Example 47);
1-(Cyclopropylmethyl)-5-(3,5-dimethylisoxazol-4-yl)pyridin-2(1H)-one (Example 48);

1-(Cyclobutylmethyl)-5-(3,5-dimethylisoxazol-4-yl)pyridin-2(1H)-one (Example 49);
1-(3-(Difluoromethyl)benzyl)-5-(3,5-dimethylisoxazol-4-yl)pyridin-2(1H)-one (Example 50);
5-(3,5-Dimethylisoxazol-4-yl)-1-(2-phenoxyethyl)pyridin-2(1H)-one (Example 51);
1-((5-Chloropyridin-2-yl)methyl)-5-(3,5-dimethylisoxazol-4-yl)pyridin-2(1H)-one (Example 55);
1-Benzyl-5-(3,5-dimethylisoxazol-4-yl)pyridin-2(1H)-one (Example 56);
1-Benzyl-5-(5-methylisoxazol-4-yl)pyridin-2(1H)-one (Example 57);
1-Benzyl-5-(isoxazol-4-yl)pyridin-2(1H)-one (Example 58);
1-Benzyl-5-(isothiazol-4-yl)pyridin-2(1H)-one (Example 59);
2-Benzyl-6-((3,5-dimethylisoxazol-4-yl)amino)pyridazin-3(2H)-one (Example 61);
1-Benzyl-5-(3,5-dimethylisoxazol-4-yl)-3-fluoropyridin-2(1H)-one (Example 63);
1-Benzyl-3-chloro-5-(3,5-dimethylisoxazol-4-yl)pyridin-2(1H)-one (Example 64);
1-Benzyl-5-(3,5-dimethylisoxazol-4-yl)-3-methylpyridin-2(1H)-one (Example 66);
1-Benzyl-3-cyclopropyl-5-(3,5-dimethylisoxazol-4-yl)pyridin-2(1H)-one (Example 67);
5-(3,5-Dimethylisoxazol-4-yl)-1-(4-fluorobenzoyl)pyridin-2(1H)-one (Example 68);
1-(4-Chlorobenzoyl)-5-(3,5-dimethylisoxazol-4-yl)pyridin-2(1H)-one (Example 69);
1-Benzyl-5-(3,5-dimethylisoxazol-4-yl)-3-(4-fluorophenyl)pyridin-2(1H)-one (Example 70);
N-(1-Benzyl-5-(3,5-dimethylisoxazol-4-yl)-2-oxo-1,2-dihydropyridin-3-yl)acetamide (Example 71);
1-Benzyl-5-(3,5-dimethylisoxazol-4-yl)-3-(phenylamino)pyridin-2(1H)-one (Example 72);
3-Amino-1-benzyl-5-(3,5-dimethylisoxazol-4-yl)pyridin-2(1H)-one (Example 73);
1-Benzyl-3-(benzylamino)-5-(3,5-dimethylisoxazol-4-yl)pyridin-2(1H)-one (Example 74);
1-Benzyl-5-(3,5-dimethylisoxazol-4-yl)-3-(methylamino)pyridin-2(1H)-one (Example 75);
6-(3,5-Dimethylisoxazol-4-yl)-2-(4-(trifluoromethoxy)benzyl)pyridazin-3(2H)-one (Example 76);
6-(3,5-Dimethylisoxazol-4-yl)-2-(naphthalen-2-ylmethyl)pyridazin-3(2H)-one (Example 77);
5-(3,5-Dimethylisoxazol-4-yl)-1-(3-methoxybenzyl)pyridin-2(1H)-one (Example 78);
5-(3,5-Dimethylisoxazol-4-yl)-1-(thiophen-3-ylmethyl)pyridin-2(1H)-one (Example 79);
1-Benzyl-5-(thiazol-5-yl)pyridin-2(1H)-one (Example 80);
1-Benzyl-5-(5-methyl-1H-imidazol-4-yl)pyridin-2(1H)-one (Example 81);
6-(3,5-Dimethylisoxazol-4-yl)-2-(2-fluorobenzyl)-4-methylpyridazin-3(2H)-one (Example 84);
2-(Cyclopropylmethyl)-6-(3,5-dimethylisoxazol-4-yl)-4-methylpyridazin-3(2H)-one (Example 85);
2-Benzyl-6-(3,5-dimethyl-1H-pyrazol-4-yl)pyridazin-3(2H)-one (Example 86);
6-(3,5-Dimethylisoxazol-4-yl)-4-methyl-2-(pyridin-4-ylmethyl)pyridazin-3(2H)-one (Example 87);
2-(Cyclobutylmethyl)-6-(3,5-dimethylisoxazol-4-yl)pyridazin-3(2H)-one (Example 88);
4-((3-(3,5-Dimethylisoxazol-4-yl)-6-oxopyridazin-1(6H)-yl)methyl)-N-methylbenzamide (Example 89);
2-(2,6-Difluorobenzyl)-6-(3,5-dimethylisoxazol-4-yl)pyridazin-3(2H)-one (Example 90);
6-(3,5-Dimethylisoxazol-4-yl)-2-(4-(trifluoromethyl)benzyl)pyridazin-3(2H)-one (Example 91);
6-(3,5-Dimethylisoxazol-4-yl)-2-(2,4,6-trifluorobenzyl)pyridazin-3(2H)-one (Example 92);
6-(3,5-Dimethylisoxazol-4-yl)-2-(2-fluorobenzyl)pyridazin-3(2H)-one (Example 93);
6-(3,5-Dimethylisoxazol-4-yl)-2-(2-(trifluoromethyl)benzyl)pyridazin-3(2H)-one (Example 94);
6-(3,5-Dimethylisoxazol-4-yl)-2-(1-(2-fluorophenyl)ethyl)pyridazin-3(2H)-one (Example 95);
2-(2-Chloro-6-fluorobenzyl)-6-(3,5-dimethylisoxazol-4-yl)pyridazin-3(2H)-one (Example 96);
6-(3,5-Dimethylisoxazol-4-yl)-2-(isoxazol-4-ylmethyl)pyridazin-3(2H)-one (Example 97);
5-(5-Amino-3-methylisoxazol-4-yl)-1-benzylpyridin-2(1H)-one trifluoroacetic acid (Example 98);
5-(3,5-Dimethylisoxazol-4-yl)-1-(1-(4-fluorophenyl)ethyl)pyridin-2(1H)-one (Example 101);
6-(3,5-Dimethylisoxazol-4-yl)-2-(quinolin-8-ylmethyl)pyridazin-3(2H)-one (Example 102);
1-(1-(2-Chlorophenyl)ethyl)-5-(3,5-dimethylisoxazol-4-yl)pyridin-2(1H)-one (Example 103);
5-(3,5-Dimethylisoxazol-4-yl)-1-(1-(3-fluorophenyl)ethyl)pyridin-2(1H)-one (Example 104);
1-(1-(4-Chlorophenyl)ethyl)-5-(3,5-dimethylisoxazol-4-yl)pyridin-2(1H)-one (Example 105);
5-(3,5-Dimethylisoxazol-4-yl)-1-(2-phenylpropan-2-yl)pyridin-2(1H)-one (Example 106);
6-(3,5-Dimethylisoxazol-4-yl)-2-(thiophen-3-ylmethyl)pyridazin-3(2H)-one (Example 107);
(R)-6-(3,5-Dimethylisoxazol-4-yl)-2-(1-phenylethyl)pyridazin-3(2H)-one (Example 108);
(S)-6-(3,5-Dimethylisoxazol-4-yl)-2-(1-phenylethyl)pyridazin-3(2H)-one (Example 109);
(S)-5-(3,5-Dimethylisoxazol-4-yl)-1-(1-(4-fluorophenyl)ethyl)pyridin-2(1H)-one (Example 110);
(R)-5-(3,5-Dimethylisoxazol-4-yl)-1-(1-(4-fluorophenyl)ethyl)pyridin-2(1H)-one (Example 111);
5-(3,5-Dimethylisoxazol-4-yl)-1-(1-(pyridin-2-yl)ethyl)pyridin-2(1H)-one (Example 112);
1-(1-(3-Chlorophenyl)ethyl)-5-(3,5-dimethylisoxazol-4-yl)pyridin-2(1H)-one (Example 113);
1-Benzyl-6-chloro-5-(3,5-dimethylisoxazol-4-yl)pyridin-2(1H)-one (Example 114);
1-Benzyl-5-(3,5-dimethylisoxazol-4-yl)-6-methylpyridin-2(1H)-one (Example 115);
5-(3,5-Dimethylisoxazol-4-yl)-1-(2-methylbenzyl)pyridin-2(1H)-one (Example 121);
5-(3,5-Dimethylisoxazol-4-yl)-1-(3-methylbenzyl)pyridin-2(1H)-one (Example 122);
5-(3,5-Dimethylisoxazol-4-yl)-1-(2-(trifluoromethyl)benzyl)pyridin-2(1H)-one (Example 123);
5-(3,5-Dimethylisoxazol-4-yl)-1-(1-(2-fluorophenyl)ethyl)pyridin-2(1H)-one (Example 124);
5-(3,5-Dimethylisoxazol-4-yl)-1-(1-phenylethyl)pyridin-2(1H)-one (Example 125);
1-(3-Chlorobenzyl)-5-(3,5-dimethylisoxazol-4-yl)pyridin-2(1H)-one (Example 126);
1-(2-Chlorobenzyl)-5-(3,5-dimethylisoxazol-4-yl)pyridin-2(1H)-one (Example 127);
1-(4-Chlorobenzyl)-5-(3,5-dimethylisoxazol-4-yl)pyridin-2(1H)-one (Example 128);
5-(3,5-Dimethylisoxazol-4-yl)-1-(pyridin-4-ylmethyl)pyridin-2(1H)-one (Example 129);
5-(3,5-Dimethylisoxazol-4-yl)-1-(4-methoxybenzyl)pyridin-2(1H)-one (Example 130);

1-(3,4-Dimethoxybenzyl)-5-(3,5-dimethylisoxazol-4-yl)pyridin-2(1H)-one (Example 131);
5-(3,5-Dimethylisoxazol-4-yl)-1-(4-fluorobenzyl)pyridin-2(1H)-one (Example 132);
(S)-5-(3,5-Dimethylisoxazol-4-yl)-1-(1-phenylethyl)pyridin-2(1H)-one (Example 133);
(R)-5-(3,5-Dimethylisoxazol-4-yl)-1-(1-phenylethyl)pyridin-2(1H)-one (Example 134);
2-((5-(3,5-Dimethylisoxazol-4-yl)-2-oxopyridin-1(2H)-yl)methyl)benzonitrile (Example 135);
1-(2,4-Dichlorobenzyl)-5-(3,5-dimethylisoxazol-4-yl)pyridin-2(1H)-one (Example 136);
4-((5-(3,5-Dimethylisoxazol-4-yl)-2-oxopyridin-1(2H)-yl)methyl)benzonitrile (Example 137);
1-(2,4-Difluorobenzyl)-5-(3,5-dimethylisoxazol-4-yl)pyridin-2(1H)-one (Example 138);
1-(4-Chloro-2-fluorobenzyl)-5-(3,5-dimethylisoxazol-4-yl)pyridin-2(1H)-one (Example 139);
1-(2-Chloro-4-fluorobenzyl)-5-(3,5-dimethylisoxazol-4-yl)pyridin-2(1H)-one (Example 140);
1-(4-Chloro-3-fluorobenzyl)-5-(3,5-dimethylisoxazol-4-yl)pyridin-2(1H)-one (Example 141);
5-(3,5-Dimethylisoxazol-4-yl)-1-(3,4,5-trifluorobenzyl)pyridin-2(1H)-one (Example 142);
2-((1H-Benzo[d]imidazol-5-yl)methyl)-6-(3,5-dimethylisoxazol-4-yl)pyridazin-3(2H)-one (Example 143);
6-(3,5-Dimethylisoxazol-4-yl)-2-(3,4,5-trifluorobenzyl)pyridazin-3(2H)-one (Example 144);
5-(3,5-Dimethylisoxazol-4-yl)-1-(4-(methylsulfonyl)benzyl)pyridin-2(1H)-one (Example 145);
1-((1H-Benzo[d]imidazol-5-yl)methyl)-5-(3,5-dimethylisoxazol-4-yl)pyridin-2(1H)-one (Example 146);
1-(3-Chloro-4-fluorobenzyl)-5-(3,5-dimethylisoxazol-4-yl)pyridin-2(1H)-one (Example 147);
1-((1H-Indazol-5-yl)methyl)-5-(3,5-dimethylisoxazol-4-yl)pyridin-2(1H)-one (Example 148);
1-((1H-Indol-4-yl)methyl)-5-(3,5-dimethylisoxazol-4-yl)pyridin-2(1H)-one (Example 149);
1-((4-Chlorophenyl)sulfonyl)-5-(3,5-dimethylisoxazol-4-yl)pyridin-2(1H)-one (Example 150);
5-(3-Amino-5-methylisoxazol-4-yl)-1-benzylpyridin-2(1H)-one (Example 151);
3-Amino-1-(4-chlorobenzyl)-5-(3,5-dimethylisoxazol-4-yl)pyridin-2(1H)-one (Example 152);
1-Benzyl-5-(3,5-dimethylisoxazol-4-yl)-3-(4-methylpiperazin-1-yl)pyridin-2(1H)-one Hydrochloride (Example 153);
1-Benzyl-5-(3,5-dimethylisoxazol-4-yl)-4-methoxypyridin-2(1H)-one (Example 154);
1-(3,4-Dichlorobenzyl)-5-(3,5-dimethylisoxazol-4-yl)pyridin-2(1H)-one (Example 155);
1-Benzyl-5-(3,5-dimethylisoxazol-4-yl)-3-((4-fluorophenyl)amino)pyridin-2(1H)-one (Example 156);
1-Benzyl-5-(3,5-dimethylisoxazol-4-yl)-3-((3-fluorophenyl)amino)pyridin-2(1H)-one (Example 157);
1-Benzyl-5-(3-(hydroxymethyl)-5-methylisoxazol-4-yl)pyridin-2(1H)-one (Example 158);
1-(4-Chlorobenzyl)-5-(3-(hydroxymethyl)-5-methylisoxazol-4-yl)pyridin-2(1H)-one (Example 159);
1-Benzyl-5-(3-methylisothiazol-4-yl)pyridin-2(1H)-one (Example 160);
1-Benzyl-5-(3,5-dimethylisoxazol-4-yl)-3-(piperazin-1-yl)pyridin-2(1H)-one Hydrochloride (Example 161);
5-(3,5-Dimethylisoxazol-4-yl)-1-(2-methoxybenzyl)pyridin-2(1H)-one (Example 162);
5-(3,5-Dimethylisoxazol-4-yl)-1-(pyrimidin-2-ylmethyl)pyridin-2(1H)-one (Example 163);
2-Benzyl-4-(3,5-dimethylisoxazol-4-yl)isoquinolin-1(2H)-one (Example 167);
2-Benzyl-4-(3,5-dimethylisoxazol-4-yl)-2H-phthalazin-1-one (Example 170);
6-Benzyl-8-(3,5-dimethylisoxazol-4-yl)-1,6-naphthyridin-5(6H)-one (Example 173);
7-Benzyl-5-(3,5-dimethylisoxazol-4-yl)-1,7-naphthyridin-8(7H)-one (Example 174);
2-Benzyl-4-(3,5-dimethylisoxazol-4-yl)-2,7-naphthyridin-1(2H)-one (Example 175);
2-Benzyl-4-(3,5-dimethylisoxazol-4-yl)-2,6-naphthyridin-1(2H)-one (Example 176);
3-amino-5-(3,5-dimethylisoxazol-4-yl)-1-(4-fluorobenzyl)pyridin-2(1H)-one (Example 180);
3-chloro-5-(3,5-dimethylisoxazol-4-yl)-1-(4-fluorobenzyl)pyridin-2(1H)-one (Example 181);
5-(3,5-dimethylisoxazol-4-yl)-1-(4-fluorobenzyl)-3-(phenylamino)pyridin-2(1H)-one (Example 182);
3-(azetidin-1-yl)-1-benzyl-5-(3,5-dimethylisoxazol-4-yl)pyridin-2(1H)-one (Example 183);
1-benzyl-5-(3,5-dimethylisoxazol-4-yl)-3-((1-methyl-1H-pyrazol-3-yl)amino)pyridin-2(1H)-one (Example 184);
3-(1-benzyl-5-(3,5-dimethylisoxazol-4-yl)-2-oxo-1,2-dihydropyridin-3-yl)benzamide (Example 185);
1-benzyl-5-(3,5-dimethylisoxazol-4-yl)-3-(ethylamino)pyridin-2(1H)-one (Example 186);
1-benzyl-5-(3-(methoxymethyl)-5-methylisoxazol-4-yl)pyridin-2(1H)-one (Example 187);
1-(4-chlorobenzyl)-5-(3,5-dimethylisoxazol-4-yl)-3-(phenylamino)pyridin-2(1H)-one (Example 188);
3-amino-1-benzyl-5-(3-(hydroxymethyl)-5-methylisoxazol-4-yl)pyridin-2(1H)-one (Example 189);
1-benzyl-5-(3,5-dimethylisoxazol-4-yl)-3-morpholinopyridin-2(1H)-one (Example 190);
1-benzyl-3-(benzyloxy)-5-(3,5-dimethylisoxazol-4-yl)pyridin-2(1H)-one (Example 191);
1-benzyl-5-(3,5-dimethylisoxazol-4-yl)-3-(isopropylamino)pyridin-2(1H)-one (Example 192);
1-benzyl-5-(3,5-dimethylisoxazol-4-yl)-3-(pyridin-2-ylamino)pyridin-2(1H)-one (Example 193);
1-benzyl-5-(3,5-dimethylisoxazol-4-yl)-3-(pyridin-3-ylamino)pyridin-2(1H)-one (Example 194);
1-benzyl-5-(3,5-dimethylisoxazol-4-yl)-3-(pyridin-4-ylamino)pyridin-2(1H)-one (Example 195);
1-benzyl-5-(3,5-dimethylisothiazol-4-yl)pyridin-2(1H)-one (Example 196);
1-benzyl-5-(3,5-dimethylisoxazol-4-yl)-2-oxo-1,2-dihydropyridine-3-carbonitrile (Example 198);
methyl 4-(1-(4-chlorobenzyl)-6-oxo-1,6-dihydropyridin-3-yl)-5-methylisoxazole-3-carboxylate (Example 199);
N-(1-benzyl-5-(3,5-dimethylisoxazol-4-yl)-2-oxo-1,2-dihydropyridin-3-yl)methanesulfonamide (Example 200);
2-benzyl-6-(((3,5-dimethylisoxazol-4-yl)methyl)amino)pyridazin-3(2H)-one (Example 201);
4-(1-(4-chlorobenzyl)-6-oxo-1,6-dihydropyridin-3-yl)-5-methylisoxazole-3-carboxamide (Example 202);
3-amino-1-(4-chloro-3-fluorobenzyl)-5-(3,5-dimethylisoxazol-4-yl)pyridin-2(1H)-one (Example 203);
1-benzyl-5-(3,5-dimethylisoxazol-4-yl)-3-(1H-imidazol-1-yl)pyridin-2(1H)-one (Example 204);
3-amino-1-(4-chlorobenzyl)-5-(3-(hydroxymethyl)-5-methylisoxazol-4-yl)pyridin-2(1H)-one (Example 205);
3-amino-1-(4-chloro-2-fluorobenzyl)-5-(3,5-dimethylisoxazol-4-yl)pyridin-2(1H)-one (Example 206);
3-amino-1-(2-chloro-4-fluorobenzyl)-5-(3,5-dimethylisoxazol-4-yl)pyridin-2(1H)-one (Example 207);

1-benzyl-3-(cyclopentylamino)-5-(3,5-dimethylisoxazol-4-yl)pyridin-2(1H)-one (Example 208);
1-benzyl-5-(3,5-dimethylisoxazol-4-yl)-3-hydroxypyridin-2(1H)-one (Example 209);
1-benzyl-5-(3,5-dimethylisoxazol-4-yl)-3-methoxypyridin-2(1H)-one (Example 210);
3-amino-1-(3,4-difluorobenzyl)-5-(3,5-dimethylisoxazol-4-yl)pyridin-2(1H)-one (Example 211);
3-amino-1-(3-chloro-4-fluorobenzyl)-5-(3,5-dimethylisoxazol-4-yl)pyridin-2(1H)-one (Example 212);
3-amino-1-(3,4-dichlorobenzyl)-5-(3,5-dimethylisoxazol-4-yl)pyridin-2(1H)-one (Example 213);
1-benzyl-5-(5-(hydroxymethyl)-3-methylisoxazol-4-yl)pyridin-2(1H)-one (Example 214);
3-amino-5-(3,5-dimethylisoxazol-4-yl)-1-(thiazol-2-ylmethyl)pyridin-2(1H)-one (Example 215);
4-((3-amino-5-(3,5-dimethylisoxazol-4-yl)-2-oxopyridin-1(2H)-yl)methyl)benzonitrile (Example 216);
1-benzyl-5-(3,5-dimethylisoxazol-4-yl)-3-((3,5-dimethylisoxazol-4-yl)amino)pyridin-2(1H)-one (Example 217);
5-(3,5-dimethylisoxazol-4-yl)-1-(4-vinylbenzyl)pyridin-2(1H)-one (Example 218);
3-amino-5-(3,5-dimethylisoxazol-4-yl)-1-(thiophen-3-ylmethyl)pyridin-2(1H)-one (Example 219);
3-amino-5-(3,5-dimethylisoxazol-4-yl)-1-(4-methoxybenzyl)pyridin-2(1H)-one (Example 220);
1-benzyl-5-(3,5-dimethylisoxazol-4-yl)-3-(pyridazin-3-ylamino)pyridin-2(1H)-one (Example 221);
3-amino-1-((5-chlorothiophen-2-yl)methyl)-5-(3,5-dimethylisoxazol-4-yl)pyridin-2(1H)-one (Example 222);
1-benzyl-5-(3,5-dimethylisoxazol-4-yl)-3-((5-fluoropyridin-3-yl)amino)pyridin-2(1H)-one (Example 223);
3-amino-5-(3,5-dimethylisoxazol-4-yl)-1-methylpyridin-2(1H)-one (Example 224);
4-(1-(4-chlorobenzyl)-6-oxo-1,6-dihydropyridin-3-yl)-5-methylisoxazole-3-carboxylic acid (Example 225);
3-amino-5-(3,5-dimethylisoxazol-4-yl)-1-(4-(trifluoromethoxy)benzyl)pyridin-2(1H)-one (Example 226);
3-amino-1-(2-chlorobenzyl)-5-(3,5-dimethylisoxazol-4-yl)pyridin-2(1H)-one (Example 227);
3-amino-5-(3,5-dimethylisoxazol-4-yl)-1-(4-(trifluoromethyl)benzyl)pyridin-2(1H)-one (Example 228);
1-benzyl-5-(3,5-dimethylisoxazol-4-yl)-2-oxo-1,2-dihydropyridine-3-carboxylic acid (Example 229);
1-benzyl-5-(3,5-dimethylisoxazol-4-yl)-2-oxo-1,2-dihydropyridine-3-carboxamide (Example 230);
1-benzyl-5-(3,5-dimethylisoxazol-4-yl)-3-((5-methoxypyridin-3-yl)amino)pyridin-2(1H)-one (Example 231);
5-((1-benzyl-5-(3,5-dimethylisoxazol-4-yl)-2-oxo-1,2-dihydropyridin-3-yl)amino)picolinonitrile (Example 232);
4-amino-2-(4-chlorobenzyl)-6-(3,5-dimethylisoxazol-4-yl)pyridazin-3(2H)-one (Example 233);
1-benzyl-5-(3,5-dimethylisoxazol-4-yl)-3-((6-methoxypyridin-3-yl)amino)pyridin-2(1H)-one (Example 234);
1-benzyl-5-(3,5-dimethylisoxazol-4-yl)-3-(pyrazin-2-ylamino)pyridin-2(1H)-one (Example 235);
1-benzyl-5-(3,5-dimethylisoxazol-4-yl)-3-(pyrimidin-5-ylamino)pyridin-2(1H)-one (Example 236);
3-amino-1-(4-(azetidin-1-yl)benzyl)-5-(3,5-dimethylisoxazol-4-yl)pyridin-2(1H)-one (Example 237);
3-amino-5-(3,5-dimethylisoxazol-4-yl)-1-(4-morpholinobenzyl)pyridin-2(1H)-one (Example 238);
1-benzyl-5-(3,5-dimethylisoxazol-4-yl)-3-(pyrrolidin-3-ylamino)pyridin-2(1H)-one (Example 239);
3-amino-5-(3,5-dimethylisoxazol-4-yl)-1-((3-methylisoxazol-5-yl)methyl)pyridin-2(1H)-one (Example 240);
3-amino-1-(4-bromobenzyl)-5-(3,5-dimethylisoxazol-4-yl)pyridin-2(1H)-one (Example 241);
3-amino-5-(3,5-dimethylisoxazol-4-yl)-1-(4-isopropylbenzyl)pyridin-2(1H)-one (Example 242);
1-(4-chlorobenzyl)-5-(3,5-dimethylisoxazol-4-yl)-3-((2,2,2-trifluoroethyl)amino)pyridin-2(1H)-one (Example 243);
3-amino-5-(3,5-dimethylisoxazol-4-yl)-1-((6-methylpyridin-2-yl)methyl)pyridin-2(1H)-one (Example 244);
1-benzyl-5-(3,5-dimethylisoxazol-4-yl)-3-((6-methylpyridin-3-yl)amino)pyridin-2(1H)-one (Example 245);
1-benzyl-5-(3,5-dimethylisoxazol-4-yl)-3-((5-methylpyridin-3-yl)amino)pyridin-2(1H)-one (Example 246);
1-((1H-indol-4-yl)methyl)-3-amino-5-(3,5-dimethylisoxazol-4-yl)pyridin-2(1H)-one (Example 247);
2-benzyl-6-(3,5-dimethylisoxazol-4-yl)-4-(pyridin-3-ylamino)pyridazin-3(2H)-one (Example 248);
4-(1-benzyl-6-oxo-1,6-dihydropyridin-3-yl)-N-methoxy-N,5-dimethylisoxazole-3-carboxamide (Example 249);
4-amino-2-benzyl-6-(3,5-dimethylisoxazol-4-yl)pyridazin-3(2H)-one (Example 250);
3-amino-5-(3,5-dimethylisoxazol-4-yl)-1-((2,5-dimethylthiophen-3-yl)methyl)pyridin-2(1H)-one (Example 251);
3-amino-1-((5-chloropyridin-3-yl)methyl)-5-(3,5-dimethylisoxazol-4-yl)pyridin-2(1H)-one (Example 252);
3-amino-1-((3-chloropyridin-4-yl)methyl)-5-(3,5-dimethylisoxazol-4-yl)pyridin-2(1H)-one (Example 253);
3-amino-1-((3-chloropyridin-2-yl)methyl)-5-(3,5-dimethylisoxazol-4-yl)pyridin-2(1H)-one (Example 254);
3-amino-1-((5-chloropyridin-2-yl)methyl)-5-(3,5-dimethylisoxazol-4-yl)pyridin-2(1H)-one (Example 255);
3-amino-1-(benzo[d][1,3]dioxol-5-ylmethyl)-5-(3,5-dimethylisoxazol-4-yl)pyridin-2(1H)-one (Example 256);
3-amino-1-(benzo[d][1,3]dioxol-4-ylmethyl)-5-(3,5-dimethylisoxazol-4-yl)pyridin-2(1H)-one (Example 257);
3-amino-5-(3,5-dimethylisoxazol-4-yl)-1-((6-methylpyridin-3-yl)methyl)pyridin-2(1H)-one (Example 258);
methyl 4-(1-(4-chlorobenzyl)-6-oxo-1,6-dihydropyridin-3-yl)-3-methylisoxazole-5-carboxylate (Example 259);
4-(1-(4-chlorobenzyl)-6-oxo-1,6-dihydropyridin-3-yl)-3-methylisoxazole-5-carboxylic acid (Example 260);
4-((3-amino-5-(3,5-dimethylisoxazol-4-yl)-2-oxopyridin-1(2H)-yl)methyl)-3-fluorobenzonitrile (Example 261);
4-((3-amino-5-(3,5-dimethylisoxazol-4-yl)-2-oxopyridin-1(2H)-yl)methyl)-2-fluorobenzonitrile (Example 262);
3-amino-5-(3,5-dimethylisoxazol-4-yl)-1-(1-phenylethyl)pyridin-2(1H)-one (Example 263);
5-((3-amino-5-(3,5-dimethylisoxazol-4-yl)-2-oxopyridin-1(2H)-yl)methyl)thiophene-2-carbonitrile (Example 264);
4-(1-(4-chlorobenzyl)-6-oxo-1,6-dihydropyridin-3-yl)-N,3-dimethylisoxazole-5-carboxamide (Example 265);
3-(aminomethyl)-1-benzyl-5-(3,5-dimethylisoxazol-4-yl)pyridin-2(1H)-one (Example 266);
3-amino-5-(3,5-dimethylisoxazol-4-yl)-1-(4-iodobenzyl)pyridin-2(1H)-one (Example 267);
1-benzyl-5-(5-oxopyrrolidin-3-yl)pyridin-2(1H)-one (Example 268);
4-(1-(3-amino-5-(3,5-dimethylisoxazol-4-yl)-2-oxopyridin-1(2H)-yl)ethyl)benzonitrile (Example 269);
1-((1H-indol-3-yl)methyl)-3-amino-5-(3,5-dimethylisoxazol-4-yl)pyridin-2(1H)-one (Example 270);
3-amino-5-(3,5-dimethylisoxazol-4-yl)-1-((3-methyl-1H-indol-4-yl)methyl)pyridin-2(1H)-one (Example 271);
5-((3-amino-5-(3,5-dimethylisoxazol-4-yl)-2-oxopyridin-1(2H)-yl)methyl)-2-bromobenzonitrile (Example 272);
4-((3-amino-5-(3,5-dimethylisoxazol-4-yl)-2-oxopyridin-1(2H)-yl)methyl)-2-bromobenzonitrile (Example 276); and 3-amino-5-(3,5-dimethylisoxazol-4-yl)-1-(quinolin-5-ylmethyl)pyridin-2(1H)-one (Example 274).

40. A compound of Formula III:

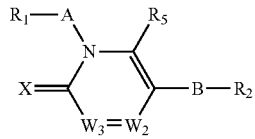

Formula III or a stereoisomer, tautomer, pharmaceutical acceptable salt, or hydrate thereof,
wherein:
$W_2$ is selected from N and $CR_4$,
$W_3$ is selected from N and $CR_3$,
each W may be the same or different from each other;
$R_1$ is a carbocycle or heterocycle,
$R_2$ is selected from a 6-membered monocyclic carbocycle or monocyclic heterocycle,
$R_3$, $R_4$, and $R_5$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN,
with the proviso that $R_4$ is not —OH and $R_5$ is not —COOH or -ester;
$R_3$ and $R_4$ may be connected to form an optionally substituted 5-, 6-, or 7-membered carbocycle or heterocycle;
$R_4$ may be connected to B or $R_2$ to form a carbocycle or heterocycle;
X is selected from O and S;
A is selected from —CR$_x$R$_y$—, C=O, —C(O)CR$_x$R$_y$—, —CR$_x$R$_y$CR$_z$R$_v$—, —SO$_2$—, —CR$_x$R$_y$CR$_z$R$_v$O—, —CR$_x$R$_y$CR$_z$R$_v$N—, —CR$_x$R$_y$CR$_z$R$_v$S—, and —CR$_x$R$_y$CR$_z$R$_v$CR$_Q$R$_R$—;
with the proviso that $R_x$ and R, cannot both be an unsubstituted phenyl ring,
and with the proviso that if A is —CH$_2$CH$_2$CH$_2$— and $W_3$ is N then $R_4$ is not —OH,
and with the proviso that if A is —CH$_2$CH$_2$O— then $R_1$ is not

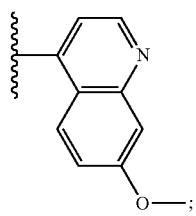 [SMILES: *c1ccnc2cc(OC)ccc12]

$R_x$, $R_y$, $R_z$, $R_v$, $R_Q$, and $R_R$ are each independently selected from hydrogen, alkyl($C_1$-$C_8$), halogen, —OH, —CF$_3$, amino, alkoxy ($C_1$-$C_8$), carboxyl, —CN, sulfone, sulfoxide, sulfide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;

B is selected from —(CR$_a$R$_b$)$_n$—, —(CR$_a$R$_b$CR$_c$R$_d$)—, —O—, —OCR$_a$R$_b$—, —CR$_a$R$_b$O—, —NH—, —NHCR$_a$R$_b$—, —CR$_a$R$_b$NH—, —S—, —SCR$_a$R$_b$—, —CR$_a$R$_b$S—, —S(O)—, —S(O)CR$_a$R$_b$—, —CR$_a$R$_b$S(O)—, —SO$_2$—, —SO$_2$CR$_a$R$_b$—, and —CR$_a$R$_b$SO$_2$—;

n is selected from 0 and 1, meaning if n=0 then B is absent;

and $R_a$, $R_b$, $R_c$, and $R_d$ are each independently selected from hydrogen, alkyl($C_1$-$C_3$), and alkoxy($C_1$-$C_3$).

41. The compound according to embodiment 40, wherein if $W_2$ is N and $R_2$ is

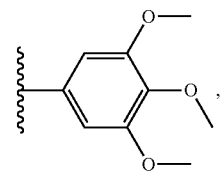 [SMILES: *c1cc(OC)c(OC)c(OC)c1]

then $R_5$ is not hydrogen.

42. The compound according to embodiment 40, wherein if $W_3$ is N then neither $R_5$ nor $R_4$ is —OH.

43. The compound according to embodiment 40, wherein $R_1$-A is not

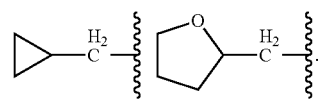

44. The compound according to embodiment 40, wherein if $R_1$-A is

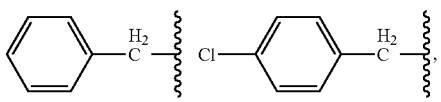

then at least one of $Q_1$, $Q_2$, $Q_3$, or $Q_4$ is not hydrogen.

45. The compound according to embodiment 40, wherein if $R_1$-A is

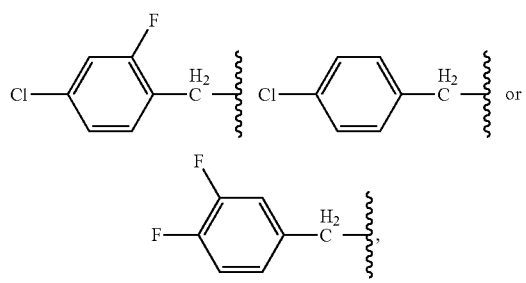

then at least one of $R_3$ and $R_4$ is not hydrogen.

46. The compound according to embodiment 40, wherein if $R_1$ is

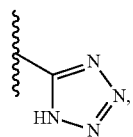

then $R_2$ is not

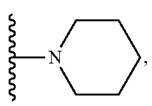

47. The compound according to embodiment 40, wherein if $R_1$ is

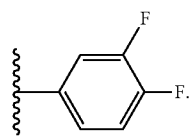 [SMILES: *c1ccc(F)c(F)c1]

then $R_2$ is not

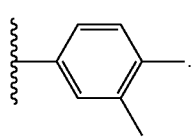 [SMILES: *c1ccc(C)c(C)c1]

48. The compound according to embodiment 40, wherein $R_2$ is not

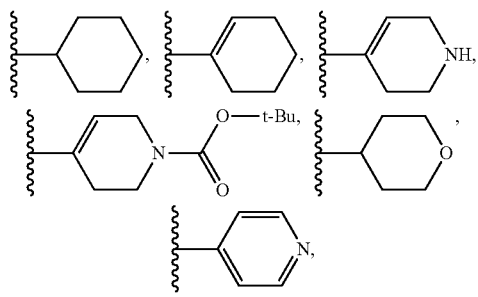

or an optionally substituted

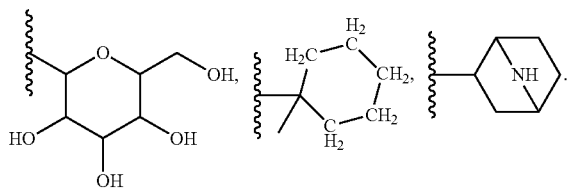

49. The compound according to embodiment 40, wherein if $R_2$ is

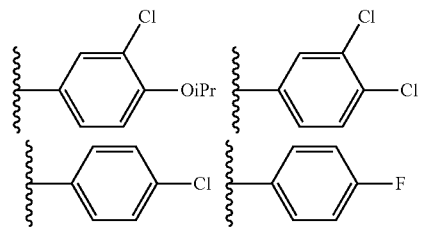

then at least one of $R_3$ and $R_4$ is not hydrogen

50. The compound according to embodiment 40, wherein if $R_3$ is —CN, then $R_2$ is not

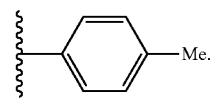

51. The compound according to embodiment 40, wherein if $R_2$ is

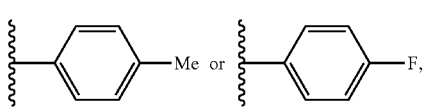

then $R_1$ is not

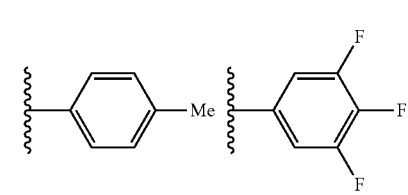

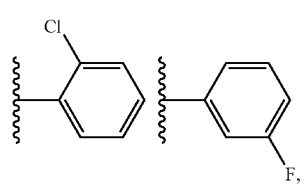

or if R₂ is

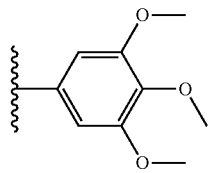 [SMILES: *c1cc(OC)c(OC)c(OC)c1]

then R₅ is not —COOMe; or if R₄ is —NH₂ then R₂ is not

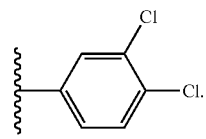 [SMILES: *c1ccc(Cl)c(Cl)c1]

52. The compound according to any one of embodiments 40 to 51, wherein R₂ is selected from an optionally substituted 6-membered monocyclic carbocycle (such as phenyl) or heterocycle (such as pyridyl, pyrimidine, pyrazine, and triazine), where the heterocycle is connected to the rest of the molecule via a carbon-carbon bond.

53. The compound according to any one of embodiments 39 to 50, wherein R₂ is selected from

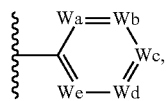

wherein:
$W_a$ is selected from N and $CQ_1$;
$W_b$ is selected from N and $CQ_2$;
$W_c$ is selected from N and $CQ_3$;
$W_d$ is selected from N and $CQ_4$;
$W_e$ is selected from N and $CQ_5$;
Each W may be the same or different from each other;
$Q_1, Q_2, Q_4, Q_5$ are each independently selected from hydrogen, —OH, —NH₂, halogen, —CF₃, —CN, —Ac, alkyl ($C_1$-$C_3$), alkoxy($C_1$-$C_3$), —S(O)Alkyl($C_1$-$C_3$), —SO₂Alkyl ($C_1$-$C_3$), —Salkyl($C_1$-$C_3$), —NHAlkyl($C_1$-$C_3$), —N(Alkyl)₂ ($C_1$-$C_3$), which may be optionally substituted with groups independently selected from F, Cl, Br, —OH, —NH₂, —OMe, —OEt, —NHMe, —SMe, —S(O)Me, -Me, and -Et;
$Q_3$ is selected from —OH, —NH₂, F, Cl, alkyl($C_1$-$C_3$), alkoxy($C_1$-$C_3$), —S(O)Alkyl($C_1$-$C_3$), —SO₂Alkyl($C_1$-$C_3$), —Salkyl($C_1$-$C_3$), —NHAlkyl($C_1$-$C_3$), and —N(Alkyl)₂ ($C_1$-$C_3$), which may be optionally substituted with groups independently selected from F, Cl, —OH, —NH₂, —OMe, —OEt, -Me, and -Et.

54. The compound according to any one of embodiments 40 to 51, wherein R₂ is selected from

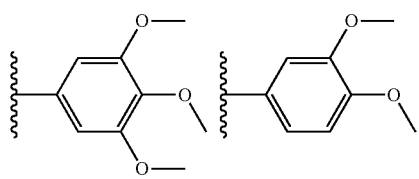

-continued

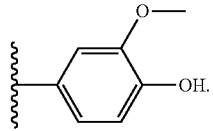

55. The compound according to any one of embodiments 40 to 51, wherein R₁ is selected from a 3, 4-, 5-, or 6-membered carbocycle or heterocycle.

56. The compound according to embodiment 55, wherein R₁ is selected from an optionally substituted phenyl.

57. The compound according to any one of embodiments 40 to 51, wherein R₁ is optionally substituted with hydrogen, —OH, —NH₂, halogen, —CF₃, —CN, —Ac, Alkyl($C_1$-$C_3$), Alkoxy($C_1$-$C_3$), —S(O)Alkyl($C_1$-$C_3$), —SO₂Alkyl($C_1$-$C_3$), —SAlkyl($C_1$-$C_3$), —NHAlkyl($C_1$-$C_3$), and —N(Alkyl)₂ ($C_1$-$C_3$), any of which may be optionally substituted.

58. The compound according to any one of embodiments 40 to 51, wherein R₃ is selected from hydrogen, —CN, —NH₂, amino (such as —NHMe, —NHethyl, —NHcyclopropyl, —NHPh, —NHBn, —NMe₂, —NHpyridyl, —NHcyclopentyl), amido (such as —NHAc, —NHC(O)Et, —NHC(O)Pr, —NHC(O)phenyl, —C(O)NHMe, —C(O)NH₂, —C(O)NHEt, —C(O)NMe₂), sulfone, Sulfoxide, sulfonamide (such as —SO₂NH₂, —NHSO₂Me), carbocycle (phenyl, cyclopropyl, cyclobutyl, cyclopentyl), or heterocycle, any of which may be optionally substituted.

59. The compound according to any one of embodiments 40 to 51, wherein R₃ is selected from hydrogen, —NH₂, amino (such as —NHMe, —NHEt, —NHcyclopropyl, —NHPh, —NHBn, —NMe₂, —NHpyridyl, —NHcyclopentyl), and —NHheterocycle or heterocycle (such as,

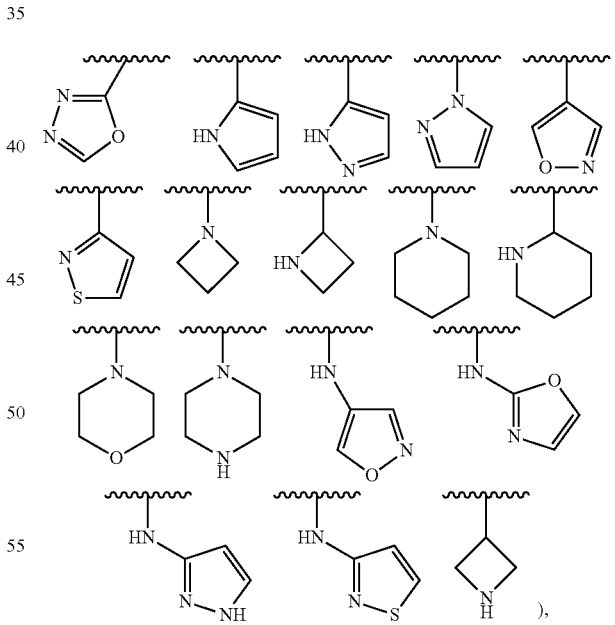), any of which may be optionally substituted with groups independently selected from hydrogen, alkyl, —OH, —NH₂, thioalkyl, alkoxy, ketone, ester, carboxylic acid, urea, carbamate, carbonate, amino, amide, halogen, oxo, and thio-oxo.

60. The compound according to any one of embodiments 40 to 51, wherein R₃, R₄, and R₅ may be optionally substituted with groups independently selected from hydrogen, alkyl, —OH, —NH$_2$, thioalkyl, alkoxy, ketone, ester, carboxylic acid, urea, carbamate, carbonate, amino, amide, and halogen.

61. The compound according to any one of embodiments 40 to 51, wherein R$_3$ and R$_4$ may be connected to form an optionally substituted 5-, 6-, or 7-membered carbocycle or heterocycle such as

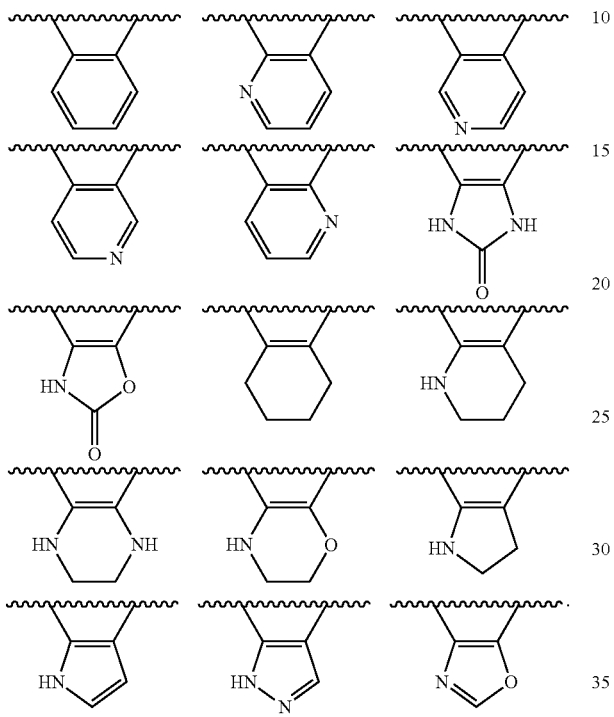

62. The compound according to any one of embodiments 40 to 51, wherein R$_5$ is hydrogen.
63. The compound according to any one of embodiments 40 to 51, wherein R$_4$ is hydrogen.
64. The compound according to any one of embodiments 40 to 51, wherein X is oxygen.
65. The compound according to any one of embodiments 40 to 51, wherein n=0, meaning B is absent.
66. The compound according to any one of embodiments 40 to 51, wherein B is selected from —(CR$_a$R$_b$)$_n$—, —O—, —NH—, —S—, where n is 0 or 1, meaning if n=0 then B is absent.
67. The compound according to any one of embodiments 40 to 51, wherein A is selected from C=O and —CR$_x$R$_y$—.
68. The compound according to any one of embodiments 40 to 51, wherein the compound of Formula III is selected from:
1-Benzyl-5-(3,4,5-trimethoxyphenyl)pyridin-2(1H)-one (Example 52);
2-((2-Oxo-5-(3,4,5-trimethoxyphenyl)pyridin-1(2H)-yl)methyl)benzonitrile (Example 53);
1-Benzyl-2'-hydroxy-[3,4'-bipyridin]-6(1H)-one (Example 62);
1-Benzyl-5-((3,4-dimethoxyphenyl)amino)pyridin-2(1H)-one (Example 65);
2-Benzyl-4-(3,4-dimethoxyphenyl)isoquinolin-1(2H)-one (Example 166);
2-Benzyl-4-(3,4,5-trimethoxyphenyl)isoquinolin-1(2H)-one (Example 168);
2-Benzyl-4-(4-hydroxy-3-methoxyphenyl)isoquinolin-1(2H)-one (Example 169); and
2-Benzyl-4-((3,4,5-trimethoxyphenyl)amino)isoquinolin-1(2H)-one (Example 172).

69. A compound of Formula IV:

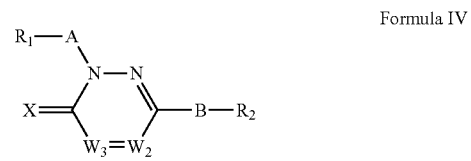

Formula IV or a stereoisomer, tautomer, pharmaceutically acceptable salt, or hydrate thereof,
wherein:
W$_2$ is selected from N and CR$_4$,
W$_3$ is selected from N and CR$_3$,
each W may be the same or different from each other;
R$_1$ is a carbocycle or heterocycle,
R$_2$ is selected from a 6-membered monocyclic carbocycle or monocyclic heterocycle,
R$_3$ and R$_4$ are each independently selected from hydrogen, alkyl, —OH, —NH$_2$, thioalkyl, alkoxy, ketone, ester, carboxylic acid, urea, carbamate, carbonate, amino, amide, halogen, carbocycle, heterocycle, sulfone, sulfoxide, sulfide, sulfonamide, and —CN,
with the proviso that R$_4$ is not —OH;
R$_3$ and R$_4$ may be connected to form an optionally substituted 5-, 6-, or 7-membered carbocycle or heterocycle,
with the proviso that R$_3$ and R$_4$ are not connected to form

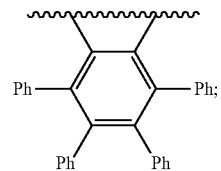

R$_4$ may be connected to B or R$_2$ to form a carbocycle or heterocycle;
X is selected from O and S;
A is selected from —CR$_x$R$_y$—, C=O, —C(O)CR$_x$R$_y$—, —CR$_x$R$_y$CR$_z$R$_v$—, —SO$_2$—, —CR$_x$R$_y$CR$_z$R$_v$O—, —CR$_x$R$_y$CR$_z$R$_v$N—, —CR$_x$R$_y$CR$_z$R$_v$S—, and —CR$_x$R$_y$CR$_z$R$_v$CR$_Q$R$_R$—;
with the proviso that if A is C=O, then R$_2$ is not an optionally substituted

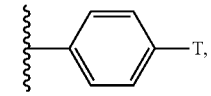

where T is halogen,
and with the proviso that R$_x$ and R$_y$ cannot both be an unsubstituted phenyl ring,
and with the proviso that if A is —CH$_2$CH$_2$CH$_2$— and W$_3$ is N then R$_4$ is not —OH,
and with the proviso that if A is —CH$_2$CH$_2$O— then R$_1$ is not

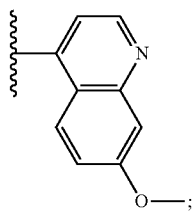 [SMILES: *c1ccnc2cc(OC)ccc12]

$R_x$, $R_y$, $R_z$, $R_v$, $R_Q$, and $R_R$ are each independently selected from hydrogen, alkyl($C_1$-$C_8$), halogen, —OH, —$CF_3$, amino, alkoxy ($C_1$-$C_8$), carboxyl, —CN, sulfone, sulfoxide, carbocycle, and heterocycle, or two substituents selected from $R_x$, $R_y$, $R_z$, $R_v$, $R_Q$ and $R_R$ may form an oxo or thio-oxo group, or two substituents selected from $R_x$, $R_y$, $R_z$, $R_v$, $R_5$, and $R_1$ may be connected in a 5- or 6-membered ring to form a bicyclic carbocycle or bicyclic heterocycle;

B is selected from —$(CR_aR_b)_n$—, —$(CR_aR_bCR_cR_d)$—, —O—, —$OCR_aR_b$—, —$CR_aR_bO$—, —NH—, —$NHCR_aR_b$—, —$CR_aR_bNH$—, —S—, —$SCR_aR_b$—, —$CR_aR_bS$—, —S(O)—, —$S(O)CR_aR_b$—, —$CR_aR_bS(O)$—, —$SO_2$—, —$SO_2CR_aR_b$—, and —$CR_aR_bSO_2$—;

n is selected from 0 and 1, meaning if n=0 then B is absent;

$R_a$, $R_b$, $R_c$, and $R_d$ are each independently selected from hydrogen, alkyl($C_1$-$C_3$), and alkoxy($C_1$-$C_3$).

70. The compound according to embodiment 69, wherein if $W_2$ is N and $R_2$ is

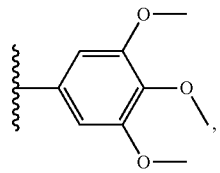

then $R_5$ is not hydrogen.

71. The compound according to embodiment 69, wherein if $W_3$ is N then neither $R_5$ nor $R_4$ is —OH.

72. The compound according to embodiment 69, wherein $R_1$ is not an amino group with nitrogen attached to A, a substituted napthyl, or cyclohexyl.

73. The compound according to embodiment 69, wherein $R_1$-A is not

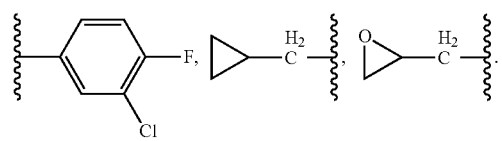

74. The compound according to embodiment 69, wherein if $R_1$-A is

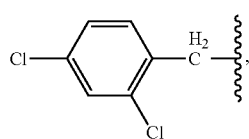 [SMILES: *Cc1ccc(Cl)cc1Cl]

then $R_2$ is not an optionally substituted

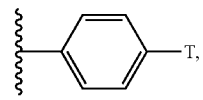

where T is halogen.

75. The compound according to embodiment 69, wherein if $R_1$-A is

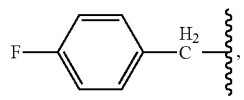

then $R_2$ is not

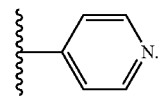

76. The compound according to embodiment 69, wherein if $R_1$A is

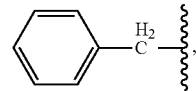

then $R_2$ is not substituted with —OH or —$NH_2$.

77. The compound according to embodiment 68, wherein $R_2$ is not an unsubstituted thiophene, furan, cyclopentyl, cyclohexyl, or

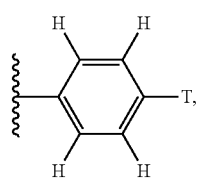

where T is any atom.

78. The compound according to embodiment 69, wherein $R_2$ is not

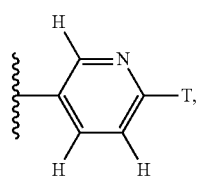

where T is Cl, Br, —OMe, or Me.

79. The compound according to embodiment 69, wherein $R_2$ is not

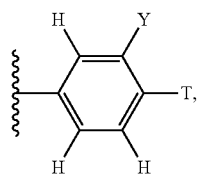

where T and Y are independently selected from Cl, F, -Me, —CN, or —OH.

80. The compound according to embodiment 69, wherein $R_2$ is not

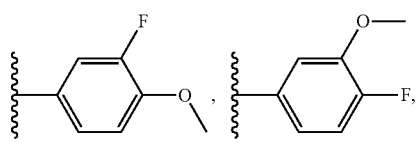

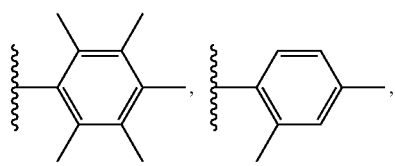

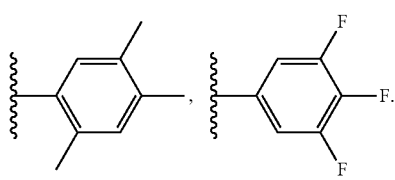

81. The compound according to embodiment 69, wherein if $R_2$ is

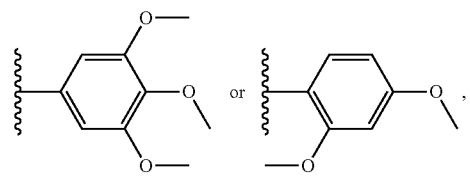 [SMILES: *c1cc(OC)c(OC)c(OC)c1 ; *c1ccc(OC)cc1OC]

then $R_1$-A is not

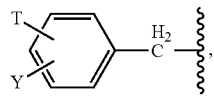

where T and Y are independently selected from hydrogen, F, Cl, Br, —CF$_3$, and -Me, and $R_1$ is not unsubstituted pyridyl, substituted furan, or unsubstituted naphthyl.

82. The compound according to embodiment 69, wherein if $R_2$ is

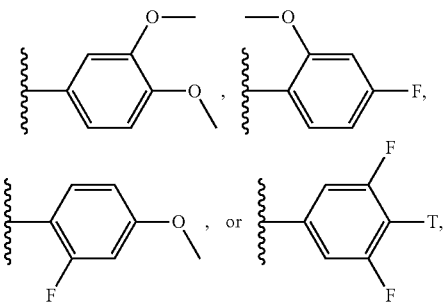

where T is an —OH, Alkoxy, —OAcyl, —NH$_2$, amino, amide, carbamate, or urea substituent, then at least one of $R_3$ and $R_4$ is not hydrogen.

83. The compound according to embodiment 69, wherein if $R_2$ is an unsubstituted pyridyl, then at least one of $R_3$ and $R_4$ is not hydrogen, or $R_1$-A is not

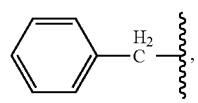

or $R_3$ and $R_4$ are not connected to form an unsubstituted benzene ring.

84. The compound according to embodiment 69, wherein if $R_2$ is

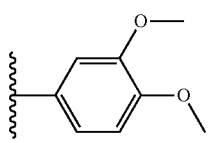 [SMILES: *c1ccc(OC)c(OC)c1]

then $R_3$ is not methyl, at least one of $R_3$ and $R_4$ cannot be connected to

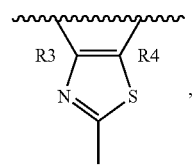

or $R_1$-A cannot be

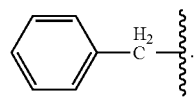

85. The compound according to any one of embodiments 69 to 84, wherein $R_2$ is selected from an optionally substituted 6-membered monocyclic carbocycle (such as phenyl) or heterocycle (such as pyridyl, pyrimidine, pyrazine, and triazine), where the heterocycle is connected to the rest of the molecule via a carbon-carbon bond.

86. The compound according to any one of embodiments 69 to 84, wherein $R_2$ is selected from

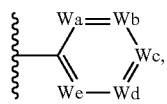

wherein:
$W_a$ is selected from N and $CQ_1$;
$W_b$ is selected from N and $CQ_2$;
$W_c$ is selected from N and $CQ_3$;
$W_d$ is selected from N and $CQ_4$;
$W_e$ is selected from N and $CQ_5$;
Each of $W_a$, $W_b$, $W_c$, $W_d$, and $W_e$ may be the same or different from each other;
$Q_1$, $Q_2$, $Q_4$, $Q_5$ are each independently selected from hydrogen, —OH, —$NH_2$, halogen, —$CF_3$, —CN, —Ac, alkyl ($C_1$-$C_3$), alkoxy($C_1$-$C_3$), —S(O)Alkyl($C_1$-$C_3$), —$SO_2$Alkyl ($C_1$-$C_3$), —Salkyl($C_1$-$C_3$), —NHAlkyl($C_1$-$C_3$), and —N(Alkyl)$_2$($C_1$-$C_3$), which may be optionally substituted with groups independently selected from F, Cl, Br, —OH, —$NH_2$, —OMe, —OEt, —NHMe, —SMe, —S(O)Me, -Me, and -Et;
$Q_3$ is selected from —OH, —$NH_2$, F, Cl, alkyl($C_1$-$C_3$), alkoxy($C_1$-$C_3$), —S(O)Alkyl($C_1$-$C_3$), —$SO_2$Alkyl($C_1$-$C_3$), —Salkyl($C_1$-$C_3$), —NHAlkyl($C_1$-$C_3$), —N(Alkyl)$_2$ ($C_1$-$C_3$), which may be optionally substituted with groups independently selected from F, Cl, —OH, —$NH_2$, —OMe, —OEt, -Me, and -Et.

87. The compound according to any one of embodiments 69 to 84, wherein $R_2$ is selected from

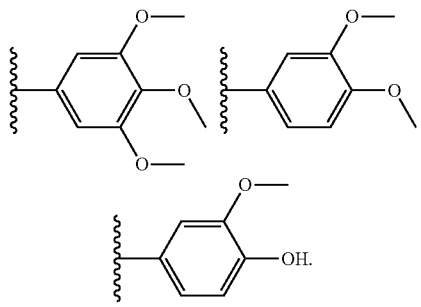

88. The compound according to any one of embodiments 69 to 84, wherein $R_1$ is selected from a 3, 4-, 5-, or 6-membered carbocycle or heterocycle.

89. The compound according to embodiment 87, wherein $R_1$ is an optionally substituted phenyl.

90. The compound according to any one of embodiments 68 to 83, wherein $R_1$ is optionally substituted with hydrogen, —OH, —$NH_2$, halogen, —$CF_3$, —CN, —Ac, Alkyl($C_1$-$C_3$), Alkoxy($C_1$-$C_3$), —S(O)Alkyl($C_1$-$C_3$), —$SO_2$Alkyl($C_1$-$C_3$), —SAlkyl($C_1$-$C_3$), —NHAlkyl($C_1$-$C_3$), and —N(Alkyl)$_2$ ($C_1$-$C_3$), any of which may be optionally substituted.

91. The compound according to any one of embodiments 69 to 84, wherein $R_3$ is selected from hydrogen, —CN, —$NH_2$, amino (such as —NHMe, —NHethyl, —NHcyclopropyl, —NHPh, —NHBn, —NMe$_2$, —NHpyridyl, —NHcyclopentyl), amido (such as —NHAc, —NHC(O)Et, —NHC(O)Pr, —NHC(O)phenyl, —C(O)NHMe, —C(O) NH$_2$, —C(O)NHEt, —C(O)NMe$_2$), sulfone, Sulfoxide, sulfonamide (such as —$SO_2NH_2$, —$NHSO_2Me$), carbocycle (phenyl, cyclopropyl, cyclobutyl, cyclopentyl), or heterocycle, any of which may be optionally substituted.

92. The compound according to any one of embodiments 69 to 84, wherein $R_3$ is selected from hydrogen, —$NH_2$, amino (such as —NHMe, —NHEt, —NHcyclopropyl, —NHPh, —NHBn, —NMe$_2$, —NHpyridyl, —NHcyclopentyl), and —NHheterocycle or heterocycle (such as,

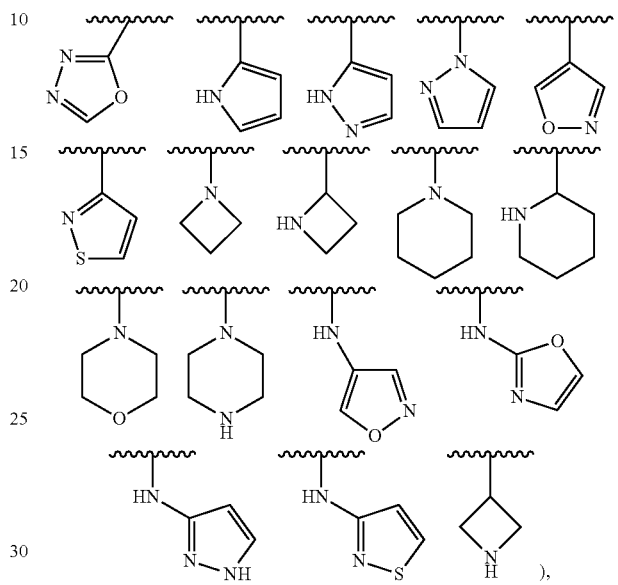

), any of which may be optionally substituted with groups independently selected from hydrogen, alkyl, —OH, —$NH_2$, thioalkyl, alkoxy, ketone, ester, carboxylic acid, urea, carbamate, carbonate, amino, amide, and halogen.

93. The compound according to any one of embodiments 69 to 84, wherein $R_3$, $R_4$, and $R_5$ may be optionally substituted with groups independently selected from hydrogen, alkyl, —OH, —$NH_2$, thioalkyl, alkoxy, ketone, ester, carboxylic acid, urea, carbamate, carbonate, amino, amide, and halogen.

94. The compound according to any one of embodiments 69 to 84, wherein $R_3$ and $R_4$ may be connected to form an optionally substituted 5-, 6-, or 7-membered carbocycle or heterocycle such as

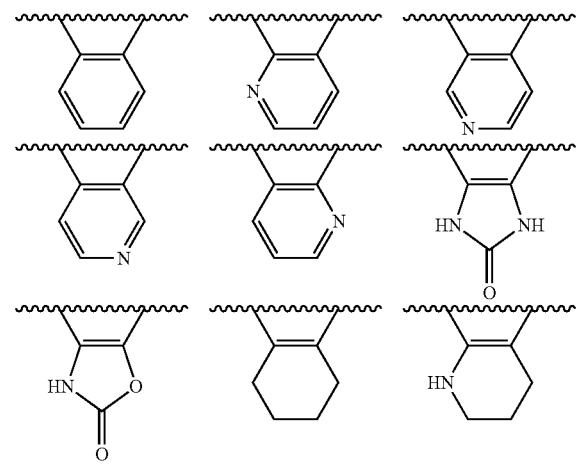

-continued

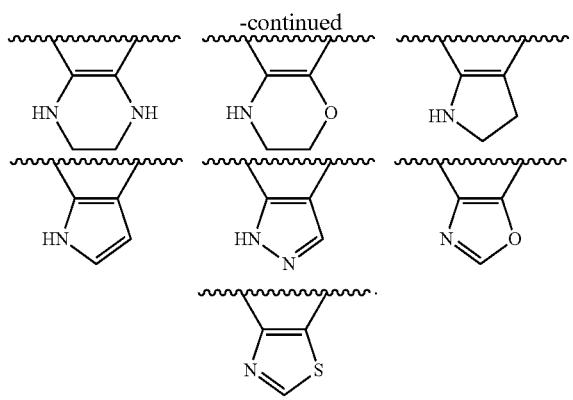

95. The compound according to any one of embodiments 69 to 84, wherein R₄ is hydrogen.

96. The compound according to any one of embodiments 69 to 84, wherein X is oxygen.

97. The compound according to any one of embodiments 69 to 84, wherein n=0, meaning B is absent.

98. The compound according to any one of embodiments 69 to 84, wherein B is selected from —(CR$_a$R$_b$)$_n$—, —O—, —NH—, —S—, where n is 0 or 1, meaning if n=0 then B is absent.

99. The compound according to any one of embodiments 69 to 84, wherein A is selected from C=O and —CR$_x$R$_y$—.

100. The compound according to any one of embodiments 69 to 84, wherein the compound of Formula IV is selected from:
3-((6-Oxo-3-(3,4,5-trimethoxyphenyl)pyridazin-1(6H)-yl) methyl)benzonitrile (Example 15)
4-((6-Oxo-3-(3,4,5-trimethoxyphenyl)pyridazin-1(6H)-yl) methyl)benzonitrile (Example 16);
N-(3-((6-Oxo-3-(3,4,5-trimethoxyphenyl)pyridazin-1(6H)-yl)methyl)phenyl)acetamide (Example 17);
2-Benzyl-6-((3,4,5-trimethoxyphenyl)amino)pyridazin-3(2H)-one (Example 54);
2-Benzyl-6-((3,4-dimethoxyphenyl)amino)pyridazin-3(2H)-one (Example 60);
N-(4-((6-Oxo-3-(3,4,5-trimethoxyphenyl)pyridazin-1(6H)-yl)methyl)phenyl)acetamide (Example 82);
2-Benzyl-6-(4-hydroxy-3-methoxyphenyl)pyridazin-3(2H)-one (Example 83);
2-Benzyl-6-((5,6-dimethoxypyridin-2-yl)amino)pyridazin-3(2H)-one (Example 99);
2-Benzyl-6-(3,4-dimethoxyphenoxy)pyridazin-3(2H)-one (Example 100);
2-(4-(Methylsulfonyl)benzyl)-6-(3,4,5-trimethoxyphenyl) pyridazin-3(2H)-one (Example 116);
2-(4-Methoxybenzyl)-6-(3,4,5-trimethoxyphenyl)pyridazin-3(2H)-one (Example 117);
2-((6-Oxo-3-(3,4,5-trimethoxyphenyl)pyridazin-1(6H)-yl) methyl)benzonitrile (Example 118);
2-(3-Methoxybenzyl)-6-(3,4,5-trimethoxyphenyl)pyridazin-3(2H)-one (Example 119);
2-(4-(tert-Butyl)benzyl)-6-(3,4,5-trimethoxyphenyl) pyridazin-3(2H)-one (Example 120);
2-Benzyl-4-(2-hydroxy-3,4-dimethoxyphenyl)phthalazin-1(2H)-one (Example 164);
2-Benzyl-4-(4-hydroxy-3-methoxyphenyl)-2H-phthalazin-1-one (Example 165);
2-Benzyl-4-(3,4,5-trimethoxyphenylamino)-2H-phthalazin-1-one (Example 171);
2-Benzyl-4-(2,3,4-trimethoxyphenyl)phthalazin-1(2H)-one (Example 177); 6-(4-hydroxyphenyl)-2-(1-phenylethyl) pyridazin-3(2H)-one (Example 178); and
2-benzyl-6-(4-methyl-3-oxopiperazin-1-yl)pyridazin-3 (2H)-one (Example 179).

101. A pharmaceutical composition comprising a compound according to any one of embodiments 1 to 99.

102. A compound according to any one of embodiments 1 to 100 for use as a medicament.

103. A method for inhibiting BET proteins in a mammal comprising administering a therapeutically effective amount of a compound according to any one of embodiments 1 to 100.

104. A method for treating a disease that is sensitive to a BET inhibitor comprising administering a therapeutically effective amount of a compound according to any one of embodiments 1 to 100.

105. A method for treating an autoimmune disease in a mammal comprising administering a therapeutically effective amount of a compound according to any one of embodiments 1 to 100.

106. The method of embodiment 105, wherein the autoimmune disease is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

107. A method for treating inflammatory diseases or disorders in a mammal comprising administering a therapeutically effective amount of a compound according to any one of embodiments 1 to 100.

108. The method of embodiment 107 wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

109. A method for treating or preventing a cancer in a mammal comprising administering a therapeutically effective amount of a compound according to any one of embodiments 1 to 100.

110. The method of embodiment 109 wherein the cancer is a midline carcinoma.

111. The method of embodiment 109 wherein the cancer exhibits overexpression, translocation, amplification, or rearrangement of a myc family oncoproteins.

112. The method of embodiment 109 wherein the cancer is characterized by overexpression of c-myc.

113. The method of embodiment 109 wherein the cancer is characterized by is characterized by overexpression n-myc.

114. The method of embodiment 109 wherein the cancer results from aberrant regulation of BET proteins.

115. The method of embodiment 109 wherein the cancer is characterized by recruitment of pTEFb to regulate oncogenes.

116. The method of embodiment 109 wherein the cancer is characterized by upregulation of CDK6, Bcl2, TYRO3, MYB and/or hTERT.

117. The method of embodiment 109 wherein the cancer is selected from: B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, nodular melanoma, neuroblastoma, oesophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, B-cell lymphoma, non-small cell lung cancer, esophageal cancer and head and neck squamous cell carcinoma, chronic lymphocytic leukemia, follicular lymphoma, diffuse large B cell lymphoma with germinal center phenotype, Burkitt's lymphoma, Hodgkin's lymphoma, follicular lymphomas, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, hepatoma, pro-myelocytic leukemia, chronic lymphocytic leukemia, and mantle cell lymphoma.

118. The method of any one of embodiments 109 to 117 wherein the compound of Formula I is administered in combination with another anticancer agent.

119. The method of embodiment 118, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

120. A method of treating a cardiovascular disease comprising administering a therapeutically effective amount of a compound according to any one of embodiments 1 to 100.

121. The method of embodiment 120, wherein the cardiovascular disease is dyslipidemia, atherosclerosis, hypercholesterolemia, or metabolic syndrome.

122. A method of treating insulin resistance diabetes comprising administering a therapeutically effective amount of a compound according to any one of embodiments 1 to 100.

123. A method of treating a neurological disorder comprising administering a therapeutically effective amount of a compound according to any one of embodiments 1 to 100.

124. The method of embodiment 123 wherein the neurological disorder is Alzheimer's disease, Parkinson's disease, Huntington disease, bipolar disorder, schizophrenia, Rubinstein-Taybi syndrome, or epilepsy.

125. A method of male contraception comprising administering a therapeutically effective amount of a compound according to any one of embodiments 1 to 100.

126. A method of treating HIV comprising administering a therapeutically effective amount of a compound according to any one of embodiments 1 to 100.

127. A method of treating a cancer associated with a viral infection comprising administering a therapeutically effective amount of a compound according to any one of embodiments 1 to 100.

128. The method of embodiment 127 wherein the virus is selected from Epstein-Barr Virus, hepatitis B virus, hepatitis C virus, Kaposi's sarcoma associated virus, human papilloma virus, Merkel cell polyomavirus, and human cytomegalovirus.

129. The compound of embodiment 1, wherein the compound of formula I is 1-(4-chlorobenzyl)-5-(3,5-dimethyl-4H-1,2,4-triazol-4-yl)pyridin-2(1H)-one (Example 197).

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A compound selected from:
 3-amino-5-(3, 5-dimethylisoxazol-4-yl)-1-(4-fluorobenzyl)pyridin-2(1H)-one;
 3-chloro-5-(3, 5-dimethylisoxazol-4-yl)-1-(4-fluorobenzyl)pyridin-2(1H)-one;
 5-(3, 5-dimethylisoxazol-4-yl)-1-(4-fluorobenzyl)-3-(phenylamino)pyridin-2(1H)-one;
 3-(azetidin-1-yl)-1-benzyl-5-(3,5-dimethylisoxazol-4-yl)pyridin-2(1H)-one;
 1-benzyl-5-(3,5-dimethylisoxazol-4-yl)-3-((1-methyl-1H-pyrazol-3-yl)amino)pyridin-2(1H)-one;
 3-(1-benzyl-5-(3,5-dimethylisoxazol-4-yl)-2-oxo-1,2-dihydropyridin-3-yl)benzamide;
 1-benzyl-5-(3, 5-dimethylisoxazol-4-yl)-3-(ethylamino)pyridin-2(1H)-one;
 1-benzyl-5-(3-(methoxymethyl)-5-methylisoxazol-4-yl)pyridin-2(1H)-one;
 1-(4-chlorobenzyl)-5-(3,5-dimethylisoxazol-4-yl)-3-(phenylamino)pyridin-2(1H)-one;
 3-amino-1-benzyl-5-(3-(hydroxymethyl)-5-methylisoxazol-4-yl)pyridin-2(1H)-one;
 1-benzyl-5-(3, 5-dimethylisoxazol-4-yl)-3-morpholinopyridin-2(1H)-one;
 1-benzyl-3-(benzyloxy)-5-(3, 5-dimethylisoxazol-4-yl)pyridin-2(1H)-one;
 1-benzyl-5-(3, 5-dimethylisoxazol-4-yl)-3-(isopropylamino)pyridin-2(1H)-one;

1-benzyl-5-(3,5-dimethylisoxazol-4-yl)-3-(pyridin-2-ylamino)pyridin-2(1H)-one;
1-benzyl-5-(3, 5-dimethylisoxazol-4-yl)-3-(pyridin-3-ylamino)pyridin-2(1H)-one;
1-benzyl-5-(3, 5-dimethylisoxazol-4-yl)-3-(pyridin-4-ylamino)pyridin-2(1H)-one;
1-benzyl-5-(3,5-dimethylisothiazol-4-yl)pyridin-2(1H)-one;
1-benzyl-5-(3, 5-dimethylisoxazol-4-yl)-2-oxo-1,2-dihydropyridine-3-carbonitrile;
methyl 4-(1-(4-chlorobenzyl)-6-oxo-1,6-dihydropyridin-3-yl)-5-methylisoxazole-3-carboxylate;
N-(1-benzyl-5-(3, 5-dimethylisoxazol-4-yl)-2-oxo-1,2-dihydropyridin-3-yl)methanesulfonamide;
4-(1-(4-chlorobenzyl)-6-oxo-1,6-dihydropyridin-3-yl)-5-methylisoxazole-3-carboxamide;
3-amino-1-(4-chloro-3-fluorobenzyl)-5-(3,5-dimethylisoxazol-4-yl)pyridin-2(1H)-one;
1-benzyl-5-(3, 5-dimethylisoxazol-4-yl)-3-(1H-imidazol-1-yl)pyridin-2(1H)-one;
3-amino-1-(4-chlorobenzyl)-5-(3-(hydroxymethyl)-5-methylisoxazol-4-yl)pyridin-2(1H)-one;
3-amino-1-(4-chloro-2-fluorobenzyl)-5-(3, 5-dimethylisoxazol-4-yl)pyridin-2(1H)-one;
3-amino-1-(2-chloro-4-fluorobenzyl)-5-(3,5-dimethylisoxazol-4-yl)pyridin-2(1H)-one;
1-benzyl-3-(cyclopentylamino)-5-(3,5-dimethylisoxazol-4-yl)pyridin-2(1H)-one;
1-benzyl-5-(3,5-dimethylisoxazol-4-yl)-3-hydroxypyridin-2(1H)-one;
1-benzyl-5-(3, 5-dimethylisoxazol-4-yl)-3-methoxypyridin-2(1H)-one;
3-amino-1-(3,4-difluorobenzyl)-5-(3,5-dimethylisoxazol-4-yl)pyridin-2(1H)-one;
3-amino-1-(3-chloro-4-fluorobenzyl)-5-(3, 5-dimethylisoxazol-4-yl)pyridin-2(1H)-one;
3-amino-1-(3,4-dichlorobenzyl)-5-(3, 5-dimethylisoxazol-4-yl)pyridin-2(1H)-one;
1-benzyl-5-(5-(hydroxymethyl)-3-methylisoxazol-4-yl)pyridin-2(1H)-one;
3-amino-5-(3, 5-dimethylisoxazol-4-yl)-1-(thiazol-2-ylmethyl)pyridin-2(1H)-one;
4-((3-amino-5-(3, 5-dimethylisoxazol-4-yl)-2-oxopyridin-1 (2H)-yl)methyl)benzonitrile;
1-benzyl-5-(3, 5-dimethylisoxazol-4-yl)-3-((3, 5-dimethylisoxazol-4-yl)amino)pyridin-2(1H)-one;
5-(3,5-dimethylisoxazol-4-yl)-1-(4-vinylbenzyl)pyridin-2(1H)-one;
3-amino-5-(3, 5-dimethylisoxazol-4-yl)-1-(thiophen-3-ylmethyl)pyridin-2(1H)-one;
3-amino-5-(3,5-dimethylisoxazol-4-yl)-1-(4-methoxybenzyl)pyridin-2(1H)-one;
1-benzyl-5-(3,5-dimethylisoxazol-4-yl)-3-(pyridazin-3-ylamino)pyridin-2(1H)-one;
3-amino-1-((5-chlorothiophen-2-yl)methyl)-5-(3,5-dimethylisoxazol-4-yl)pyridin-2(1H)-one;
1-benzyl-5-(3,5-dimethylisoxazol-4-yl)-3-((5-fluoropyridin-3-yl)amino)pyridin-2(1H)-one;
3-amino-5-(3,5-dimethylisoxazol-4-yl)-1-methylpyridin-2(1H)-one;
4-(1-(4-chlorobenzyl)-6-oxo-1,6-dihydropyridin-3-yl)-5-methylisoxazole-3-carboxylic acid;
3-amino-5-(3,5-dimethylisoxazol-4-yl)-1-(4-(trifluoromethoxy)benzyl)pyridin-2(1H)-one;
3-amino-1-(2-chlorobenzyl)-5-(3, 5-dimethylisoxazol-4-yl)pyridin-2(1H)-one;
3-amino-5-(3,5-dimethylisoxazol-4-yl)-1-(4-(trifluoromethyl)benzyl)pyridin-2(1H)-one;
1-benzyl-5-(3, 5-dimethylisoxazol-4-yl)-2-oxo-1,2-dihydropyridine-3-carboxylic acid;
1-benzyl-5-(3, 5-dimethylisoxazol-4-yl)-2-oxo-1,2-dihydropyridine-3-carboxamide;
1-benzyl-5-(3, 5-dimethylisoxazol-4-yl)-3-((5-methoxypyridin-3-yl)amino)pyridin-2(1H)-one;
5-((1-benzyl-5-(3,5-dimethylisoxazol-4-yl)-2-oxo-1,2-dihydropyridin-3-yl)amino)picolinonitrile;
1-benzyl-5-(3, 5-dimethylisoxazol-4-yl)-3-((6-methoxypyridin-3-yl)amino)pyridin-2(1H)-one;
1-benzyl-5-(3,5-dimethylisoxazol-4-yl)-3-(pyrazin-2-ylamino)pyridin-2(1H)-one;
1-benzyl-5-(3,5-dimethylisoxazol-4-yl)-3-(pyrimidin-5-ylamino)pyridin-2(1H)-one;
3-amino-1-(4-(azetidin-1-yl)benzyl)-5-(3, 5-dimethylisoxazol-4-yl)pyridin-2(1H)-one;
3-amino-5-(3,5-dimethylisoxazol-4-yl)-1-(4-morpholinobenzyl)pyridin-2(1H)-one;
1-benzyl-5-(3,5-dimethylisoxazol-4-yl)-3-(pyrrolidin-3-ylamino)pyridin-2(1H)-one;
3-amino-5-(3, 5-dimethylisoxazol-4-yl)-1-((3-methylisoxazol-5-yl)methyl)pyridin-2(1H)-one;
3-amino-1-(4-bromobenzyl)-5-(3,5-dimethylisoxazol-4-yl)pyridin-2(1H)-one;
3-amino-5-(3, 5-dimethylisoxazol-4-yl)-1-(4-isopropylbenzyl)pyridin-2(1H)-one;
1-(4-chlorobenzyl)-5-(3,5-dimethylisoxazol-4-yl)-3-((2,2,2-trifluoroethyl)amino)pyridin-2(1H)-one;
3-amino-5-(3, 5-dimethylisoxazol-4-yl)-1-((6-methylpyridin-2-yl)methyl)pyridin-2(1H)-one;
1-benzyl-5-(3, 5-dimethylisoxazol-4-yl)-3-((6-methylpyridin-3-yl)amino)pyridin-2(1H)-one;
1-benzyl-5-(3, 5-dimethylisoxazol-4-yl)-3-((5-methylpyridin-3-yl)amino)pyridin-2(1H)-one;
1-((1H-indol-4-yl)methyl)-3-amino-5-(3, 5-dimethylisoxazol-4-yl)pyridin-2(1H)-one;
4-(1-benzyl-6-oxo-1,6-dihydropyridin-3-yl)-N-methoxy-N,5-dimethylisoxazole-3-carboxamide;
3-amino-5-(3,5-dimethylisoxazol-4-yl)-1-((2,5-dimethylthiophen-3-yl)methyl)pyridin-2(1H)-one;
3-amino-1-((5-chloropyridin-3-yl)methyl)-5-(3, 5-dimethylisoxazol-4-yl)pyridin-2(1H)-one;
3-amino-1-((3-chloropyridin-4-yl)methyl)-5-(3, 5-dimethylisoxazol-4-yl)pyridin-2(1H)-one;
3-amino-1-((3-chloropyridin-2-yl)methyl)-5-(3, 5-dimethylisoxazol-4-yl)pyridin-2(1H)-one;
3-amino-1-((5-chloropyridin-2-yl)methyl)-5-(3, 5-dimethylisoxazol-4-yl)pyridin-2(1H)-one;
3-amino-1-(benzo[d][1,3]dioxol-5-ylmethyl)-5-(3,5-dimethylisoxazol-4-yl)pyridin-2(1H)-one;
3-amino-1-(benzo[d][1,3]dioxol-4-ylmethyl)-5-(3, 5-dimethylisoxazol-4-yl)pyridin-2(1H)-one;
3-amino-5-(3, 5-dimethylisoxazol-4-yl)-1-((6-methylpyridin-3-yl)methyl)pyridin-2(1H)-one;
methyl 4-(1-(4-chlorobenzyl)-6-oxo-1,6-dihydropyridin-3-yl)-3-methylisoxazole-5-carboxylate;
4-(1-(4-chlorobenzyl)-6-oxo-1,6-dihydropyridin-3-yl)-3-methylisoxazole-5-carboxylic acid;
4-((3-amino-5-(3,5-dimethylisoxazol-1-yl)-2-oxopyridin-1(2H)-yl)methyl)-3-fluorobenzonitrile;
4-((3-amino-5-(3,5-dimethylisoxazol-4-yl)-2-oxopyridin-1(2H)-yl)methyl)-2-fluorobenzonitrile;
3-amino-5-(3,5-dimethylisoxazol-4-yl)-1-(1-phenylethyl)pyridin-2(1H)-one;

5-((3-amino-5-(3,5-dimethylisoxazol-4-yl)-2-oxopyridin-1(2H)-yl)methyl)thiophene-2-carbonitrile;

4-(1-(4-chlorobenzyl)-6-oxo-1,6-dihydropyridin-3-yl)-N,3-dimethylisoxazole-5-carboxamide;

3-(aminomethyl)-1-benzyl-5-(3,5-dimethylisoxazol-4-yl)pyridin-2(1H)-one;

3-amino-5-(3,5-dimethylisoxazol-4-yl)-1-(4-iodobenzyl)pyridin-2(1H)-one;

1-benzyl-5-(5-oxopyrrolidin-3-yl)pyridin-2(1H)-one;

4-(1-(3-amino-5-(3,5-dimethylisoxazol-4-yl)-2-oxopyridin-1(2H)-yl)ethyl)benzonitrile;

1-((1H-indol-3-yl)methyl)-3-amino-5-(3,5-dimethylisoxazol-4-yl)pyridin-2(1H)-one;

3-amino-5-(3,5-dimethylisoxazol-4-yl)-1-((3-methyl-1H-indol-4-yl)methyl)pyridin-2(1H)-one;

5-((3-amino-5-(3,5-dimethylisoxazol-4-yl)-2-oxopyridin-1 (2H)-yl)methyl)-2-bromobenzonitrile;

4-((3-amino-5-(3, 5-dimethylisoxazol-4-yl)-2-oxopyridin-1 (2H)-yl)methyl)-2-bromobenzonitrile;

3-amino-5-(3,5-dimethylisoxazol-4-yl)-1-(quinolin-5-ylmethyl)pyridin-2(1H)-one;

and stereoisomers, tautomers, pharmaceutical acceptable salts, and hydrates thereof.

2. A pharmaceutical composition comprising a compound according to claim 1, or a stereoisomer, tautomer, pharmaceutically acceptable salt, or hydrate thereof.

3. A compound selected from:

2-benzyl-6-(((3, 5-dimethylisoxazol-4-yl)methyl)amino)pyridazin-3(2H)-one;

4-amino-2-(4-chlorobenzyl)-6-(3, 5-dimethylisoxazol-4-yl)pyridazin-3(2H)-one;

2-benzyl-6-(3, 5-dimethylisoxazol-4-yl)-4-(pyridin-3-ylamino)pyridazin-3(2H)-one;

4-amino-2-benzyl-6-(3,5-dimethylisoxazol-4-yl)pyridazin-3(2H)-one; and stereoisomers, tautomers, pharmaceutical acceptable salts, and hydrates thereof.

4. A pharmaceutical composition comprising a compound according to claim 3, or a stereoisomer, tautomer, pharmaceutically acceptable salt, or hydrate thereof.

* * * * *